US012528848B2

(12) United States Patent
Duperret et al.

(10) Patent No.: US 12,528,848 B2
(45) Date of Patent: Jan. 20, 2026

(54) TUMOR-SPECIFIC NEOANTIGENS AND METHODS OF USING THE SAME

(71) Applicants: The Wistar Institute of Anatomy & Biology, Philadelphia, PA (US); INOVIO PHARMACEUTICALS, INC., Plymouth Meeting, PA (US); GENEOS THERAPEUTICS, INC., Plymouth Meeting, PA (US)

(72) Inventors: Elizabeth Kennedy Duperret, Philadelphia, PA (US); Alfredo Perales Puchalt, Philadelphia, PA (US); David Weiner, Merion, PA (US); Niranjan Y. Sardesai, Blue Bell, PA (US)

(73) Assignees: The Wistar Institute of Anatomy and Biology; Inovio Pharmaceuticals, Inc.; Geneos Therapeutica, Inc.

(*) Notice: Subject to any disclaimer, the term of this patent is extended or adjusted under 35 U.S.C. 154(b) by 1054 days.

(21) Appl. No.: 17/058,999

(22) PCT Filed: May 28, 2019

(86) PCT No.: PCT/US2019/034229
§ 371 (c)(1),
(2) Date: Nov. 25, 2020

(87) PCT Pub. No.: WO2019/227106
PCT Pub. Date: Nov. 28, 2019

(65) Prior Publication Data

US 2021/0361755 A1 Nov. 25, 2021

Related U.S. Application Data

(60) Provisional application No. 62/676,563, filed on May 25, 2018.

(51) Int. Cl.

| | |
|---|---|
| ***C07K 14/47*** | (2006.01) |
| ***A61K 39/00*** | (2006.01) |
| ***A61K 40/11*** | (2025.01) |
| ***A61K 40/42*** | (2025.01) |
| ***A61K 45/06*** | (2006.01) |
| ***A61P 35/00*** | (2006.01) |
| ***C12Q 1/6886*** | (2018.01) |

(52) U.S. Cl.
CPC .......... *C07K 14/4748* (2013.01); *A61K 39/00* (2013.01); *A61K 39/0011* (2013.01); *A61K 39/00119* (2018.08); *A61K 40/11* (2025.01); *A61K 40/4201* (2025.01); *A61K 40/4271* (2025.01); *A61K 45/06* (2013.01); *A61P 35/00* (2018.01); *C12Q 1/6886* (2013.01); *A61K 2039/53* (2013.01); *C12Q 2600/156* (2013.01)

(58) Field of Classification Search
CPC ................ A61K 39/0011; A61K 39/00; A61K 39/00119; A61K 40/11; A61K 40/4201; A61K 40/4271; A61K 45/06; A61K 2039/53; A61K 2039/545; A61K 2039/57; A61K 38/179; A61K 38/193; A61K 38/20; A61K 38/00; C07K 14/4748; C07K 14/5434; C07K 14/71; C07K 2319/00; C07K 2319/50; C07K 14/47; C07K 14/4702; C07K 14/4703; A61P 35/00; C12Q 1/6886; C12Q 2600/156; C12N 15/62
See application file for complete search history.

(56) References Cited

U.S. PATENT DOCUMENTS

| | | | |
|---|---|---|---|
| 2009/0041792 A1 | 2/2009 | Belardelli et al. | |
| 2011/0142865 A1 | 6/2011 | Dengjel | |
| 2013/0267686 A1 | 10/2013 | Brinkmann et al. | |
| 2014/0178438 A1 | 6/2014 | Sahin et al. | |
| 2016/0101170 A1 | 4/2016 | Hacohen et al. | |
| 2016/0303225 A1 | 10/2016 | Cui et al. | |
| 2017/0202939 A1 | 7/2017 | Carreno | |
| 2019/0008938 A1* | 1/2019 | Ciaramella | A61K 39/001114 |

FOREIGN PATENT DOCUMENTS

| | | | |
|---|---|---|---|
| CN | 103160473 A | * | 6/2013 |
| CN | 103180730 A | | 6/2013 |
| CN | 103608033 A1 | | 2/2014 |
| CN | 108025048 A | | 5/2018 |
| JP | 2013539463 A | | 10/2013 |
| JP | 2017500298 A | | 1/2017 |
| WO | 2012159643 A1 | | 11/2012 |
| WO | 2014168874 A2 | | 10/2014 |
| WO | 2017118702 A1 | | 7/2017 |

(Continued)

OTHER PUBLICATIONS

Egerer et al. (Mol. Ther. Jul. 2011; 19 (7): 1236-44).*
Young et al. (Adv. Genet. 2015: 89: 49-88; author manuscript; pp. 1-33).*
Guo Y, Lei K, Tang L. Neoantigen Vaccine Delivery for Personalized Anticancer Immunotherapy. Front Immunol. Jul. 2, 2018;9:1499. doi: 10.3389/fimmu.2018.01499. PMID: 30013560; PMCID: PMC6036114 (Year: 2018).*
Goodman AM, Kato S, Bazhenova L, Patel SP, Frampton GM, Miller V, Stephens PJ, Daniels GA, Kurzrock R. Tumor Mutational Burden as an Independent Predictor of Response to Immunotherapy in Diverse Cancers. Mol Cancer Ther. Nov. 2017;16(11):2598-2608. doi: 10.1158/1535-7163.MCT-17-0386. Epub Aug. 23, 2017. (Year: 2017).*

(Continued)

*Primary Examiner* — Anand U Desai
*Assistant Examiner* — Kathleen Cunningchen
(74) *Attorney, Agent, or Firm* — The Wistar Institute of Anatomy & Biology c/o The Belles Group, P.C.

(57) ABSTRACT

The disclosure relates to methods of manufacturing individualized vaccines that comprise nucleic acid molecules that encode one or more neoantigens specific for antigens that are expressed by a tumor in a subject. Compositions comprising coding regions encoding neoantigens organized in a pattern of nucleic acid sequences are also disclosed as well as methods of immunizing a subject using the same.

25 Claims, 66 Drawing Sheets

Specification includes a Sequence Listing.

(56) References Cited

FOREIGN PATENT DOCUMENTS

| | | | | | |
|---|---|---|---|---|---|
| WO | 2017139498 | A1 | | 8/2017 | |
| WO | 2017152042 | A2 | | 9/2017 | |
| WO | WO-2017222619 | A2 | * | 12/2017 | ............. A61K 35/17 |
| WO | WO-2018144082 | A1 | * | 8/2018 | ......... A61K 31/7088 |
| WO | WO-2019191494 | A1 | * | 10/2019 | ........... A61K 35/761 |

OTHER PUBLICATIONS

Lichtman MA et al. The Oncologist2017; 22(5); 542-548 (Year: 2017).*

Hanahan D et al. Cell 2011 144(5) p. 646-674 (Year: 2011).*

Lee KW et al. Nature Reviews Cancer Nov. 2011 211-218 (Year: 2011).*

Bloquel C, Fabre E, Bureau MF, Scherman D. Plasmid DNA electrotransfer for intracellular and secreted proteins expression: new methodological developments and applications. J Gene Med. Feb. 2004;6 Suppl 1:S11-23. doi: 10.1002/jgm.508. PMID: 14978747 (Year: 2004).*

Genexine "Dose-finding, Safety Study of Plasmid DNA Therapeutic Vaccine to Treat Cervical Intraepithelial Neoplasia", NCT02139267, first published May 13, 2014 (Year: 2014).*

CN-103160473-A machine translation from wipo.patentscope.int (Year: 2013).*

Kim JH, et al. High cleavage efficiency of a 2A peptide derived from porcine teschovirus-1 in human cell lines, zebrafish and mice. PLoS One. 2011;6(4):e18556. doi: 10.1371/journal.pone.0018556. Epub Apr. 29, 2011. PMID: 21602908; PMCID: PMC3084703 (Year: 2011).*

Aurisicchio, L., et al., "A novel minigene scaffold for therapeutic cancer vaccines", Oncoimmunology, 3/1, p. e27529, Jan. 3, 2014 (Jan. 3, 2014).

Canadian Office Action 3100974 Issued Jul. 27, 2023.

Luigi Aurisicchio et al. "A novel minigene scaffoldfor therapeutic cancer vaccines" Oncolmmunology 3, pp. e27529-1 to e27529-13; Jan. 2014; © 2014 Landes Bioscience,www.landesbioscience.com.

First Chinese Office Action 201980039164.6, Issued May 27, 2023.

Szymczak AL. et al., "Correction of multi-gene deficiency in vivo using a single 'self-cleaving' 2A peptide-based retroviral vector", Nature Biotechnology vol. 22, No. 5, May 2004, pp. 1-8.

Office Action issued in counterpart Japanese Application No. 2021-516553 on Dec. 26, 2023.

Sinu Paul, et al, HLA Class I Alleles Are Associated with Peptide-Binding Repertoires of Different Size, Affinity, and Immunogenicity, The Journal of Immunology, vol. 191, Issue 12, pp. 5831-5839.

Kreiter, S. et al. "Mutant MHC Class II Epitopes Drive Therapeutic Immune Responses to Cancer" (2015) Nature 520 (7549): 692-696.

Sahin, U. et al. "Personalized RNA Mutanome Vaccines Mobilize Poly-Specific Therapeutic Immunity Against Cancer" (2017) Nature 547(7662): 222-226.

Rojas, L.A. "Personalized RNA Neoantigen Vaccines Stimulate T Cells in Pancreatic Cancer" (2023) Nature 618 (7963): 144-150.

Keskin, D. B. "Neoantigen Vaccine Generates Intratumoral T Cell Responses in Phase Ib Glioblastoma Trial" (2019) 565(7738): 234-239.

* cited by examiner

FIG. 2A

GGATCCGCCACC
ATGCACCTCGGCAACTTCGCTTCCTCACTGTCTGGGGTCAGATGTATGGTCCTGGTTCTCCACTCGGGGAGCA
CCTCTCGGCGGCGCCCCTACCGCCGCTAGGGGCAGAAAGAGGAGATCTGCTCAGAGAAACAGCAACCCAATCATC
GCCGAGCTGTCCCAGGCTATGAACTCTGGCACACTGCTGTCCAAGCCCTCTCCCCCTCTGCCACCCAAGAGGAGG
GGAAGGAAGAGGAGAAGCGGAGAGTCCAAGGGACCTCTGGACAGCTCCTTCAGCCAGTACCTGGGCCGGTCCTGC
CTGCTGGATCAGAGAGAGGCCAAGCGGAAGGGAGAGGGACTGAGGGGAAGGAAGCGGCGCAGCCTGGCCAGGGAC
GAGTTCAACCTGCAGAAGATGATGGTCATGGTGACCGCTTCCGGCAAGCTGTTTGGAATCGAGTCTAGCTCCGGC
ACAATCCTGTGGAGGGGAAGAAAGAGGAGAAGCGAGACAACAGTGAAGTACCTGGACGGCGAGAAGCTGAGCGTG
CTGTGCCACGACAACTACCTGACCCAGGATTCCGAGGAGATGGTGTGCAAGGATGGAAGAGGCAGGAAGCGGCGC
TCTGACAGCTTCCAGATCATCCTGGATTCTCTGCTGCTGTTTGGCCAGTGCTCTAGCACACCTCTGAGCGAGGCC
TTCCACCCAACCGTGACAGGCGAGTCTAGGGGACGCAAAAGGAGAAGCGAGTGTAAGGAGGCCGCCGTGAGCCAC
GCTGGATCTATGCACAGGGAGAGGCGCACCTTTCTGAGGTCCGCCCTGAAGGAGCTGGCTACAGTGCTGTCCCGG
GGCCGCAAGAGGAGATCTCAGGGAAAGTACATCCTGAAGGTGTGCGGCTGTGACGAGTACTTCCTGGAGAAGTTT
CCACTGAGCCAGTACAAGTACATCAGATCCTGCATCATGCTGAGGGGAAGAAAGCGGCGCAGCAAGTTTATCAGC
GTGCTGTGCACCTCCCTGGCCACAATGCTGCACGTGGAGCTGCCCCACGTGAACCTGCTGTCTAAGATGGACCTG
ATCGAGCACTATAGAGGTAGAAAGAGGAGATCTGCCGAGGATACCCAGGAGAACCTGCACAGCGGAAAGTCCCAG
TCTAGAAGCTTCCCCAAGGTGCTGGCTGACTCTGATGAGAGCGATATGGAGGAGACAAGGGGCAGAAAGCGGCGC
TCCTCTGGACACGTGGGACTGAGGAACCTGGGAAACACCCTGCCACAGTGCTTTCTGAACGCTATGCTGCAGTGT
CTGAGCTCCACAAGACCCCTGCGGGACCGCGGAAGGAAGAGGAGATCCGAGCCAAAGCGGGACCGGCGCGATCCT
TCTACCGATAAGAGCGGTCCTGATACCTTCCCCGTGGAAGTGCTGGAGAGAAAGCCCCCTGAAAAAACATAC
TGATAACTCGAG

FIG. 2B

MHLGNFASSLSGGQMYGPGSPLGGAPLGGAPTAARGRKRRSAQRNSNPIIAELSQAMNSG
TLLSKPSPPLPPKRRGRKRRSGESKGPLDSSFSQYLGRSCLLDQREAKRKGEGLRGRKRR
SLARDEFNLQKMMVMVTASGKLFGIESSSGTILWRGRKRRSETTVKYLDGEKLSVLCHDN
YLTQDSEEMVCKDGRGRKRRSDSFQIILDSLLLFGQCSSTPLSEAFHPTVTGESRGRKRR
SECKEAAVSHAGSMHRERRTFLRSALKELATVLSRGRKRRSQGKYILKVCGCDEYFLEKF
PLSQYKYIRSCIMLRGRKRRSKFISVLCTSLATMLHVELPHVNLLSKMDLIEHYRGRKRR
SAEDTQENLHSGKSQSRSFPKVLADSDESDMEETRGRKRRSSGHVGLRNLGNTLPQCFLN
AMLQCLSSTRPLRDRGRKRRSEPKRDRRDPSTDKSGPDTFPVEVLERKPPEKTY

FIG. 2C

GGATCCGCCACC
ATGAACTCAGGGGTCGATAACGCCATTACAAAAAGCCAGATGCTGGTCGATCAGTATTTCCCACTCACTCAGGAA
GAGCTGGAGATGGAGGCCAAGAAGGTGCGGGCAAGGAAGAGGAGAAGCCTGCGGCCTTCCACCCTGTCTCAGGAG
GTGTACAAGACAGTGTCCATGCGCCTGAACGTGGTGTCTCCAGACCTGACCGGCAAGGGACTGGTGCTGCCCAGG
GGCAGAAAGCGGCGCTCCTTCCTGCAGCTGAAGCTGGTGGTGAAGAAGGGAAAGCAGACCGAGAACCTGTACATC
GAGCTGACACTGCCACAGTTCTACTCCTTTCTGCACGAGATGCGGGGCCGCAAGAGGAGATCTCTGACCCACCCT
TACGGCAAGGGATGGGACCTGATGCAGAACATCATGGACGATGTGCCAATCTACATGTACAGCGTGTGCAACGTG
GTGAGCGGCGATAGGGGAAGAAAGCGGCGCTCCGCCTGTAGCTCCTCTTACAACTCTGCTGTGATGGAGAGCTCC
TCTGTGAACGTGTCCATGGTGCACAGCTCCTCTAAGGAGAACCTGTGCCCCAAGAAGCGGGGTAGAAAGAGGAGA
TCTCAGCACGTGATCCACAAGTACTTCCTGCCTAGGGCCTACGCTGTGCTGCTGCCACTGCCTGCTGGCCTGCTG
CTGCTGCTGTTTGTGGGCAAGAGCCCCAGGGGAAGGAAACGGCGCTCCCAGCACGGCATCCAGCTGCTGAACGGA
CACGCTCCTGCTGCTGGACCAAACCTGAGCGGACTGCCACAGGCTAACAGGCACCACGGCCTGCTGGGCGGAAGG
GGAAGGAAGAGGAGGAGCAGGGACCCCTACGCTCTGGACCTGATCGATAAGCTGCTGGTGCCAGACCCCGCTCAG
AGGATCGATAGCGACGATGCTCTGAACCACGATTTCTTTTGGAGAGGTAGAAAGCGGCGCTCTCGCAGATCGCT
GTGGAGCACAACAACCTGGGAAAGGCCGTGTACAGCAGGATGGCTAGAATCTGTAAGAACGACATGGGCGGATCT
CAGAGAGTGCTGAGGGCACCCAAGAGGAGAAGCAACACCCAGATCCAGAAGCTGACAGGCAGCCCCTTCAGGAGC
AGGGAGTACGTGCAGACCATGGAGAGCCGAGTCCGAGCACTCTTACCCTCCTCCCGGAAGGGGAAGGAAGCGGCGC
TCTCTGAGCCAGACACCCCCTCCAGCCCCTCCTCCCAGCGCCGGCTCCGAGCCACTGGCTAGGCTGCCTCAGAAG
GATAGCGTGGGAAAGCACTCCGGCGCTAGGGGAAGAAAGAGGAGAAGCCGGATGAGGGAGCAGCAGCTGGCCAGA
GAGGCTGAGGCTTGGGCAGAACGGGAGGCAGAGGCAAGACGCAGGGAGGAACAGGAAGCCAGGGAAAAAGCA
TGATAACTCGAG

FIG. 2D

MNSGVDNAITKSEMLVDQYFPLTQEELEMEAKKVRGRKRRSLRPSTLSQEVYKTVSMRLN
VVSPDLSGKGLVLPRGRKRRSFLQLKLVVKKGKQTENLYIELTLPQFYSFLHEMRGRKRR
SLTHPYGKGWDLMQNIMDDVPIYMYSVCNVVSGDRGRKRRSACSSSYNSAVMESSSVNVS
MVHSSSKENLCPKKRGRKRRSQHVIHKYFLPRAYAVLLPLPAGLLLLLFVGKSPRGRKRR
SQHGIQLLNGHAPAAGPNLSGLPQANRHHGLLGGRGRKRRSRDPYALDLIDKLLVPDPAQ
RIDSDDALNHDFFWRGRKRRSREIAVEHNNLGKAVYSRMARICKNDMGGSQRVLRGRKRR
SNTQIQKLTGSPFRSREYVQTMESESEHSYPPPGRGRKRRSLSQTPPPAPPPSAGSEPLA
RLPQKDSVGKHSGARGRKRRSRMREEQLAREAEAWAEREAEARRREEQEAREKA

FIG. 2E

GGATCCGCCACC
ATGGAGGGGGAGTCAACCAATACATCAAAAGTCGCTAAAAAGTCATCAGTCCACTACAGCCTGCTCGCCGAACAC
GAAGAAACCCAGTCCCTGGGCACCAAGCGGGGACGCAAGAGGAGATCCACAGGCTCTATGAACGTGATCCACATG
CTGGAGTCTTTCACCTTTAGGAACAACGTGTGCATGGCCTTCGAGCTGCTGTCTATCGACCTGTACGAGCTGAGG
GGCAGAAAGCGGCGCAGCAACTGCAACTTCGACTTTCCCGAGGAGACATGTGGATGGGTGTACGATCACGCCAAG
CTGCTGAGGTCTACATGGATCAGCTCCGCTAACCCTAACGACAGGGGAAGGAAGAGGAGAAGCCTGCCAGCCAGA
CTGGAGATCCAGGGAACCGATCCTATGTCCGCTGTGACACTGTCTCTGCTGGACCCTGAGACACAGGAGGACCCC
AGCAGCTGGACAAGGGGCAGGAAACGGCGCAGCGGACTGTCCCTGAACATCAAGAAGTACCTGCTGGTGTCTATG
CCTCTGTGGGCTAAGCACATGAGCGATGAGCAGATCCAGGGCTTTGTGGAGAACCTGAGAGGCCGCAAGAGGAGA
AGCATCTCCATGGGCGGACACATGGCTAGCCTGGCCGTGTGCAACTGGCCCAAGCCTATGCCACTGATCCCATGT
CTGTCTTGGAGCACCGCTTCCGGCGTGAGGGGAAGAAAGCGGCGCTCTGAGCCCATCGAGGTGAACCTGTTCGGC
CTGATCAACGTGACACCCAACATGCTGCCTCTGGTGAAGAAGGCTCGGGGCCGCGTGATCAACGTGTCCTCTAGG
GGAAGAAAGAGGAGATCCGTGGACTTTAACAAGATCTGTGGACAGGCCTACGATTCTGCTACAAACTTCCGGGTG
AAGCTGAACGAGGTGGTGGCCGAGTTTAAGAAGGAGGAGCCACGGGGCAGGAAGCGGCGCAGCGCCGAGGTGCTG
ATCGACGCTCTGGTGGATGGACAGGTGGTGGCCCTGCTGGTGCAGAACCTGGAGCGGCTGGACGAGAGCGTGCGC
GAGGAGGCTGATAGGGGCAGAAAGAGGAGATCCGACGAGGAGGAGTCTGTGGATCTGAGCATCCCCGGAGCCTGC
TACCTGAGACTGCTGACCATCACAGCTCCATCCGTGCTGCCCGCTCTGGAGGAGTTCCGGGGACGCAAGCGGCGC
AGCAAGCTGCTGGTGTACTCCGCTCACGACACCACACTGGTGGCCCTGCAGATGGCTCTGAACCTGTACAACGGC
AAGCAGGCCCCTTACGCTAGCTGTCACAGAGGCAGGAAAAGGAGATCCGGCGAGGACGAGGGAGATAAGCCAGAG
GCCAAGCAGGTGGTGCTGATTGGGTCATCCTACCTCTGCCAGTTTTGTCCTTCTAAATTCTCCACCTACTTT
TGATAACTCGAG

FIG. 2F

MEGESTNTSKVAKKSSVHYSLLAEHEETQSLGTKRGRKRRSTGSMNVIHMLESFTFRNNV
CMAFELLSIDLYELRGRKRRSNCNFDFPEETCGWVYDHAKLLRSTWISSANPNDRGRKRR
SLPARLEIQGTDPMSAVTLSLLDPETQEDPSSWTRGRKRRSGLSLNIKKYLLVSMPLWAK
HMSDEQIQGFVENLRGRKRRSISMGGHMASLAVCNWPKPMPLIPCLSWSTASGVRGRKRR
SEPIEVNLFGLINVTPNMLPLVKKARGRVINVSSRGRKRRSVDFNKICGQAYDSATNFRV
KLNEVVAEFKKEEPRGRKRRSAEVLIDALVDGQVVALLVQNLERLDESVREEADRGRKRR
SDEEESVDLSIPGACYLRLLTITAPSVLPALEEFRGRKRRSKLLVYSAHDTTLVALQMAL
NLYNGKQAPYASCHRGRKRRSGEDEGDKPEAKQVVLIGSSYLCQFCPSKFSTYF

FIG. 3A

GGATCCGCCACC

ATGCTCCTCGCTCGCACTCACCCTGGTTGTGGTAATATCGTCACTTTTGCTCATTTCCTCTTTATCGCAGTCGAA
GGTTTCCTGTTCGAGGCTAACCTGGGAAGAGGCAGGAAGCGCAGATCTTCCCACGTGCAGAGACTGGTGCACAGG
GACAGCACAATCTCCAACGAGGCCTTTATCTCGGTGGACGATCTGGAGCCATCCGGACCACAGGATCTGGAGCGG
GGAAGGAAGAGGAGATCCGACTACATCGCTCTGAACGAGGATCTGAAGACCTGGACAGCTGCCGCTATGGCTGCC
CTGATCACAAAGCACAAGTGGGAGCAGGCCGGCGAGGCTGAGAGGGGAAGAAAGCGGAGGTCCGGCGGAAAGGTG
TGGAACGAGCAGGAGAAGAACACCTACGCCGACAAGCTGTTCGATTGTATCGAGGCTTACGCTCCTGGATTCAAG
AGAAGCGTGCTGAGAGGCCGGAAGCGCAGATCCAAGCTGGTGTTCGTGAGCACCTCTGGCGGATCTCTGTGGAAC
CTGAAGGCCATCCACTCCATGTGCAGGATCGAGCAGGAGCAGGAGGGAAGCGTGCGGAGAGGAAGGAAGCGCAGG
TCCCCAAAGATGTGCTCTCAGCCTGCTGTGAGCCAGCTGCAGTCTAACATCAGATCCCAGTGCATCTCCCACACC
GCCCTGGTGCTGCAGGGCAGCCTGACAAGAGGAAGGAAGAGACGGTCCATCCAGGGATGGCTGGGCACCAAGGTG
AGGACAAACCTGCGGAGAGAGCCATTCTCTCTGGTGCCTAAGAACGCTAAGGACGGAAACTCCTTCCAGGGACGC
GGAAGGAAGAGACGCTCTAACACCATGACAACCAAGGAGTGCCTGCACAGGTTTTGTGCCGACTGTATCATCACC
GGCCTGAGGAGCGGAAACAAGGAGTGCCCTACCTGCAGAAAGAGGGGCAGAAAGCGGAGAAGCAACGGATACGAT
ACATACGTGCACGATGCCTACGGACTGTTCCAGGAGTGCAGGTCTAGGGTGGCCCACTGGGGCTGGCCTCTGGGA
CCCGCCCCACTGAGAGGAAGAAAGAGGAGGTCCGACCACCTGCAGCTGAAGGACATCCTGAGAAAGCAGGACGAG
TACCACATGGTGCACCTGCTGTGCGCCTCTAGATCCCCTCCCAGCTCCCCCAAGTCCAGGGGACGGAAGAGGCGG
AGCGCCCCAGAGCTGACATTCGACTTTACCATCGAGACCGTGCTGTGCCTGCAGGACAGCGTGCTGGCCTTCTGG
AGCCACGGAATGCAGGGACGGTCCCTGAGAGGACGCAAGAGGAGAAGCACAACAACCAGCAGGGCCATCTGCCAG
CTGGTGAAGGAGTACATTGGATACAGGGATGGCATTTGGGATGTCAGCGTCACACGGACTCAGCCTATTGTC
TGATAACTCGAG

FIG. 3B

MLLARTHPGCGNIVTFAHFLFIAVEGFLFEANLGRGRKRRSSHVQRLVHRDSTISNDAFI
SVDDLEPSGPQDLERGRKRRSDYIALNEDLKTWTAAAMAALITKHKWEQAGEAERGRKRR
SGGKVWNEQEKNTYADKLFDCIEAYAPGFKRSVLRGRKRRSKLVFVSTSGGSLWNLKAIH
SMCRIEQEQEGSVRRGRKRRSPKMCSQPAVSQLQSNIRSQCISHTALVLQGSLTRGRKRR
SIQGWLGTKVRTNLRREPFSLVPKNAKDGNSFQGRGRKRRSNTMTTKECLHRFCADCIIT
GLRSGNKECPTCRKRGRKRRSNGYDTYVHDAYGLFQECRSRVAHWGWPLGPAPLRGRKRR
SDHLQLKDILRKQDEYHMVHLLCASRSPPSSPKSRGRKRRSAPELTFDFTIETVLCLQDS
VLAFWSHGMQGRSLRGRKRRSTTTSRAICQLVKEYIGYRDGIWDVSVTRTQPIV

FIG. 3C

GGATCCGCCACC
ATGGGGAACAATATCACTGTGAAAACCGAGAGCACCGTCAAAACCAATGTCTTTAGCTGTAATCTGGGGGAGAAA
TTCGATGAAACCACCGCCGACGGCAGGAGAGGAAGAAAGCGGCGCTCCGTGGAGCACAAGAAGCGGCCAAAGGTG
GAGCTGATGCCCGGCATGAGGAGACTGCAGTCTCTGCTGGATACCAGATGCGTGTACATCCTGGACTGTTGGAGG
GGAAGGAAGCGGCGCAGCACACAGGGATGCAAGCTGGTGGATACCAACAAGACACGCACCACATGCGCCTGTAGG
CACCTGACAAACTTCGCCATCCTGATGGCTCACCGCGAGATCAGGGGCAGAAAGAGGAGATCTCAGAGCAAGAAG
AGGCTGCACATCGAGGATTACTCCGTGTCTCAGCCTACCCTGGACCAGGTGTTCGTGAACTTTGCTAAGGATCAG
AGCGACGATGACAGAGGCAGGAAGCGGCGCTCCTGGAACACATGGCTGTACGCCCCTGGACTGCCCCCTGTGAAG
CCAAACTACGACGCTACCCTGACAAACGCCTGCATCGCTCTGTCCCAGAGATGGGTGAGGGGTAGGAAGAGGAGA
TCCCTGGGATCTTACACCGAGGATAACGCTTCTCAGGCTCGGGTGGACGGACACAGATGTATCGTGAGGGCCCTG
AAGGACCCCAACGCTTTCCTGTTTGACAGAGGTAGGAAGCGGCGCAGCCAGAGGGACAACCTGACACAGTTCTTT
CCCCAGAACTACTTCCCTCTGCTGGGACAGGAGCTGGTGCAGGCCCTGAAGGCTGTGGTGAACTTTCTGCAGAGA
GGTAGAAAGAGGAGAAGCACCGCTTCCGGAACACAGGACCCCCACTCCGCTGAGACACTGGGAGTGTGCCGCAGC
CCACCCCCTCCATGTTCCCCTATCCTGGAGGCTTCTGATGACAGAGGGAGGAAGCGGCGCTCTGGACAGGTCATC
CAGGCTCAGGGAAGAGCTAGCCCAACCATGGCCACACTGCCTGCTCCAATGGCCTCCGCTCCCCCTCTGTCTGAG
CTGTACCCAAACAGGGGAAGAAAGAGGAGAAGCGACTCCAAGCGGCGCAAGGAGCAGTTCCCCGTGCTGTCTCAC
CTGCTGAGCATCGCCCAGCTGCCACCCAACAAGGATGCTACCTACCTGTCTCGGAGCCGCGGCAGGAAGAGGAGA
AGCTCCATCCTGCGCAACCACAGGTACAGGAGGGATGCTAGGACCCTGGAGGACAAGGAGGAGATGTGGTTTAAC
ACAGATGAGGATGACATGGAGGACGGCAGAGGACGGAAGAGGAGAAGCTGGATGAAGTGCGTGAAGGGACAGCCT
CACGACCACAAGCACCTCATGCCAACTCAGATTATTCCCGGCTCCGTGCTCACAGACCTCCTGGATGCTATG
TGATAACTCGAG

FIG. 3D

MGNNITVKTESTVKTNVFSCNLGEKFDETTADGRRGRKRRSVEHKKRPKVELMPGMRRLQ
SLLDTRCVYILDCWRGRKRRSTQGCKLVDTNKTRTTCACRHLTNFAILMAHREIRGRKRR
SQSKKRLHIEDYSVSQPTLDQVFVNFAKDQSDDDRGRKRRSWNTWLYAPGLPPVKPNYDA
TLTNACIALSQRWVRGRKRRSLGSYTEDNASQARVDGHRCIVRALKDPNAFLFDRGRKRR
SQRDNLTQFFPQNYFPLLGQELVQALKAVVNFLQRGRKRRSTASGTQDPHSAETLGVCRS
PPPPCSPILEASDDRGRKRRSGQVIQAQGRASPTMATLPAPMASAPPLSELYPNRGRKRR
SDSKRRKEQFPVLSHLLSIAQLPPNKDATYLSRSRGRKRRSSILRNHRYRRDARTLEDKE
EMWFNTDEDDMEDGRGRKRRSWMKCVKGQPHDHKHLMPTQIIPGSVLTDLLDAM

FIG. 4A

GGATCCGCCACC
ATGGCAACTGATATGTCCCAGGGAGAACTGATTCATCCTAAGGCTTTTCCACTCATTGTCGGGGCACAGCTCATT
CACGCAGATAAGCTGGGCGAGAAGAGGGGAAGAAAGAGGAGAAGCACATGCTACCTGGACGCTGGCCTGGCTAGG
ACCACAACCGGAAACAAGTTCTTTGGCGCCCTGAAGGGAGCTGTGGATGGCGGACTGTCCATCCCACACAGGGGA
AGGAAGCGGCGCAGCTGGCTGCTGTCCAGACCTGAGGCCCCAGAGGACTTCCAGACCTTTCACGCTAGCCTGCAG
CTGAGGAAGCAGTCCCTGGCTCGCAAGCACATCTACCTGAGGGGCAGAAAGAGGAGATCCGCCAACGCTGTGCAC
TCTATGGAGAAAGTGATGGATATCCACTCCAAGTACTGCAGGTGTCTGCAGAGACTGAGCTCCACAGTGGCCAC
TCTCTGATTAGAGGAAGGAAGCGGCGCTCTCCCGGCCTGCTGAGCGTGGACCTGTTCCACGTGCTGGTGTCTGCC
GTGCTGGCTTTTCCAAGCCTGTACTGGGACGATACCGTGGATCTGCAGCCCTCCAGGGGCAGGAAAAGGAGATCT
GAGGTGCCCAAGCCTCTGTTCCCTGTGGCCGGAGTGCCAATGATCCAGTACCACATCGAGGCCTGCGCTCAGGTG
CCTGGCATGCAGGAGATCCTGCTGCGGCAGGAAGCGGCGCTCTAGCAACGAGGACAGGGAGTGGCACGAGTCC
TTTTCTCTGGTGCTGGGACCAGACGATCCTGTGGAGGCCGTGCTGGGCGATGTGACAACCGCTACAGTGAGGGGT
AGGAAGAGGAGGAGCCTGTGCCTGATGGGACACAAGCCCGTGCTGCTGAGGACCCAGTGCAGGTGTCACCCTGCC
ATCTCTGCCATCGCTAACGACCTGTTCTACGAGGGCAGCCGGGGAAGAAAACGGCGCAGCACATCCGCCGCTGAG
ACAAAGCCCCCTCTGGCTCCTTCCTCTCCACCCGCTCCTCCAGGCACAATGGTGGCTGGAAGCTCCCTGGAGGGA
CCAGCTCCCAGGGGAAGGAAAAGGAGATCTATGAGCGTGATGGTGCTGAGAACACAGGGACCAGAGGCTCCCTTT
GAGGACCACCGGCTGATCCTGCACACCTCTAGCTGCGATGCTGAGAGGGCTAGAAGAGGAAGAAAGAGGAGATCC
CTGTCTGGAAAGGACGAGCAGGAGAACAGCAACCTGGCTACCCCTGAGTACCAGGTGTCCGAGGCTGCTAGAGAG
CTGGCCTGGCTACAGCTGAGGAGCGCGGTAGGAAGCGGCGCTCCTGTCCACACATGACCGAGGACAACAAGGAT
CTGATCCAGGGTAAAGACCTCCTGACTGCTTGCTATGATGTGGACTACGAAAAGAATGCCAAAGGCTCT
TGATAACTCGAG

FIG. 4B

MATDMSQGELIHPKAFPLIVGAQLIHADKLGEKRGRKRRSTCYLDAGLARTTTGNKFFGA

LKGAVDGGLSIPHRGRKRRSWLLSRPEAPEDFQTFHASLQLRKQSLARKHIYLRGRKRRS

ANAVHSMEKVMDIHSKYCRCLQRLSSTVGHSLIRGRKRRSPGLLSVDLFHVLVSAVLAFP

SLYWDDTVDLQPSRGRKRRSEVPKPLFPVAGVPMIQYHIEACAQVPGMQEILLRGRKRRS

SNEDREWHESFSLVLGPDDPVEAVLGDVTTATVRGRKRRSLCLMGHKPVLLRTQCRCHPA

ISAIANDLFYEGSRGRKRRSTSAAETKPPLAPSSPPAPPGTMVAGSSLEGPAPRGRKRRS

MSVMVLRTQGPEAPFEDHRLILHTSSCDAERARRGRKRRSLSGKDEQENSNLATPEYQVS

EAARELGLATAEERGRKRRSCPHMTEDNKDLIQGKDLLTACYDVDYEKNAKGS

FIG. 4C

GGATCCGCCACC

ATGGCTGCTACATCAGAAGGGCTCCTGTTCGCCGCATCAATCGAGAAAACTTGGGGTTCAGTCGTCAGGTCACCA
GAGGGTACTCCACAGAAGGTGAGGAGAGGAAGGAAGCGGCGCTCCACAAGAGGCCTGGCCTACCTGCACACCGAG
CTGCCACAGGGCGACCACTACAAGCCCGCTATCTCTCACAGAGATCTGAACAGCCGGAACGTGCTGGTGAGAGGC
CGGAAGAGGAGATCCATCCACCGGGAGCAGAACTCCCTGTCTCTGCTGGAGGCCTCTGAGGCTGACGGCGATGCC
GTGAACGACAAGAAGAGGACACCCAACGAGGCTCCTTCTCGCGGAAGGAAGCGGCGCAGCTACCAGGTGAAGGGC
AAGAAGAACATCAGAGCCACAGAGCGGGCTCTGAGCTGGGATTCCTTCAACACCGGCGACTGCCTGATCCTGGAT
CTGGGCCAGAGAGGACGGAAGAGGAGAAGCAGGTCCCTGCAGGAGCTGCTGGCTAGGAGGACCTACTACTCCGGC
GACCCCCTGTTCTCTGTGGATATCCTGCGGAACCTGACAGACACCTTTAAGAGAAGGGGCAGAAAGCGGCGCTCC
GGCGGACACGTGTGCTGGATGAGAGAGGGCGTGGAGCTGTGCCCAGGAAACAAGTACGAGATGAGGAGACACGGA
ACCAGACACAGCCTGGTCATCCACAGGGGCCGCAAGCGGCGCAGCTCCATGGCTCTGTCCCTGCGCCTGGCCCTG
GCTAGGTCTAGCATCGAGAGATCCTCTACAGCTAGCGACCCCCAGGGAGATCTGCTGTTTCTGCTGGATAGGGGT
CGGAAGAGGAGATCTCTGAGCAAGCACAAGCAGATCCCTGGACTGATCCAGAACATGACCGTGAGGTGCTGTGAG
CTGCCCTACCCTGAGCAGGCTTGCTGTGGAGAGGAGGAGAGGGGCAGGAAACGGCGCAGCTCCAACAGCGGACCA
AGACCCTCCAACACCACAACCTCTAGCAACTCCCAGTCTAACAGCCTGCCTCGCCCATCTAACAGGGGCAGCATC
TCTAACTACAGGGGACGGAAGAGGAGATCTGCTGGCAGCCCAGGAATGCAGCGGCGCAGGAGACGGGTGCTGAAC
ACAAGCGTGGCCTACGTGAGAGGCGAGGAGAACCTGGCTGGATGGCGGCCCAGGAGGGGACGCAAGAGACGGTCC
ATCAAGTCTTGCCCTGAGTGTCGGATCACCAGCAACTTCGTGATCCCATCCGAGTACTGGGTGGAGGAGAAGGAG
GAGAAGCAGAAGCTGATCCAGAAGAGGGGAAGGAAGCGCAGGAGCGCCGAGGACGAGATCGAGGATATCCAGCAG
GAGATCACAGCTCTCAGCCAGTGTGATAGCCCTTACATTACCAGATACTTCGGTTCCTACCTCAAATCC
TGATAACTCGAG

FIG. 4D

MAATSEGLLFAASIEKTWGSVVRSPEGTPQKVRRGRKRRSTRGLAYLHTELPQGDHYKPA
ISHRDLNSRNVLVRGRKRRSIHREQNSLSLLEASEADGDAVNDKKRTPNEAPSRGRKRRS
YQVKGKKNIRATERALSWDSFNTGDCLILDLGQRGRKRRSRSLQELLARRTYYSGDPLFS
VDILRNVTDTFKRRGRKRRSGGHVCWMREGVELCPGNKYEMRRHGTTHSLVIHRGRKRRS
SMALSLRLALARSSIERSSTASDPQGDLLFLLDRGRKRRSLSKHKQIPGLIQNMTVRCCE
LPYPEQACCGEEERGRKRRSSNSGPRPSNTTTSSNSQSNSLPRPSNRGSISNYRGRKRRS
AGSPGMQRRRRRVLNTSVAYVRGEENLAGWRPRRGRKRRSIKSCPECRITSNFVIPSEYW
VEEKEEKQKLIQKRGRKRRSAEDEIEDIQQEITALSQCDSPYITRYFGSYLKS

FIG. 23A gctgcttcgcgatgtacgggccagatatacgcgttgacattgattattgactagttattaatagtaatcaattacggggtcattagttcatagcccatata
tggagttccgcgttacataacttacggtaaatggcccgcctggctgaccgcccaacgacccccgcccattgacgtcaataatgacgtatgttcccatag
taacgccaatagggactttccattgacgtcaatgggtggagtatttacggtaaactgcccacttggcagtacatcaagtgtatcatatgccaagtacgc
cccctattgacgtcaatgacggtaaatggcccgcctggcattatgcccagtacatgaccttatgggactttcctacttggcagtacatctacgtattagtc
atcgctattaccatggtgatgcggttttggcagtacatcaatgggcgtggatagcggtttgactcacggggatttccaagtctccaccccattgacgtca
atgggagtttgttttggcaccaaaatcaacgggactttccaaaatgtcgtaacaactccgccccattgacgcaaatgggcggtaggcgtgtacggtgg
gaggtctatataagcagagctctctggctaactagagaacccactgcttactggcttatcgaaattaatacgactcactatagggagacccaagctgg
ctagcgtttaaacttaagcttggtaccgagctcggatccgccaccatggactggacctggattctgttcctggtggccgctgccacacgggtgcacagc
cgcgagggagtggagctgtgcccaggaaacaagtacgagatgaggagacacggcaccacacactccctggtcatccacgacccatctaagcccagc
ttccaggagtttgtggattgggagaacgtgtcccctgagctgaactctaccgaccagccattcctggatagcggctccccctttcctgctgccgtgatcct
gagggatgctctgcacatggcccggggactgaagtacctgcaccagtgataactcgagtctagagggcccgtttaaacccgctgatcagcctcgactg
tgccttctagttgccagccatctgttgtttgcccctcccccgtgccttccttgaccctggaaggtgccactcccactgtcctttcctaataaaatgaggaaa
ttgcatcgcattgtctgagtaggtgtcattctattctggggggtggggtggggcaggacagcaagggggaggattgggaagacaatagcaggcatgct
ggggatgcggtgggctctatggcttctactgggcggttttatggacagcaagcgaaccggaattgccagctggggcgccctctggtaaggttgggaag
ccctgcaaagtaaactggatggctttcttgccgccaaggatctgatggcgcaggggatcaagctctgatcaagagacaggatgaggatcgtttcgcat
gattgaacaagatggattgcacgcaggttctccggccgcttgggtggagaggctattcggctatgactgggcacaacagacaatcggctgctctgatg
ccgccgtgttccggctgtcagcgcaggggcgcccggttctttttgtcaagaccgacctgtccggtgccctgaatgaactgcaagacgaggcagcgcgg
ctatcgtggctggccacgacgggcgttccttgcgcagctgtgctcgacgttgtcactgaagcgggaagggactggctgctattgggcgaagtgccggg
gcaggatctcctgtcatctcaccttgctcctgccgagaaagtatccatcatggctgatgcaatgcggcggctgcatacgcttgatccggctacctgccca
ttcgaccaccaagcgaaacatcgcatcgagcgagcacgtactcggatggaagccggtcttgtcgatcaggatgatctggacgaagagcatcaggggc
tcgcgccagccgaactgttcgccaggctcaaggcgagcatgcccgacggcgaggatctcgtcgtgacccatggcgatgcctgcttgccgaatatcatg
gtggaaaatggccgcttttctggattcatcgactgtggccggctgggtgtggcggaccgctatcaggacatagcgttggctacccgtgatattgctgaa
gagcttggcggcgaatgggctgaccgcttcctcgtgctttacggtatcgccgctcccgattcgcagcgcatcgccttctatcgccttcttgacgagttctt
ctgaattattaacgcttacaatttcctgatgcggtattttctccttacgcatctgtgcggtatttcacaccgcatcaggtggcacttttcggggaaatgtgc
gcggaacccctatttgtttatttttctaaatacattcaaatatgtatccgctcatgagacaataaccctgataaatgcttcaataatagcacgtgctaaaa
cttcatttttaatttaaaaggatctaggtgaagatcctttttgataatctcatgaccaaaatcccttaacgtgagttttcgttccactgagcgtcagacccc
gtagaaaagatcaaaggatcttcttgagatcctttttttctgcgcgtaatctgctgcttgcaaacaaaaaaaccaccgctaccagcggtggtttgtttgc
cggatcaagagctaccaactctttttccgaaggtaactggcttcagcagagcgcagataccaaatactgttcttctagtgtagccgtagttaggccacc
acttcaagaactctgtagcaccgcctacatacctcgctctgctaatcctgttaccagtggctgctgccagtggcgataagtcgtgtcttaccgggttgga
ctcaagacgatagttaccggataaggcgcagcggtcgggctgaacggggggttcgtgcacacagcccagcttggagcgaacgacctacaccgaact
gagatacctacagcgtgagctatgagaaagcgccacgcttcccgaagggagaaaggcggacaggtatccggtaagcggcagggtcggaacaggag
agcgcacgagggagcttccagggggaaacgcctggtatctttatagtcctgtcgggtttcgccacctctgacttgagcgtcgatttttgtgatgctcgtc
aggggggcggagcctatggaaaaacgccagcaacgcggcctttttacggttcctggccttttgctggccttttgctcacatgttctt

FIG. 24A gctgcttcgcgatgtacgggccagatatacgcgttgacattgattattgactagttattaatagtaatcaattacggggtcattagttcatag
cccatatatggagttccgcgttacataacttacggtaaatggcccgcctggctgaccgcccaacgacccccgcccattgacgtcaataatgacgtatgt
tcccatagtaacgccaatagggactttccattgacgtcaatgggtggagtatttacggtaaactgcccacttggcagtacatcaagtgtatcatatgcca
agtacgccccctattgacgtcaatgacggtaaatggcccgcctggcattatgcccagtacatgaccttatgggactttcctacttggcagtacatctacg
tattagtcatcgctattaccatggtgatgcggttttggcagtacatcaatgggcgtggatagcggtttgactcacggggatttccaagtctccacccatt
gacgtcaatgggagtttgttttggcaccaaaatcaacgggactttccaaaatgtcgtaacaactccgccccattgacgcaaatgggcggtaggcgtgt
acggtgggaggtctatataagcagagctctctggctaactagagaacccactgcttactggcttatcgaaattaatacgactcactatagggagaccc
aagctggctagcgtttaaacttaagcttggtaccgagctcggatccgccaccatggactggacctggattctgttcctggtggctgctgctacacgggtg
cactcccgcgagggcgtggagctgtgcccaggaaacaagtacgagatgaggagacacggcaccacacactctctggtcatccacgataggggaaga
aagcggcgcagcccttccaagccaagcttccaggagtttgtggactgggagaacgtgtcccccgagctgaactctaccgatcagcctttcctgggcag
cggagctacaaacttttccctgctgaagcaggctggcgacgtggaggagaacccaggacctgattctggaagcccatttcccgctgccgtgatcctga
gggacgctctgcacatggccaggggactgaagtacctgcaccagtgataactcgagtctagagggcccgtttaaacccgctgatcagcctcgactgtg
ccttctagttgccagccatctgttgtttgcccctcccccgtgccttccttgaccctggaaggtgccactcccactgtcctttcctaataaaatgaggaaatt
gcatcgcattgtctgagtaggtgtcattctattctggggggtggggtggggcaggacagcaagggggaggattgggaagacaatagcaggcatgctg
gggatgcggtgggctctatggcttctactgggcggttttatggacagcaagcgaaccggaattgccagctggggcgccctctggtaaggttgggaagc
cctgcaaagtaaactggatggctttcttgccgccaaggatctgatggcgcaggggatcaagctctgatcaagagacaggatgaggatcgtttcgcatg
attgaacaagatggattgcacgcaggttctccggccgcttgggtggagaggctattcggctatgactgggcacaacagacaatcggctgctctgatgc
cgccgtgttccggctgtcagcgcaggggcgcccggttctttttgtcaagaccgacctgtccggtgccctgaatgaactgcaagacgaggcagcgcggct
atcgtggctggccacgacgggcgttccttgcgcagctgtgctcgacgttgtcactgaagcgggaagggactggctgctattgggcgaagtgccggggc
aggatctcctgtcatctcaccttgctcctgccgagaaagtatccatcatggctgatgcaatgcggcggctgcatacgcttgatccggctacctgcccatt
cgaccaccaagcgaaacatcgcatcgagcgagcacgtactcggatggaagccggtcttgtcgatcaggatgatctggacgaagagcatcaggggct
cgcgccagccgaactgttcgccaggctcaaggcgagcatgcccgacggcgaggatctcgtcgtgacccatggcgatgcctgcttgccgaatatcatgg
tggaaaatggccgcttttctggattcatcgactgtggccggctgggtgtggcggaccgctatcaggacatagcgttggctacccgtgatattgctgaag
agcttggcggcgaatgggctgaccgcttcctcgtgctttacggtatcgccgctcccgattcgcagcgcatcgccttctatcgccttcttgacgagttcttct
gaattattaacgcttacaatttcctgatgcggtattttctccttacgcatctgtgcggtatttcacaccgcatcaggtggcacttttcggggaaatgtgcgc
ggaacccctatttgtttatttttctaaatacattcaaatatgtatccgctcatgagacaataaccctgataaatgcttcaataatagcacgtgctaaaact
tcatttttaatttaaaaggatctaggtgaagatcctttttgataatctcatgaccaaaatcccttaacgtgagttttcgttccactgagcgtcagaccccgt
agaaaagatcaaaggatcttcttgagatcctttttttctgcgcgtaatctgctgcttgcaaacaaaaaaaccaccgctaccagcggtggtttgtttgccg
gatcaagagctaccaactctttttccgaaggtaactggcttcagcagagcgcagataccaaatactgttcttctagtgtagccgtagttaggccaccact
tcaagaactctgtagcaccgcctacatacctcgctctgctaatcctgttaccagtggctgctgccagtggcgataagtcgtgtcttaccgggttggactc
aagacgatagttaccggataaggcgcagcggtcgggctgaacggggggttcgtgcacacagcccagcttggagcgaacgacctacaccgaactgag
atacctacagcgtgagctatgagaaagcgccacgcttcccgaagggagaaaggcggacaggtatccggtaagcggcagggtcggaacaggagagc
gcacgagggagcttccagggggaaacgcctggtatctttatagtcctgtcgggtttcgccacctctgacttgagcgtcgatttttgtgatgctcgtcagg
ggggcggagcctatggaaaaacgccagcaacgcggcctttttacggttcctggccttttgctggccttttgctcacatgttctt

FIG. 25A gctgcttcgcgatgtacgggccagatatacgcgttgacattgattattgactagttattaatagtaatcaattacggggtcattagttcatag
cccatatatggagttccgcgttacataacttacggtaaatggcccgcctggctgaccgcccaacgacccccgcccattgacgtcaataatgacgtatgt
tcccatagtaacgccaatagggactttccattgacgtcaatgggtggagtatttacggtaaactgcccacttggcagtacatcaagtgtatcatatgcca
agtacgccccctattgacgtcaatgacggtaaatggcccgcctggcattatgcccagtacatgaccttatgggactttcctacttggcagtacatctacg
tattagtcatcgctattaccatggtgatgcggttttggcagtacatcaatgggcgtggatagcggtttgactcacggggatttccaagtctccacccatt
gacgtcaatgggagtttgttttggcaccaaaatcaacgggactttccaaaatgtcgtaacaactccgccccattgacgcaaatgggcggtaggcgtgt
acggtgggaggtctatataagcagagctctctggctaactagagaacccactgcttactggcttatcgaaattaatacgactcactatagggagaccc
aagctggctagcgtttaaacttaagcttggtaccgagctcggatccgccaccatggactggacctggattctgttcctggtggccgctgccacaagggt
gcactctcaggctatcgtgcggggatgcagcatgccaggaccttggcggtccggccgcctgctggtgtccaggagatggtctgtggagccactgctgc
ccttctaccctcccgatgaggctctggagatcggactggagctgaacagctccgccctgccacccaccgaagtgatcctgcctcaggctccatctggcc
ccagctacgccacctacctgcagcctgctcaggcccagatgctgacacctccatgataactcgagtctagagggcccgtttaaacccgctgatcagcct
cgactgtgccttctagttgccagccatctgttgtttgcccctcccccgtgccttccttgaccctggaaggtgccactcccactgtcctttcctaataaaatg
aggaaattgcatcgcattgtctgagtaggtgtcattctattctggggggtggggtggggcaggacagcaagggggaggattgggaagacaatagcag
gcatgctggggatgcggtgggctctatggcttctactgggcggttttatggacagcaagcgaaccggaattgccagctggggcgccctctggtaaggtt
gggaagccctgcaaagtaaactggatggctttcttgccgccaaggatctgatggcgcaggggatcaagctctgatcaagagacaggatgaggatcgt
ttcgcatgattgaacaagatggattgcacgcaggttctccggccgcttgggtggagaggctattcggctatgactgggcacaacagacaatcggctgc
tctgatgccgccgtgttccggctgtcagcgcaggggcgcccggttctttttgtcaagaccgacctgtccggtgccctgaatgaactgcaagacgaggca
gcgcggctatcgtggctggccacgacgggcgttccttgcgcagctgtgctcgacgttgtcactgaagcgggaagggactggctgctattgggcgaagt
gccggggcaggatctcctgtcatctcaccttgctcctgccgagaaagtatccatcatggctgatgcaatgcggcggctgcatacgcttgatccggctac
ctgcccattcgaccaccaagcgaaacatcgcatcgagcgagcacgtactcggatggaagccggtcttgtcgatcaggatgatctggacgaagagcat
caggggctcgcgccagccgaactgttcgccaggctcaaggcgagcatgcccgacggcgaggatctcgtcgtgacccatggcgatgcctgcttgccga
atatcatggtggaaaatggccgcttttctggattcatcgactgtggccggctgggtgtggcggaccgctatcaggacatagcgttggctacccgtgatat
tgctgaagagcttggcggcgaatgggctgaccgcttcctcgtgctttacggtatcgccgctcccgattcgcagcgcatcgccttctatcgccttcttgacg
agttcttctgaattattaacgcttacaatttcctgatgcggtattttctccttacgcatctgtgcggtatttcacaccgcatcaggtggcacttttcggggaa
atgtgcgcggaacccctatttgtttatttttctaaatacattcaaatatgtatccgctcatgagacaataaccctgataaatgcttcaataatagcacgtg
ctaaaacttcatttttaatttaaaaggatctaggtgaagatcctttttgataatctcatgaccaaaatcccttaacgtgagttttcgttccactgagcgtca
gaccccgtagaaaagatcaaaggatcttcttgagatcctttttttctgcgcgtaatctgctgcttgcaaacaaaaaaaccaccgctaccagcggtggttt
gtttgccggatcaagagctaccaactctttttccgaaggtaactggcttcagcagagcgcagataccaaatactgttcttctagtgtagccgtagttagg
ccaccacttcaagaactctgtagcaccgcctacatacctcgctctgctaatcctgttaccagtggctgctgccagtggcgataagtcgtgtcttaccggg
ttggactcaagacgatagttaccggataaggcgcagcggtcgggctgaacggggggttcgtgcacacagcccagcttggagcgaacgacctacacc
gaactgagatacctacagcgtgagctatgagaaagcgccacgcttcccgaagggagaaaggcggacaggtatccggtaagcggcagggtcggaac
aggagagcgcacgagggagcttccagggggaaacgcctggtatctttatagtcctgtcgggtttcgccacctctgacttgagcgtcgatttttgtgatgc
tcgtcaggggggcggagcctatggaaaaacgccagcaacgcggcctttttacggttcctggccttttgctggccttttgctcacatgttctt

FIG. 26A gctgcttcgcgatgtacgggccagatatacgcgttgacattgattattgactagttattaatagtaatcaattacggggtcattagttcatag
cccatatatggagttccgcgttacataacttacggtaaatggcccgcctggctgaccgcccaacgacccccgcccattgacgtcaataatgacgtatgt
tcccatagtaacgccaatagggactttccattgacgtcaatgggtggagtatttacggtaaactgcccacttggcagtacatcaagtgtatcatatgcca
agtacgccccctattgacgtcaatgacggtaaatggcccgcctggcattatgcccagtacatgaccttatgggactttcctacttggcagtacatctacg
tattagtcatcgctattaccatggtgatgcggttttggcagtacatcaatgggcgtggatagcggtttgactcacggggatttccaagtctccacccatt
gacgtcaatgggagtttgttttggcaccaaaatcaacgggactttccaaaatgtcgtaacaactccgccccattgacgcaaatgggcggtaggcgtgt
acggtgggaggtctatataagcagagctctctggctaactagagaacccactgcttactggcttatcgaaattaatacgactcactatagggagaccc
aagctggctagcgtttaaacttaagcttggtaccgagctcggatccgccaccatggactggacctggattctgttcctggtggccgctgccacaagggt
gcactctcaggctatcgtgagaggctgcagcatgccaggaccttggcggtccggccgcctgctggtgtccaggagatggtctgtggagaggggaagg
aagcggcgcagcccactgctgcccttctaccctcccgatgaggctctggagatcggactggagctgaacagctccgccctgccacccaccgagaggg
gcagaaagaggagatccgtgatcctgcctcaggctccatctggacccagctacgccacctacctgcagcctgctcaggcccagatgctgacacctcca
tgataactcgagtctagagggcccgtttaaacccgctgatcagcctcgactgtgccttctagttgccagccatctgttgtttgcccctcccccgtgccttcc
ttgaccctggaaggtgccactcccactgtcctttcctaataaaatgaggaaattgcatcgcattgtctgagtaggtgtcattctattctggggggtggggt
ggggcaggacagcaagggggaggattgggaagacaatagcaggcatgctggggatgcggtgggctctatggcttctactgggcggttttatggacag
caagcgaaccggaattgccagctggggcgccctctggtaaggttgggaagccctgcaaagtaaactggatggctttcttgccgccaaggatctgatgg
cgcaggggatcaagctctgatcaagagacaggatgaggatcgtttcgcatgattgaacaagatggattgcacgcaggttctccggccgcttgggtgga
gaggctattcggctatgactgggcacaacagacaatcggctgctctgatgccgccgtgttccggctgtcagcgcaggggcgcccggttctttttgtcaa
gaccgacctgtccggtgccctgaatgaactgcaagacgaggcagcgcggctatcgtggctggccacgacgggcgttccttgcgcagctgtgctcgacg
ttgtcactgaagcgggaagggactggctgctattgggcgaagtgccggggcaggatctcctgtcatctcaccttgctcctgccgagaaagtatccatca
tggctgatgcaatgcggcggctgcatacgcttgatccggctacctgcccattcgaccaccaagcgaaacatcgcatcgagcgagcacgtactcggatg
gaagccggtcttgtcgatcaggatgatctggacgaagagcatcaggggctcgcgccagccgaactgttcgccaggctcaaggcgagcatgcccgacg
gcgaggatctcgtcgtgacccatggcgatgcctgcttgccgaatatcatggtggaaaatggccgcttttctggattcatcgactgtggccggctgggtgt
ggcggaccgctatcaggacatagcgttggctacccgtgatattgctgaagagcttggcggcgaatgggctgaccgcttcctcgtgctttacggtatcgc
cgctcccgattcgcagcgcatcgccttctatcgccttcttgacgagttcttctgaattattaacgcttacaatttcctgatgcggtattttctccttacgcat
ctgtgcggtatttcacaccgcatcaggtggcacttttcggggaaatgtgcgcggaacccctatttgtttatttttctaaatacattcaaatatgtatccgct
catgagacaataaccctgataaatgcttcaataatagcacgtgctaaaacttcatttttaatttaaaaggatctaggtgaagatcctttttgataatctc
atgaccaaaatcccttaacgtgagttttcgttccactgagcgtcagaccccgtagaaaagatcaaaggatcttcttgagatcctttttttctgcgcgtaat
ctgctgcttgcaaacaaaaaaaccaccgctaccagcggtggtttgtttgccggatcaagagctaccaactctttttccgaaggtaactggcttcagcag
agcgcagataccaaatactgttcttctagtgtagccgtagttaggccaccacttcaagaactctgtagcaccgcctacatacctcgctctgctaatcctg
ttaccagtggctgctgccagtggcgataagtcgtgtcttaccgggttggactcaagacgatagttaccggataaggcgcagcggtcgggctgaacggg
gggttcgtgcacacagcccagcttggagcgaacgacctacaccgaactgagatacctacagcgtgagctatgagaaagcgccacgcttcccgaagg
gagaaaggcggacaggtatccggtaagcggcagggtcggaacaggagagcgcacgagggagcttccagggggaaacgcctggtatctttatagtcc
tgtcgggtttcgccacctctgacttgagcgtcgatttttgtgatgctcgtcaggggggcggagcctatggaaaaacgccagcaacgcggcctttttacgg
ttcctggccttttgctggccttttgctcacatgttctt

FIG. 27A gctgcttcgcgatgtacgggccagatatacgcgttgacattgattattgactagttattaatagtaatcaattacggggtcattagttcatag
cccatatatggagttccgcgttacataacttacggtaaatggcccgcctggctgaccgcccaacgacccccgcccattgacgtcaataatgacgtatgt
tcccatagtaacgccaatagggactttccattgacgtcaatgggtggagtatttacggtaaactgcccacttggcagtacatcaagtgtatcatatgcca
agtacgccccctattgacgtcaatgacggtaaatggcccgcctggcattatgcccagtacatgaccttatgggactttcctacttggcagtacatctacg
tattagtcatcgctattaccatggtgatgcggttttggcagtacatcaatgggcgtggatagcggtttgactcacggggatttccaagtctccacccatt
gacgtcaatgggagtttgttttggcaccaaaatcaacgggactttccaaaatgtcgtaacaactccgccccattgacgcaaatgggcggtaggcgtgt
acggtgggaggtctatataagcagagctctctggctaactagagaacccactgcttactggcttatcgaaattaatacgactcactatagggagaccc
aagctggctagcgtttaaacttaagcttggtaccgagctcggatccgccaccatggactggacctggattctgttcctggtggctgctgctacaagggtg
cactcccaggccatcgtgaggggctgctctatgccaggaccttggcggagcggccgcctgctggtgtccaggagatggtctgtggagaggggaagaa
agcggcgctctcctctgctgcccttctaccctcccgacgaggctctggagatcggcctggagctgaacagctccgctctgccacccaccgagggcagcg
gagccacaaacttttccctgctgaagcaggctggagatgtggaggagaacccaggacccgtgatcctgccacaggctccttctggaccaagctacgct
acctacctgcagccagctcaggctcagatgctgacacctccatgataactcgagtctagagggcccgtttaaacccgctgatcagcctcgactgtgcct
tctagttgccagccatctgttgtttgcccctcccccgtgccttccttgaccctggaaggtgccactcccactgtcctttcctaataaaatgaggaaattgca
tcgcattgtctgagtaggtgtcattctattctggggggtggggtggggcaggacagcaagggggaggattgggaagacaatagcaggcatgctgggg
atgcggtgggctctatggcttctactgggcggttttatggacagcaagcgaaccggaattgccagctggggcgccctctggtaaggttgggaagccctg
caaagtaaactggatggctttcttgccgccaaggatctgatggcgcaggggatcaagctctgatcaagagacaggatgaggatcgtttcgcatgattg
aacaagatggattgcacgcaggttctccggccgcttgggtggagaggctattcggctatgactgggcacaacagacaatcggctgctctgatgccgcc
gtgttccggctgtcagcgcaggggcgcccggttctttttgtcaagaccgacctgtccggtgccctgaatgaactgcaagacgaggcagcgcggctatcg
tggctggccacgacgggcgttccttgcgcagctgtgctcgacgttgtcactgaagcgggaagggactggctgctattgggcgaagtgccggggcagga
tctcctgtcatctcaccttgctcctgccgagaaagtatccatcatggctgatgcaatgcggcggctgcatacgcttgatccggctacctgcccattcgacc
accaagcgaaacatcgcatcgagcgagcacgtactcggatggaagccggtcttgtcgatcaggatgatctggacgaagagcatcaggggctcgcgc
cagccgaactgttcgccaggctcaaggcgagcatgcccgacggcgaggatctcgtcgtgacccatggcgatgcctgcttgccgaatatcatggtggaa
aatggccgcttttctggattcatcgactgtggccggctgggtgtggcggaccgctatcaggacatagcgttggctacccgtgatattgctgaagagcttg
gcggcgaatgggctgaccgcttcctcgtgctttacggtatcgccgctcccgattcgcagcgcatcgccttctatcgccttcttgacgagttcttctgaatta
ttaacgcttacaatttcctgatgcggtattttctccttacgcatctgtgcggtatttcacaccgcatcaggtggcacttttcggggaaatgtgcgcggaac
ccctatttgtttatttttctaaatacattcaaatatgtatccgctcatgagacaataaccctgataaatgcttcaataatagcacgtgctaaaacttcattt
ttaatttaaaaggatctaggtgaagatcctttttgataatctcatgaccaaaatcccttaacgtgagttttcgttccactgagcgtcagaccccgtagaa
aagatcaaaggatcttcttgagatcctttttttctgcgcgtaatctgctgcttgcaaacaaaaaaaccaccgctaccagcggtggtttgtttgccggatca
agagctaccaactctttttccgaaggtaactggcttcagcagagcgcagataccaaatactgttcttctagtgtagccgtagttaggccaccacttcaag
aactctgtagcaccgcctacatacctcgctctgctaatcctgttaccagtggctgctgccagtggcgataagtcgtgtcttaccgggttggactcaagac
gatagttaccggataaggcgcagcggtcgggctgaacggggggttcgtgcacacagcccagcttggagcgaacgacctacaccgaactgagatacc
tacagcgtgagctatgagaaagcgccacgcttcccgaagggagaaaggcggacaggtatccggtaagcggcagggtcggaacaggagagcgcacg
agggagcttccagggggaaacgcctggtatctttatagtcctgtcgggtttcgccacctctgacttgagcgtcgatttttgtgatgctcgtcaggggggc
ggagcctatggaaaaacgccagcaacgcggcctttttacggttcctggccttttgctggccttttgctcacatgttctt A map of the plasmid follows:

TUMOR-SPECIFIC NEOANTIGENS AND METHODS OF USING THE SAME

CROSS-REFERENCE TO RELATED APPLICATIONS

This application is a national stage application filed under 35 U.S.C. § 371 of International Application No. PCT/US2019/034229, filed May 28, 2019, which claims benefit of U.S. Provisional Application No. 62/676,563, filed May 25, 2018, the content of each of the aforementioned applications is hereby incorporated by reference in its entirety.

The Sequence Listing associated with this application is filed in electronic format via Patent Center and hereby incorporated by reference into the specification in its entirety. The name of the text file containing the Sequence Listing is WIST-003-US_SL.txt. The size of the text file is 251,030 bytes and the text file was created on May 8, 2024.

FIELD

The disclosure relates to vaccines, nucleic acid sequence that are components of vaccines and methods of manufacturing and using the same for inducing antigen-specific immune responses in a subject.

BACKGROUND

The immune system can be classified into two functional subsystems: the innate and the acquired immune system. The innate immune system is the first line of defense against infections, and most potential pathogens are rapidly neutralized by this system before they can cause, for example, a noticeable infection. The acquired immune system reacts to molecular structures, referred to as antigens, of the intruding organism. There are two types of acquired immune reactions, which include the humoral immune reaction and the cell-mediated immune reaction. In the humoral immune reaction, antibodies secreted by B cells into bodily fluids bind to pathogen-derived antigens, leading to the elimination of the pathogen through a variety of mechanisms, e.g. complement-mediated lysis. In the cell-mediated immune reaction, T-cells capable of destroying other cells are activated. For example, if proteins associated with a disease are present in a cell, they are fragmented proteolytically to peptides within the cell. Specific cell proteins then attach themselves to the antigen or peptide formed in this manner and transport them to the surface of the cell, where they are presented to the molecular defense mechanisms, in particular T-cells, of the body. Cytotoxic T cells recognize these antigens and kill the cells that harbor the antigens.

The molecules that transport and present peptides on the cell surface are referred to as proteins of the major histocompatibility complex (MHC). MHC proteins are classified into two types, referred to as MHC class I and MHC class II. The structures of the proteins of the two MHC classes are very similar; however, they have very different functions. Proteins of MHC class I are present on the surface of almost all cells of the body, including most tumor cells. MHC class I proteins are loaded with antigens that usually originate from endogenous proteins or from pathogens present inside cells, and are then presented to naive or cytotoxic T-lymphocytes (CTLs). MHC class II proteins are present on dendritic cells, B-lymphocytes, macrophages and other antigen-presenting cells. They mainly present peptides, which are processed from external antigen sources, i.e. outside of the cells, to T-helper (Th) cells. Most of the peptides bound by the MHC class I proteins originate from cytoplasmic proteins produced in the healthy host cells of an organism itself, and do not normally stimulate an immune reaction. Accordingly, cytotoxic T-lymphocytes (CTLs) that recognize such self-peptide-presenting MHC molecules of class I are deleted in the thymus (central tolerance) or, after their release from the thymus, are deleted or inactivated, i.e. tolerized (peripheral tolerance). MHC molecules are capable of stimulating an immune reaction when they present peptides to non-tolerized T-lymphocytes. Cytotoxic T-lymphocytes have both T-cell receptors (TCR) and cluster of differentiation (CD) molecules on their surface. T-Cell receptors are capable of recognizing and binding peptides complexed with the molecules of MHC class I. Each cytotoxic T-lymphocyte expresses a unique T-cell receptor which is capable of binding specific MHC/peptide complexes.

The peptide antigens attach themselves to the molecules of MHC class I by competitive affinity binding within the endoplasmic reticulum, before they are presented on the cell surface. Here, the affinity of an individual peptide antigen is directly linked to its amino acid sequence and the presence of specific binding motifs in defined positions within the amino acid sequence. If the sequence of such a peptide is known, it is possible to manipulate the immune system against diseased cells using, for example, peptide vaccines.

One of the critical barriers to developing curative and tumor-specific immunotherapy is the identification and selection of highly specific and restricted tumor antigens to avoid autoimmunity. Cancer neoantigens, epitopes derived from tumor-specific somatic mutations that are presented on MHCs, are emerging as promising targets for personalized immunotherapy. These epitopes are thought to be more robust immunotherapy targets compared to shared, overexpressed tumor-associated self-antigens due to i) their high frequency in human cancers (ranging from approximately 33-163 expressed, non-synonymous mutations for common solid tumors in adults) (Vogelstein et al. Science (80-). 2013; 339:1546-58), ii) their lack of expression in normal somatic tissues, and iii) their high potential for immunogenicity due to lack of central and peripheral tolerance. Indeed, effective immune checkpoint blockade therapy has been associated with specific targeting of tumor neoantigens (Gubin et al. Nature. 2014; 515:577-81; McGranahan et al. Science. 2016; 351:1463-9). However, the same immunogenic neoantigens are rarely shared across multiple patients (Rech et al., Cancer Immunol Res. 2018); therefore, this type of therapy is highly personalized and requires rapid, efficient and affordable sequencing and manufacturing processes. Furthermore, the vast majority of these mutations are passenger mutations, and not drivers of the malignancy; thus, there is a high likelihood of tumor escape.

In 2017, there were an estimated 1,688,780 new cancer cases diagnosed, and 600,920 cancer deaths in the US. Over the past few decades there been significant improvements in the detection, diagnosis, and treatment of cancer, which have significantly increased the survival rate for many types of cancer. The number of cancer deaths (cancer mortality) is 171.2 per 100,000 men and women per year (based on 2008-2012 deaths), which makes cancer among the leading causes of death in the United States.

Existing cancer therapies include ablation techniques (e.g., surgical procedures, cryogenic/heat treatment, ultrasound, radiofrequency, and radiation) and chemical techniques (e.g., pharmaceutical agents, cytotoxic/chemotherapeutic agents, monoclonal antibodies, and various combinations thereof). Unfortunately, such therapies are frequently associated with serious risk, toxic side effects, and extremely high costs, as well as uncertain efficacy.

Cancer vaccines are typically composed of tumor antigens and immunostimulatory molecules (e.g., cytokines or TLR ligands) that work together to induce antigen-specific cytotoxic T cells that target and destroy tumor cells. Current cancer vaccines typically contain shared tumor antigens, which are native proteins (i.e. —proteins encoded by the DNA of ail the normal cells in the individual) that are selectively expressed or over-expressed in tumors found in many individuals. While such shared tumor antigens are useful in identifying particular types of tumors, they are not ideal as immunogens for targeting a T-cell response to a particular tumor type because they are subject to the immune dampening effects of self-tolerance.

Early clinical trials using synthetic long peptides (15-30mer) delivered with poly(I:C), dendritic cells loaded with short HLA class I restricted peptides, or RNA vaccines encoding long (27mer) neo-epitope peptides have shown immune responses directed against a significant fraction of mutated epitopes delivered (Ott et al. Nature. Nature Publishing Group; 2017; 547:217-21; Sahin et al. Nature. Nature Publishing Group; 2017; 547:222-6; Carreno et al. Science. 2015; 348:803-8). The vast majority of these responses driven by RNA or synthetic long peptides have been MHC class II restricted, both in these early clinical studies as well as in pre-clinical mouse studies (70-95% in mice and 72.5-79% in humans) (Ott et al. 2017; Sahin et al. 2017; Kretier et al. Nature; 2015; 520:692-6; Martin et al. PLoS One. 2016; 11). This strong induction of $CD4^+$ T cell responses occurs despite the fact that the epitopes were selected in silico for high MHCI binding affinity (Ott et al. 2017; Sahin et al. 2017; Kreiter et al. 2015).

SUMMARY OF THE DISCLOSURE

The disclosure describes the development of DNA vaccines encoding neoantigens that are capable of generating robust MHC class I-restricted immune responses against neoantigens in a greater proportion than those immune responses generated by RNA and peptide vaccine platforms. Neoantigen targeted immunotherapies are based on the specific activation of certain well-defined tumor antigens that have been mapped to the patient's specific tumor. These are antigens that have been shown to be expressed in the tumor and presented to the immune system of that patient, and thus are specifically targeted to the patient's tumor without the risk of non-specific/bystander targeting from a broad activation of innate immunity.

The DNA vaccines described in the present disclosure surprisingly generate a much larger proportion of $CD8^+$ T cell responses for the immunogenic epitopes. The present disclosure describes for the first time that inclusion of only high affinity MHC class I epitopes selected for a larger proportion of immunogenic epitopes, and selected for 100% $CD8^+$ or $CD8^+/CD4^+$ T cell epitopes. Moreover, the present disclosure described for the first time that DNA vaccines encoding neo-antigens were able to control tumor growth in vivo in a therapeutic setting, and T cells expanded from immunized mice were able to kill tumor cells ex vivo. Thus, the DNA vaccines targeting neoantigens described in the present disclosure can overcome many of the limitations of other vaccine platforms, and may be able to work synergistically with other platforms for effective immunotherapy approaches.

In some embodiments, a nucleic acid molecule comprising a nucleic acid sequence comprising Formula I: $[(AED^n)\text{-}(linker)]_n\text{-}[AED^{n+1}]$, wherein the AED is an antigen expression domain comprising an expressible nucleic acid sequence. Each linker is independently selectable from about 0 to about 125 natural or non-natural nucleic acids in length. The antigen expression domain 1 is independently selectable from about 24 to about 250 nucleotides in length and encodes an epitope. The antigen expression domain 2 is independently selectable from about 24 to about 250 nucleotides in length and encodes an epitope, and n is any positive integer from about 1 to about 500.

In some embodiments, the antigen expression domain 1 and the antigen expression domain 2 are independently selectable from about 20 to about 2,000 nucleotides in length.

In some embodiments, the antigen expression domain 1 or antigen expression domain 2 is independently selectable from about 50 to about 10,000 nucleotides in length and n is any positive integer from about 6 to about 26.

In some embodiments, the antigen expression domain 1 and/or the antigen expression domain 2 are independently selectable from about 15 to about 150, about 15 to about 100, or about 15 to about 50 nucleotides in length.

In some embodiments, n is a positive integer from about 5 to about 30, about 2 to about 100, about 2 to about 58, or about 2 to about 29.

In some embodiments, at least one linker comprises from about 15 to about 300 nucleotides and encodes a cleavage site. Optionally, the at least one linker comprises a furin protease cleavage site or a porcine teschovirus-1 2A (P2A) cleavage site.

In some embodiments, at least one linker comprises from about 15 to about 300 nucleotides, encodes a cleavage site, and Formula I comprises at least a first linker and a second linker, wherein the first and second linker comprise a furin protease cleavage site.

In some embodiments, at least one linker comprises from about 15 to about 300 nucleotides, encodes a cleavage site, n is a positive integer from about 5 to about 50, and each linker comprises a furin protease cleavage site. The nucleic acid molecule of this embodiment may further comprise at least one regulatory sequence, and wherein at least one nucleic acid sequence of Formula I is operably linked to the regulatory sequence.

In some embodiments, the antigen expression domain 1 is independently selectable from about 12 to about 15,000 nucleotides in length and encodes an epitope from one or a plurality of cancer cells from a subject. The antigen expression domain 2 is independently selectable from about 12 to about 15,000 nucleotides in length and encodes an epitope from one or a plurality of cancer cells from the subject.

In some embodiments, the nucleic acid molecule is in an amount sufficient to elicit a CD8+ T cell response and/or a CD4+ T cell response against any one or plurality of amino acid sequences encoded by one or plurality of antigen expression domains.

In some embodiments, the nucleic acid molecule further comprises a leader sequence, such as an IgE leader sequence.

In some embodiments, the nucleic acid molecule is a plasmid. In some embodiments, the nucleic acid sequence of Formula I is positioned with the multiple cloning site of a plasmid is (i) selected from the group consisting of: LLC, TC1, ID8, pGX4501, pGX4503, pGX4504, pGX4505, and pGX4506, or (ii) a plasmid having at least 70% homology with a plasmid selected from the group consisting of: LLC, TC1, ID8, pGX4501, pGX4503, pGX4504, pGX4505, and pGX4506. It should be appreciated that host cells can be transformed with such plasmids.

In some embodiments, a composition comprises one or a plurality of nucleic acid molecules as described herein.

In some embodiments, a pharmaceutical composition comprises (i) one or a plurality of any of the nucleic acid molecules described herein, or a pharmaceutically acceptable salt thereof and (ii) a pharmaceutically acceptable carrier. Optionally, the pharmaceutical composition may further comprise one or more therapeutic agents, such as a biologic therapeutic or a small molecule. In some embodiment, one of the therapeutic agents is (i) a checkpoint inhibitor or functional fragment thereof, or (ii) a nucleic acid sequence that encodes a checkpoint inhibitor or functional fragment thereof. In some embodiments, the checkpoint inhibitor or functional fragment thereof associates or inhibits a checkpoint protein selected from the group consisting of CTLA-4, PDL1, PDL2, PD1, B7-H3, B7-H4, BTLA, HVEM, TIM3, GAL9, LAG3, VISTA, KIR, 2B4, CD160, CGEN-15049, CHK 1, CHK2, A2aR, and B-7 family ligands or a combination thereof. In some embodiments, the checkpoint inhibitor is an inhibitor of the programmed death-1 (PD-1) pathway. In some embodiments, the checkpoint inhibitor is an anti-cytotoxic T-lymphocyte-associated antigen 4 (CTLA4) antibody. In some embodiments, a pharmaceutical composition comprises a pharmaceutically effective amount of: (i) one or a plurality of any of the nucleic acid molecules described herein or nucleic acid sequences that are about 70%, 75%, 80%, 85%, 90%, 91%, 92%, 93%, 94%, 95%, 96%, 97%, 98%, or 99% homologous to any nuclecui acid sequence listed herein, or a pharmaceutically acceptable salt thereof; and (ii) a pharmaceutically acceptable carrier.

In some embodiments, the therapeutic agent is an adjuvant or functional fragment thereof. In some embodiments, the adjuvant or functional fragment thereof is (i) selected from the group consisting of: poly-ICLC, 1018 ISS, aluminum salts, Amplivax. AS15, BCG, CP-870,893, CpG7909, CyaA, GM-CSF, IC30, IC31, Imiquimod, ImuFact 1MP321, IS Patch, ISS, ISCOMATRIX, JuvImmune, LipoVac, monophosphoryf lipid A, Montanide IMS 1312, Montanide ISA 206, Montanide ISA 50V, Montanide ISA-51, OK-432, OM-174, OM-197-MP-EC, ONTAK, PEPTEL, vector system, PLGA microparticles, resiquimod, S L172, Virosomes and other Virus-like particles, YF-17D, VEGF trap, R848, beta-gluean, Pam3Cys, acrylic or methacrylic polymers, copolymers of maleic anhydride and Aquila's QS21 stimulon, and a functional fragment of any thereof; or (ii) a nucleic acid molecule encoding an adjuvant selected from the group consisting of: poly-ICLC, 1018 ISS, Amplivax AS15, BCG, CP-870,893, CpG7909, CyaA, GM-CSF, IC30, IC31, Imiquimod, ImuFact 1MP321, IS Patch, ISS, ISCOMATRIX, JuvImmune, LipoVac, monophosphoryf lipid A, Montanide IMS 1312, Montanide ISA 206, Montanide ISA 50V, Montanide ISA-51, OK-432, OM-174, OM-197-MP-EC, ONTAK, PEPTEL, vector system, resiquimod, S L172, Virosomes and other Virus-like particles, YF-17D, VEGF trap, R848, beta-gluean, Pam3Cys, and Aquila's QS21 stimulon, or functional fragment thereof. IL-12, IL-15 (protein or plasmid or NA)

In some embodiments, the therapeutic agent is: (i) an immunostimulatory agent or functional fragment thereof; or (ii) a nucleic acid sequence encoding an immunostimulatory agent or a functional fragment thereof. In some embodiments, the immunostimulatory agent is an interleukin or a functional fragment thereof. In some embodiments, the therapeutic agent is: (i) an chemotherapeutic agent or functional fragment thereof; or (ii) a nucleic acid sequence encoding an chemotherapeutic agent or a functional fragment thereof.

In some embodiments, a method of treating and/or preventing cancer in a subject comprises administering to the subject in need thereof a pharmaceutically effective amount of any of the nucleic acid molecules, or any of the pharmaceutical compositions described in this disclosure. In some embodiments, treatment is determined by a clinical outcome, an increase, enhancement or prolongation of anti-tumor activity by T cells, an increase in the number of anti-tumor T cells or activated T cells as compared with the number prior to treatment, or a combination thereof. In some embodiments, the clinical outcome is selected from the group consisting of tumor regression, tumor shrinkage, tumor necrosis, anti-tumor response by the immune system, tumor expansion, recurrence or spread, or a combination thereof. In some embodiments, the cancer has a high mutational load.

In some embodiments, the cancer is selected from the group consisting of: non-small cell lung cancer, melanoma, ovarian cancer, cervical cancer, glioblastoma, urogenital cancer, gynecological cancer, lung cancer, gastrointestinal cancer, head and neck cancer, non-metastatic or metastatic breast cancer, malignant melanoma, Merkel Cell Carcinoma or bone and soft tissue sarcomas, haematologic neoplasias, multiple myeloma, acute myelogenous leukemia, chronic myelogenous leukemia, myelodysplastic syndrome and acute lymphoblastic leukemia, breast cancer, metastatic colorectal cancers, hormone sensitive or hormone refractory prostate cancer, colorectal cancer, ovarian cancer, hepatocellular cancer, renal cell cancer, pancreatic cancer, gastric cancer, oesophageal cancers, hepatocellular cancers, cholangiocellular cancers, head and neck squamous cell cancer soft tissue sarcoma, and small cell lung cancer.

In some embodiments, a method of enhancing an immune response against a plurality of heterogeneous hyperproliferative cells in a subject comprises administering to the subject in need thereof a pharmaceutically effective amount of any of the nucleic acid molecules or any of the pharmaceutical composition of as described in this disclosure. In some embodiments, the immune response is of a sufficient magnitude or efficacy to inhibit or retard tumor growth, induce tumor cell death, induce tumor regression, prevent or delay tumor recurrence, prevent tumor growth, prevent tumor spread and/or induce tumor elimination.

In some embodiments, of enhancing an immune response against a plurality of heterogeneous hyperproliferative cells in a subject further comprises administration of one or more therapeutic agents, as disclosed herein. In some embodiments, the additional therapeutic agent is a biologic therapeutic or a small molecule. In some embodiments, the therapeutic agent is: (i) a checkpoint inhibitor or functional fragment thereof; or (ii) a nucleic acid molecule encoding a checkpoint inhibitor or a functional fragment thereof. In some embodiments, the checkpoint inhibitor associates with or inhibits a checkpoint protein selected from the group consisting of CTLA-4, PDL1, PDL2, PD1, B7-H3, B7-H4, BTLA, HVEM, TIM3, GAL9, LAG3, VISTA, KIR, 2B4, CD160, CGEN-15049, CHK 1, CHK2, A2aR, and B-7 family ligands, IDO inhibitors, or a combination thereof. In some embodiments, the checkpoint inhibitor is an inhibitor of the programmed death-1 (PD-1) pathway. In some embodiments, the checkpoint inhibitor is an anti-cytotoxic T-lymphocyte-associated antigen 4 (CTLA4) antibody or functional fragment thereof. In some embodiments, the therapeutic agent is selected from the adjuvants as disclosed herein, or an immunostimulatory agent or functional fragment thereof. In some embodiments. the immunostimulatory agent is an interleukin or functional fragment thereof. In some embodiments, the therapeutic agent is a chemotherapeutic agent.

In some embodiments, the subject has cancer. In some embodiments, the the subject has not responded to checkpoint inhibitor therapy.

In some embodiments, the nucleic acid molecule is administered to the subject by electroporation.

In some embodiments, a method of inducing an immune response in a subject comprises administering to the subject in need thereof a pharmaceutically effective amount of any of the nucleic acid molecules or any of the pharmaceutical composition of the present disclosure. In some embodiments, the immune response is a CD8+ T cell immune response. In some embodiments, inducing the CD8+ T cell immune response comprises activating 0.01% to about 50% CD8+ T cells. In some embodiments, inducing the CD8+ T cell immune response comprises expanding CD8+ T cells.

In some embodiments, a method of enhancing an immune response in a subject comprises administering to the subject in need thereof a pharmaceutically effective amount of any of the nucleic acid molecules or any of the pharmaceutical compositions disclosed herein.

In some embodiments, the immune response is a CD8+ T cell immune response. In some embodiments, enhancing the CD8+ T cell immune response comprises activating 0.01% to about 50% CD8+ T cells. In some embodiments, enhancing the CD8+ T cell immune response comprises expanding CD8+ T cells.

In some embodiments, a method of identifying one or more subject-specific DNA neoantigen mutations in a subject, wherein the subject has a cancer characterized by the presence or quantity of a plurality of neoantigen mutations comprises:

- sequencing a nucleic acid sample from a tumor of the subject and of a non-tumor sample of the subject;
- analyzing the sequence to determine coding and non-coding regions;
- identifying sequences comprising tumor-specific non-synonymous or non-silent mutations not present in the non-tumor sample;
- identifying single nucleotide variations and single nucleotide insertions and deletions;
- producing subject-specific peptides encoded by the sequences comprising tumor-specific non-synonymous or non-silent mutations not present in the non-tumor sample; and
- measuring the binding characteristics of the of the subject-specific peptides,
- wherein each subject-specific peptide is an expression product of subject-specific DNA neoantigen not present in the non-tumor sample, thereby identifying one or more subject-specific DNA neoantigens in a subject.

In some embodiments, the step of measuring the binding characteristics of the of the subject-specific peptides is carried out by one or more of:

- measuring the binding of the subject-specific peptides to T-cell receptor;
- measuring the binding of the subject-specific peptides to a HLA protein of the subject; or
- measuring the binding of the subject-specific peptides to transporter associated with antigen processing (TAP).

In some embodiments, the subject-specific peptides bind to HLA proteins of the subject with an IC50 of less than about 500 nM. In some embodiments, the step of ranking the subject-specific peptides based on the binding characteristics. In some embodiments, the method further comprises the step of measuring the CD8+ T cell immune response generated by the subject-specific peptides. In some embodiments, the method further comprises formulating the subject-specific DNA neoantigens into a immunogenic composition for administration to the subject. In some embodiments, about 200 ranked neoantigen mutations are included in the immunogenic composition.

In some embodiments, the method further comprises steps of providing a culture comprising dendritic cells obtained from the subject, and contacting the dendritic cells with the immunogenic composition. In some embodiments, the method further comprises steps of: administering to the subject the dendritic cells, obtaining a population of CD8+ T cells from a peripheral blood sample from the subject, wherein the CD8+ cells recognize the at least one neoantigen, and expanding the population of CD8+ T cells that recognizes the neoantigen. In some embodiments, the method further comprises administering to the subject the expanded population of CD8+ T cells.

In some embodiments, a method of making an individualized cancer vaccine for a subject suspected of having or diagnosed with a cancer comprises:

- identifying a plurality of mutations in a sample from the subject;
- analyzing the plurality of mutations to identify one or more neoantigen mutations; and
- producing, based on the identified subset, a personalized cancer vaccine.

In some embodiments, the step of identifying comprises sequencing the cancer. In some embodiments, the step of analyzing further comprises determining one or more binding characteristics associated with the neoantigen mutation, the binding characteristics selected from the group consisting of binding of the subject-specific peptides to T-cell receptor, binding of the subject-specific peptides to a HLA protein of the subject and binding of the subject-specific peptides to transporter associated with antigen processing (TAP), and ranking, based on the determined characteristics, each of the neo-antigenic mutations.

In some embodiments, the method comprises cloning nucleic acid sequences encoding the one or plurality of neoantigen mutations into a nucleic acid molecule, such as a plasmid. In some embodiments, the nucleic acid molecule comprises a nucleic acid sequence of Formula I that is positioned within the multiple cloning site of a plasmid selected from the group consisting of: pGX4501, pGX4503, pGX 4504, pGX4505, and pGX4506.

DESCRIPTION OF THE DRAWINGS

FIG. 1A. Experimental setup. C57Bl/6 mice were implanted with LLC, TC1 or ID8 tumor cells subcutaneously (LLC and TC1) or in the peritoneum (ID8). Tumors and normal tail tissue were harvested 3 weeks after implantation for RNA and DNA isolation and sequencing. Mutations were identified through comparison with normal tissue. FIG. 1B. Number of mutations identified for each tumor type with the indicated MHC class I affinity (NetMHCons v1.1). Mutations were included if they were expressed with an Alt allele depth in RNA-seq ≥1, a proteasomal cleavage score ≥10 and a TAP processing score ≤0.5. FIG. 1C. Plasmid DNA design. The predicted 9mer epitopes were flanked by 12 amino acids on each side (SEQ ID NO: 4). Each epitope was separated by a furin cleavage site (SEQ ID NO: 41). FIG. 1D. Mice were immunized with each plasmid (n=5 mice per group) with 25 μg of DNA followed by electroporation (EP) three times at two week intervals, and were sacrificed for IFNγ ELISpot and flow cytometry analysis one week after final immunization. FIG. 1E. Percentage of epitopes that generated immune responses (>50 SFU/million splenocytes) for each tumor type.

FIG. 2A-FIG. 2F. FIG. 2A shows the nucleotide sequence (SEQ ID NO: 115) of LLC Plasmid #1 and FIG. 2B shows the amino acid sequence (SEQ ID NO: 116) of LLC Plasmid #1. FIG. 2C shows the nucleotide sequence (SEQ ID NO: 117) of LLC Plasmid #2 and FIG. 2D shows the amino acid sequence (SEQ ID NO: 118) of LLC Plasmid #2. FIG. 2E shows the nucleotide sequence (SEQ ID NO: 119) of LLC Plasmid #1 and FIG. 2F shows the amino acid sequence (SEQ ID NO: 120) of LLC Plasmid #3.

FIG. 3A-FIG. 3D. FIG. 3A shows the nucleotide sequence (SEQ ID NO: 121) of TC1 Plasmid #1 and FIG. 3B shows the amino acid sequence (SEQ ID NO: 122) of TC1 Plasmid #1. FIG. 3C shows the nucleotide sequence (SEQ ID NO: 123) of TC1 Plasmid #2 and FIG. 3D shows the amino acid sequence (SEQ ID NO: 124) of TC1 Plasmid #2.

FIG. 4A-FIG. 4D. FIG. 4A shows the nucleotide sequence (SEQ ID NO: 125) of ID8 Plasmid #1 and FIG. 4B shows the amino acid sequence (SEQ ID NO: 126) of ID8 Plasmid #1. FIG. 4C shows the nucleotide sequence (SEQ ID NO: 127) of ID8 Plasmid #2 and FIG. 4D shows the amino acid sequence (SEQ ID NO: 128) of ID8 Plasmid #2.

FIG. 6A-F shows intracellular cytokine staining of splenocytes isolated from control (pVax) or neoantigen immunized mice, stimulated with the corresponding neoantigen-specific peptides for 5 hours. Shown are the percentage of CD8+ T cells that are IFNγ+(FIG. 6A), TNFα+(FIG. 6B) and IL-2+ (FIG. 6C), and CD4+ T cells that are IFNγ+(FIG. 6D), TNFα+(FIG. 6E) and IL-2+ (FIG. 6F). N=5 mice per group. Significance was calculated using a two-tailed student's t-test. Error bars indicate ±SEM. *p<0.05, p<0.01, *p<0.001, ****p<0.0001.

FIG. 7A is a graph of IFNγ ELISpot responses for each epitope that generated a significant immune response (>50SFU/million splenocytes, statistically significantly greater response compared to pVax immunized mice). Bars with upward diagonal lines indicate responses that are exclusively $CD8^+$ T cells, bars with downward diagonal lines bars indicate responses that are exclusively CD4+ T cells, and bars with intermediate diagonal lines bars indicate responses that are both $CD8^+$ and $CD4^+$ T cells. FIG. 7B and FIG. 7C show example flow cytometry data from mice immunized with a TC1 plasmid containing Sgsm2 (FIG. 7B) or Lta4h (FIG. 7C). Shown are IFNγ and TNFα responses for CD4 and CD8 T cells. FIG. 7D shows IFNγ ELISpot responses from (FIG. 7A), displayed according to MHC class I affinity (NetMHC-Cons v1.1). Dark grey bars indicate high affinity (<500 nM), medium grey bars indicate medium affinity (500 nM-2000 nM), and light grey bars indicate low affinity (>2000 nM). FIG. 7E shows percentage of epitopes that generate CD4 versus CD8 T cell responses, organized according to MHC class I affinity. All data shown is ±SEM. N=5 mice per group.

FIG. 8A-FIG. 8F show polyfunctional cytokine analysis of data shown in FIG. 6. Shown are the percentage of CD8+ T cells that co-express IFNγ, T-bet and CD107a (FIG. 8A), CD8+ T cells that co-express IFNγ and TNFα (FIG. 8B), and CD8+ T cells that co-express IFNγ, TNFα and IL-2 (FIG. 5C). Also shown are the percentage of CD4+ T cells that co-express IFNγ, T-bet and CD107a (FIG. 8D), CD8+ T cells that co-express IFNγ and TNFα (FIG. 8E), and CD8+ T cells that co-express IFNγ, TNFα and IL-2 (FIG. 8F). N=5 mice per group. Significance was calculated using a two-tailed student's t-test. Error bars indicate ±SEM. *p<0.05, p<0.01, *p<0.001, ****p<0.0001.

FIG. 10A shows a comparison of IFNγ ELISpot responses against the mutated neoantigen epitope (MUT) to responses against the corresponding wild-type, non-mutated epitope (WT). FIG. 10B. The data from A, expressed in terms of fold change between responses to the MUT and WT epitopes (MUT/WT). Bars with upward diagonal lines indicate epitopes with >2 fold increase in response, bars with downward diagonal lines indicate epitopes with >1.5 fold increase in response, bars with intermediate diagonal lines indicate epitopes with <1.5 fold change in response, and bars Bars with roughly vertical lines indicate epitopes with >1.5 fold decrease in response. N=5 mice per group. Error bars indicate ±SEM.

FIG. 11A shows flow cytometry plots showing IFNg expressing CD4 and CD8 T cells that resulted from the expansion of Herpud2 and Lta4h reactive T cells. Cytotoxicity of T-cells derived from TC1 plasmids. FIG. 11B Sgmsm2 FIG. 11C Herpud2 and FIG. 11C Lta4h expanded with their corresponding overlapping peptides (5 μg/ml) four weeks co-cultured for 24 hours with either TC1 or ID8 tumor cells measured by luciferase expression after co-culture of 24 hours (triplicates, similar results with 5-hour incubation). FIG. 11D shows RNA expression levels of Sgmsm2, Herpud2 and Lta4h in TC1 tumors grown in vivo compared to TC1 cells grown in vitro. FIG. 11E shows flow cytometry histograms showing surface expression of MHC class II on B16 melanoma, TC1, ID8 and LLC tumor cells in normal conditions or after being exposed to 50 ng/ml of interferon gamma. FIG. 11F Histograms showing basal and IFNγ-induced expression of MHC class II in the B16 melanoma, TC1, LLC and ID8 measured by flow cytometry. Two-way ANOVA. Error bars indicate ±SEM. ***p<0.001.

FIG. 14A Schematic of tumor challenge experiments: we implanted 100,000 TC1 tumor cells subcutaneously and 7 days later started weekly immunizations with TC1 plasmid 1, 2, both or pVax empty vector. FIG. 14B Tumor volume of mice bearing TC1 treated TC1 plasmid 1, 2, both or pVax. FIG. 14C Survival curve of mice bearing TC1 treated TC1 plasmid 1, 2, both or pVax (n=10 mice per group). Log rank and two-way ANOVA. Error bars indicate ±SEM. *p<0.05,  p<0.01, **p<0.0001.

FIG. 23A and FIG. 23B. FIG. 23A shows the pGX4501 Full Length DNA Sequence (SEQ ID NO: 129). FIG. 23B shows the pGX4501 plasmid map.

FIG. 24A and FIG. 24B. FIG. 24A shows the pGX4503 Full Length DNA Sequence (SEQ ID NO: 131). FIG. 24B shows the pGX4503 plasmid map.

FIG. 25A and FIG. 25B. FIG. 25A shows the pGX4504 Full Length DNA Sequence (SEQ ID NO: 130). FIG. 25B shows the pGX4504 plasmid map.

FIG. 26A and FIG. 26B. FIG. 26A shows the pGX4505 Full Length DNA Sequence (SEQ ID NO: 132). FIG. 26B shows the pGX4505 plasmid map.

FIG. 27A and FIG. 27B. FIG. 27A shows the pGX4506 Full Length DNA Sequence (SEQ ID NO: 133). FIG. 27B shows the pGX4506 plasmid map.

FIG. 29 depicts survival analysis for mice bearing ID8 tumors treated with ID8 plasmid cocktail (25 micrograms of ID8 plasmid 1 and 25 micrograms id ID8 plasmid 2 formulated together) or 50 micrograms of pVax control plasmid. For this experiment, mice were euthanized upon development of ascites. For all studies, N=10 mice/group. Two-way ANOVA. Gehan-Brelow-Wilcoxon test. *, P<0.01; ****, P<0.0001

DETAILED DESCRIPTION

Figure 1A:
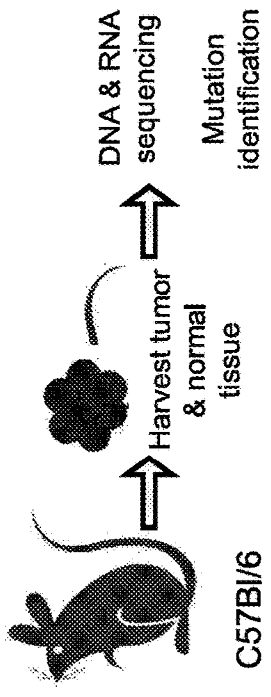
FIG. 1A-FIG. 1E shows DNA vaccine neo-epitope dodecamers induce frequent immune responses.

The present disclosure relates to personalized strategies for the treatment of cancer, by administering a therapeutically effective amount of a pharmaceutical composition (e.g., a cancer vaccine) comprising a plurality of tumor specific neo-antigens to a subject (e.g., a mammal such as a human).

Definitions

The term "about" as used herein when referring to a measurable value such as an amount, a temporal duration, and the like, is meant to encompass variations of ±20%, ±10%, ±5%, ±1%, ±0.5%, or ±0.1% from the specified value, as such variations are appropriate to perform the disclosed methods.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, In some embodiments, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of" will refer to the inclusion of exactly one element of a number or list of elements. In general, the term "or" as used herein shall only be interpreted as indicating exclusive alternatives (i.e. "one or the other but not both") when preceded by terms of exclusivity, "either," "one of" "only one of" or "exactly one of" "Consisting essentially of," when used in the claims, shall have its ordinary meaning as used in the field of patent law.

As used herein, the terms "activate," "stimulate," "enhance" "increase" and/or "induce" (and like terms) are used interchangeably to generally refer to the act of improving or increasing, either directly or indirectly, a concentration, level, function, activity, or behavior relative to the natural, expected, or average, or relative to a control condition. "Activate" refers to a primary response induced by ligation of a cell surface moiety. For example, in the context of receptors, such stimulation entails the ligation of a receptor and a subsequent signal transduction event. Further, the stimulation event may activate a cell and upregulate or downregulate expression or secretion of a molecule. Thus, ligation of cell surface moieties, even in the absence of a direct signal transduction event, may result in the reorganization of cytoskeletal structures, or in the coalescing of cell surface moieties, each of which could serve to enhance, modify, or alter subsequent cellular responses.

As used herein, the terms "activating CD8+ T cells" or "CD8+ T cell activation" refer to a process (e.g., a signaling event) causing or resulting in one or more cellular responses of a CD8+ T cell (CTL), selected from: proliferation, differentiation, cytokine secretion, cytotoxic effector molecule release, cytotoxic activity, and expression of activation markers. As used herein, an "activated CD8+ T cell" refers to a CD8+ T cell that has received an activating signal, and thus demonstrates one or more cellular responses, selected from proliferation, differentiation, cytokine secretion, cytotoxic effector molecule release, cytotoxic activity, and expression of activation markers. Suitable assays to measure CD8+ T cell activation are known in the art and are described herein.

As used herein, the term "adjuvant" is meant to refer to any molecule added to the DNA plasmid vaccines described herein to enhance the immunogenicity of the antigens encoded by the DNA plasmids and the encoding nucleic acid sequences described hereinafter.

As used herein an "antigen" is meant to refer to any substance that will elicit an immune response.

As used herein, the term "anti-tumor response" refers to an immune system response including but not limited to activating T-cells to attack an antigen or an antigen presenting cell.

The term "cancer" as used herein is meant to refer to any disease that is caused by, or results in, inappropriately high levels of cell division, inappropriately low levels of apoptosis, or both. Specific examples of cancer include, but are not limited to, Acute Lymphoblastic Leukemia, Adult; Acute Lymphoblastic Leukemia, Childhood; Acute Myeloid Leukemia, Adult; Adrenocortical Carcinoma; Adrenocortical Carcinoma, Childhood; AIDS-Related Lymphoma; AIDS-Related Malignancies; Anal Cancer; Astrocytoma, Childhood Cerebellar; Astrocytoma, Childhood Cerebral; Bile Duct Cancer, Extrahepatic; Bladder Cancer; Bladder Cancer, Childhood; Bone Cancer, Osteosarcoma/Malignant Fibrous Histiocytoma; Brain Stem Glioma, Childhood; Brain Tumor, Adult; Brain Tumor, Brain Stem Glioma, Childhood; Brain Tumor, Cerebellar Astrocytoma, Childhood; Brain Tumor, Cerebral Astrocytoma/Malignant Glioma, Childhood; Brain Tumor, Ependymoma, Childhood; Brain Tumor, Medulloblastoma, Childhood; Brain Tumor, Supratentorial Primitive Neuroectodermal Tumors, Childhood; Brain Tumor, Visual Pathway and Hypothalamic Glioma, Childhood; Brain Tumor, Childhood (Other); Breast Cancer; Breast Cancer and Pregnancy; Breast Cancer, Childhood; Breast Cancer, Male; Bronchial Adenomas/Carcinoids, Childhood: Carcinoid Tumor, Childhood; Carcinoid Tumor, Gastrointestinal; Carcinoma, Adrenocortical; Carcinoma, Islet Cell; Carcinoma of Unknown Primary; Central Nervous System Lymphoma, Primary; Cerebellar Astrocytoma, Childhood; Cerebral Astrocytoma/Malignant Glioma, Childhood; Cervical Cancer; Childhood Cancers; Chronic Lymphocytic Leukemia; Chronic Myelogenous Leukemia; Chronic Myeloproliferative Disorders; Clear Cell Sarcoma of Tendon Sheaths; Colon Cancer; Colorectal Cancer, Childhood; Cutaneous T-Cell Lymphoma; Endometrial Cancer; Ependymoma, Childhood; Epithelial Cancer, Ovarian; Esophageal Cancer; Esophageal Cancer, Childhood; Ewing's Family of Tumors; Extracranial Germ Cell Tumor, Childhood; Extragonadal Germ Cell Tumor; Extrahepatic Bile Duct Cancer; Eye Cancer, Intraocular Melanoma; Eye Cancer, Retinoblastoma; Gallbladder Cancer; Gastric (Stomach) Cancer; Gastric (Stomach) Cancer, Childhood; Gastrointestinal Carcinoid Tumor; Germ Cell Tumor, Extracranial, Childhood; Germ Cell Tumor, Extragonadal; Germ Cell Tumor, Ovarian; Gestational Trophoblastic Tumor; Glioma. Childhood Brain Stem; Glioma. Childhood Visual Pathway and Hypothalamic; Hairy Cell Leukemia; Head and Neck Cancer; Hepatocellular (Liver) Cancer, Adult (Primary); Hepatocellular (Liver) Cancer, Childhood (Primary); Hodgkin's Lymphoma, Adult; Hodgkin's Lymphoma, Childhood; Hodgkin's Lymphoma During Pregnancy; Hypopharyngeal Cancer; Hypothalamic and Visual Pathway Glioma, Childhood; Intraocular Melanoma; Islet Cell Carcinoma (Endocrine Pancreas); Kaposi's Sarcoma; Kidney Cancer; Laryngeal Cancer; Laryngeal Cancer, Childhood; Leukemia, Acute Lymphoblastic, Adult; Leukemia, Acute Lymphoblastic, Childhood; Leukemia, Acute Myeloid, Adult; Leukemia, Acute Myeloid, Childhood; Leukemia, Chronic Lymphocytic; Leukemia, Chronic Myelogenous; Leukemia, Hairy Cell; Lip and Oral Cavity Cancer; Liver Cancer, Adult (Primary); Liver Cancer, Childhood (Primary); Lung Cancer, Non-Small Cell; Lung Cancer, Small Cell; Lymphoblastic Leukemia, Adult Acute; Lymphoblastic Leukemia, Childhood Acute; Lymphocytic Leukemia, Chronic; Lymphoma, AIDS-Related; Lymphoma, Central Nervous System (Primary); Lymphoma, Cutaneous T-Cell; Lymphoma, Hodgkin's, Adult; Lymphoma, Hodgkin's; Childhood; Lymphoma, Hodgkin's During Pregnancy; Lymphoma, Non-Hodgkin's, Adult; Lymphoma, Non-Hodgkin's, Childhood; Lymphoma, Non-Hodgkin's During Pregnancy; Lymphoma, Primary Central Nervous System; Macroglobulinemia, Waldenstrom's; Male Breast Cancer; Malignant Mesothelioma, Adult; Malignant Mesothelioma, Childhood; Malignant Thymoma; Medulloblastoma, Childhood; Melanoma; Melanoma, Intraocular; Merkel Cell Carcinoma; Mesothelioma, Malignant; Metastatic Squamous Neck Cancer with Occult Primary; Multiple Endocrine Neoplasia Syndrome, Childhood; Multiple Myeloma/Plasma Cell Neoplasm; Mycosis Fungoides; Myelodysplasia Syndromes; Myelogenous Leukemia, Chronic; Myeloid Leukemia, Childhood Acute; Myeloma, Multiple; Myeloproliferative Disorders, Chronic; Nasal Cavity and Paranasal Sinus Cancer; Nasopharyngeal Cancer; Nasopharyngeal Cancer, Childhood; Neuroblastoma; Neurofibroma; Non-Hodgkin's Lymphoma, Adult; Non-Hodgkin's Lymphoma, Childhood; Non-Hodgkin's Lymphoma During Pregnancy; Non-Small Cell Lung Cancer; Oral Cancer, Childhood; Oral Cavity and Lip Cancer; Oropharyngeal Cancer; Osteosarcoma/Malignant Fibrous Histiocytoma of Bone; Ovarian Cancer, Childhood; Ovarian Epithelial Cancer; Ovarian Germ Cell Tumor; Ovarian Low Malignant Potential Tumor; Pancreatic Cancer; Pancreatic Cancer, Childhood', Pancreatic Cancer, Islet Cell; Paranasal Sinus and Nasal Cavity Cancer; Parathyroid Cancer; Penile Cancer; Pheochromocytoma; Pineal and Supratentorial Primitive Neuroectodermal Tumors, Childhood; Pituitary Tumor; Plasma Cell Neoplasm/Multiple Myeloma; Pleuropulmonary Blastoma; Pregnancy and Breast Cancer; Pregnancy and Hodgkin's Lymphoma; Pregnancy and Non-Hodgkin's Lymphoma; Primary Central Nervous System Lymphoma; Primary Liver Cancer, Adult; Primary Liver Cancer, Childhood; Prostate Cancer; Rectal Cancer; Renal Cell (Kidney) Cancer; Renal Cell Cancer, Childhood; Renal Pelvis and Ureter, Transitional Cell Cancer; Retinoblastoma; Rhabdomyosarcoma, Childhood; Salivary Gland Cancer; Salivary Gland Cancer, Childhood; Sarcoma, Ewing's Family of Tumors; Sarcoma, Kaposi's; Sarcoma (Osteosarcoma)/Malignant Fibrous Histiocytoma of Bone; Sarcoma, Rhabdomyosarcoma, Childhood; Sarcoma, Soft Tissue, Adult; Sarcoma, Soft Tissue, Childhood; Sezary Syndrome; Skin Cancer; Skin Cancer, Childhood; Skin Cancer (Melanoma); Skin Carcinoma, Merkel Cell; Small Cell Lung Cancer; Small Intestine Cancer; Soft Tissue Sarcoma, Adult; Soft Tissue Sarcoma, Childhood; Squamous Neck Cancer with Occult Primary, Metastatic; Stomach (Gastric) Cancer; Stomach (Gastric) Cancer, Childhood; Supratentorial Primitive Neuroectodermal Tumors, Childhood; T-Cell Lymphoma, Cutaneous; Testicular Cancer; Thymoma, Childhood; Thymoma, Malignant; Thyroid Cancer; Thyroid Cancer, Childhood; Transitional Cell Cancer of the Renal Pelvis and Ureter; Trophoblastic Tumor, Gestational; Unknown Primary Site, Cancer of, Childhood; Unusual Cancers of Childhood; Ureter and Renal Pelvis, Transitional Cell Cancer; Urethral Cancer; Uterine Sarcoma; Vaginal Cancer; Visual Pathway and Hypothalamic Glioma, Childhood; Vulvar Cancer; Waldenstrom's Macro globulinemia; and Wilms' Tumor.

In certain embodiments, the cancer is selected from the group consisting of non small cell lung cancer, melanoma, ovarian cancer, cervical cancer, glioblastoma, urogenital cancer, gynecological cancer, lung cancer, gastrointestinal cancer, head and neck cancer, non-metastatic or metastatic breast cancer, malignant melanoma, Merkel Cell Carcinoma or bone and soft tissue sarcomas, haematologic neoplasias, multiple myeloma, acute myelogenous leukemia, chronic myelogenous leukemia, myelodysplastic syndrome and acute lymphoblastic leukemia, breast cancer, metastatic colorectal cancers, hormone sensitive or hormone refractory prostate cancer, colorectal cancer, ovarian cancer, hepatocellular cancer, renal cell cancer, pancreatic cancer, gastric cancer, oesophageal cancers, hepatocellular cancers, cholangiocellular cancers, head and neck squamous cell cancer soft tissue sarcoma, and small cell lung cancer.

The term "checkpoint inhibitor" as used herein is meant to refer to any small molecule chemical compound, antibody, nucleic acid molecule, or polypeptide, or fragments thereof, that inhibits the inhibitory pathways, allowing more extensive immune activity. In certain embodiments, the checkpoint inhibitor is an inhibitor of the programmed death-1 (PD-1) pathway, for example an anti-PD1 antibody, such as, but not limited to Nivoiumab. In other embodiments, the checkpoint inhibitor is an anti-cytotoxic T-lymphocyte-associated antigen (CTLA-4) antibody. In further additional embodiments, the checkpoint inhibitor is targeted at a member of the TNF superfamily such as CD40, OX40, CD 137, GITR, CD27 or TIM-3. In some cases targeting a checkpoint inhibitor is accomplished with an inhibitory antibody or similar molecule. In other cases, it is accomplished with an agonist for the target; examples of this class include the stimulatory targets OX40 and GITR.

The term "combination therapy" as used herein is meant to refer to administration of one or more therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single capsule having a fixed ratio of each therapeutic agent or in multiple, single capsules for each of the therapeutic agents. For example, one combination of the present invention may comprise a pooled sample of tumor specific neoantigens and a checkpoint inhibitor administered at the same or different times, or the)' can be formulated as a single, co-formulated pharmaceutical composition comprising the two compounds. As another example, a combination of the present invention (e.g., DNA neoantigen vaccines and a checkpoint inhibitor) may be formulated as separate pharmaceutical compositions that can be administered at the same or different time. As used herein, the term "simultaneously" is meant to refer to administration of one or more agents at the same time. For example, in certain embodiments, a cancer vaccine or immunogenic composition and a checkpoint inhibitor are administered simultaneously). Simultaneously includes administration contemporaneously, that is during the same period of time. In certain embodiments, the one or more agents are administered simultaneously in the same hour, or simultaneously in the same day. Sequential or substantially simultaneous administration of each therapeutic agent can be effected by any appropriate route including, but not limited to, oral routes, intravenous routes, subcutaneous routes, intramuscular routes, direct absorption through mucous membrane tissues (e.g., nasal, mouth, vaginal, and rectal), and ocular routes (e.g., intravitreal, intraocular, etc.). The therapeutic agents can be administered by the same route or by different routes. For example, one component of a particular combination may be administered by intravenous injection while the other component(s) of the combination may be administered orally. The components may be administered in any therapeutically effective sequence. A "combination" embraces groups of compounds or non-drug therapies useful as part of a combination therapy.

As used herein, the term "electroporation," "electro-permeabilization," or "electro-kinetic enhancement" ("EP"), are used interchangeably and are meant to refer to the use of a transmembrane electric field pulse to induce microscopic pathways (pores) in a bio-membrane; their presence allows biomolecules such as plasmids, oligonucleotides, siRNA, drugs, ions, and/or water to pass from one side of the cellular membrane to the other.

By "fragment" is meant a portion of a polypeptide or nucleic acid molecule. This portion contains, preferably, at least 5%, 10%, 20%, 30%, 40%, 50%, 60%, 70%, 80%, or 90% of the entire length of the reference nucleic acid molecule or polypeptide. A fragment may contain 5, 10, 20, 30, 40, 50, 60, 70, 80, 90, or 100, 200, 300, 400, 500, 600, 700, 800, 900, 1000 or more nucleotides or amino acids.

As used herein, the term "genetic construct" is meant to refer to the DNA or RNA molecules that comprise a nucleotide sequence which encodes protein. The coding sequence includes initiation and termination signals operably linked to regulatory elements including a promoter and polyadenylation signal capable of directing expression in the cells of the individual to whom the nucleic acid molecule is administered.

The term "host cell" as used herein is meant to refer to a cell that can be used to express a nucleic acid, e.g., a nucleic acid of the disclosure. can be, but is not limited to, a eukaryotic cell, a bacterial cell, an insect cell, or a human cell. Suitable eukaryotic cells include, but are not limited to, Vero cells, HeLa cells, COS cells, CHO cells, HEK293 cells, BHK cells and MDCKII cells. Suitable insect cells include, but are not limited to, Sf9 cells. The phrase "recombinant host cell" can be used to denote a host cell that has been transformed or transfected with a nucleic acid to be expressed. A host cell also can be a cell that comprises the nucleic acid but does not express it at a desired level unless a regulatory sequence is introduced into the host cell such that it becomes operably linked with the nucleic acid. It is understood that the term host cell refers not only to the particular subject cell but also to the progeny or potential progeny of such a cell. Because certain modifications may occur in succeeding generations due to, e.g., mutation or environmental influence, such progeny may not, in fact, be identical to the parent cell, but are still included within the scope of the term as used herein.

The term "hybridize" as used herein is meant pair to form a double-stranded molecule between complementary polynucleotide sequences (e.g., a gene described herein), or portions thereof, under various conditions of stringency. (See, e.g., Wahl, G. M. and S. L. Berger (1987) Methods Enzymol. 152:399; Kimmel, A. R. (1987) Methods Enzymol. 152:507).

The term "immune checkpoint" as used herein is meant to refer to inhibitory pathways that slow down or stop immune reactions and prevent excessive tissue damage from uncontrolled activity of immune cells.

The term "immune response" is used herein is meant to refer to the activation of a host's immune system, e.g., that of a mammal, in response to the introduction of nucleic acid molecules comprising a nucleotide sequence encoding neoantigens a described herein.

The term "isolated" as used herein means that the polynucleotide or polypeptide or fragment, variant, or derivative thereof has been essentially removed from other biological materials with which it is naturally associated, or essentially free from other biological materials derived, e.g., from a recombinant host cell that has been genetically engineered to express the polypeptide of the invention.

The term "ligand" as used herein is meant to refer to a molecule which has a structure complementary to that of a receptor and is capable of forming a complex with this receptor. According to embodiments of the invention, a ligand is to be understood as meaning in particular a peptide or peptide fragment which has a suitable length and suitable binding motives in its amino acid sequence, so that the peptide or peptide fragment is capable of forming a complex with proteins of MHC class I or MHC class II.

The terms "MHC molecules", "MHC proteins" or "HLA proteins" as used herein are meant to refer to proteins capable of binding peptides resulting from the proteolytic cleavage of protein antigens and representing potential T-cell epitopes, transporting them to the cell surface and presenting them there to specific cells, in particular cytotoxic T-lymphocytes or T-helper cells. The major histocompatibility complex in the genome comprises the genetic region whose gene products expressed on the cell surface are important for binding and presenting endogenous and/or foreign antigens and thus for regulating immunological processes. The major histocompatibility complex is classified into two gene groups coding for different proteins, namely molecules of MEW class I and molecules of MHC class II. The molecules of the two MHC classes are specialized for different antigen sources. The molecules of MEW class I present endogenously synthesized antigens, for example viral proteins and tumor antigens. The molecules of MHC class II present protein antigens originating from exogenous sources, for example bacterial products. The cellular biology and the expression patterns of the two MEW classes are adapted to these different roles.

MEW molecules of class I consist of a heavy chain and a light chain and are capable of binding a peptide of about 8 to 11 amino acids, but usually 9 or 10 amino acids, if this peptide has suitable binding motifs, and presenting it to cytotoxic T-lymphocytes. The peptide bound by the MHC molecules of class I originates from an endogenous protein antigen. The heavy chain of the MHC molecules of class I is preferably an HLA-A, HLA-B or HLA-C monomer, and the light chain is β-2-microglobulin.

MHC molecules of class II consist of an α-chain and a β-chain and are capable of binding a peptide of about 15 to 24 amino acids if this peptide has suitable binding motifs, and presenting it to T-helper cells. The peptide bound by the MEW molecules of class II usually originates from an extracellular of exogenous protein antigen. The α-chain and the β-chain are in particular HLA-DR, HLA-DQ and HLA-DP monomers.

The term "neoantigen" as used herein is meant to refer to a class of tumor antigens which arises from tumor-specific mutations in expressed protein of a subject. In some embodiments, the neoantigen is derived directly from a tumor of a subject. This is as opposed to a known tumor associated antigen which may be a consensus sequence known to elicit an immune response against a cell expressing the tumor antigen but not necessarily expressed by a tumor derived the subject.

The term "neoantigen mutation" as used herein refers to a mutation that is predicted to encode a neoantigenic peptide.

The term "pharmaceutically acceptable" as used herein refers to approved or approvable by a regulatory agency of the Federal or a state government or listed in the U.S. Pharmacopeia or other generally recognized pharmacopeia for use in animals, including humans.

The term "pharmaceutically acceptable excipient, carrier or diluent" as used herein is meant to refer to an excipient, carrier or diluent that can be administered to a subject, together with an agent, and which does not destroy the pharmacological activity thereof and is nontoxic when administered in doses sufficient to deliver a therapeutic amount of the agent.

The term "pharmaceutically acceptable salt" of tumor specific neoantigens as used herein may be an acid or base salt that is generally considered in the art to be suitable for use in contact with the tissues of human beings or animals without excessive toxicity, irritation, allergic response, or other problem or complication. Such salts include mineral and organic acid salts of basic residues such as amines, as well as alkali or organic salts of acidic residues such as carboxylic acids. Specific pharmaceutical salts include, but are not limited to, salts of acids such as hydrochloric, phosphoric, hydrobromic, malic, glycolic, fumaric, sulfuric, sulfamic, suifanilic, formic, toluenesulfonie, methanesulfonic, benzene sulfonic, ethane disulfonic, 2-hydroxyethyl sulfonic, nitric, benzoic, 2-acetoxybenzoic, citric, tartaric, lactic, stearic, salicylic, glutamic, ascorbic, pamoic, succinic, fumaric, maleic, propionic, hydroxymaleic, hydroiodic, phenylacetic, a!kanoic such as acetic, HOOC—(CH2)n-COOH where n is 0-4, and the like. Similarly, pharmaceutically acceptable cations include, but are not limited to sodium, potassium, calcium, aluminum, lithium and ammonium. Those of ordinary skill in the art will recognize from this disclosure and the knowledge in the art that further pharmaceutically acceptable salts for the pooled tumor specific neoantigens provided herein, including those listed by Remington's Pharmaceutical Sciences, 17th ed., Mack Publishing Company, Easton, PA, p. 1418 (1985). In general, a pharmaceutically acceptable acid or base salt can be synthesized from a parent compound that contains a basic or acidic moiety by any conventional chemical method. Briefly, such salts can be prepared by reacting the free acid or base forms of these compounds with a stoichiometric amount of the appropriate base or acid in an appropriate solvent.

As used herein, the terms "prevent," "preventing," "prevention," "prophylactic treatment," and the like, are meant to refer to reducing the probability of developing a disease or condition in a subject, who does not have, but is at risk of or susceptible to developing a disease or condition.

As used herein, the term "purified" means that the polynucleotide or polypeptide or fragment, variant, or derivative thereof is substantially free of other biological material with which it is naturally associated, or free from other biological materials derived, e.g., from a recombinant host cell that has been genetically engineered to express the polypeptide of the invention. That is, e.g., a purified polypeptide of the present invention is a polypeptide that is at least from about 70 to about 100% pure, i.e., the polypeptide is present in a composition wherein the polypeptide constitutes from about 70 to about 100% by weight of the total composition. In some embodiments, the purified polypeptide of the present invention is from about 75% to about 99% by weight pure, from about 80% to about 99% by weight pure, from about 90 to about 99% by weight pure, or from about 95% to about 99% by weight pure.

The term "receptor" as used herein, is meant to refer to a biological molecule or a molecule grouping capable of binding a ligand. A receptor may serve, to transmit information in a cell, a cell formation or an organism. The receptor comprises at least one receptor unit and preferably two receptor units, where each receptor unit may consist of a protein molecule, in particular a glycoprotein molecule. The receptor has a structure which complements that of a ligand and may complex the ligand as a binding partner. The information is transmitted in particular by conformational changes of the receptor following complexation of the ligand on the surface of a cell. According to embodiments of the invention, a receptor is to be understood as meaning in particular proteins of MHC classes I and II capable of forming a receptor/ligand complex with a ligand, in particular a peptide or peptide fragment of suitable length.

As used herein, the term "small molecule" refers to a low molecular weight (<900 daltons) organic compound that may help regulate a biological process, with a size on the order of 10 9 m. Most drugs are small molecules.

As used herein, the terms "subject," "individual," "host," and "patient," are used interchangeably herein and refer to any mammalian subject for whom diagnosis, treatment, or therapy is desired, particularly humans. The methods described herein are applicable to both human therapy and veterinary applications. In some embodiments, the subject is a mammal, and in other embodiments the subject is a human.

As used herein, "patient in need thereof" or "subject in need thereof" refers to a living organism suffering from or prone to a disease or condition that can be treated by administration of a vaccine (or pharmaceutical composition comprising a neoantigen DNA vaccine) according to the described invention. A "patient in need thereof" or "subject in need" may also refer to a living organism that is receiving a neoantigen DNA vaccine (or pharmaceutical composition comprising a neoantigen DNA vaccine) according to the described invention, or has received a neoantigen DNA vaccine (or pharmaceutical composition comprising a neoantigen DNA vaccine) according to the described invention; or has a tumor or Non-limiting examples include humans, other mammals, bovines, rats, mice, dogs, monkeys, goat, sheep, cows, deer, and other non-mammalian animals. In embodiments, a patient or subject is human.

The term "T-cell epitope" as used herein is meant to refer to a peptide sequence which can be bound by the MHC molecules of class I or II in the form of a peptide-presenting MHC molecule or MHC complex and then, in this form, be recognized and bound by cytotoxic T-lymphocytes or T-helper cells, respectively.

The term "therapeutic effect" as used herein is meant to refer to some extent of relief of one or more of the symptoms of a disorder (e.g., a neoplasia or tumor) or its associated pathology. A "therapeutically effective amount" as used herein is meant to refer to an amount of an agent which is effective, upon single or multiple dose administration to the cell or subject, in prolonging the survivability of the patient with such a disorder, reducing one or more signs or symptoms of the disorder, preventing or delaying, and the like beyond that expected in the absence of such treatment. A "therapeutically effective amount" is intended to qualify the amount required to achieve a therapeutic effect. A physician or veterinarian having ordinary skill in the art can readily determine and prescribe the "therapeutically effective amount" (e.g., ED50) of the pharmaceutical composition required. For example, the physician or veterinarian could start doses of the compounds of the invention employed in a pharmaceutical composition at levels lower than that required in order to achieve the desired therapeutic effect and gradually increase the dosage until the desired effect is achieved. In some embodiments, the therapeutically effective amount is an amount effective to shrink a solid tumor by about 2% in total mass as compared to its mass or estimated mass before treatment, by about 4% in total mass, by about 6% in total mass, by about 8% in total mass, by about 10% in total mass, by about 15% in total mass, by about 20% in total mass, by about 25% in total mass, by about 30% in total mass, by about 35% in total mass, by about 40% in total mass, by about 45% in total mass, or by about 50% in total mass as compared to the total mass of the solid tumor before the treatment.

The terms "treat," "treated," "treating," "treatment," and the like as used herein are meant to refer to reducing or ameliorating a disorder and/or symptoms associated therewith (e.g., a cancer or tumor). "Treating" may refer to administration of the neoantigen vaccines described herein to a subject after the onset, or suspected onset, of a cancer. "Treating" includes the concepts of "alleviating", which refers to lessening the frequency of occurrence or recurrence, or the severity, of any symptoms or other ill effects related to a cancer and/or the side effects associated with cancer therapy. The term "treating" also encompasses the concept of "managing" which refers to reducing the severity of a particular disease or disorder in a patient or delaying its recurrence, e.g., lengthening the period of remission in a patient who had suffered from the disease. It is appreciated that, although not precluded, treating a disorder or condition does not require that the disorder, condition, or symptoms associated therewith be completely eliminated.

As used herein, the term "treating cancer" is not intended to be an absolute term. In some aspects, the compositions and methods of the invention seek to reduce the size of a tumor or number of cancer cells, cause a cancer to go into remission, or prevent growth in size or cell number of cancer cells. In some circumstances, treatment with the leads to an improved prognosis.

The term "therapeutic effect" as used herein is meant to refer to some extent of relief of one or more of the symptoms of a disorder (e.g., a neoplasia or tumor) or its associated pathology. A "therapeutically effective amount" as used herein is meant to refer to an amount of an agent which is effective, upon single or multiple dose administration to the cell or subject, in prolonging the survivability of the patient with such a disorder, reducing one or more signs or symptoms of the disorder, preventing or delaying, and the like beyond that expected in the absence of such treatment. A "therapeutically effective amount" is intended to qualify the amount required to achieve a therapeutic effect. A physician or veterinarian having ordinary skill in the art can readily determine and prescribe the "therapeutically effective amount" (e.g., ED50) of the pharmaceutical composition required. For example, the physician or veterinarian could start doses of the compounds of the invention employed in a pharmaceutical composition at levels lower than that required in order to achieve the desired therapeutic effect and gradually increase the dosage until the desired effect is achieved.

For any therapeutic agent described herein the therapeutically effective amount may be initially determined from preliminary in vitro studies and/or animal models. A therapeutically effective dose may also be determined from human data. The applied dose may be adjusted based on the relative bioavailability and potency of the administered agent Adjusting the dose to achieve maximal efficacy based on the methods described above and other well-known methods is within the capabilities of the ordinarily skilled artisan. General principles for determining therapeutic effectiveness, which may be found in Chapter 1 of Goodman and Gilman's The Pharmacological Basis of Therapeutics, 10th Edition, McGraw-Hill (New York) (2001), incorporated herein by reference, are summarized below.

Pharmacokinetic principles provide a basis for modifying a dosage regimen to obtain a desired degree of therapeutic efficacy with a minimum of unacceptable adverse effects. In situations where the drug's plasma concentration can be measured and related to the therapeutic window, additional guidance for dosage modification can be obtained.

Drug products are considered to be pharmaceutical equivalents if they contain the same active ingredients and are identical in strength or concentration, dosage form, and route of administration. Two pharmaceutically equivalent drug products are considered to be bioequivalent when the rates and extents of bioavailability of the active ingredient in the two products are not significantly different under suitable test conditions.

The terms "polynucleotide," "oligonucleotide" and "nucleic acid" are used interchangeably throughout and include DNA molecules (e.g., cDNA or genomic DNA), RNA molecules (e.g., mRNA), analogs of the DNA or RNA generated using nucleotide analogs (e.g., peptide nucleic acids and non-naturally occurring nucleotide analogs), and hybrids thereof. The nucleic acid molecule can be single-stranded or double-stranded. In some embodiments, the nucleic acid molecules of the disclosure comprise a contiguous open reading frame encoding an antibody, or a fragment thereof, as described herein. "Nucleic acid" or "oligonucleotide" or "polynucleotide" as used herein may mean at least two nucleotides covalently linked together. The depiction of a single strand also defines the sequence of the complementary strand. Thus, a nucleic acid also encompasses the complementary strand of a depicted single strand. Many variants of a nucleic acid may be used for the same purpose as a given nucleic acid. Thus, a nucleic acid also encompasses substantially identical nucleic acids and complements thereof. A single strand provides a probe that may hybridize to a target sequence under stringent hybridization conditions. Thus, a nucleic acid also encompasses a probe that hybridizes under stringent hybridization conditions. Nucleic acids may be single stranded or double stranded, or may contain portions of both double stranded and single stranded sequence. The nucleic acid may be DNA, both genomic and cDNA, RNA, or a hybrid, where the nucleic acid may contain combinations of deoxyribo- and ribo-nucleotides, and combinations of bases including uracil, adenine, thymine, cytosine, guanine, inosine, xanthine hypoxanthine, isocytosine and isoguanine Nucleic acids may be obtained by chemical synthesis methods or by recombinant methods. A nucleic acid will generally contain phosphodiester bonds, although nucleic acid analogs may be included that may have at least one different linkage, e.g., phosphoramidate, phosphorothioate, phosphorodithioate, or O-methylphosphoroamidite linkages and peptide nucleic acid backbones and linkages. Other analog nucleic acids include those with positive backbones; non-ionic backbones, and non-ribose backbones, including those described in U.S. Pat. Nos. 5,235,033 and 5,034,506, which are incorporated by reference in their entireties. Nucleic acids containing one or more non-naturally occurring or modified nucleotides are also included within one definition of nucleic acids. The modified nucleotide analog may be located for example at the 5'-end and/or the 3'-end of the nucleic acid molecule. Representative examples of nucleotide analogs may be selected from sugar- or backbone-modified ribonucleotides. It should be noted, however, that also nucleobase-modified ribonucleotides, i.e. ribonucleotides, containing a non-naturally occurring nucleobase instead of a naturally occurring nucleobase such as uridines or cytidines modified at the 5-position, e.g. 5-(2-amino)propyl uridine, 5-bromo uridine; adenosines and guanosines modified at the 8-position, e.g. 8-bromo guanosine; deaza nucleotides, e.g. 7-deaza-adenosine; O- and N-alkylated nucleotides, e.g. N6-methyl adenosine are suitable. The 2'-OH-group may be replaced by a group selected from H, OR, R, halo, SH, SR, NH.sub.2, NHR, N.sub.2 or CN, wherein R is C.sub.1-C.sub.6 alkyl, alkenyl or alkynyl and halo is F, Cl, Br or I. Modified nucleotides also include nucleotides conjugated with cholesterol through, e.g., a hydroxyprolinol linkage as described in Krutzfeldt et al., Nature (Oct. 30, 2005), Soutschek et al., Nature 432:173-178 (2004), and U.S. Patent Publication No. 20050107325, which are incorporated herein by reference in their entireties. Modified nucleotides and nucleic acids may also include locked nucleic acids (LNA), as described in U.S. Patent No. 20020115080, which is incorporated herein by reference. Additional modified nucleotides and nucleic acids are described in U.S. Patent Publication No. 20050182005, which is incorporated herein by reference in its entirety. Modifications of the ribose-phosphate backbone may be done for a variety of reasons, e.g., to increase the stability and half-life of such molecules in physiological environments, to enhance diffusion across cell membranes, or as probes on a biochip. Mixtures of naturally occurring nucleic acids and analogs may be made; alternatively, mixtures of different nucleic acid analogs, and mixtures of naturally occurring nucleic acids and analogs may be made.

As used herein, the term "nucleic acid molecule" comprises one or more nucleotide sequences that encode one or more proteins. In some embodiments, a nucleic acid molecule comprises initiation and termination signals operably linked to regulatory elements including a promoter and polyadenylation signal capable of directing expression in the cells of the individual to whom the nucleic acid molecule is administered. In some embodiments, the nucleic acid molecule also includes a plasmid containing one or more nucleotide sequences that encode one or a plurality of neoantigens. In some embodiments, the disclosure relates to a pharmaceutical composition comprising a first, second, third or more nucleic acid molecule, each of which encoding one or a plurality of neoantigens and at least one of each plasmid comprising one or more of the Formulae disclosed herein.

The terms "polypeptide", "peptide" and "protein" are used interchangeably herein to refer to polymers of amino acids of any length. The polymer may be linear or branched, it may comprise modified amino acids, and it may be interrupted by non-natural amino acids or chemical groups that are not amino acids. The terms also encompass an amino acid polymer that has been modified; for example, disulfide bond formation, glycosylation, lipidation, acetylation, phosphorylation, or any other manipulation, such as conjugation with a labeling component. As used herein the term "amino acid" includes natural and/or unnatural or synthetic amino acids, including glycine and both the D or L optical isomers, and amino acid analogs and peptidomimetics.

The "percent identity" or "percent homology" of two polynucleotide or two polypeptide sequences is determined by comparing the sequences using the GAP computer program (a part of the GCG Wisconsin Package, version 10.3 (Accelrys, San Diego, Calif.)) using its default parameters. "Identical" or "identity" as used herein in the context of two or more nucleic acids or amino acid sequences, may mean that the sequences have a specified percentage of residues that are the same over a specified region. The percentage may be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of single sequence are included in the denominator but not the numerator of the calculation. When comparing DNA and RNA, thymine (T) and uracil (U) may be considered equivalent. Identity may be performed manually or by using a computer sequence algorithm such as BLAST or BLAST 2.0. Briefly, the BLAST algorithm, which stands for Basic Local Alignment Search Tool is suitable for determining sequence similarity. Software for performing BLAST analyses is publicly available through the National Center for Biotechnology Information (http://www.ncbi.nlm.nih.gov). This algorithm involves first identifying high scoring sequence pair (HSPs) by identifying short words of length Win the query sequence that either match or satisfy some positive-valued threshold score T when aligned with a word of the same length in a database sequence. T is referred to as the neighborhood word score threshold (Altschul et al., supra). These initial neighborhood word hits act as seeds for initiating searches to find HSPs containing them. The word hits are extended in both directions along each sequence for as far as the cumulative alignment score can be increased. Extension for the word hits in each direction are halted when: 1) the cumulative alignment score falls off by the quantity X from its maximum achieved value; 2) the cumulative score goes to zero or below, due to the accumulation of one or more negative-scoring residue alignments; or 3) the end of either sequence is reached. The Blast algorithm parameters W, T and X determine the sensitivity and speed of the alignment. The Blast program uses as defaults a word length (W) of 11, the BLOSUM62 scoring matrix (see Henikoff et al., Proc. Natl. Acad. Sci. USA, 1992, 89, 10915-10919, which is incorporated herein by reference in its entirety) alignments (B) of 50, expectation (E) of 10, M=5, N=4, and a comparison of both strands. The BLAST algorithm (Karlin et al., Proc. Natl. Acad. Sci. USA, 1993, 90, 5873-5787, which is incorporated herein by reference in its entirety) and Gapped BLAST perform a statistical analysis of the similarity between two sequences. One measure of similarity provided by the BLAST algorithm is the smallest sum probability (P(N)), which provides an indication of the probability by which a match between two nucleotide sequences would occur by chance. For example, a nucleic acid is considered similar to another if the smallest sum probability in comparison of the test nucleic acid to the other nucleic acid is less than about 1, less than about 0.1, less than about 0.01, and less than about 0.001. Two single-stranded polynucleotides are "the complement" of each other if their sequences can be aligned in an anti-parallel orientation such that every nucleotide in one polynucleotide is opposite its complementary nucleotide in the other polynucleotide, without the introduction of gaps, and without unpaired nucleotides at the 5' or the 3' end of either sequence. A polynucleotide is "complementary" to another polynucleotide if the two polynucleotides can hybridize to one another under moderately stringent conditions. Thus, a polynucleotide can be complementary to another polynucleotide without being its complement.

The phrase "stringent hybridization conditions" or "stringent conditions" as used herein is meant to refer to conditions under which a nucleic acid molecule will hybridize another nucleic acid molecule, but to no other sequences. Stringent conditions are sequence-dependent and will be different in different circumstances. Longer sequences hybridize specifically at higher temperatures. Generally, stringent conditions are selected to be about 5° C. lower than the thermal melting point (Tm) for the specific sequence at a defined ionic strength and pH. The Tm is the temperature (under defined ionic strength, pH and nucleic acid concentration) at which 50% of the probes complementary to the target sequence hybridize to the target sequence at equilibrium. Since the target sequences are generally present in excess, at Tm, 50% of the probes are occupied at equilibrium. Typically, stringent conditions will be those in which the salt concentration is less than about 1.0 M sodium ion, typically about 0.01 to 1.0 M sodium ion (or other salts) at pH 7.0 to 8.3 and the temperature is at least about 30° C. for short probes, primers or oligonucleotides (e.g. 10 to 50 nucleotides) and at least about 600 C for longer probes, primers or oligonucleotides. Stringent conditions may also be achieved with the addition of destabilizing agents, such as formamide.

By "substantially identical" is meant nucleic acid molecule (or polypeptide) exhibiting at least 50% identity to a reference amino acid sequence (for example, any one of the amino acid sequences described herein) or nucleic acid sequence (for example, any one of the nucleic acid sequences described herein). Preferably, such a sequence is at least 60%, more preferably 80% or 85%, and more preferably 90%, 95% or even 99% identical at the amino acid level or nucleic acid to the sequence used for comparison.

A nucleotide sequence is "operably linked" to a regulatory sequence if the regulatory sequence affects the expression (e.g., the level, timing, or location of expression) of the nucleotide sequence. A "regulatory sequence" is a nucleic acid that affects the expression (e.g., the level, timing, or location of expression) of a nucleic acid to which it is operably linked. The regulatory sequence can, for example, exert its effects directly on the regulated nucleic acid, or through the action of one or more other molecules (e.g., polypeptides that bind to the regulatory sequence and/or the nucleic acid). Examples of regulatory sequences include promoters, enhancers and other expression control elements (e.g., polyadenylation signals). Further examples of regulatory sequences are described in, for example, Goeddel, 1990, Gene Expression Technology: *Methods in Enzymology* 185, Academic Press, San Diego, Calif. and Baron et al., 1995, *Nucleic Acids Res.* 23:3605-06.

As used herein, the term "sample" refers generally to a limited quantity of something which is intended to be similar to and represent a larger amount of that something. In the present disclosure, a sample is a collection, swab, brushing, scraping, biopsy, removed tissue, or surgical resection that is to be testing for the absence, presence or grading of a hyperproliferative tissue, which, in some cases is cancerous tissue or one or a plurality of cells. In some embodiments, samples are taken from a patient or subject that is believed to have a cancer, hyperplasia, pre-cancerous or comprise one or more tumor cells. In some embodiments, a sample believed to contain one or more hyperproliferative cells is compared to a "control sample" that is known not to contain one or more hyperproliferative cells. This disclosure contemplates using any one or a plurality of disclosed samples herein to identify, detect, sequence and/or quantify the amount of neoantigens (highly or minimally immunogenic) within a particular sample. In some embodiments, the methods relate to the step of exposing a swab, brushing or other sample from an environment to a set of reagents sufficient to isolate and/or sequence the DNA and RNA of one or a plurality of cells in the sample.

A "vector" is a nucleic acid that can be used to introduce another nucleic acid linked to it into a cell. One type of vector is a "plasmid," which refers to a linear or circular double stranded DNA molecule into which additional nucleic acid segments can be ligated. Another type of vector is a viral vector (e.g., replication defective retroviruses, adenoviruses and adeno-associated viruses), wherein additional DNA segments can be introduced into the viral genome. Certain vectors are capable of autonomous replication in a host cell into which they are introduced (e.g., bacterial vectors comprising a bacterial origin of replication and episomal mammalian vectors). Other vectors (e.g., non-episomal mammalian vectors) are integrated into the genome of a host cell upon introduction into the host cell, and thereby are replicated along with the host genome. An "expression vector" is a type of vector that can direct the expression of a chosen polynucleotide. The disclosure relates to any one or plurality of vectors that comprise nucleic acid sequences encoding any one or plurality of amino acid sequence disclosed herein.

The term "vaccine" as used herein is meant to refer to a composition for generating immunity for the prophylaxis and/or treatment of diseases (e.g., cancer). Accordingly, vaccines are medicaments which comprise antigens and are intended to be used in humans or animals for generating specific defense and protective substance by vaccination. A "vaccine composition" or a "neoantigen vaccine composition" can include a pharmaceutically acceptable excipient, earner or diluent.

Compositions

The present disclosure is based, at least in part, on the ability to identify all, or substantially all, of the mutations within a cancer/tumor (e.g., translocations, inversions, large and small deletions and insertions, missense mutations, splice site mutations, etc.). In particular, these mutations are present in the genome of cancer/tumor cells of a subject, but not in normal tissue from the subject. The disclosure relates to the innovative discovery that administering pharmaceutical compositions comprising the nucleic acid sequences that encode from about 1 to about 100 different amino acid sequences that represent a milleu of mutations in several different cancer cells Such mutations are of particular interest if they lead to changes that result in a protein with an altered amino acid sequence that is unique to the patient's cancer/tumor (e.g., a neo-antigen).

In one aspect, the present disclosure features a nucleic acid molecule comprising a nucleic acid sequence comprising Formula I:

$$[(AED^{n})\text{-}(linker)]_{n}\text{-}[AED^{n+1}],$$

wherein the AED is an independently selectable antigen expression domain comprising an expressible nucleic acid sequence, wherein $AED^n$ is referred to as antigen expression domain and wherein AEDn+1 is referred to as antigen expression domain 2; wherein the each linker is independently selectable from about 0 to about 300 natural or non-natural nucleic acids in length, wherein the antigen expression domain 1 is independently selectable from about 12 to about 15,000 nucleotides in length and encodes an epitope; wherein the antigen expression domain 2 is independently selectable from about 12 to about 15,000 nucleotides in length and encodes an epitope; and wherein n is any positive integer from about 1 to about 500.

In some embodiments, each linker is independently selectable from about 0 to about 25, about 1 to about 25, about 2 to about 25, about 3 to about 25, about 4 to about 25, about 5 to about 25, about 6 to about 25, about 7 to about 25, about 8 to about 25, about 9 to about 25, about 10 to about 25, about 11 to about 25, about 12 to about 25, about 13 to about 25, about 14 to about 25, about 15 to about 25, about 16 to about 25, about 17 to about 25, about 18 to about 25, about 19 to about 25, about 20 to about 25, about 21 to about 25, about 22 to about 25, about 23 to about 25, about 24 to about 25 natural or non-natural nucleic acids in length. In some embodiments, each linker is about 0, about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25 natural or non-natural nucleic acids in length. In some embodiments, each linker is independently selectable from a linker that is about 0, about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25 natural or non-natural nucleic acids in length. In some embodiments, each linker is about 21 natural or non-natural nucleic acids in length.

In some embodiments, the length of each linker according to Formula I is different. For example, in some embodiments, the length of a first linker is about 0, about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25 natural or non-natural nucleic acids in length, and the length of a second linker is about 0, about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25 natural or non-natural nucleic acids in length, where the length of the first linker is different from the length of the second linker. Various configurations can be envisioned by the present disclosure, where Formula I comprises 1, 2, 3, 4, 5, 6, 7, 8, 9, 10 or more linkers wherein the linkers are of similar or different lengths.

In certain embodiments, two linkers can be used together, in a nucleotide sequence that encodes a fusion peptide. Accordingly, in some embodiments, the first linker is independently selectable from about 0 to about 25 natural or non-natural nucleic acids in length, about 0 to about 25, about 1 to about 25, about 2 to about 25, about 3 to about 25, about 4 to about 25, about 5 to about 25, about 6 to about 25, about 7 to about 25, about 8 to about 25, about 9 to about 25, about 10 to about 25, about 11 to about 25, about 12 to about 25, about 13 to about 25, about 14 to about 25, about 15 to about 25, about 16 to about 25, about 17 to about 25, about 18 to about 25, about 19 to about 25, about 20 to about 25, about 21 to about 25, about 22 to about 25, about 23 to about 25, about 24 to about 25 natural or non-natural nucleic acids in length. In some embodiments, the second linker is independently selectable from about 0 to about 25, about 1 to about 25, about 2 to about 25, about 3 to about 25, about 4 to about 25, about 5 to about 25, about 6 to about 25, about 7 to about 25, about 8 to about 25, about 9 to about 25, about 10 to about 25, about 11 to about 25, about 12 to about 25, about 13 to about 25, about 14 to about 25, about 15 to about 25, about 16 to about 25, about 17 to about 25, about 18 to about 25, about 19 to about 25, about 20 to about 25, about 21 to about 25, about 22 to about 25, about 23 to about 25, about 24 to about 25 natural or non-natural nucleic acids in length. In some embodiments, the first linker is independently selectable from a linker that is about 0, about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25 natural or non-natural nucleic acids in length. In some embodiments, the second linker is independently selectable from a linker that is about 0, about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25 natural or non-natural nucleic acids in length.

In certain embodiments, antigen expression domain 1 and antigen expression domain 2 comprise a nucleic acid sequence that encodes a particular tumor neoantigen. In some embodiments, antigen expression domain 1 encodes a CD4 neoepitope. In some embodiments, antigen expression domain 1 encodes a CD8 neoepitope. In some embodiments, antigen expression domain 2 encodes a CD4 neoepitope. In some embodiments, antigen expression domain 2 encodes a CD8 neoepitope. In some embodiments, antigen domain 1 encodes a CD8 neoepitope and antigen expression domain 2 encodes a CD8 neoepitope. A CD4 neoepitope is an epitope that is recognized by CD4+ T cells. A CD8 neoepitope is an epitope that is recognized by CD8+ T cells.

The disclosures relates to a nucleic acid sequence comprising a plurality of antigen expression domains encoding at least two neoantigens separated by one or a plurality of linkers. In some embodiments, the antigen expression domain encodes an amino acid sequence from about 3 to about 100 amino acids in length. In some embodiments, there is at least one linker encoding a linker from about 3 to about 25 amino acids in length. In some embodiment, the linker sequence separate each antigen expression domain. In some embodiments, the nucleic acid sequence comprises 1, 2, 3, 4, 5, 6, 7, 8, 9, or 10 or more linkers. In some embodiments, the nucleic acid sequence comprises 1, 2, 3, 4, 5, 6, 7, 8, 9, or 10 or more linkers, at least one or more are comprise furin linkers. In some embodiments, the nucleic acid sequence comprises at least 2, 3, 4, 5, 6, 7, 8, 9, or 10 or more linker domains and the nucleic acid sequence comprises Formula I(a):

$$(AED^1)\text{-(linker)-}(AED^2)\text{-(linker)}]_n$$

wherein each AED is independently selectable from any one or plurality of tumor associated antigens from a subject and wherein n is any positive integer from about 1 to about 50 and wherein each "linker" is a nucleic acid sequence encoding one or a plurality of amino acid cleavage sites. Each linker may be the same or independently selectable to comprise one or a plurality of the linkers disclosed herein. In some embodiments, the linker is a furin cleavage site from about 9 to about 105 nucleotides in length and encodes an amino acid sequence that is an amino acid cleavage site.

In some embodiments, the nucleic acid sequence is a component of a nucleic acid molecule. In some compositions contemplated herein, the composition comprises 1, 2, 3, 4, 5, or more nucleic acid molecules each of which expressing any of the patterns or formulae of AEDs disclosed herein.

The disclosures also relates to a nucleic acid sequence comprising a coding region and a non-coding region, the coding region consisting of the Formula I(b):

$$[(AED^1)\text{-(linker)-}(AED^2)\text{-(linker)}]_{n}\text{-}(AED^3)]_{n+1},$$

wherein n is a positive integer from about 1 to about 20, wherein each "linker" encode one or a plurality of amino acid cleavages sequences, and wherein the non-coding region comprises at least one regulatory sequence operably linked to one or more AEDs; and wherein, in the 5' of 3' orientation, $AED^3$ is the terminal antigen expression domain in a sequence of AEDs. In some embodiments, the regulatory is any of the regulatory sequences depicted in the Figures or a functional fragment that comprises at least 70%, 75%, 80%, 85%, 90%, 91%, 92%, 93%, 94%, 95%, 96% 97%, 98% or 99% homologous to the regulatory sequence depicted in the Figures.

In some embodiments, the nucleic acid molecule or sequence of the disclosure comprises a plurality of antigen expression domains encoding at least two neoantigens separated by one or a plurality of linkers. In some embodiments, the antigen expression domain encodes an amino acid sequence from about 3 to about 100 amino acids in length. In some embodiments, there is at least one linker encoding a linker from about 3 to about 25 amino acids in length. In some embodiment, the linker sequence separate each antigen expression domain. In some embodiments, the nucleic acid sequence comprises 1, 2, 3, 4, 5, 6, 7, 8, 9, or 10 or more linkers. In some embodiments, the nucleic acid sequence comprises 1, 2, 3, 4, 5, 6, 7, 8, 9, or 10 or more linkers, at least one or more are comprise furin linkers. In some embodiments, the nucleic acid sequence comprises at least 2, 3, 4, 5, 6, 7, 8, 9, or 10 or more linker domains and the nucleic acid sequence comprises $$(AED^1)\text{-(linker)-}(AED^2)\text{-(linker)}]_n \qquad \text{Formula I(a):}$$

wherein each AED is independently selectable from any one or plurality of tumor associated antigens from a subject and wherein n is any positive integer from about 1 to about 50 and wherein each "linker" is a nucleic acid sequence encoding one or a plurality of amino acid cleavage sites. Each linker may be the same or independently selectable to comprise one or a plurality of the linkers disclosed herein.

In some embodiments, the antigen expression domain 1 and/or 2 is independently selectable from about 12 to about 15,000 nucleotides in length, about 50 to about 15,000 nucleotides in length, about 100 to about 15,000 nucleotides in length, about 500 to about 15,000 nucleotides in length, about 1,000 to about 15,000 nucleotides in length, about 5,000 to about 15,000 nucleotides in length, about 10,000 to about 15,000 nucleotides in length. In other embodiments, the antigen expression domain 1 is about 12, about 25, about 50, about 75, about 100, about 200, about 300, about 400, about 500, about 600, about 700, about 800, about 900, about 1,000, about 2,000, about 3,000, about 4,000, about 5,000, about 6,000, about 7,000, about 8,000, about 9,000, about 10,000, about 11,000, about 12,000, about 13,000, about 14,000, about 15,000 nucleotides in length. In some embodiments, the antigen expression domain 2 is independently selectable from about 12 to about 15,000 nucleotides in length, about 50 to about 15,000 nucleotides in length, about 100 to about 15,000 nucleotides in length, about 500 to about 15,000 nucleotides in length, about 1,000 to about 15,000 nucleotides in length, about 5,000 to about 15,000 nucleotides in length, about 10,000 to about 15,000 nucleotides in length. In another embodiment, the antigen expression domain 2 is about 12, about 25, about 50, about 75, about 100, about 200, about 300, about 400, about 500, about 600, about 700, about 800, about 900, about 1,000, about 2,000, about 3,000, about 4,000, about 5,000, about 6,000, about 7,000, about 8,000, about 9,000, about 10,000, about 11,000, about 12,000, about 13,000, about 14,000 about 15,000 nucleotides in length.

In other embodiments, the antigen expression domain 1 or the antigen expression domain 2 are independently selectable from about 20 to about 2,000 nucleotides in length. In some embodiments, the antigen expression domain 1 is about 20 to about 2,000 nucleotides in length, about 50 to about 2,000 nucleotides in length, about 100 to about 2,000 nucleotides in length, about 500 to about 2,000 nucleotides in length, about 1500 to about 2,000 nucleotides in length. In other embodiments, the antigen expression domain 1 is about 20, about 30, about 40, about 50, about 60, about 70, about 80, about 90, about 100, about 200, about 300, about 400, about 500, about 600, about 700, about 800, about 900, about 1000, about 1,100, about 1,200, about 1,300, about 1,400, about 1,500, about 1,600, about 1,700, about 1,800, about 1900, about 2000 nucleotides in length. In some embodiments, the antigen expression domain 2 is about 20 to about 2,000 nucleotides in length, about 50 to about 2,000 nucleotides in length, about 100 to about 2,000 nucleotides in length, about 500 to about 2,000 nucleotides in length, about 1500 to about 2,000 nucleotides in length. In other embodiments, the antigen expression domain 2 is about 20, about 30, about 40, about 50, about 60, about 70, about 80, about 90, about 100, about 200, about 300, about 400, about 500, about 600, about 700, about 800, about 900, about 1000, about 1,100, about 1,200, about 1,300, about 1,400, about 1,500, about 1,600, about 1,700, about 1,800, about 1900, about 2000 nucleotides in length.

In some embodiments, the antigen expression domain 1 and/or the antigen expression domain 2 are independently selectable from about 15 to about 150 nucleotides in length, for example about 15 to about 150 nucleotides in length, about 15 to about 125 nucleotides in length, about 15 to about 100, about 15 to about 90 nucleotides in length, about 15 to about 90 nucleotides in length, about 15 to about 80 nucleotides in length, about 15 to about 70 nucleotides in length, about 15 to about 60 nucleotides in length, about 15 to about 50 nucleotides in length, about 15 to about 40 nucleotides in length, about 15 to about 30 nucleotides in length, about 15 to about 20 nucleotides in length.

In some embodiments, the antigen expression domain 1 and/or antigen expression domain 2 is independently selectable from about 15 to about 100 nucleotides in length, for example about 3 to about 120 nucleotides in length, from about 15 to about 100, from about 15 to about 90 nucleotides in length, about 15 to about 90 nucleotides in length, about 15 to about 80 nucleotides in length, about 15 to about 70 nucleotides in length, about 15 to about 60 nucleotides in length, about 15 to about 50 nucleotides in length, about 15 to about 40 nucleotides in length, about 15 to about 30 nucleotides in length, about 15 to about 20 nucleotides in length.

In some embodiments, the antigen expression domain 1 and/or antigen expression domain 2 is independently selectable from about 15 to about 50 nucleotides in length, for example about 15 to about 50 nucleotides in length, about 15 to about 40 nucleotides in length, about 15 to about 30 nucleotides in length, about 15 to about 20 nucleotides in length.

In some embodiments, n is any positive integer from about 1 to about 500. In some embodiments, n is any positive integer from about 1 to about 500, from about 10 to about 500, from about 50 to about 500, from about 100 to about 500, from about 200 to about 500, from about 300 to about 500, from about 400 to about 500. In other embodiments, n is any positive integer of about 1, about 5, about 10, about 15, about 20, about 25, about 30, about 35, about 40, about 45, about 50, about 55, about 60, about 65, about 70, about 75, about 80, about 85, about 90, about 95, about 100, about 105, about 110, about 115, about 120, about 125, about 130, about 135, about 140, about 145, about 150, about 155, about 160, about 165, about 170, about 175, about 180, about 185, about 190, about 195, about 200, about 205, about 210, about 215, about 220, about 225, about 230, about 235, about 240, about 245, about 250, about 255, about 260, about 265, about 270, about 275, about 280, about 285, about 290, about 295, about 300, about 305, about 310, about 315, about 120, about 325, about 330, about 335, about 340, about 345, about 350, about 355, about 360, about 365, about 370, about 375, about 380, about 385, about 390, about 395, about 400, about 405, about 410, about 415, about 420, about 425, about 430, about 435, about 440, about 445, about 450, about 455, about 460, about 465, about 470, about 475, about 480, about 485, about 490, about 495, about 500.

In some embodiments, n is a positive integer from about 5 to about 30, from about 5 to about 25, from about 5 to about 20, from about 5 to about 15, from about 5 to about 10.

In some embodiments, n is a positive integer from about 2 to about 100, from about 2 to about 90, from about 2 to about 80, from about 2 to about 70, from about 2 to about 60, from about 2 to about 50, from about 2 to about 40, from about 2 to about 30, from about 2 to about 20, from about 2 to about 10.

In some embodiments, n is a positive integer from about 2 to about 58, from about 3 to about 58, from about 4 to about 58, from about 5 to about 58, from about 6 to about 58, from about 7 to about 58, from about 8 to about 58, from about 9 to about 58, from about 10 to about 58, from about 11 to about 58, from about 12 to about 58, from about 13 to about 58, from about 14 to about 58, from about 15 to about 58, from about 16 to about 58, from about 17 to about 58, from about 18 to about 58, from about 19 to about 58, from about 20 to about 58, from about 21 to about 58, from about 22 to about 58, from about 23 to about 58, from about 24 to about 58, from about 25 to about 58, from about 26 to about 58, from about 27 to about 58, from about 28 to about 58, from about 29 to about 58, from about 30 to about 58, from about 31 to about 58, from about 32 to about 58, from about 33 to about 58, from about 34 to about 58, from about 35 to about 58, from about 36 to about 58, from about 37 to about 58, from about 38 to about 58, from about 39 to about 58, from about 40 to about 58, from about 41 to about 58, from about 42 to about 58, from about 43 to about 58, from about 44 to about 58, from about 45 to about 58, from about 46 to about 58, from about 47 to about 58, from about 48 to about 58, from about 49 to about 58, from about 50 to about 58, from about 51 to about 58, from about 52 to about 58, from about 53 to about 58, from about 54 to about 58, from about 55 to about 58, from about 56 to about 58, from about 57 to about 58.

In one In some embodiments, n is a positive integer from about 2 to about 29, from about 3 to about 29, from about 4 to about 29, from about 5 to about 29, from about 6 to about 58, from about 7 to about 29, from about 8 to about 29, from about 9 to about 29, from about 10 to about 29, from about 11 to about 29, from about 12 to about 29, from about 13 to about 29, from about 14 to about 29, from about 15 to about 29, from about 16 to about 29, from about 17 to about 29, from about 18 to about 29, from about 19 to about 29, from about 20 to about 29, from about 21 to about 29, from about 22 to about 29, from about 23 to about 29, from about 24 to about 29, from about 25 to about 29, from about 26 to about 29, from about 27 to about 29, from about 28 to about 29.

In some embodiments, the antigen expression domain 1 or antigen expression domain 2 is independently selectable from about 50 to about 10,000 nucleotides in length, for example about 50 to about 15,000 nucleotides in length, about 100 to about 15,000 nucleotides in length, about 500 to about 15,000 nucleotides in length, about 1,000 to about 15,000 nucleotides in length, about 5,000 to about 15,000 nucleotides in length, about 10,000 to about 15,000 nucleotides in length, and n is any positive integer from about 6 to about 26, for example about 6, about 7, about 8, about 9, about 10, about 11, about 12, about 13, about 14, about 15, about 16, about 17, about 18, about 19, about 20, about 21, about 22, about 23, about 24, about 25, or about 26.

In some embodiments, a nucleic acid molecule comprises a nucleic acid sequence comprising Formula I ([(AED$^n$)-(linker)]$_n$-[AED$^{n+1}$]), wherein the each linker is independently selectable from about 0 to about 25 natural or non-natural nucleic acids in length. In some embodiments, a nucleic acid molecule comprises a nucleic acid sequence comprising Formula I ([(AED$^n$)-(linker)]$_n$-[AED$^{n+1}$]), wherein the each linker is independently selectable from about 0 to about 25 natural or non-natural nucleic acids in length, about 0 to about 25, about 1 to about 25, about 2 to about 25, about 3 to about 25, about 4 to about 25, about 5 to about 25, about 6 to about 25, about 7 to about 25, about 8 to about 25, about 9 to about 25, about 10 to about 25, about 11 to about 25, about 12 to about 25, about 13 to about 25, about 14 to about 25, about 15 to about 25, about 16 to about 25, about 17 to about 25, about 18 to about 25, about 19 to about 25, about 20 to about 25, about 21 to about 25, about 22 to about 25, about 23 to about 25, about 24 to about 25. In some embodiments, each linker is about 0, about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25 natural or non-natural nucleic acids in length. In some embodiments, each linker is about 21 natural or non-natural nucleic acids in length. In certain embodiments, two linkers can be used together, in a fusion. Accordingly, in some embodiments, the first linker is independently selectable from about 0 to about 25 natural or non-natural nucleic acids in length, about 0 to about 25, about 1 to about 25, about 2 to about 25, about 3 to about 25, about 4 to about 25, about 5 to about 25, about 6 to about 25, about 7 to about 25, about 8 to about 25, about 9 to about 25, about 10 to about 25, about 11 to about 25, about 12 to about 25, about 13 to about 25, about 14 to about 25, about 15 to about 25, about 16 to about 25, about 17 to about 25, about 18 to about 25, about 19 to about 25, about 20 to about 25, about 21 to about 25, about 22 to about 25, about 23 to about 25, about 24 to about 25 natural or non-natural nucleic acids in length. In some embodiments, the second linker is independently selectable from about 0 to about 25, about 1 to about 25, about 2 to about 25, about 3 to about 25, about 4 to about 25, about 5 to about 25, about 6 to about 25, about 7 to about 25, about 8 to about 25, about 9 to about 25, about 10 to about 25, about 11 to about 25, about 12 to about 25, about 13 to about 25, about 14 to about 25, about 15 to about 25, about 16 to about 25, about 17 to about 25, about 18 to about 25, about 19 to about 25, about 20 to about 25, about 21 to about 25, about 22 to about 25, about 23 to about 25, about 24 to about 25 natural or non-natural nucleic acids in length. In some embodiments, the first linker is independently selectable from a linker that is about 0, about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25 natural or non-natural nucleic acids in length. In some embodiments, the second linker is independently selectable from a linker that is about 0, about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25 natural or non-natural nucleic acids in length.

In some embodiments, the at least one linker comprises from about 15 to about 300 nucleotides and encodes a n amino acid cleavage site. In some embodiments, each linker positioned between each AED is the same nucleotide sequence comprising from about 15 to about 120 nucleotides and encodes an amino acid cleavage site In some embodiments, the formula (e.g. $[(AED^n)\text{-}(linker)]_n\text{–}[AED^{n+1}]$) comprises at least 1, 2, 3, 4, 5, 6, 7, 8, 9, 10 or more linkers.

In some embodiments, the formula comprises at least a first linker and a second linker.

In some embodiments, the formula comprises at least a first linker, a second linker, and a third linker.

In some embodiments, the formula comprises at least a first linker, a second linker, a third linker, and a fourth linker.

In some embodiments, the formula comprises at least a first linker, a second linker, a third linker, a fourth linker, and a fifth linker.

In a further embodiment, the at least one linker comprises a furin protease cleavage site.

Furin is a protease which resides in the trans-Golgi network of eukaryotic cells. Its function is to cleave proteins at a step just prior to their delivery to their final cellular destination.

Furin recognizes a consensus amino acid sequence, RXRR, RXRK or KXKR (where X is any amino acid, Moehring et al., 1993, incorporated by reference in its entirety herein) and cuts proteins which contain these sequences when they reach the trans-Golgi network. Furin is a Ca2+-dependent serine endoprotease that cleaves protein precursors with a high specificity after the multiple basic motifs shown in Table 1 below.

TABLE 1

| | |
|---|---|
| Canonic | $\text{-}R^{P4}\text{-}X^{P3}\text{-}(K/R)^{P2}\text{-}R^{P1}\downarrow X^{P1'}\text{-}X^{P2'}\text{-}X^{P3'}\text{-}X^{P4'}$ |
| Alternative | $\text{-}R^{P6}\text{-}X^{P5}\text{-}X^{P4}\text{-}X^{P3}\text{-}(K/R)^{P2}\text{-}R^{P1}\downarrow X^{P1'}\text{-}X^{P2'}\text{-}X^{P3'}\text{-}X^{P4'}$ |
| Minimal | $\text{-}R^{P4}\text{-}X^{P3}\text{-}X^{P2}\text{-}R^{P1}\downarrow X^{P1'}\text{-}X^{P2'}\text{-}X^{P3'}\text{-}X^{P4'}$ |

In certain embodiments, the one or plurality of nucleic acid molecules encode a furin-sensitive cleavage site selected from the sequence R-X-[R/K]-R, where R denotes arginine, X is any amino acid, and K is lysine. The "R/K" indicates that this amino acid may be either arginine or lysine.

In certain embodiments, a furin cleavage site is introduced after the antigen domain 1 and/or the antigen domain 2 (e.g. $[(AED^n)\text{-}(linker)]_n\text{–}[AED^{n+1}]$).

In some embodiments, the at least one linker comprises from about 15 to about 300 nucleotides and encodes a cleavage site, wherein the at least one linker comprises a 2A cleavage site. In some embodiments, the at least one linker comprises from about 15 to about 300 nucleotides and encodes a cleavage site, wherein the at least one linker comprises a porcine teschovirus-1 2A (P2A) cleavage site.

A 2A peptide is a "self-cleaving" small peptide. The average length of 2A peptides is 18-22 amino acids. The designation "2A" refers to a specific region of picornavirus polyproteins. Of the 2A peptides identified to date, four are widely used in research: FMDV 2A (abbreviated herein as F2A); equine rhinitis A virus (ERAV) 2A (E2A); porcine teschovirus-1 2A (P2A) and Thoseaasigna virus 2A (T2A). The former three viruses belong to picornaviruses and the latter is an insect virus. DNA and corresponding amino acid sequences of various 2A peptides are shown below in Table 2. Underlined sequences encode amino acids GSG, which were added to improve cleavage efficiency. P2A indicates porcine teschovirus-1 2A; T2A, Thoseaasigna virus 2A; E2A, equine rhinitis A virus (ERAV) 2A; F2A, FMDV 2A.

TABLE 2

```
                                                    (SEQ ID NO: 106)
P2A  GGA AGC GGA GCT ACT AAC TTC AGC CTG CTG AAG CAG GCT GGA
      G   S   G   A   T   N   F   S   L   L   K   Q   A   G

     GAC GTG GAG GAG AAC CCT GGA CCT
      D   V   E   E   N   P   G   P

                                                    (SEQ ID NO: 108)
T2A  GGA AGC GGA GAG GGC AGA GGA AGT CTG CTA ACA TGC GGT GAC
      G   S   G   E   G   R   G   S   L   L   T   C   G   D

     GTC GAG GAG AAT CCT GGA CCT
      V   E   E   N   P   G   P

                                                    (SEQ ID NO: 110)
E2A  GGA AGC GGA CAG TGT ACT AAT TAT GCT CTC TTG AAA TTG GCT
      G   S   G   Q   C   T   N   Y   A   L   L   K   L   A

     GGA GAT GTT GAG AGC AAC CCT GGA CCT
      G   D   V   E   S   N   P   G   P
```

TABLE 2-continued

```
                                               (SEQ ID NO: 112)
F2A  GGA AGC GGA GTG AAA CAG ACT TTG AAT TTT GAC CTT CTC AAG
      G   S   G   V   K   Q   T   L   N   F   D   L   L   K

     TTG GCG GGA GAC GTG GAG TCC AAC CCT GGA CCT
      L   A   G   D   V   E   S   N   P   G   P
```

In some embodiments, the formula comprises at least a first linker and a second linker, wherein the first and second linker comprise a furin protease cleavage site.

In some embodiments, the formula comprises at least a first linker, a second linker, and a third linker, wherein the first, second and third linker comprise a furin protease cleavage site.

In some embodiments, the formula comprises at least a first linker, a second linker, a third linker, and a fourth linker, wherein the first, second, third and fourth linker comprise a furin protease cleavage site.

In some embodiments, the formula comprises at least a first linker, a second linker, a third linker, a fourth linker, and a fifth linker, wherein the first, second, third, fourth and fifth linker comprise a furin protease cleavage site.

In some embodiments, the formula comprises at least a first linker, a second linker, a third linker, a fourth linker, and a fifth linker, wherein the first, second, third, fourth and fifth linker comprise a furin protease cleavage site.

In another embodiment, the formula comprises at least a first linker and a second linker, wherein the first and second linker comprise a P2A protease cleavage site.

In some embodiments, the formula comprises at least a first linker, a second linker, and a third linker, wherein the first, second and third linker comprise a P2A cleavage site.

In some embodiments, the formula comprises at least a first linker, a second linker, a third linker, and a fourth linker, wherein the first, second, third and fourth linker comprise a P2A cleavage site.

In some embodiments, the formula comprises at least a first linker, a second linker, a third linker, a fourth linker, and a fifth linker, wherein the first, second, third, fourth and fifth linker comprise a P2A cleavage site.

In some embodiments, the formula comprises at least a first linker, a second linker, a third linker, a fourth linker, a fifth linker, or more wherein the first, second, third, fourth, fifth linker, or more linkers comprise a P2A protease cleavage site.

In some embodiments, the formula comprises at least a first linker and a second linker, wherein at least one of the first or second linkers comprise a furin protease cleavage site.

In some embodiments, the formula comprises at least a first linker, a second linker, and a third linker, wherein at least one of the first, second or third linkers comprise a furin protease cleavage site.

In some embodiments, the formula comprises at least a first linker, a second linker, a third linker, and a fourth linker, at least one of the first, second, third or fourth linkers comprise a furin protease cleavage site.

In some embodiments, the formula comprises at least a first linker, a second linker, a third linker, a fourth linker, and a fifth linker, at least one of the first, second, third, fourth or fifth linkers comprise a furin protease cleavage site.

In some embodiments, the formula comprises at least a first linker and a second linker, wherein at least one of the first or second linkers comprise a P2A protease cleavage site.

In some embodiments, the formula comprises at least a first linker, a second linker, and a third linker, wherein at least one of the first, second or third linkers comprise a P2A protease cleavage site.

In some embodiments, the formula comprises at least a first linker, a second linker, a third linker, and a fourth linker, at least one of the first, second, third or fourth linkers comprise a P2A protease cleavage site.

In some embodiments, the formula comprises at least a first linker, a second linker, a third linker, a fourth linker, and a fifth linker, at least one of the first, second, third, fourth or fifth linkers comprise a P2A protease cleavage site.

Nucleic acid molecules useful in the methods of the invention include any nucleic acid molecule that encodes a neoantigen, or a fragment thereof; any nucleic acid that encodes a linker, any nucleic acid that encodes a regulatory sequence, any nucleic acid that encodes a leader sequence. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. In some embodiments, the some embodiments, the nucleic acid sequence or molecules of the disclosure relate to nucleic acid sequences comprising a nucleic acid sequence at least about 70%, 80%, 85%, 90%, 95%, 96%, 97%, 98% 99% or 100% sequence identity to SEQ ID NO:68, the sequence of FIG. 2A, 2C, 2E, 3A, 3C, 4A or FIG. 4C. In some embodiments, the nucleic acid sequence or molecules of the disclosure relate to nucleic acid sequences comprising a nucleic acid sequence with at least about 70%, 80%, 85%, 90%, 95%, 96%, 97%, 98% 99% or 100% sequence identity to SEQ ID NO:68, the sequence of FIG. 2A, 2C, 2E, 3A, 3C, 4A or FIG. 4C, and comprise Formula I, I(a), or II(a) within their multiple cloning site. In some embodiments, the some embodiments, the nucleic acid sequence or molecules of the disclosure relate to nucleic acid sequences comprising a nucleic acid sequence encoding an amino acid sequence encoded by a nucleic acid sequence with at least about 70%, 80%, 85%, 90%, 95%, 96%, 97%, 98% 99% or 100% sequence identity to SEQ ID NO:68, the sequence of FIG. 2A, 2C, 2E, 3A, 3C, 4A or FIG. 4C.

In some embodiments, the disclosure relates to a nucleic acid molecule that is pVax or with at least about 70%, 80%, 85%, 90%, 95%, 96%, 97%, 98% 99% or 100% sequence identity to SEQ ID NO:68. In some embodiments, the disclosure relates to a nucleic acid molecule that is pVax or with at least about 70%, 80%, 85%, 90%, 95%, 96%, 97%, 98% 99% or 100% sequence identity to SEQ ID NO:68 comprising a coding sequence comprising any one or plurality of nucleic acid sequences with at least about 70%, 80%, 85%, 90%, 95%, 96%, 97%, 98% 99% or 100% sequence identity to SEQ ID Nos:1-40. In some embodiments, the disclosure relates to a nucleic acid molecule that is pVax or with at least about 70%, 80%, 85%, 90%, 95%, 96%, 97%, 98% 99% or 100% sequence identity to SEQ ID NO:68 comprising a coding sequence comprising any one or plurality of nucleic acid sequences with at least about 70%, 80%, 85%, 90%, 95%, 96%, 97%, 98% 99% or 100% sequence identity to SEQ ID Nos:1-40, and, optionally, one or plurality of nucleic acid sequences encoding one or a plurality of amino acid sequences with at least about 70%, 80%, 85%, 90%, 95%, 96%, 97%, 98% 99% or 100% sequence identity to SEQ ID NO:61-66.

In some embodiments, an exemplary leader sequence is an IgE leader amino acid sequence as set forth in the sequence below and described in US20160175427, incorporated by reference in its entirety herein.

In some embodiments, the nucleic acid comprises a coding region consisting of any of Formulae I, I(a) and/or I(b) and one or a plurality of leader sequences. In some embodiments, the leader sequence is an IgE leader sequence: Met Asp Trp Thr Trp Ile Leu Phe Leu Val Ala Ala Ala Thr Arg Val (SEQ ID NO:69) or a leader sequence that is a functional fragment thereof comprising at least about 70%, 80%, 85%, 90%, 95%, 96%, 97%, 98% or 99% homologous to the IgE leader sequence identified in the aforementioned sentence. In some embodiments, the nucleic acid sequence or molecules of the disclosure relate to nucleic acid sequences comprising a leader with at least about 70%, 80%, 85%, 90%, 95%, 96%, 97%, 98% 99% or 100% sequence identity to SEQ ID NO:69.

For example, stringent salt concentration will ordinarily be less than about 750 mM NaCl and 75 mM trisodium citrate, preferably less than about 500 mM NaCl and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred: embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 μg/ml denatured salmon sperm DNA (ssDNA). In a most preferred embodiment, hybridization will occur at 42° C. in 250 mM NaCl, 25 mM trisodium citrate, 1% SDS, 50% formamide, and 200 μg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and even more preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42° C. in 15 mM NaCl, 1.5 mM trisodium citrate, and 0.1% SDS. In a more preferred embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196:180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., Molecular Cloning: A Laboratory Manual, Cold Spring Harbor Laboratory Press, New York.

The nucleic acid sequences may be used in association with other polynucleotide sequences coding for regulatory proteins that control the expression of the neo antigen sequence. For example, the nucleic acid molecule according to the invention may additionally contain recognition, regulatory, leader and promoter sequences.

In some embodiments, the nucleic acid molecule further comprises at least one regulatory sequence, wherein at least one nucleic acid sequence of Formula I is operably linked to the regulatory sequence.

In another embodiment, the nucleic acid molecule further comprises a leader sequence.

In some embodiments, an exemplary leader sequence is an IgE leader amino acid sequence as described in US20160175427, incorporated by reference in its entirety herein.

In some embodiments, the nucleic acid molecule comprises a nucleic acid sequence comprising Formula I ($[(AED^n)\text{-(linker)}]_n\text{–}[AED^{n+1}]$), wherein the antigen expression domain 1 is independently selectable from about 12 to about 15,000 nucleotides in length and encodes an epitope from one or a plurality of cancer cells from a subject; and the antigen expression domain 2 is independently selectable from about 12 to about 15,000 nucleotides in length and encodes an epitope from one or a plurality of cancer cells from the subject.

In some embodiments, the nucleic acid molecule comprising a nucleic acid sequence comprising Formula I ($[(AED^n)\text{-(linker)}]_n\text{–}[AED^{n+1}]$) is in an amount sufficient to elicit a cellular immune response. A "cellular immune response" is meant to include a cellular response directed to cells characterized by presentation of an antigen with class I or class II MHC. The cellular response relates to cells called T cells or T-lymphocytes which act as either "helpers" or "killers". The helper T cells (also termed $CD4^+$ T cells) play a central role by regulating the immune response and the killer cells (also termed cytotoxic T cells, cytolytic T cells, $CD8^+$ T cells or CTLs) kill diseased cells such as cancer cells, preventing the production of more diseased cells. In preferred embodiments, the present invention involves the stimulation of an anti-tumor CTL response against tumor cells expressing one or more tumor expressed antigens and preferably presenting such tumor expressed antigens with class I MHC.

In some embodiments, the nucleic acid molecule comprising a nucleic acid sequence comprising Formula I ($[(AED^n)\text{-(linker)}]_n\text{–}[AED^{n+1}]$) is in an amount sufficient to elicit a CD8+ T cell response against any one or plurality of amino acid sequences encoded by one or plurality of antigen expression domains. In some embodiments, the nucleic acid molecule comprising a nucleic acid sequence comprising Formula I ([(AED$^n$)–[AED$^{n+1}$]) is in an amount sufficient to elicit a CD8+ T and/or CD4+ T cell response against any one or plurality of amino acid sequences encoded by one or plurality of antigen expression domains.

In some embodiments, the nucleic acid molecule comprising a nucleic acid sequence comprising Formula I ([(AED$^n$)-(linker)]$_n$–[AED$^{n+1}$]) is in an amount sufficient to elicit a CD4+ T cell response against any one or plurality of amino acid sequences encoded by one or plurality of antigen expression domains. In some embodiments, the nucleic acid molecule comprising a nucleic acid sequence comprising Formula I ([(AED$^n$)-(linker)]$_n$–[AED$^{n+1}$]) is in an amount sufficient to elicit a subpopulation of T cells that are greater than at least about 40% CD4+ T cells in response against any one or plurality of amino acid sequences encoded by one or plurality of antigen expression domains as compared to the response generated without the nucleic acid sequences disclosed herein. In some embodiments, the nucleic acid molecule comprising a nucleic acid sequence comprising Formula I ([(AED$^n$)-(linker)]$_n$–[AED$^{n+1}$]) is in an amount sufficient to elicit a subpopulation of T cells that are greater than at least about 40% CD8+ T cells in response against any one or plurality of amino acid sequences encoded by one or plurality of antigen expression domains as compared to the response generated without the nucleic acid sequences disclosed herein. In some embodiments, the nucleic acid molecule comprising a nucleic acid sequence comprising Formula I ([(AED$^n$)-(linker)]$_n$–[AED$^{n+1}$]) is in an amount sufficient to elicit a subpopulation of T cells that comprise greater than at least about 40% CD4+ T cells and that comprise greater than 40% CD8+ T cells in response against any one or plurality of amino acid sequences encoded by one or plurality of antigen expression domains as compared to the response generated without the nucleic acid sequences disclosed herein.

In a still further aspect, the nucleic acid molecule described in any of the aspects and embodiments herein is a plasmid. In certain embodiments, an expression vector comprises the nucleic acid molecule described in any of the aspects and embodiments. In certain embodiments, the nucleic acid expression vector is a plasmid. The vector can be capable of expressing one or a plurality of consensus neoantigen sequences in the cell of a mammal in a quantity effective to elicit an immune response in the mammal. The vector can be recombinant. The vector can comprise heterologous nucleic acid encoding the neoantigen. The vector can be a plasmid. The vector can be useful for transfecting cells with nucleic acid encoding a neoantigen, which the transformed host cell is cultured and maintained under conditions wherein expression of the neoantigen takes place. In some embodiments, the vector is capable of expressing one or a plurality of neoantigen sequences in the cell of a mammal in a quantity effective to elicit an immune response in the mammal. In some embodiments, a cell comprising the nucleic acid molecule is capable of expressing one or a plurality of consensus neoantigen sequences in the cell of a mammal in a quantity effective to elicit an immune response in the mammal that shrinks a tumor by more than about 5, 10, 15, 20, 30, 40, 50, 60, 70 or more percent. In some embodiments, a cell comprising the nucleic acid molecule is capable of expressing one or a plurality of neoantigen amino acid sequences in the cell of a mammal in a quantity effective to elicit an clonal expansion of CD8+ T cells from about 0.1 to about 50% of the total T cell stimulation against the one or plurality of neoantigens.

The vector can comprise heterologous nucleic acid encoding a neoantigen and can further comprise an initiation codon, which can be upstream of the neoantigen coding sequence, and a stop codon, which can be downstream of the neoantigen coding sequence. The initiation and termination codon can be in frame with the neoantigen coding sequence. The vector can also comprise a promoter that is operably linked to the neoantigen coding sequence. The promoter operably linked to the neoantigen coding sequence can be a promoter from simian virus 40 (SV40), a mouse mammary tumor virus (MMTV) promoter, a human immunodeficiency virus (HIV) promoter such as the bovine immunodeficiency virus (BIV) long terminal repeat (LTR) promoter, a Moloney virus promoter, an avian leukosis virus (ALV) promoter, a cytomegalovirus (CMV) promoter such as the CMV immediate early promoter, Epstein Barr virus (EBV) promoter, or a Rous sarcoma virus (RSV) promoter. The promoter can also be a promoter from a human gene such as human actin, human myosin, human hemoglobin, human muscle creatine, or human metalothionein. The promoter can also be a tissue specific promoter, such as a muscle or skin specific promoter, natural or synthetic. Examples of such promoters are described in US patent application publication no. US20040175727, the contents of which are incorporated herein in its entirety.

The vector can also comprise a polyadenylation signal, which can be downstream of the HA coding sequence. The polyadenylation signal can be a SV40 polyadenylation signal, LTR polyadenylation signal, bovine growth hormone (bGH) polyadenylation signal, human growth hormone (hGH) polyadenylation signal, or human .beta.-globin polyadenylation signal. The SV40 polyadenylation signal can be a polyadenylation signal from a pCEP4 vector (Invitrogen, San Diego, Calif.).

The vector can also comprise an enhancer upstream of the neoantigen coding. The enhancer can be necessary for DNA expression. The enhancer can be human actin, human myosin, human hemoglobin, human muscle creatine or a viral enhancer such as one from CMV, HA, RSV or EBV. Polynucleotide function enhances are described in U.S. Pat. Nos. 5,593,972, 5,962,428, and WO94/016737, the contents of each are fully incorporated by reference.

The vector can also comprise a mammalian origin of replication in order to maintain the vector extrachromosomally and produce multiple copies of the vector in a cell. In some embodiments, the vector can be LLC, TC1, ID8, pGX4501, pGX4503, pGX 4504, pGX4505, and/or pGX4506 or any one or more regulatory or non-coding sequences of LLC, TC1, ID8, pGX4501, pGX4503, pGX 4504, pGX4505, and/or pGX4506. In some embodiments, the vector comprises the sequence that is pVAX1. The backbone of the vector can be pAV0242. The vector can be a replication defective adenovirus type 5 (Ad5) vector.

The vector can also comprise a regulatory sequence, which can be well suited for gene expression in a mammalian or human cell into which the vector is administered. The neoantigen coding sequence can comprise a codon, which can allow more efficient transcription of the coding sequence in the host cell.

The vector can be pSE420 (Invitrogen, San Diego, Calif.), which can be used for protein production in *Escherichia coli* (*E. coli*). The vector can also be pYES2 (Invitrogen, San Diego, Calif.), which can be used for protein production in *Saccharomyces cerevisiae* strains of yeast. The vector can also be of the MAXBAC.™ complete baculovirus expression system (Invitrogen, San Diego, Calif.), which can be used for protein production in insect cells. The vector can also be pcDNA I or pcDNA3 (Invitrogen, San Diego, Calif.), which can be used for protein production in mammalian cells such as Chinese hamster ovary (CHO) cells. The vector can be expression vectors or systems to produce protein by routine techniques and readily available starting materials including Sambrook et al., Molecular Cloning: A Laboratory Manual, Second Ed., Cold Spring Harbor (1989), which is incorporated fully by reference.

Expression vectors for different cell types are well known in the art and can be selected without undue experimentation. Generally, the DNA is inserted into an expression vector, such as a plasmid, in proper orientation and correct reading frame for expression. If necessary, the DNA may be linked to the appropriate transcriptional and translational regulatory control nucleotide sequences recognized by the desired host (e.g., bacteria), although such controls are generally available in the expression vector. The vector is then introduced into the host bacteria for cloning using standard techniques (see, e.g., Sambrook et al. (1989) Molecular Cloning, A Laboratory Manual, Cold Spring Harbor Laboratory, Cold Spring Harbor, N.Y.).

In some embodiments, the nucleic acid sequence of Formula I is positioned with the multiple cloning site of a plasmid selected from the group consisting of LLC, TC1, ID8, pGX4501, pGX4503, pGX4504, pGX4505, and pGX4506. In some embodiments, the nucleic acid sequence of Formula I is positioned with the multiple cloning site of LLC. In some embodiments, the nucleic acid sequence of Formula I is positioned with the multiple cloning site of TC1. In some embodiments, the nucleic acid sequence of Formula I is positioned with the multiple cloning site of ID8. In some embodiments, the nucleic acid sequence of Formula I is positioned with the multiple cloning site of pGX4501. In some embodiments, the nucleic acid sequence of Formula I is positioned with the multiple cloning site of pGX4503. In some embodiments, the nucleic acid sequence of Formula I is positioned with the multiple cloning site of pGX4504. In some embodiments, the nucleic acid sequence of Formula I is positioned within the multiple cloning site of pGX4505. In some embodiments, the nucleic acid sequence of Formula I is positioned with the multiple cloning site of pGX4506. In preferred embodiments, the plasmid is pGX4505 or a sequence that is 70%, 80%, 90%, 91%, 92%, 93%, 94%, 95%, 96%, 97%, 98%, 99% homolgous to each of the above-identified nucleotide sequences.

In another embodiment, a host cell is transformed with the plasmids described herein.

The invention also provides that the one or more neo-antigenic peptides of the invention may be encoded by a single expression vector. The invention also provides that the one or more neo-antigenic peptides of the invention may be encoded and expressed in vivo using a viral based system (e.g., an adenovirus system).

The term “polynucleotide encoding a polypeptide” encompasses a polynucleotide which includes only coding sequences for the polypeptide as well as a polynucleotide which includes additional coding and/or non-coding sequences. The polynucleotides of the invention can be in the form of RNA or in the form of DNA. DNA includes cDNA, genomic DNA, and synthetic DNA; and can be double-stranded or single-stranded, and if single stranded can be the coding strand or non-coding (anti-sense) strand.

In some embodiments, the polynucleotides may comprise the coding sequence for the tumor specific neo-antigenic peptide fused in the same reading frame to a polynucleotide which aids, for example, in expression and/or secretion of a polypeptide from a host cell (e.g., a leader sequence which functions as a secretory sequence for controlling transport of a polypeptide from the cell). The polypeptide having a leader sequence is a preprotein and can have the leader sequence cleaved by the host cell to form the mature form of the polypeptide.

In some embodiments, the polynucleotides can comprise the coding sequence for the tumor specific neo-antigenic peptide fused in the same reading frame to a marker sequence that allows, for example, for purification of the encoded polypeptide, which may then be incorporated into the personalized neoplasia vaccine. For example, the marker sequence can be a hexa-histidine tag supplied by a pQE-9 vector to provide for purification of the mature polypeptide fused to the marker in the case of a bacterial host, or the marker sequence can be a hemagglutinin (HA) tag derived from the influenza hemagglutinin protein when a mammalian host (e.g., COS-7 cells) is used. Additional tags include, but are not limited to, Calmodulin tags, FLAG tags, Myc tags, S tags, SBP tags, Softag 1, Softag 3, V5 tag, Xpress tag, Isopeptag, SpyTag, Biotin Carboxyl Carrier Protein (BCCP) tags, GST tags, fluorescent protein tags (e.g., green fluorescent protein tags), maltose binding protein tags, Nus tags, Strep-tag, thioredoxin tag, TC tag, Ty tag, and the like.

In embodiments, the polynucleotides may comprise the coding sequence for one or more of the tumor specific neo-antigenic peptides fused in the same reading frame to create a single concatamerized neo-antigenic peptide construct capable of producing multiple neo-antigenic peptides.

In embodiments, the present invention provides isolated nucleic acid molecules having a nucleotide sequence at least 60% identical, at least 65% identical, at least 70% identical, at least 75% identical, at least 80% identical, at least 85% identical, at least 90% identical, at least 95% identical, or at least 96%, 97%, 98% or 99% identical to a polynucleotide encoding a tumor specific neo-antigenic peptide of the present invention.

By a polynucleotide having a nucleotide sequence at least, for example, 95% “identical” to a reference nucleotide sequence is intended that the nucleotide sequence of the polynucleotide is identical to the reference sequence except that the polynucleotide sequence can include up to five point mutations per each 100 nucleotides of the reference nucleotide sequence. In other words, to obtain a polynucleotide having a nucleotide sequence at least 95% identical to a reference nucleotide sequence, up to 5% of the nucleotides in the reference sequence can be deleted or substituted with another nucleotide, or a number of nucleotides up to 5% of the total nucleotides in the reference sequence can be inserted into the reference sequence. These mutations of the reference sequence can occur at the amino- or carboxy-terminal positions of the reference nucleotide sequence or anywhere between those terminal positions, interspersed either individually among nucleotides in the reference sequence or in one or more contiguous groups within the reference sequence.

As a practical matter, whether any particular nucleic acid molecule is at least 80% identical, at least 85% identical, at least 90% identical, and in some embodiments, at least 95%, 96%, 97%, 98%, or 99% identical to a reference sequence can be determined conventionally using known computer programs such as the Bestfit program (Wisconsin Sequence Analysis Package, Version 8 for Unix, Genetics Computer Group, University Research Park, 575 Science Drive, Madison, Wis. 53711). Bestfit uses the local homology algorithm of Smith and Waterman, Advances in Applied Mathematics 2:482-489 (1981), to find the best segment of homology between two sequences. When using Bestfit or any other sequence alignment program to determine whether a particular sequence is, for instance, 95% identical to a reference sequence according to the present invention, the parameters are set such that the percentage of identity is calculated over the full length of the reference nucleotide sequence and that gaps in homology of up to 5% of the total number of nucleotides in the reference sequence are allowed.

The present disclosure also includes a composition comprising one or a plurality of nucleic acid molecules described herein.

The present disclosure also contemplates the use of nucleic acid molecules as vehicles for delivering neo-antigens to the subject in vivo in the form of, e.g., DNA/RNA vaccines (see, e.g., WO2012/159643, and WO2012/159754, hereby incorporated by reference in their entirety).

In some embodiments, the personalized neoplasia vaccine may include separate DNA plasmids encoding, for example, one or more neo-antigenic peptides/polypeptides as identified in according to the invention. As discussed above, the exact choice of expression vectors will depend upon the peptide/polypeptides to be expressed, and is well within the skill of the ordinary artisan. The expected persistence of the DNA constructs (e.g., in an episomal, non-replicating, non-integrated form in the muscle cells) is expected to provide an increased duration of protection. In some embodiments, the composition comprises the a first, second or third nucleic acid molecule, wherein at least the first nucleic acid molecule encodes one or more neoantigens. In some embodiments, the second nucleic acid molecule comprises one or more neoantigens. In some embodiments, the second nucleic acid molecule comprising a nucleic acid sequence that encodes one or more adjuvants. In other embodiments, the personalized neoplasia vaccine may include separate RNA or cDNA molecules encoding neo-antigenic peptides/polypeptides of the invention.

In another embodiment the personalized neoplasia vaccine may include a viral based vector for use in a human patient such as, for example, and adenovirus system (see, e.g., Baden et al. First-in-human evaluation of the safety and immunogenicity of a recombinant adenovirus serotype 26 HIV-1 Env vaccine (IPCAVD 001). J Infect Dis. 2013 Jan. 15; 207(2):240-7, hereby incorporated by reference in its entirety).

Methods of Identifying Neoantigens

As described in more detail herein, a population of neoplasia/tumor specific neoantigens may be identified by sequencing the neoplasia/tumor and normal DNA of each patient to identify tumor-specific mutations, and determining the patient's HLA allotype. The population of neoplasia/tumor specific neo-antigens and their cognate native antigens may be subject to bioinformatic analysis using validated algorithms to predict which tumor-specific mutations create epitopes that could bind to the patient's HLA allotype, and in particular which tumor-specific mutations create epitopes that could bind to the patient's HLA allotype more effectively than the cognate native antigen. Based on this analysis, identified nucleotide sequences corresponding to these mutations may be designed for each patient, and used together for use as a cancer vaccine in immunizing the subject.

In one aspect, the disclosure features a method of identifying one or more subject-specific neoantigen mutations in a subject, wherein the subject has been diagnosed with, suspected of having or comprises one or more hyperproliferative cells (e.g. such as a tumor). In some embodiments, the disclosure features a method of identifying one or more subject-specific neoantigen mutations in a subject, wherein the subject has been diagnosed with, suspected of having or comprises one or more hyperproliferative cells (e.g. such as a tumor) characterized by the presence or quantity of a plurality of neoantigen mutations, the method comprising sequencing a nucleic acid sample from a tumor of the subject and of a non-tumor sample of the subject; analyzing the sequence to determine coding and non-coding regions; identifying sequences comprising tumor-specific non-synonymous or non-silent mutations not present in the non-tumor sample; identifying single nucleotide variations and single nucleotide insertions and deletions; producing subject-specific peptides encoded by the sequences comprising tumor-specific non-synonymous or non-silent mutations not present in the non-tumor sample; and measuring the binding characteristics of the of the subject-specific peptides, wherein each subject-specific peptide is an expression product of subject-specific DNA neoantigen not present in the non-tumor sample, thereby identifying one or more subject-specific DNA neoantigens in a subject. measuring the binding characteristics of the of the subject-specific peptides is carried out by one or more of measuring the binding of the subject-specific peptides to T-cell receptor; measuring the binding of the subject-specific peptides to a HLA protein of the subject; or measuring the binding of the subject-specific peptides to transporter associated with antigen processing (TAP).

Efficiently choosing which particular mutations to utilize as immunogen requires identification of the patient HLA type and the ability to predict which mutated peptides would efficiently bind to the patient's HLA alleles. Therefore, In some embodiments, measuring the binding of the subject-specific peptides to T-cell receptor comprises measuring the binding of the subject-specific peptides to a HLA protein of the subject or sample.

In some embodiments, the subject-specific peptides bind to HLA proteins of the subject with an IC50 of less than about 550 nM. In some embodiments, the subject-specific peptides bind to HLA proteins of the subject with an IC50 of less than about 500 nM. In some embodiments, the subject-specific peptides bind to HLA proteins of the subject with an IC50 of less than about 450 nM. In some embodiments, the subject-specific peptides bind to HLA proteins of the subject with an IC50 of less than about 400 nM. In some embodiments, the subject-specific peptides bind to HLA proteins of the subject with an IC50 of less than about 350 nM. In some embodiments, the subject-specific peptides bind to HLA proteins of the subject with an IC50 of less than about 300 nM.

In another embodiment, the method of identifying one or more subject-specific DNA neoantigen mutations in a subject further comprises the step of ranking the subject-specific peptides based on the binding characteristics.

In another embodiment, the method of identifying one or more subject-specific DNA neoantigen mutations in a subject, further comprises the step of measuring the CD8+ T cell immune response generated by the subject-specific peptides. Methods of measuring the CD8+ T cell response are known in the art and described herein.

In a further embodiment, the method of identifying one or more subject-specific DNA neoantigen mutations in a subject further comprises formulating the subject-specific DNA neoantigens into a immunogenic composition for administration to the subject. In some embodiments, the top 200 ranked neo-antigen mutations are included or subcloned into the immunogenic composition, which in some embodiments, is one or a plurality of plasmids. In another embodiment, the top 150 ranked neo-antigen mutations are included in the immunogenic composition. In another embodiment, the top 100 ranked neo-antigen mutations are included in the immunogenic composition. In another embodiment, the top 50 ranked neo-antigen mutations are included in the immunogenic composition. In another embodiment, the top 25 ranked neo-antigen mutations are included in the immunogenic composition. In another embodiment, the top 10 ranked neo-antigen mutations are included in the immunogenic composition. In another embodiment, the top 5 ranked neo-antigen mutations are included in the immunogenic composition. In another embodiment, the top 5-20 ranked noe-antigen mutations are included in the immunogenic composition. In another embodiment, the top 10-50 ranked neo-antigen mutations are included in the immunogenic composition. In another embodiment, the top 25-100 ranked neo-antigen mutations are included in the immunogenic composition. In another embodiment, the top 50-100 ranked neo-antigen mutations are included in the immunogenic composition. In another embodiment, the top 100-200 ranked neo-antigen mutations are included in the immunogenic composition.

In another embodiment, the method of identifying one or more subject-specific DNA neoantigen mutations in a subject further comprises providing a culture comprising dendritic cells (DCs) obtained from the subject; and contacting the dendritic cells with the immunogenic composition. DCs are potent antigen-presenting cells that initiate T cell immunity and can be used as cancer vaccines when loaded with one or more neoantigens of interest. In a further embodiment, the method further comprises administering to the subject the dendritic cells; obtaining a population of CD8+ T cells from a peripheral blood sample from the subject, wherein the CD8+ cells recognize the at least one neoantigen; and expanding the population of CD8+ T cells that recognizes the neoantigen.

In some embodiments, the expanded population of CD8+ T cells is administered to the subject.

Preferably, any suitable sequencing-by-synthesis platform can be used to identify mutations. Four major sequencing-by-synthesis platforms are currently available: the Genome Sequencers from Roche/454 Life Sciences, the HiSeq Analyzer from Illumina/Solexa, the SOLiD system from Applied BioSystems, and the Heliscope system from Helicos Biosciences. Sequencing-by-synthesis platforms have also been described by Pacific Biosciences and VisiGen Biotechnologies. Each of these platforms can be used in the methods of the invention. In some embodiments, a plurality of nucleic acid molecules being sequenced is bound to a support (e.g., solid support). To immobilize the nucleic acid on a support, a capture sequence/universal priming site can be added at the 3' and/or 5' end of the template. The nucleic acids may be bound to the support by hybridizing the capture sequence to a complementary sequence covalently attached to the support. The capture sequence (also referred to as a universal capture sequence) is a nucleic acid sequence complementary to a sequence attached to a support that may dually serve as a universal primer.

As an alternative to a capture sequence, a member of a coupling pair (such as, e.g., antibody/antigen, receptor/ligand, or the avidin-biotin pair as described in, e.g., U.S. Patent Application No. 2006/0252077) may be linked to each fragment to be captured on a surface coated with a respective second member of that coupling pair. Subsequent to the capture, the sequence may be analyzed, for example, by single molecule detection/sequencing, e.g., as described in the Examples and in U.S. Pat. No. 7,283,337, including template-dependent sequencing-by-synthesis. In sequencing-by-synthesis, the surface-bound molecule is exposed to a plurality of labeled nucleotide triphosphates in the presence of polymerase. The sequence of the template is determined by the order of labeled nucleotides incorporated into the 3' end of the growing chain. This can be done in real time or in a step-and-repeat mode. For real-time analysis, different optical labels to each nucleotide may be incorporated and multiple lasers may be utilized for stimulation of incorporated nucleotides.

Any cell type or tissue may be utilized to obtain nucleic acid samples for use in the sequencing methods described herein. In a preferred embodiment, the DNA or RNA sample is obtained from a neoplasia, a tumor or a bodily fluid, e.g., blood, obtained by known techniques (e.g. venipuncture) or saliva. Alternatively, nucleic acid tests can be performed on dry samples (e.g. hair or skin).

A variety of methods are available for detecting the presence of a particular mutation or allele in an individual's DNA or RNA. Advancements in this field have provided accurate, easy, and inexpensive large-scale SNP genotyping. Most recently, for example, several new techniques have been described including dynamic allele-specific hybridization (DASH), microplate array diagonal gel electrophoresis (MADGE), pyrosequencing, oligonucleotide-specific ligation, the TaqMan system as well as various DNA "chip" technologies such as the Affymetrix SNP chips. These methods require amplification of the target genetic region, typically by PCR. Still other newly developed methods, based on the generation of small signal molecules by invasive cleavage followed by mass spectrometry or immobilized padlock probes and rolling-circle amplification, might eventually eliminate the need for PCR. Several of the methods known in the art for detecting specific single nucleotide polymorphisms are summarized below. The method of the present invention is understood to include all available methods.

PCR based detection means may include multiplex amplification of a plurality of markers simultaneously. For example, it is well known in the art to select PCR primers to generate PCR products that do not overlap in size and can be analyzed simultaneously.

Alternatively, it is possible to amplify different markers with primers that are differentially labeled and thus can each be differentially detected. Of course, hybridization based detection means allow the differential detection of multiple PCR products in a sample. Other techniques are known in the art to allow multiplex analyses of a plurality of markers.

Several methods have been developed to facilitate analysis of single nucleotide polymorphisms in genomic DNA or cellular RNA. In some embodiments, the single base polymorphism can be detected by using a specialized exonuclease-resistant nucleotide, as disclosed, e.g., U.S. Pat. No. 4,656,127. According to the method, a primer complementary to the allelic sequence immediately 3' to the polymorphic site is permitted to hybridize to a target molecule obtained from a particular animal or human. If the polymorphic site on the target molecule contains a nucleotide that is complementary to the particular exonuclease-resistant nucleotide derivative present, then that derivative will be incorporated onto the end of the hybridized primer. Such incorporation renders the primer resistant to exonuclease, and thereby permits its detection. Since the identity of the exonuclease-resistant derivative of the sample is known, a finding that the primer has become resistant to exonucleases reveals that the nucleotide present in the polymorphic site of the target molecule was complementary to that of the nucleotide derivative used in the reaction. This method has the advantage that it does not require the determination of large amounts of extraneous sequence data.

In another embodiment of the invention, a solution-based method is used for determining the identity of the nucleotide of a polymorphic site. Cohen et al. (French Patent No. 2,650,840; PCT Application No. WO1991/02087). As in the method of U.S. Pat. No. 4,656,127, a primer may be employed that is complementary to allelic sequences immediately 3' to a polymorphic site. The method determines the identity of the nucleotide of that site using labeled dideoxynucleotide derivatives, which, if complementary to the nucleotide of the polymorphic site, will become incorporated onto the terminus of the primer.

An alternative method, known as Genetic Bit Analysis or GBA is described in PCT Application No. WO1992/15712). GBA uses mixtures of labeled terminators and a primer that is complementary to the sequence 3' to a polymorphic site. The labeled terminator that is incorporated is thus determined by, and complementary to, the nucleotide present in the polymorphic site of the target molecule being evaluated. In contrast to the method of Cohen et al. (French Patent 2,650,840; PCT Application No. WO1991/02087) the GBA method is preferably a heterogeneous phase assay, in which the primer or the target molecule is immobilized to a solid phase.

Several primer-guided nucleotide incorporation procedures for assaying polymorphic sites in DNA have been described (Komher, J. S. et al., Nucl. Acids. Res. 17:7779-7784 (1989); Sokolov, B. P., Nucl. Acids Res. 18:3671 (1990); Syvanen, A.-C, et al., Genomics 8:684-692 (1990); Kuppuswamy, M. N. et al., Proc. Natl. Acad. Sci. (U.S.A.) 88: 1143-1147 (1991); Prezant, T. R. et al., Hum. Mutat. 1: 159-164 (1992); Ugozzoli, L. et al., GATA 9: 107-112 (1992); Nyren, P. et al., *Anal. Biochem.* 208: 171-175 (1993)). These methods differ from GBA in that they all rely on the incorporation of labeled deoxynucleotides to discriminate between bases at a polymorphic site. In such a format, since the signal is proportional to the number of deoxynucleotides incorporated, polymorphisms that occur in runs of the same nucleotide can result in signals that are proportional to the length of the run (Syvanen, A.-C, et al., Amer. J. Hum. Genet. 52:46-59 (1993)).

The disclosure generally relates to a method of identifying or selecting one or a plurality of neoantigens from a sample, the method comprising (a) sequencing the DNA/RNA from a sample, and (b) measuring the binding of the subject-specific peptides to T-cell receptor comprises measuring the binding of the subject-specific peptides to a HLA protein of the subject or sample, and (c) selecting or a plurality of neoantigens from a sample if the HLA protein from the subject binds to HLA proteins of the subject with an IC50 of less than about 500 nM, 400 nM, 300 nM, 200 nM, or 100 nM; and, optionally (d) ordering the neoantigens in order of lowest IC50 value to highest IC50 value.

In some embodiments, the disclosure relates to generating a vaccine or manufacturing a pharmaceutical composition comprising performing any one or more of the aforementioned steps and further comprising subcloning a nucleic acid sequence encoding the one or plurality of neoantigens into one or more nucleic acid molecules; and, optionally, suspending the nucleic acid molecules in one or more pharmaceutically acceptable carriers.

In some embodiments, the nucleic acid sequence encoding the neoantigens also comprises a linker. In some embodiments, the nucleic acid molecule is free of a nucleic acid sequence that encodes a P2A linker. In some embodiments, the nucleic acid molecule is free of a nucleic acid sequence that encodes two different linkers. In some embodiments, the nucleic acid molecule is free of a nucleic acid sequence that encodes a linker, such that at least two or a plurality of AED sequences, from the 5' to 3' orientation is encoded as a separate polypeptide or as a large contiguous fusion protein. In another embodiment, the method of identifying one or more subject-specific DNA neoantigen mutations in a subject further comprises providing a culture comprising dendritic cells (DCs) obtained from the subject; and contacting the dendritic cells with the immunogenic composition. DCs are potent antigen-presenting cells that initiate T cell immunity and can be used as cancer vaccines when loaded with one or more neoantigens of interest. In a further embodiment, the method further comprises administering to the subject the dendritic cells; obtaining a population of CD8+ T cells from a peripheral blood sample from the subject, wherein the CD8+ cells recognize the at least one neoantigen; and expanding the population of CD8+ T cells that recognizes the neoantigen.

In some embodiments, the expanded population of CD8+ T cells is administered to the subject.

Preferably, any suitable sequencing-by-synthesis platform can be used to identify mutations. Four major sequencing-by-synthesis platforms are currently available: the Genome Sequencers from Roche/454 Life Sciences, the HiSeq Analyzer from Illumina/Solexa, the SOLiD system from Applied BioSystems, and the Heliscope system from Helicos Biosciences. Sequencing-by-synthesis platforms have also been described by Pacific Biosciences and VisiGen Biotechnologies. Each of these platforms can be used in the methods of the invention. In some embodiments, a plurality of nucleic acid molecules being sequenced is bound to a support (e.g., solid support). To immobilize the nucleic acid on a support, a capture sequence/universal priming site can be added at the 3' and/or 5' end of the template. The nucleic acids may be bound to the support by hybridizing the capture sequence to a complementary sequence covalently attached to the support. The capture sequence (also referred to as a universal capture sequence) is a nucleic acid sequence complementary to a sequence attached to a support that may dually serve as a universal primer.

As an alternative to a capture sequence, a member of a coupling pair (such as, e.g., antibody/antigen, receptor/ligand, or the avidin-biotin pair as described in, e.g., U.S. Patent Application No. 2006/0252077) may be linked to each fragment to be captured on a surface coated with a respective second member of that coupling pair. Subsequent to the capture, the sequence may be analyzed, for example, by single molecule detection/sequencing, e.g., as described in the Examples and in U.S. Pat. No. 7,283,337, including template-dependent sequencing-by-synthesis. In sequencing-by-synthesis, the surface-bound molecule is exposed to a plurality of labeled nucleotide triphosphates in the presence of polymerase. The sequence of the template is determined by the order of labeled nucleotides incorporated into the 3' end of the growing chain. This can be done in real time or in a step-and-repeat mode. For real-time analysis, different optical labels to each nucleotide may be incorporated and multiple lasers may be utilized for stimulation of incorporated nucleotides.

Any cell type or tissue may be utilized to obtain nucleic acid samples for use in the sequencing methods described herein. In a preferred embodiment, the DNA or RNA sample is obtained from a neoplasia/tumor or a bodily fluid, e.g., blood, obtained by known techniques (e.g. venipuncture) or saliva. Alternatively, nucleic acid tests can be performed on dry samples (e.g. hair or skin).

A variety of methods are available for detecting the presence of a particular mutation or allele in an individual's DNA or RNA. Advancements in this field have provided accurate, easy, and inexpensive large-scale SNP genotyping. Most recently, for example, several new techniques have been described including dynamic allele-specific hybridization (DASH), microplate array diagonal gel electrophoresis (MADGE), pyrosequencing, oligonucleotide-specific ligation, the TaqMan system as well as various DNA "chip" technologies such as the Affymetrix SNP chips. These methods require amplification of the target genetic region, typically by PCR. Still other newly developed methods, based on the generation of small signal molecules by invasive cleavage followed by mass spectrometry or immobilized padlock probes and rolling-circle amplification, might eventually eliminate the need for PCR. Several of the methods known in the art for detecting specific single nucleotide polymorphisms are summarized below. The method of the present invention is understood to include all available methods.

PCR based detection means may include multiplex amplification of a plurality of markers simultaneously. For example, it is well known in the art to select PCR primers to generate PCR products that do not overlap in size and can be analyzed simultaneously.

Alternatively, it is possible to amplify different markers with primers that are differentially labeled and thus can each be differentially detected. Of course, hybridization based detection means allow the differential detection of multiple PCR products in a sample. Other techniques are known in the art to allow multiplex analyses of a plurality of markers.

Several methods have been developed to facilitate analysis of single nucleotide polymorphisms in genomic DNA or cellular RNA. In some embodiments, the single base polymorphism can be detected by using a specialized exonuclease-resistant nucleotide, as disclosed, e.g., U.S. Pat. No. 4,656,127. According to the method, a primer complementary to the allelic sequence immediately 3' to the polymorphic site is permitted to hybridize to a target molecule obtained from a particular animal or human. If the polymorphic site on the target molecule contains a nucleotide that is complementary to the particular exonuclease-resistant nucleotide derivative present, then that derivative will be incorporated onto the end of the hybridized primer. Such incorporation renders the primer resistant to exonuclease, and thereby permits its detection. Since the identity of the exonuclease-resistant derivative of the sample is known, a finding that the primer has become resistant to exonucleases reveals that the nucleotide present in the polymorphic site of the target molecule was complementary to that of the nucleotide derivative used in the reaction. This method has the advantage that it does not require the determination of large amounts of extraneous sequence data.

In another embodiment of the invention, a solution-based method is used for determining the identity of the nucleotide of a polymorphic site. Cohen et al. (French Patent No. 2,650,840; PCT Application No. WO1991/02087). As in the method of U.S. Pat. No. 4,656,127, a primer may be employed that is complementary to allelic sequences immediately 3' to a polymorphic site. The method determines the identity of the nucleotide of that site using labeled dideoxynucleotide derivatives, which, if complementary to the nucleotide of the polymorphic site, will become incorporated onto the terminus of the primer.

An alternative method, known as Genetic Bit Analysis or GBA is described in PCT Application No. WO1992/15712). GBA uses mixtures of labeled terminators and a primer that is complementary to the sequence 3' to a polymorphic site. The labeled terminator that is incorporated is thus determined by, and complementary to, the nucleotide present in the polymorphic site of the target molecule being evaluated. In contrast to the method of Cohen et al. (French Patent 2,650,840; PCT Application No. WO1991/02087) the GBA method is preferably a heterogeneous phase assay, in which the primer or the target molecule is immobilized to a solid phase.

Several primer-guided nucleotide incorporation procedures for assaying polymorphic sites in DNA have been described (Komher, J. S. et al., Nucl. Acids. Res. 17:7779-7784 (1989); Sokolov, B. P., Nucl. Acids Res. 18:3671 (1990); Syvanen, A.-C, et al., Genomics 8:684-692 (1990); Kuppuswamy, M. N. et al., Proc. Natl. Acad. Sci. (U.S.A.) 88: 1143-1147 (1991); Prezant, T. R. et al., Hum. Mutat. 1: 159-164 (1992); Ugozzoli, L. et al., GATA 9: 107-112 (1992); Nyren, P. et al., *Anal. Biochem.* 208: 171-175 (1993)). These methods differ from GBA in that they all rely on the incorporation of labeled deoxynucleotides to discriminate between bases at a polymorphic site. In such a format, since the signal is proportional to the number of deoxynucleotides incorporated, polymorphisms that occur in runs of the same nucleotide can result in signals that are proportional to the length of the run (Syvanen, A.-C, et al., Amer. J. Hum. Genet. 52:46-59 (1993)).

Methods of Treating Cancer

The disclosure further provides a method of inducing a neoplasia/tumor-specific immune response in a subject, vaccinating against a neoplasia/tumor, treating and/or alleviating a symptom of cancer in a subject by administering to the subject the nucleic acid sequences as described herein.

In one aspect, the disclosure provides a method of treating and/or preventing cancer in a subject, the method comprising administering to the subject in need thereof a pharmaceutically effective amount of any of the nucleic acid molecules as described herein (e.g. a nucleic acid molecule comprising a nucleic acid sequence comprising Formula I: $[[(AED^n)\text{-(linker)}]_n\text{–}[AED^{n+1}]$) or any of the pharmaceutical compositions described herein.

In some embodiments, the nucleic acid molecule is administered to the subject by electroporation.

In some embodiments, treatment is determined by a clinical outcome, an increase, enhancement or prolongation of anti-tumor activity by T cells, an increase in the number of anti-tumor T cells or activated T cells as compared with the number prior to treatment, or a combination thereof. In a further embodiment, clinical outcome is selected from the group consisting of tumor regression, tumor shrinkage, tumor necrosis, anti-tumor response by the immune system, tumor expansion, recurrence or spread, or a combination thereof.

Examples of cancers and cancer conditions that can be treated with the combination therapy of this document include, but are not limited to a patient in need thereof that has been diagnosed as having cancer, or at risk of developing cancer.

In some embodiments, the subject has previously been treated, and not responded to checkpoint inhibitor therapy.

The therapy described herein is also applicable where the subject has no detectable neoplasia but is at high risk for disease recurrence.

According to the disclosure, the nucleic acid molecules described herein may be used for a patient that has been diagnosed as having cancer, or at risk of developing cancer.

In certain embodiments, the cancer is a solid tumor.

In some embodiments, the cancer has a high mutational load.

In another embodiment, the cancer has a moderate mutational load.

In other embodiments, the cancer has been shown to have a poor or low response to checkpoint inhibitor therapy.

In certain embodiments, the cancer is selected from, but not limited to, Acute Lymphoblastic Leukemia, Adult; Acute Lymphoblastic Leukemia, Childhood; Acute Myeloid Leukemia, Adult; Adrenocortical Carcinoma; Adrenocortical Carcinoma, Childhood; AIDS-Related Lymphoma; AIDS-Related Malignancies; Anal Cancer; Astrocytoma, Childhood Cerebellar; Astrocytoma, Childhood Cerebral; Bile Duct Cancer, Extrahepatic; Bladder Cancer; Bladder Cancer, Childhood; Bone Cancer, Osteosarcoma/Malignant Fibrous Histiocytoma; Brain Stem Glioma, Childhood; Brain Tumor, Adult; Brain Tumor, Brain Stem Glioma, Childhood; Brain Tumor, Cerebellar Astrocytoma, Childhood; Brain Tumor, Cerebral Astrocytoma/Malignant Glioma, Childhood; Brain Tumor, Ependymoma, Childhood; Brain Tumor, Medulloblastoma, Childhood; Brain Tumor, Supratentorial Primitive Neuroectodermal Tumors, Childhood; Brain Tumor, Visual Pathway and Hypothalamic Glioma, Childhood; Brain Tumor, Childhood (Other); Breast Cancer; Breast Cancer and Pregnancy; Breast Cancer, Childhood; Breast Cancer, Male; Bronchial Adenomas/Carcinoids, Childhood: Carcinoid Tumor, Childhood; Carcinoid Tumor, Gastrointestinal; Carcinoma, Adrenocortical; Carcinoma, Islet Cell; Carcinoma of Unknown Primary; Central Nervous System Lymphoma, Primary; Cerebellar Astrocytoma, Childhood; Cerebral Astrocytoma/Malignant Glioma, Childhood; Cervical Cancer; Childhood Cancers; Chronic Lymphocytic Leukemia; Chronic Myelogenous Leukemia; Chronic Myeloproliferative Disorders; Clear Cell Sarcoma of Tendon Sheaths; Colon Cancer; Colorectal Cancer, Childhood; Cutaneous T-Cell Lymphoma; Endometrial Cancer; Ependymoma, Childhood; Epithelial Cancer, Ovarian; Esophageal Cancer; Esophageal Cancer, Childhood; Ewing's Family of Tumors; Extracranial Germ Cell Tumor, Childhood; Extragonadal Germ Cell Tumor; Extrahepatic Bile Duct Cancer; Eye Cancer, Intraocular Melanoma; Eye Cancer, Retinoblastoma; Gallbladder Cancer; Gastric (Stomach) Cancer; Gastric (Stomach) Cancer, Childhood; Gastrointestinal Carcinoid Tumor; Germ Cell Tumor, Extracranial, Childhood; Germ Cell Tumor, Extragonadal; Germ Cell Tumor, Ovarian; Gestational Trophoblastic Tumor; Glioma. Childhood Brain Stem; Glioma. Childhood Visual Pathway and Hypothalamic; Hairy Cell Leukemia; Head and Neck Cancer; Hepatocellular (Liver) Cancer, Adult (Primary); Hepatocellular (Liver) Cancer, Childhood (Primary); Hodgkin's Lymphoma, Adult; Hodgkin's Lymphoma, Childhood; Hodgkin's Lymphoma During Pregnancy; Hypopharyngeal Cancer; Hypothalamic and Visual Pathway Glioma, Childhood; Intraocular Melanoma; Islet Cell Carcinoma (Endocrine Pancreas); Kaposi's Sarcoma; Kidney Cancer; Laryngeal Cancer; Laryngeal Cancer, Childhood; Leukemia, Acute Lymphoblastic, Adult; Leukemia, Acute Lymphoblastic, Childhood; Leukemia, Acute Myeloid, Adult; Leukemia, Acute Myeloid, Childhood; Leukemia, Chronic Lymphocytic; Leukemia, Chronic Myelogenous; Leukemia, Hairy Cell; Lip and Oral Cavity Cancer; Liver Cancer, Adult (Primary); Liver Cancer, Childhood (Primary); Lung Cancer, Non-Small Cell; Lung Cancer, Small Cell; Lymphoblastic Leukemia, Adult Acute; Lymphoblastic Leukemia, Childhood Acute; Lymphocytic Leukemia, Chronic; Lymphoma, AIDS-Related; Lymphoma, Central Nervous System (Primary); Lymphoma, Cutaneous T-Cell; Lymphoma, Hodgkin's, Adult; Lymphoma, Hodgkin's; Childhood; Lymphoma, Hodgkin's During Pregnancy; Lymphoma, Non-Hodgkin's, Adult; Lymphoma, Non-Hodgkin's, Childhood; Lymphoma, Non-Hodgkin's During Pregnancy; Lymphoma, Primary Central Nervous System; Macroglobulinemia, Waldenstrom's; Male Breast Cancer; Malignant Mesothelioma, Adult; Malignant Mesothelioma, Childhood; Malignant Thymoma; Medulloblastoma, Childhood; Melanoma; Melanoma, Intraocular; Merkel Cell Carcinoma; Mesothelioma, Malignant; Metastatic Squamous Neck Cancer with Occult Primary; Multiple Endocrine Neoplasia Syndrome, Childhood; Multiple Myeloma/Plasma Cell Neoplasm; Mycosis Fungoides; Myelodysplasia Syndromes; Myelogenous Leukemia, Chronic; Myeloid Leukemia, Childhood Acute; Myeloma, Multiple; Myeloproliferative Disorders, Chronic; Nasal Cavity and Paranasal Sinus Cancer; Nasopharyngeal Cancer; Nasopharyngeal Cancer, Childhood; Neuroblastoma; Neurofibroma; Non-Hodgkin's Lymphoma, Adult; Non-Hodgkin's Lymphoma, Childhood; Non-Hodgkin's Lymphoma During Pregnancy; Non-Small Cell Lung Cancer; Oral Cancer, Childhood; Oral Cavity and Lip Cancer; Oropharyngeal Cancer; Osteosarcoma/Malignant Fibrous Histiocytoma of Bone; Ovarian Cancer, Childhood; Ovarian Epithelial Cancer; Ovarian Germ Cell Tumor; Ovarian Low Malignant Potential Tumor; Pancreatic Cancer; Pancreatic Cancer, Childhood', Pancreatic Cancer, Islet Cell; Paranasal Sinus and Nasal Cavity Cancer; Parathyroid Cancer; Penile Cancer; Pheochromocytoma; Pineal and Supratentorial Primitive Neuroectodermal Tumors, Childhood; Pituitary Tumor; Plasma Cell Neoplasm/Multiple Myeloma; Pleuropulmonary Blastoma; Pregnancy and Breast Cancer; Pregnancy and Hodgkin's Lymphoma; Pregnancy and Non-Hodgkin's Lymphoma; Primary Central Nervous System Lymphoma; Primary Liver Cancer, Adult; Primary Liver Cancer, Childhood; Prostate Cancer; Rectal Cancer; Renal Cell (Kidney) Cancer; Renal Cell Cancer, Childhood; Renal Pelvis and Ureter, Transitional Cell Cancer; Retinoblastoma; Rhabdomyosarcoma, Childhood; Salivary Gland Cancer; Salivary Gland'Cancer, Childhood; Sarcoma, Ewing's Family of Tumors; Sarcoma, Kaposi's; Sarcoma (Osteosarcoma)/Malignant Fibrous Histiocytoma of Bone; Sarcoma, Rhabdomyosarcoma, Childhood; Sarcoma, Soft Tissue, Adult; Sarcoma, Soft Tissue, Childhood; Sezary Syndrome; Skin Cancer; Skin Cancer, Childhood; Skin Cancer (Melanoma); Skin Carcinoma, Merkel Cell; Small Cell Lung Cancer; Small Intestine Cancer; Soft Tissue Sarcoma, Adult; Soft Tissue Sarcoma, Childhood; Squamous Neck Cancer with Occult Primary, Metastatic; Stomach (Gastric) Cancer; Stomach (Gastric) Cancer, Childhood; Supratentorial Primitive Neuroectodermal Tumors, Childhood; T-Cell Lymphoma, Cutaneous; Testicular Cancer; Thymoma, Childhood; Thymoma, Malignant; Thyroid Cancer; Thyroid Cancer, Childhood; Transitional Cell Cancer of the Renal Pelvis and Ureter; Trophoblastic Tumor, Gestational; Unknown Primary Site, Cancer of, Childhood; Unusual Cancers of Childhood; Ureter and Renal Pelvis, Transitional Cell Cancer; Urethral Cancer; Uterine Sarcoma; Vaginal Cancer; Visual Pathway and Hypothalamic Glioma, Childhood; Vulvar Cancer; Waldenstrom's Macro globulinemia; and Wilms' Tumor.

In further embodiments, the cancer is selected from the group consisting of non small cell lung cancer, melanoma, ovarian cancer, cervical cancer, glioblastoma, urogenital cancer, gynecological cancer, lung cancer, gastrointestinal cancer, head and neck cancer, non-metastatic or metastatic breast cancer, malignant melanoma, Merkel Cell Carcinoma or bone and soft tissue sarcomas, haematologic neoplasias, multiple myeloma, acute myelogenous leukemia, chronic myelogenous leukemia, myelodysplastic syndrome and acute lymphoblastic leukemia, breast cancer, metastatic colorectal cancers, hormone sensitive or hormone refractory prostate cancer, colorectal cancer, ovarian cancer, hepatocellular cancer, renal cell cancer, pancreatic cancer, gastric cancer, oesophageal cancers, hepatocellular cancers, cholangiocellular cancers, head and neck squamous cell cancer soft tissue sarcoma, and small cell lung cancer.

In certain embodiments, the cancer is non-small cell lung carcinoma or melanoma, both of which have been shown to have a high mutational load.

In other embodiments, the cancer is ovarian cancer or glioblastoma multiforme, both of which show a moderate mutational load and have been shown to have a poor or low response to checkpoint inhibitor therapy.

Methods of Inducing/Enhancing Immune Response

In one aspect, the present disclosure features a method of inducing an immune response in a subject, the method comprising administering to the subject in need thereof a pharmaceutically effective amount of any of the nucleic acid molecules of any one of the aspects or embodiments herein, or any one of the pharmaceutical compositions of any one of the aspects and embodiments herein. In some embodiments, the method comprises the steps of taking a sample from a subject, identifying one or more neoantigens expressed by hyperoliferative cells in a the sample, synthesizing one or more cDNA libraries based upon expression of neoantigens in the sample, cloning the one or more nucleic acid sequences that encode one or more epitopes of the neoantigens, into a nucleic acid molecule that comprises one or more components disclosed herein, and administering the nucleic acid molecule to the subject.

In one aspect, the present disclosure features a method of inducing a CD8+ T cell immune response in a subject, the method comprising administering to the subject in need thereof a pharmaceutically effective amount of any of the nucleic acid molecules of any one of the aspects or embodiments herein, or any one of the pharmaceutical compositions of any one of the aspects and embodiments herein.

In one aspect, the present disclosure features a method of enhancing an immune response in a subject, the method comprising administering to the subject in need thereof a pharmaceutically effective amount of any of the nucleic acid molecules of any one of the aspects or embodiments herein, or any one of the pharmaceutical compositions of any one of the aspects and embodiments herein.

In some aspects, the present disclosure features a method of enhancing a CD8+ T cell immune response in a subject, the method comprising administering to the subject in need thereof a pharmaceutically effective amount of any of the nucleic acid molecules of any one of the aspects or embodiments herein, or any one of the pharmaceutical compositions of any one of the aspects and embodiments herein.

In some embodiments, the subject has cancer. In another embodiment, the subject has previously been treated, and not responded to checkpoint inhibitor therapy.

In some embodiments, the nucleic acid molecule is administered to the subject by electroporation.

In some embodiments, enhancing the CD8+ T cell immune response comprises activating from about 0.01% to about 50% CD8+ T cells. In some embodiments, enhancing the CD8+ T cell immune response comprises activating from about 0.01% to about 50% that are IFN-T positive. In some embodiments, the activation of T cells is accomplished after no more than 1, 2, 3, 4, 5, 6, 8, 9, 10 or more hours of contact with antigen preventing cells expressing or plasmids comprising the nucleotic acid sequences disclosed herein or expressed by a hyperproliferative cell in a subject. CD8+ T cells. In some embodiments, enhancing the CD8+ T cell immune response comprises expanding CD8+ T cells. In some embodiments, enhancing the CD8+ T cell immune response comprises activating from about 0.05% to about 50% CD8+ T cells In some embodiments, enhancing the CD8+ T cell immune response comprises activating from about 0.10% to about 50% CD8+ T cells In some embodiments, enhancing the CD8+ T cell immune response comprises activating from about 0.2% to about 50% CD8+ T cells In some embodiments, enhancing the CD8+ T cell immune response comprises activating from about 0.3% to about 50% CD8+ T cells In some embodiments, enhancing the CD8+ T cell immune response comprises activating from about 0.4% to about 50% CD8+ T cells In some embodiments, enhancing the CD8+ T cell immune response comprises activating from about 0.5% to about 50% CD8+ T cells In some embodiments, enhancing the CD8+ T cell immune response comprises activating from about 0.6% to about 50% CD8+ T cells In some embodiments, enhancing the CD8+ T cell immune response comprises activating from about 0.7% to about 50% CD8+ T cells In some embodiments, enhancing the CD8+ T cell immune response comprises activating from about 0.8% to about 50% CD8+ T cells In some embodiments, enhancing the CD8+ T cell immune response comprises activating from about 0.9% to about 50% CD8+ T cells In some embodiments, enhancing the CD8+ T cell immune response comprises activating from about 1.00% to about 50% CD8+ T cells. In some embodiments, enhancing the CD8+ T cell immune response comprises activating from about 2.0% to about 50% CD8+ T cells In some embodiments, enhancing the CD8+ T cell immune response comprises activating from about 3.0% to about 50% CD8+ T cells. In some embodiments, enhancing the CD8+ T cell immune response comprises activating from about 5.0% to about 50% CD8+ T cells. In some embodiments, enhancing the CD8+ T cell immune response comprises activating from about 6.0% to about 50% CD8+ T cells. In some embodiments, enhancing the CD8+ T cell immune response comprises activating from about 7.0% to about 50% CD8+ T cells. In some embodiments, enhancing the CD8+ T cell immune response comprises activating from about 8.0% to about 50% CD8+ T cells. In some embodiments, enhancing the CD8+ T cell immune response comprises activating from about 9.0% to about 50% CD8+ T cells. In some embodiments, enhancing the CD8+ T cell immune response comprises activating from about 10% to about 50% CD8+ T cells. In some embodiments, enhancing the CD8+ T cell immune response comprises activating from about 15% to about 50% CD8+ T cells. In some embodiments, enhancing the CD8+ T cell immune response comprises activating from about 20% to about 50% CD8+ T cells.

T cell activation can be measured by various assays as described herein. For example, T cell activities that may be measured include the induction of proliferation of T cells, the induction of signaling in T cells, the induction of expression of activation markers in T cells, such as interferon-gamma (IFN-γ), the induction of cytokine secretion by T cells, and the cytotoxic activity of T cells. For example, in certain embodiments, CD8+ T cell activation is measured by a proliferation assay. In some embodiments, the activation may be measured after stimulation of cells or cell sample by the encoded nucleic acid sequences.

Cytokine Secretion

The activation of CD8+ T-cells may be assessed or measured by determining secretion of cytokines, such as gamma interferon (IFN-γ), tumor necrosis factor alpha (TNFa), interleukin-12 (IL-12) or interleukin 2 (IL-2). In some embodiments, ELISA is used to determine cytokine secretion, for example secretion of gamma interferon (IFN-γ), tumor necrosis factor alpha (TNFa), interleukin-12 (IL-12) or interleukin 2 (IL-2). The ELISPOT (enzyme-linked immunospot) technique may be used to detect T cells that secrete a given cytokine (e.g., gamma interferon (IFN-γ)) in response to stimulation with any of the nucleic acid molecules of any one of the aspects or embodiments herein, or any one of the pharmaceutical compositions of any one of the aspects and embodiments herein. T cells are cultured with, e.g. any of the nucleic acid molecules of any one of the aspects or embodiments herein wells which have been coated with anti-IFN-γ antibodies. The secreted IFN-γ is captured by the coated antibody and then revealed with a second antibody coupled to a chromogenic substrate. Thus, locally secreted cytokine molecules form spots, with each spot corresponding to one IFN-γ-secreting cell. The number of spots allows one to determine the frequency of IFN-γ-secreting cells in the analyzed sample. The ELISPOT assay has also been described for the detection of tumor necrosis factor alpha, interleukin-4 (IL-4), IL-5, IL-6, IL-10, IL-12, granulocyte-macrophage colony-stimulating factor, and granzyme B-secreting lymphocytes (Klinman D, Nutman T. Current protocols in immunology. New York, N.Y: John Wiley & Sons, Inc.; 1994. pp. 6.19.1-6.19.8, incorporated by reference in its entirety herein).

Flow cytometric analyses of intracellular cytokines may be used to measure the cytokine content in culture supernatants, but provides no information on the number of T cells that actually secrete the cytokine. When T cells are treated with inhibitors of secretion such as monensin or brefeldin A, they accumulate cytokines within their cytoplasm upon activation (e.g. with the nucleic acid molecules of the present invention). After fixation and permeabilization of the lymphocytes, intracellular cytokines can be quantified by cytometry. This technique allows the determination of the cytokines produced, the type of cells that produce these cytokines, and the quantity of cytokine produced per cell.

Cytotoxicity

The activation of CD8+ T-cells by any of the nucleic acid molecules of any one of the aspects or embodiments herein, or any one of the pharmaceutical compositions of any one of the aspects and embodiments herein may be assessed by assaying the cytotoxic activity of the CD8+ T-cells.

The cytotoxic activity of T cells may be assessed by any suitable technique known to those of skill in the art. For example, a sample comprising T cells that have been exposed to the nucleic acid molecules according to the invention can be assayed for cytotoxic activity after an appropriate period of time, in a standard cytotoxic assay. Such assays may include, but are not limited to, the chromium release CTL assay and the Alamar Blue™ fluorescence assay known in the art.

Proliferation/Expansion

The ability of the any of the nucleic acid molecules of any one of the aspects or embodiments herein, or any one of the pharmaceutical compositions of any one of the aspects and embodiments herein to expand T cells can be evaluated by using CFSE staining. To compare the initial rate of cell expansion, the cells are subject to CFSE staining to determine how well any of the nucleic acid molecules of any one of the aspects or embodiments herein, or any one of the pharmaceutical compositions of any one of the aspects and embodiments herein induced the proliferation of T cells. CFSE staining provides a much more quantitative endpoint and allows simultaneous phenotyping of the expanded cells. Every day after stimulation, an aliquot of cells is removed from each culture and analyzed by flow cytometry. CFSE staining makes cells highly fluorescent. Upon cell division, the fluorescence is halved and thus the more times a cell divides the less fluorescent it becomes. The ability of any of the nucleic acid molecules of any one of the aspects or embodiments herein, or any one of the pharmaceutical compositions of any one of the aspects and embodiments herein to induce T cell proliferation is quantitated by measuring the number of cells that divided once, twice, three times and so on. The nucleic acid molecules that induce the greatest number of cell divisions at a particular time point is deemed as the most potent expander.

To determine how well any of the nucleic acid molecules of any one of the aspects or embodiments herein, or any one of the pharmaceutical compositions of any one of the aspects and embodiments herein promote long-term growth of T cells, cell growth curves can be generated. These experiments are set up as the foregoing CFSE experiments, but no CFSE is used. Every 2-3 days of culture, T cells are removed from the respective cultures and counted using a Coulter counter which measures how many cells are present and the mean volume of the cells. The mean cell volume is the best predicator of when to restimulate the cells. In general, when T cells are properly stimulated they triple their cell volume. When this volume is reduced to more than about half of the initial blast, it may be necessary to restimulate the T cells to maintain a log linear expansion (Levine et al., 1996, Science 272:1939-1943; Levine et al., 1997, J. Immunol. 159:5921-5930). The time it takes the nucleic acid molecules of any one of the aspects or embodiments herein, or any one of the pharmaceutical compositions of any one of the aspects and embodiments herein to induce 20 population doublings is calculated. The relative differences of each nucleic acid molecule to induce this level of T cell expansion is an important criteria on which the nucleic acid molecules of any one of the aspects or embodiments herein, or any one of the pharmaceutical compositions of any one of the aspects and embodiments herein are assessed.

Apoptosis Markers

In certain embodiments of the present invention, stimulation, activation, and expansion of T cells using the nucleic acid molecules of any one of the aspects or embodiments herein, or any one of the pharmaceutical compositions of any one of the aspects and embodiments herein enhances expression of certain key molecules in T cells that protect again apoptosis or otherwise prolong survival in vivo or in vitro. Apoptosis usually results from induction of a specific signal in the T cell. Thus, the the nucleic acid molecules of any one of the aspects or embodiments herein, or any one of the pharmaceutical compositions of any one of the aspects and embodiments herein may provide for protecting a T cell from cell death resulting from stimulation of the T cell. Therefore, also included in the present invention is the enhanced T cell growth by protection from premature death or from absence or depletion of recognized T cell growth markers, such as Bcl-xL, growth factors, cytokines, or lymphokines normally necessary for T cell survival, as well as from Fas or Tumor Necrosis Factor Receptor (TNFR) cross-linking or by exposure to certain hormones or stress.

In another aspect, the disclosure features a method of enhancing an immune response against a plurality of heterogeneous hyperproliferative cells in a subject, the method comprising administering to the subject in need thereof a pharmaceutically effective amount of any of the nucleic acid molecules described herein (e.g. a nucleic acid molecule comprising a nucleic acid sequence comprising Formula I:

[[(AED$^n$)-(linker)]$_n$-[AED$^{n+1}$]), or any of the pharmaceutical compositions described herein.

In some embodiments, the subject has cancer. In another embodiment, the subject has previously been treated, and not responded to checkpoint inhibitor therapy.

In some embodiments, the nucleic acid molecule is administered to the subject by electroporation.

In some embodiments, the immune response is of a sufficient magnitude or efficacy to inhibit or retard tumor growth, induce tumor cell death, induce tumor regression, prevent or delay tumor recurrence, prevent tumor growth, prevent tumor spread and/or induce tumor elimination.

In some embodiments, the method of enhancing an immune response against a plurality of heterogeneous hyperproliferative cells in a subject further comprises administration of one or more therapeutic agents.

In some embodiments, the additional therapeutic agent is a biologic therapeutic or a small molecule.

In another embodiment, the therapeutic agent is (i) a checkpoint inhibitor or functional fragment thereof; or (ii) a nucleic acid molecule encoding a checkpoint inhibitor or a functional fragment thereof. In a further embodiment, the checkpoint inhibitor associates with or inhibits a checkpoint protein selected from the group consisting of CTLA-4, PDL1, PDL2, PD1, B7-H3, B7-H4, BTLA, HVEM, TIM3, GAL9, LAG3, VISTA, KIR, 2B4, CD160, CGEN-15049, CHK 1, CHK2, A2aR, and B-7 family ligands or a combination thereof. In an exemplary embodiment, the checkpoint inhibitor is an inhibitor of the programmed death-1 (PD-1) pathway. In another exemplary embodiment, the checkpoint inhibitor is an anti-cytotoxic T-lymphocyte-associated antigen 4 (CTLA4) antibody or functional fragment thereof.

In another embodiment, the therapeutic agent is an adjuvant. The ability of an adjuvant to increase the immune response to an antigen is typically manifested by a significant increase in immune-mediated reaction, or reduction in disease symptoms. For example, an increase in humoral immunity is typically manifested by a significant increase in the titer of antibodies raised to the antigen, and an increase in T-cell activity is typically manifested in increased cell proliferation, or cellular cytotoxicity, or cytokine secretion. An adjuvant may also alter an immune response, for example, by changing a primarily humoral or Th2 response into a primarily cellular, or Th1 response. In some embodiments, the adjuvant can be other genes that are expressed in alternative plasmid or are delivered as proteins in combination with the plasmid above in the vaccine.

In some embodiments, the adjuvant can be selected from the group consisting of: α-interferon (IFN-α), β-interferon (IFN-β), γ-interferon, platelet derived growth factor (PDGF), TNFα, TNFβ, GM-CSF, epidermal growth factor (EGF), cutaneous T cell-attracting chemokine (CTACK), epithelial thymus-expressed chemokine (TECK), mucosae-associated epithelial chemokine (MEC), IL-12, IL-15, MHC, CD80, CD86 including IL-15 having the signal sequence deleted and optionally including the signal peptide from IgE. The adjuvant can be IL-12, IL-15, IL-28, CTACK, TECK, platelet derived growth factor (PDGF), TNF.alpha., TNF.beta., GM-CSF, epidermal growth factor (EGF), IL-1, IL-2, IL-4, IL-5, IL-6, IL-10, IL-12, IL-18, or a combination thereof.

Other genes which can be useful adjuvants include those encoding: MCP-1, MW-1a, MIP-1p, IL-8, RANTES, L-selectin, P-selectin, E-selectin, CD34, GlyCAM-1, MadCAM-1, LFA-1, VLA-1, Mac-1, p150.95, PECAM, ICAM-1, ICAM-2, ICAM-3, CD2, LFA-3, M-CSF, G-CSF, IL-4, mutant forms of IL-18, CD40, CD40L, vascular growth factor, fibroblast growth factor, IL-7, nerve growth factor, vascular endothelial growth factor, Fas, TNF receptor, Flt, Apo-1, p55, WSL-1, DR3, TRAMP, Apo-3, AIR, LARD, NGRF, DR4, DR5, KILLER, TRAIL-R2, TRICK2, DR6, Caspase ICE, Fos, c-jun, Sp-1, Ap-1, Ap-2, p38, p65Rel, MyD88, IRAK, TRAF6, IkB, Inactive NIK, SAP K, SAP-1, JNK, interferon response genes, NFkB, Bax, TRAIL, TRAILrec, TRAILrecDRC5, TRAIL-R3, TRAIL-R4, RANK, RANK LIGAND, Ox40, Ox40 LIGAND, NKG2D, MICA, MICB, NKG2A, NKG2B, NKG2C, NKG2E, NKG2F, TAP1, TAP2 and functional fragments thereof.

Human IL-12 alpha subunit is set forth in GenBank® Accession Nos. NP_000873.2, NM_000882.3, incorporated by reference in their entireties herein. An exemplary human IL-12 alpha subunit amino acid sequence is shown below:

```
                                          (SEQ ID NO: 54)
MCPARSLLLV ATLVLLDHLS LARNLPVATP DPGMFPCLHH

SQNLLRAVSN MLQKARQTLE FYPCTSEEID HEDITKDKTS

TVEACLPLEL TKNESCLNSR ETSFITNGSC LASRKTSFMM

ALCLSSIYED LKMYQVEFKT MNAKLLMDPK RQIFLDQNML

AVIDELMQAL NFNSETVPQK SSLEEPDFYK TKIKLCILLH

AFRIRAVTID RVMSYLNAS
```

Human IL-12 beta subunit is set forth in GenBank® Accession No. NP_002178.2, incorporated by reference in its entirety herein. An exemplary human IL-12 beta subunit amino acid sequence is shown below:

```
                                          (SEQ ID NO: 55)
MCHQQLVISW FSLVFLASPL VAIWELKKDV YVVELDWYPD

APGEMVVLTC DTPEEDGITW TLDQSSEVLG SGKTLTIQVK

EFGDAGQYTC HKGGEVLSHS LLLLHKKEDG IWSTDILKDQ

KEPKNKTFLR CEAKNYSGRF TCWWLTTIST DLTFSVKSSR

GSSDPQGVTC GAATLSAERV RGDNKEYEYS VECQEDSACP

AAEESLPIEV MVDAVHKLKY ENYTSSFFIR DIIKPDPPKN

LQLKPLKNSR QVEVSWEYPD TWSTPHSYFS LTFCVQVQGK

SKREKKDRVF TDKTSATVIC RKNASISVRA QDRYYSSSWS

EWASVPCS
```

Human IL-15 is set forth in GenBank® Accession Nos. NP_000576.1, NP_751915.1, AAI00962.1 incorporated by reference in their entireties herein. An exemplary human IL-15 amino acid sequence is shown below:

```
                                          (SEQ ID NO: 56)
MRISKPHLRS ISIQCYLCLL LNSHFLTEAG IHVFILGCFS

AGLPKTEANW VNVISDLKKI EDLIQSMHID ATLYTESDVH

PSCKVTAMKC FLLELQVISL ESGDASIHDT VENLIILANN

SLSSNGNVTE SGCKECEELE EKNIKEFLQS FVHIVQMFIN

TS
```

Human IL-17 is set forth in GenBank® Accession Nos. NP_002181.1, NM_002190.2, incorporated by reference in their entireties herein. An exemplary human IL-17 amino acid sequence is shown below:

(SEQ ID NO: 57)
MTPGKTSLVS LLLLLSLEAI VKAGITIPRN PGCPNSEDKN

FPRTVMVNLN IHNRNTNTNP KRSSDYYNRS TSPWNLHRNE

DPERYPSVIW EAKCRHLGCI NADGNVDYHM NSVPIQQEIL

VLRREPPHCP NSFRLEKILV SVGCTCVTPI VHHVA

Human IL-8 is set forth in GenBank® Accession Nos. NP_000575.1, NM_000584.3, incorporated by reference in their entireties herein. An exemplary human IL-8 amino acid sequence is shown below:

(SEQ ID NO: 58)
MTSKLAVALL AAFLISAALC EGAVLPRSAK ELRCQCIKTY

SKPFHPKFIK ELRVIESGPH CANTEIIVKL SDGRELCLDP

KENWVQRVVE KFLKRAENS

Human C—C motif chemokine 5 (processed form RANTES (3-68)) is set forth in GenBank® Accession Nos. NP_002976.2, NM_002985.2, incorporated by reference in their entireties herein. An exemplary human C—C motif chemokine 5 amino acid sequence is shown below:

(SEQ ID NO: 59)
MKVSAAALAV ILIATALCAP ASASPYSSDT TPCCFAYIAR

PLPRAHIKEY FYTSGKCSNP AVVFVTRKNR QVCANPEKKW

VREYINSLEM S

Human Macrophage inflammatory protein 1-alpha (MIP-1a) is set forth in GenBank® Accession Nos. NP_002974.1, NM_002983.2, incorporated by reference in their entireties herein. An exemplary human C—C motif chemokine 5 amino acid sequence is shown below:

(SEQ ID NO: 60)
MQVSTAALAV LLCTMALCNQ FSASLAADTP TACCFSYTSR

QIPQNFIADY FETSSQCSKP GVIFLTKRSR QVCADPSEEW

VQKYVSDLEL SA

Other exemplary adjuvants include, but are not limited to, poly-ICLC (see Pharmacol Ther. 2015 February; 146:120-31, incorporated by reference in its entirety herein), 1018 ISS (see Vaccine. 2003 Jun. 2; 21(19-20):2461-7, incorporated by reference in its entirety herein), aluminum salts, Amplivax AS15, Bacillus Colmette-Guérin (BCG) (see Clin Immunol. 2000 January; 94(1):64-72, incorporated by reference in its entirety herein), CP-870,893, CpG7909 (GenBank® Accession No. CS576603.1), CyaA (GenBank® Accession No. KP670536.1), GM-CSF (GenBank® Accession No. M11220.1), IC30 (see Expert Rev Vaccines. 2007 October; 6(5):741-6, incorporated by reference in its entirety herein), IC31 (see Expert Rev Vaccines. 2007 October; 6 (5):741-6, incorporated by reference in its entirety herein), Imiquimod (see Vaccine. 2006 Mar. 10; 24(11):1958-6, incorporated by reference in its entirety herein), ImuFact 1MP321, IS Patch, ISS, ISCOMATRIX, Juvlmmune, LipoVac, monophosphoryl lipid A, Montanide IMS 1312, Montanide ISA 206, Montanide ISA 50V, Montanide ISA-51, OK-432, OM-174, OM-197-MP-EC, ONTAK, PEPTEL, vector system, PLGA microparticles, resiquimod, S L172, Virosomes and other Virus-like particles, YF-17D, VEGF trap, R848, beta-glucan, Pam3Cys, acrylic or methacrylic polymers, copolymers of maleic anhydride and Aquila's QS21 stimulon, and a functional fragment of any thereof; or (ii) a nucleic acid molecule encoding an adjuvant selected from the group consisting of: (i) poly-ICLC, 1018 ISS, aluminum salts, Amplivax AS15, BCG, CP-870,893, CpG7909, CyaA, GM-CSF, IC30, IC31, Imiquimod, ImuFact 1MP321, IS Patch, ISS, ISCOMATRIX, Juvlmmune, LipoVac, monophosphoryl lipid A, Montanide IMS 1312, Montanide ISA 206, Montanide ISA 50V, Montanide ISA-51, OK-432, OM-174, OM-197-MP-EC, ONTAK, PEPTEL, vector system, PLGA microparticles, resiquimod, S L172, Virosomes and other Virus-like particles, YF-17D, VEGF trap, R848, beta-glucan, Pam3Cys, acrylic or methacrylic polymers, copolymers of maleic anhydride and Aquila's QS21 stimulon, or functional fragment thereof.

In another embodiment, the therapeutic agent is an immunostimulatory agent or functional fragment thereof. For example, in some embodiments, the imunostimulatory agent is an interleukin or functional fragment thereof.

In another embodiment, the therapeutic agent is a chemotherapeutic agent. Examples of chemotherapeutic agents include, but are not limited to, aldesleukin, altretamine, amifostine, asparaginase, bleomycin, capecitabine, carboplatin, carmustine, cladribine, cisapride, cisplatin, cyclophosphamide, cytarabine, dacarbazine (DTIC), dactinomycin, docetaxel, doxorubicin, dronabinol, epoetin alpha, etoposide, filgrastim, fludarabine, fluorouracil, gemcitabine, granisetron, hydroxyurea, idarubicin, ifosfamide, interferon alpha, irinotecan, lansoprazole, levamisole, leucovorin, megestrol, mesna, methotrexate, metoclopramide, mitomycin, mitotane, mitoxantrone, omeprazole, ondansetron, paclitaxel (Taxol®), pilocarpine, prochloroperazine, rituximab, tamoxifen, taxol, topotecan hydrochloride, trastuzumab, vinblastine, vincristine and vinorelbine tartrate. For prostate cancer treatment, a preferred chemotherapeutic agent with which anti-CTLA-4 can be combined is paclitaxel (Taxol®).

In some embodiments, the adjuvant can include a nucleic acid plasmid that encodes any cytokine or functional fragment thereof that is administered sequentially with a pharmaecuticla composition comprising a plasmid encoding a plurality of neoantigens, optionally with one or a plurality of tumor associated antigens not derived from a subject. In some embodiments, the cytokine is IL-12 or a subunit of IL-12. In some embodiments, adjuvant is a nucleic acid sequence that encodes an amino acid sequence that comprises at least about 70%, 75%, 80%, 85%, 90%, 95%, 96%, 97%, 98%, 99% or 100% sequence identity to SEQ NO: 54 or a functional fragment thereof. In some embodiments, adjuvant is a nucleic acid sequence that encodes an amino acid sequence that comprises at least about 70%, 75%, 80%, 85%, 90%, 95%, 96%, 97%, 98%, 99% or 100% sequence identity to SEQ NO: 55 or a functional fragment thereof. In some embodiments, adjuvant is a first nucleic acid sequence that encodes an amino acid sequence that comprises at least about 70%, 75%, 80%, 85%, 90%, 95%, 96%, 97%, 98%, 99% or 100% sequence identity to SEQ NO: 54 and a second amino acid sequence that comprises at least about 70%, 75%, 80%, 85%, 90%, 95%, 96%, 97%, 98%, 99% or 100% sequence identity to SEQ NO: 55 or a functional fragment thereof. In some embodiments, if the nucleic acid sequence encoding a cytokine or functional fragment thereof comprise two subunits, the disclosure relates to nucleic acid molecule comprises a first nucleic acid sequence encoding the first subunit and a second nucleic acid encoding the second subunit, each of the first or second nucleic acid sequences operably linked to at least a first promoter, such as a CMV promoter. In some embodiments, if the nucleic acid sequence encoding a cytokine or functional fragment thereof comprise two subunits, the disclosure relates to nucleic acid molecule comprises a first nucleic acid sequence encoding the first subunit and a second nucleic acid encoding the second subunit, the first nucleic acid sequence is operably linked to at least a first promoter and the second nucleic acid sequence is operably linked to at least a second promoter.

In some embodiments, the IL-12 sequences and nucleic acids sequences encoding the same can be found in U.S. Pat. Nos. 9,981,036 and 9,272,024, each of which is incorporated by reference in its entirety.

Therapeutic Compositions and Administration

The present disclosure is also directed to pharmaceutical compositions comprising an effective amount of one or more nucleic acid molecules according to the present invention (including a pharmaceutically acceptable salt, thereof), optionally in combination with a pharmaceutically acceptable carrier, excipient or additive.

In embodiments, the pharmaceutical compositions contain a pharmaceutically acceptable carrier, excipient, or diluent, which includes any pharmaceutical agent that does not itself induce the production of an immune response harmful to a subject receiving the composition, and which may be administered without undue toxicity. As used herein, the term "pharmaceutically acceptable" means being approved by a regulatory agency of the Federal or a state government or listed in the U.S. Pharmacopia, European Pharmacopia or other generally recognized pharmacopia for use in mammals, and more particularly in humans. These compositions can be useful for treating and/or preventing viral infection and/or autoimmune disease.

A thorough discussion of pharmaceutically acceptable carriers, diluents, and other excipients is presented in Remington's Pharmaceutical Sciences (17th ed., Mack Publishing Company) and Remington: The Science and Practice of Pharmacy (21 st ed., Lippincott Williams & Wilkins), which are hereby incorporated by reference. The formulation of the pharmaceutical composition should suit the mode of administration. In embodiments, the pharmaceutical composition is suitable for administration to humans, and can be sterile, non-particulate and/or non-pyrogenic.

In one aspect, the disclosure provides a pharmaceutical composition comprising (i) one or a plurality of nucleic acid molecules as described herein (e.g. a nucleic acid molecule comprising a nucleic acid sequence comprising Formula I: $[([(AED^{n})\text{-}(linker)]_{n}\text{-}[AED^{n+1}])$; and (ii) a pharmaceutically acceptable carrier. In some embodiments, the nucleic acid molecule or nucleic acid sequence is free of a linker segment and the resulting plasmid comprises one or more successive nucleic acid sequences that encodes neoantigens amino acid sequences or epitopes that are from about 3 to about 30 amino acids in length. In some embodiments, the pharmaceutical composition comprises a pharmaceutically effective amount of: (i) one or a plurality of any of the nucleic acid molecules described herein comprising one or a combination of any component of a plasmid disclosed herein or nucleic acid sequences that are about 70%, 75%, 80%, 85%, 90%, 91%, 92%, 93%, 94%, 95%, 96%, 97%, 98%, or 99% homologous to any nucleic acid sequence that is a component of the plasmid listed herein. In some embodiments, the nucleic acid molecule comprises a nucleic acid seqweunce that encodes one or more nucleic acids that encode neoantigens and one or more linkers. In some embodiments, the nucleica acid molecule encodes one or a plurality of furin cleavage sequences separating one or more of the AEDs. In some embodiments, the disclosure relates to a pharmaceutical composition comprising a nucleic acid molecule that is pGX4505 or a nucleic acid sequence that is at least 70% homolgous to the sequence of pGX4505, wherein its multiple cloning site is replaced by any of the Formulae disclosed herein.

In some embodiments, the pharmaceutical composition further comprises one or more therapeutic agents.

In some embodiments, the additional therapeutic agent is a biologic therapeutic or a small molecule.

In another embodiment, the therapeutic agent is (i) a checkpoint inhibitor or functional fragment thereof; or (ii) a nucleic acid molecule encoding a checkpoint inhibitor or a functional fragment thereof. In a further embodiment, the checkpoint inhibitor associates with or inhibits a checkpoint protein selected from the group consisting of CTLA-4, PDL1, PDL2, PD1, B7-H3, B7-H4, BTLA, HVEM, TIM3, GAL9, LAG3, VISTA, KIR, 2B4, CD160, CGEN-15049, CHK 1, CHK2, A2aR, and B-7 family ligands or a combination thereof. In an exemplary embodiment, the checkpoint inhibitor is an inhibitor of the programmed death-1 (PD-1) pathway. In another exemplary embodiment, the checkpoint inhibitor is an anti-cytotoxic T-lymphocyte-associated antigen 4 (CTLA4) antibody or functional fragment thereof.

In another embodiment, the therapeutic agent is an adjuvant. The ability of an adjuvant to increase the immune response to an antigen is typically manifested by a significant increase in immune-mediated reaction, or reduction in disease symptoms. For example, an increase in humoral immunity is typically manifested by a significant increase in the titer of antibodies raised to the antigen, and an increase in T-cell activity is typically manifested in increased cell proliferation, or cellular cytotoxicity, or cytokine secretion. An adjuvant may also alter an immune response, for example, by changing a primarily humoral or Th2 response into a primarily cellular, or Th1 response. Exemplary adjuvants include, but are not limited to, poly-ICLC, 1018 ISS, aluminum salts, Amplivax AS15, BCG, CP-870,893, CpG7909, CyaA, GM-CSF, IC30, IC31, Imiquimod, ImuFact 1MP321, IS Patch, ISS, ISCOMATRIX, JuvImmune, LipoVac, monophosphoryf lipid A, Montanide IMS 1312, Montanide ISA 206, Montanide ISA 50V, Montanide ISA-51, OK-432, OM-174, OM-197-MP-EC, ONTAK, PEPTEL, vector system, PLGA microparticles, resiquimod, S L172, Virosomes and other Virus-like particles, YF-17D, VEGF trap, R848, beta-gluean, Pam3Cys, acrylic or methacrylic polymers, copolymers of maleic anhydride and Aquila's QS21 stimulon, and a functional fragment of any thereof; or (ii) a nucleic acid molecule encoding an adjuvant selected from the group consisting of: (i) poly-ICLC, 1018 ISS, aluminum salts, Amplivax AS15, BCG, CP-870,893, CpG7909, CyaA, GM-CSF, IC30, IC31, Imiquimod, ImuFact 1MP321, IS Patch, ISS, ISCOMATRIX, JuvImmune, LipoVac, monophosphoryf lipid A, Montanide IMS 1312, Montanide ISA 206, Montanide ISA 50V, Montanide ISA-51, OK-432, OM-174, OM-197-MP-EC, ONTAK, PEPTEL, vector system, PLGA microparticles, resiquimod, S L172, Virosomes and other Virus-like particles, YF-17D, VEGF trap, R848, beta-gluean, Pam3Cys, acrylic or methacrylic polymers, copolymers of maleic anhydride and Aquila's QS21 stimulon, or functional fragment thereof.

In another embodiment, the therapeutic agent is an immunostimulatory agent or functional fragment thereof. For example, in some embodiments, the imunostimulatory agent is an interleukin or functional fragment thereof.

In another embodiment, the therapeutic agent is a chemotherapeutic agent. Examples of chemotherapeutic agents include, but are not limited to, aldesleukin, altretamine, amifostine, asparaginase, bleomycin, capecitabine, carboplatin, carmustine, cladribine, cisapride, cisplatin, cyclophosphamide, cytarabine, dacarbazine (DTIC), dactinomycin, docetaxel, doxorubicin, dronabinol, epoetin alpha, etoposide, filgrastim, fludarabine, fluorouracil, gemcitabine, granisetron, hydroxyurea, idarubicin, ifosfamide, interferon alpha, irinotecan, lansoprazole, levamisole, leucovorin, megestrol, mesna, methotrexate, metoclopramide, mitomycin, mitotane, mitoxantrone, omeprazole, ondansetron, paclitaxel (Taxol®), pilocarpine, prochloroperazine, rituximab, tamoxifen, taxol, topotecan hydrochloride, trastuzumab, vinblastine, vincristine and vinorelbine tartrate. For prostate cancer treatment, a preferred chemotherapeutic agent with which anti-CTLA-4 can be combined is paclitaxel (Taxol®).

One of skill in the art can determine which therapeutic regimen is appropriate on a subject by subject basis, depending, for example, on their cancer and their immune status (e.g., T-cell, B cell or NK cell activity and/or numbers).

According to the present disclosure, a host cell can be transfected in vivo (i.e., in an animal) or ex vivo (i.e., outside of an animal). Transfection of a nucleic acid molecule into a host cell can be accomplished by any method by which a nucleic acid molecule can be inserted into the cell. Transfection techniques include, but are not limited to, transfection, electroporation, microinjection, lipofection, adsorption, and protoplast fusion.

In some embodiments, the disclosure relates to a composition comprising one, two, three or more nucleic acid molecules, each nucleic acid molecule comprising at least one coding sequence comprising Formula I. In some embodiments, the first second and/or third nucleic acid molecule comprises at least one AED that is a neoantigen and at least AED that is a tumor associated antigen that is not derived from a subject. In some embodiments, the first second and/or third nucleic acid molecule comprises at least one coding sequence comprising at least about 10 AEDs derived from a subject. In some embodiments, the first second and/or third nucleic acid molecule comprises at least one coding sequence comprising at least about 20 AEDs derived from a subject. In some embodiments, the first second and/or third nucleic acid molecule comprises at least one coding sequence comprising at least about 30 AEDs derived from a subject. In some embodiments, the first second and/or third nucleic acid molecule comprises at least one coding sequence comprising at least about 40 AEDs derived from a subject. In some embodiments, the first second and/or third nucleic acid molecule comprises at least one coding sequence comprising at least about 50 AEDs derived from a subject. In some embodiments, the first second and/or third nucleic acid molecule comprises at least one coding sequence comprising at least about 60 AEDs derived from a subject.

In some embodiments, the first second and/or third nucleic acid molecule comprises at least one coding sequence comprising at least about 10 AEDs that are each independently a tumor associated antigen that is not derived from a subject. In some embodiments, the first second and/or third nucleic acid molecule comprises at least one coding sequence comprising at least about 20 AEDs that are each independently a tumor associated antigen that is not derived from a subject. In some embodiments, the first second and/or third nucleic acid molecule comprises at least one coding sequence comprising at least about 30 AEDs that are each independently a tumor associated antigen that is not derived from a subject. In some embodiments, the first second and/or third nucleic acid molecule comprises at least one coding sequence comprising at least about 40 AEDs that are each independently a tumor associated antigen that is not derived from a subject. In some embodiments, the first second and/or third nucleic acid molecule comprises at least one coding sequence comprising at least about 50 AEDs that are each independently a tumor associated antigen that is not derived from a subject. In some embodiments, the first second and/or third nucleic acid molecule comprises at least one coding sequence comprising at least about 60 AEDs that are each independently a tumor associated antigen that is not derived from a subject. Any ratio of nucleic acid sequence encoding a neoantigen:nucleic acid sequence encoding a tumor associated antigen not derived from the subject may be included in the embodiments, such as 1:1, 2:1:, 1:2, 1:4, 4:1, 5:1, 1:5, 1:3, 3:1, etc.

In some embodiments, the nucleic acid sequence comprises at least 2, 3, 4, 5, 6, 7, 8, 9, or 10 or more linker domains and the nucleic acid sequence comprises $$(AED^1)\text{-(linker)}(AED^2)\text{-(linker)}]_n \qquad \text{Formula II(a):}$$

wherein each AED is independently selectable from any one or plurality of tumor associated antigens from a subject or one or a plurality of tumor antigens not derived from the subject and wherein n is any positive integer from about 1 to about 100 and wherein each "linker" is a nucleic acid sequence encoding one or a plurality of amino acid cleavage sites. In some embodiments, the nucleic acid sequence comprises at least one linker domain between each AED and the nucleic acid sequence comprises $$(AED^1)\text{-(linker)-}(AED^2)\text{-(linker)}]_n \qquad \text{Formula II(a):}$$

wherein each AED is independently selectable from any one or plurality of tumor associated antigens from a subject or one or a plurality of tumor antigens not derived from the subject and wherein n is any positive integer from about 25 to about 60 and wherein each "linker" is a nucleic acid sequence encoding one or a plurality of amino acid cleavage sites.

In some embodiments, the nucleic acid sequence comprises at least one linker domain between each AED and the nucleic acid sequence comprises $$(AED^1)\text{-(linker)-}(AED^2)\text{-(linker)}]_n \qquad \text{Formula II(a):}$$

wherein each AED is independently selectable from any one or plurality of tumor associated antigens from a subject or one or a plurality of tumor antigens not derived from the subject and wherein n is any positive integer from about 35 to about 50 and wherein each "linker" is a nucleic acid sequence encoding one or a plurality of amino acid cleavage sites. In some embodiments, the nucleic acid sequence comprises at least one linker domain between each AED and the nucleic acid sequence comprises $$(AED^1)\text{-(linker)-}(AED^2)\text{-(linker)}]_n \qquad \text{Formula II(a):}$$

wherein each AED is independently selectable from any one or plurality of tumor associated antigens from a subject or one or a plurality of tumor antigens not derived from the subject and wherein n is any positive integer from about 40 to about 50 and wherein each "linker" is a nucleic acid sequence encoding one or a plurality of amino acid cleavage sites.

In some embodiments, tumor associated antigens not derived from the subject comprise one or a combination of amino acids comprising at least about 70%, 75%, 80%, 85%, 90%, 91%, 92%, 93%, 94%, 95%, 96%, 97%, 98%, 99% or 100% to Survivin, MAGE A10, gp100, EGFRvIII, calreticulin and WT1.

Survivin (SEQ ID NO: 61)

MGAPTLPPAW QPFLKDHRIS TFKNWPFLEG CACTPERMAE AGFIHCPTEN

EPDLAQCFFCFKELEGWEPD DDPIEEHKKH SSGCAFLSVK KQFEELTLGE

FLKLDRERAK NKIAKETNNK KEFEETAEK VRRAIEQLAA MD

MAGE (SEQ ID: 62)

1 matsqadiet dpgisepdga taqtsadgsq aqnlesrtii rgkrtrkinn lnveenssgd 61 qrraplaagt wrsapvpvtt qnppgappnv lwqtplawqn psgwqnqtar qtpparqspp 121 arqtppawqn pvawqnpviw pnpviwqnpv iwpnpivwpg pvvwpnplaw qnppgwqtpp 181 gwqtppgwqg ppdwqgppdw plppdwplpp dwplptdwpl ppdwipadwp ippdwqnlrp 241 spnlrpspns rasqnpgaaq prdvallqer anklvkylml kdytkvpikr semlrdiire 301 ytdvypeiie racfvlekkf giqlkeidke ehlyilistp eslagilgtt kdtpklglll 361 vilgvifmng nraseavlwe alrkmglrpg vrhpllgdlr klltyefvkq kyldyrrvpn 421 snppeyeflw glrsyhetsk mkvlrfiaev qkrdprdwta qfmeaadeal daldaaaaea 481 earaeartrm gigdeaysgp wswddiefel ltwdeegdfg dpwsripftf waryhqnars 541 rfpqtfagpi igpggtasan faanfgaigf fwve

A10

(SEQ ID NO: 63)

1 mtdktekvav dpetvfkrpr ecdspsyqkr qrmallarkq gagdsliags amskekklmt 61 ghaippsqld sqiddftgfs kdgmmqkpgs napvggnvts nfsgddlecr giasspksqq 121 einadikcqv vkeirclgrk yekifemleg vqgptavrkr ffesiikeaa rcmrrdfvkh 181 lkkklkrmi gp100

(SEQ ID NO: 64)

1 mdlvlkrcll hlavigalla vgatkvprnq dwlgvsrqlr tkawnrqlyp ewteaqrldc 61 wrggqvslkv sndgptliga nasfsialnf pgsqkvlpdg qviwvnntii ngsqvwggqp 121 vypqetddac ifpdggpcps gswsqkrsfv yvwktwgqyw qvlggpvsgl sigtgramlg 181 thtmevtvyh rrgsrsyvpl ahsssaftit dqvpfsysys qlraldggnk hflrnqpltf 241 alqlhdpsgy laeadlsytw dfgdssgtli sralvvthty lepgpvtaqv vlqaaiplts 301 cgsspvpgtt dghrptaeap nttagqvptt evvgttpgqa ptaepsgtts vqvpttevis 361 tapvqmptae stgmtpekvp vsevmgttla emstpeatgm tpaevsivvl sgttaaqvtt 421 tewvettare lpipepegpd assimstesi tgslgpplldg tatlrlvkrq vpldcvlyry 481 gsfsvtldiv qgiesaeilq avpsgegdaf eltvscqggl pkeacmeiss pgcqppaqrl 541 cqpvlpspac qlvlhqilkg gsgtyclnvs ladtnslavv stqlimpgqe aglgqvpliv 601 gillvlmavv lasliyrrrl mkqdfsvpql phssshwlrl prifcscpig enspllsgqq 661 v EGFRvIII (SEQ ID NO: 65)

1 mrpsgtagaa llallaalcp asraleekkg nyvvtdhgsc vracgadsye meedgvrkck 61 kcegperkvc ngigigefkd slsinatnik hfknctsisg dlhilpvafr gdsfthtppl 121 dpqeldilkt vkeitgflli qawpenrtdl hafenleiir grtkqhgqfs lavvslnits 181 lglrslkeis dgdviisgnk nlcyantinw kklfgtsgqk tkiisnrgen sckatgqvch 241 alcspegcwg peprdcvscr nvsrgrecvd kcnllegepr efvenseciq chpeclpqam 301 nitctgrgpd nciqcahyid gphcvktcpa gvmgenntiv wkyadaghvc hlchpnctyg 361 ctgpglegcp tngpkipsia tgmvgallll lvvalgiglf mrrrhivrkr firrllgere -continued

```
421 lvepltpsge apnqallril ketefkkikv lgsgafgtvy kglwipegek vkipvaikel
481 reatspkank eildeayvma svdnphvcrl lgicltstvq litqlmpfgc lldyvrehkd
541 nigsqyllnw cvqiakgmny ledrrlvhrd laarnvlvkt pqhvkitdfg lakllgaeek
601 eyhaeggkvp ikwmalesil hriythqsdv wsygvtvwel mtfgskpydg ipaseissil
661 ekgerlpqpp ictidvymim vkcwmidads rpkfreliie fskmardpqr ylviqgderm
721 hlpsptdsnf yralmdeedm ddvvdadeyl ipqqgffssp stsrtpllss lsatsnnstv
781 acidrnglqs cpikedsflq ryssdptgal tedsiddtfl pvpeyinqsv pkrpagsvqn
841 pvyhnqpinp apsrdphyqd phstavgnpe ylntvqptcv nstfdspahw aqkgshqisl
901 dnpdyqqdff pkeakpngif kgstaenaey lrvapqssef iga
```

Calreticulin (SEQ ID NO: 66)

```
  1 mllsvplllg llglavaepa vyfkeqfldg dgwtsrwies khksdfgkfv lssgkfygde
 61 ekdkglqtsq darfyalsas fepfsnkgqt lvvqftvkhe qnidcgggyv klfpnsldqt
121 dmhgdseyni mfgpdicgpg tkkvhvifny kgknvlinkd irckddefth lytlivrpdn
181 tyevkidnsq vesgsleddw dflppkkikd pdaskpedwd erakiddptd skpedwdkpe
241 hipdpdakkp edwdeemdge weppviqnpe ykgewkprqi dnpdykgtwi hpeidnpeys
301 pdpsiyaydn fgvlgldlwq vksgtifdnf litndeayae efgnetwgvt kaaekqmkdk
361 qdeeqrlkee eedkkrkeee eaedkedded kdedeedeed keedeeedvp gqakdel
```

WT1

(SEQ ID NO: 67)

```
  1 mdflllqdpa stcvpepasq htlrsgpgcl qqpeqqgvrd pggiwaklga aeasaerlqg
 61 rrsrgasgse pqqmgsdvrd lnallpavps lgggggcalp vsgaaqwapv ldfappgasa
121 ygslggpapp papppppppp phsfikqeps wggaepheeq clsaftvhfs gqftgtagac
181 rygpfgpppp sqassgqarm fpnapylpsc lesqpairnq gystvtfdgt psyghtpshh
241 aaqfpnhsfk hedpmgqqgs lgeqqysvpp pvygchtptd sctgsqalll rtpyssdnly
301 qmtsqlecmt wnqmnlgatl kghstgyesd nhttpilcga qyrihthgvf rgiqdvrrvp
361 gvaptivrsa setsekrpfm caypgcnkry fklshlqmhs rkhtgekpyq cdfkdcerrf
421 srsdqlkrhq rrhtgvkpfq cktcqrkfsr sdhlkthtrt htgekpfscr wpscqkkfar
481 sdelvrhhnm hqrnmtklql al.
```

The disclosure relates to a nucleic acid sequence comprising one or a plurality of nucleic acid sequence encoding one or a plurality of neoantigens and one or a plurality of nucleic acid sequences encoding one or a plurality of tumor associated antigens. In some embodiments, the tumor associated antigens not derived from a subject are chosen from one or a combination of amino acid sequences comprising at least about 70%, 75%, 80%, 85%, 90%, 91%, 92%, 93%, 94%, 95%, 96%, 97%, 98%, 99% or 100% sequence identity to SEQ ID NO:61, 62, 63, 64, 65, 66 or 67, or functional fragments thereof.

The disclosure relates to a nucleic acid sequence comprising one or a plurality of nucleic acid sequence encoding one or a plurality of neoantigens and one or a plurality of nucleic acid sequences encoding one or a plurality of tumor associated antigens, wherein the one or plurality of neoantigens are chosen from one or a plurality of amino acid sequences comprising at least about 70%, 75%, 80%, 85%, 90%, 91%, 92%, 93%, 94%, 95%, 96%, 97%, 98%, 99% or 100% sequence identity to SEQ ID NO: 1-20, or functional fragments thereof.

Routes of administration include, but are not limited to, intramuscular, intranasally, intradermally, intraperitoneal, intradermal, subcutaneous, intravenous, intraarterially, intraoccularly and oral as well as topically, transdermally, by inhalation or suppository or to mucosal tissue such as by lavage to vaginal, rectal, urethral, buccal and sublingual tissue. Preferred routes of administration include intramuscular, intraperitoneal, intradermal and subcutaneous injection. Genetic constructs may be administered by means including, but not limited to, traditional syringes, needleless injection devices, "microprojectile bombardment gone guns", or other physical methods such as electroporation ("EP"), "hydrodynamic method", or ultrasound.

Examples of electroporation devices and electroporation methods preferred for facilitating delivery of the DNA vaccines of the present invention, include those described in U.S. Pat. No. 7,245,963 by Draghia-Akli, et al., U.S. Patent Application Publication No. 2005/0052630 submitted by Smith, et al., the contents of which are hereby incorporated by reference in their entirety. Also preferred, are electroporation devices and electroporation methods for facilitating delivery of the DNA vaccines provided in co-pending and co-owned U.S. patent application Ser. No. 11/874,072, filed Oct. 17, 2007, which claims the benefit under 35 USC 1 19(e) to U.S. Provisional Application Ser. No. 60/852,149, filed Oct. 17, 2006, and U.S. Provisional Application Ser. No. 60/978,982, filed Oct. 10, 2007, all of which are hereby incorporated in their entirety.

U.S. Pat. No. 7,245,963 by Draghia-Akli, et al. describes modular electrode systems and their use for facilitating the introduction of a biomolecule into cells of a selected tissue in a body or plant. The modular electrode systems comprise a plurality of needle electrodes; a hypodermic needle; an electrical connector that provides a conductive link from a programmable constant-current pulse controller to the plurality of needle electrodes; and a power source. An operator can grasp the plurality of needle electrodes that are mounted on a support structure and firmly insert them into the selected tissue in a body or plant. The biomolecules are then delivered via the hypodermic needle into the selected tissue. The programmable constant-current pulse controller is activated and constant-current electrical pulse is applied to the plurality of needle electrodes. The applied constant-current electrical pulse facilitates the introduction of the biomolecule into the cell between the plurality of electrodes. The entire content of U.S. Pat. No. 7,245,963 is hereby incorporated by reference.

U.S. Patent Application Publication No. 2005/0052630, incorporated by reference in its entirety herein, describes an electroporation device which may be used to effectively facilitate the introduction of a biomolecule into cells of a selected tissue in a body or plant. The electroporation device comprises an electro-kinetic device ("EKD device") whose operation is specified by software or firmware. The EKD device produces a series of programmable constant-current pulse patterns between electrodes in an array based on user control and input of the pulse parameters, and allows the storage and acquisition of current waveform data. The electroporation device also comprises a replaceable electrode disk having an array of needle electrodes, a central injection channel for an injection needle, and a removable guide disk.

The electrode arrays and methods described in U.S. Pat. No. 7,245,963 and U.S. Patent Application Publication No. 2005/0052630 are adapted for deep penetration into not only tissues such as muscle, but also other tissues or organs. Because of the configuration of the electrode array, the injection needle (to deliver the biomolecule of choice) is also inserted completely into the target organ, and the injection is administered perpendicular to the target issue, in the area that is pre-delineated by the electrodes. The electrodes described in U.S. Pat. No. 7,245,963 and U.S. Patent Application Publication No. 2005/005263 are preferably 20 mm long and 21 gauge.

In certain exemplary embodiments, electroporation devices can be configured to deliver to a desired tissue of a mammal a pulse of energy producing a constant current similar to a preset current input by a user. The electroporation device comprises an electroporation component and an electrode assembly or handle assembly. The electroporation component can include and incorporate one or more of the various elements of the electroporation devices, including: controller, current waveform generator, impedance tester, waveform logger, input element, status reporting element, communication port, memory component, power source, and power switch. The electroporation component can function as one element of the electroporation devices, and the other elements are separate elements (or components) in communication with the electroporation component. In some embodiments, the electroporation component can function as more than one element of the electroporation devices, which can be in communication with still other elements of the electroporation devices separate from the electroporation component. The present invention is not limited by the elements of the electroporation devices existing as parts of one electromechanical or mechanical device, as the elements can function as one device or as separate elements in communication with one another. The electroporation component is capable of delivering the pulse of energy that produces the constant current in the desired tissue, and includes a feedback mechanism. The electrode assembly includes an electrode array having a plurality of electrodes in a spatial arrangement, wherein the electrode assembly receives the pulse of energy from the electroporation component and delivers same to the desired tissue through the electrodes. At least one of the plurality of electrodes is neutral during delivery of the pulse of energy and measures impedance in the desired tissue and communicates the impedance to the electroporation component. The feedback mechanism can receive the measured impedance and can adjust the pulse of energy delivered by the electroporation component to maintain the constant current.

In some embodiments, the plurality of electrodes can deliver the pulse of energy in a decentralized pattern. In some embodiments, the plurality of electrodes can deliver the pulse of energy in the decentralized pattern through the control of the electrodes under a programmed sequence, and the programmed sequence is input by a user to the electroporation component. In some embodiments, the programmed sequence comprises a plurality of pulses delivered in sequence, wherein each pulse of the plurality of pulses is delivered by at least two active electrodes with one neutral electrode that measures impedance, and wherein a subsequent pulse of the plurality of pulses is delivered by a different one of at least two active electrodes with one neutral electrode that measures impedance.

In some embodiments, the feedback mechanism is performed by either hardware or software. Preferably, the feedback mechanism is performed by an analog closed-loop circuit. In certain embodiments, this feedback occurs every 50 μs, 20 μs, 10 μs or 1 μs, but is preferably a realtime feedback or instantaneous (i.e., substantially instantaneous as determined by available techniques for determining response time). In some embodiments, the neutral electrode measures the impedance in the desired tissue and communicates the impedance to the feedback mechanism, and the feedback mechanism responds to the impedance and adjusts the pulse of energy to maintain the constant current at a value similar to the preset current. In some embodiments, the feedback mechanism maintains the constant current continuously and instantaneously during the delivery of the pulse of energy.

For therapeutic or immunization purposes, nucleic acid molecules of the invention can also be administered to the patient. A number of methods are conveniently used to deliver the nucleic acids to the patient. For instance, the nucleic acid can be delivered directly, as "naked DNA". This approach is described, for instance, in Wolff et al., Science 247: 1465-1468 (1990) as well as U.S. Pat. Nos. 5,580,859 and 5,589,466. The nucleic acids can also be administered using ballistic delivery as described, for instance, in U.S. Pat. No. 5,204,253. Particles comprised solely of DNA can be administered. Alternatively, DNA can be adhered to particles, such as gold particles.

The nucleic acids can also be delivered complexed to cationic compounds, such as cationic lipids. Lipid-mediated gene delivery methods are described, for instance, in WO1996/18372; WO 1993/24640; Mannino & Gould-Fogerite, BioTechniques 6(7):682-691 (1988); U.S. Pat. No. 5,279,833; WO 1991/06309; and Feigner et al., Proc. Natl. Acad. Sci. USA 84: 7413-7414 (1987).

RNA encoding the peptide of interest can also be used for delivery (see, e.g., Kiken et al, 2011; Su et al, 2011).

A pharmaceutically acceptable carrier or excipient can include such functional molecules as vehicles, adjuvants, carriers or diluents, which are known and readily available to the public. In some embodiments, the pharmaceutically acceptable carrier is an adjuvant. In some embodiments, the pharmaceutically acceptable excipient is a transfection facilitating agent. Preferably, the transfection facilitating agent is a polyanion, polycation, or lipid, and more preferably poly-L-glutamate. In some embodiments, the nucleic acid molecule, or DNA plasmid, is delivered to the cells in conjunction with administration of a polynucleotide function enhancer or a genetic vaccine facilitator agent (or transfection facilitating agent). Polynucleotide function enhancers are described in U.S. Pat. Nos. 5,593,972, 5,962,428, and International Patent Application No. PCT/US94/00899 filed Jan. 26, 1994, which are each incorporated herein by reference in their entireties. Genetic vaccine facilitator agents are described in U.S. patent application Ser. No. 021,579 filed Apr. 1, 1994, which is incorporated herein by reference in its entirety. The transfection facilitating agent can be administered in conjunction with nucleic acid molecules as a mixture with the nucleic acid molecule or administered separately simultaneously, before or after administration of nucleic acid molecules. Examples of transfection facilitating agents includes surface active agents such as immune-stimulating complexes (ISCOMS), Freunds incomplete adjuvant, LPS analog including monophosphoryl lipid A, muramyl peptides, quinone analogs and vesicles such as squalene and squalene, and hyaluronic acid may also be used administered in conjunction with the genetic construct. In some embodiments, the DNA plasmid vaccines may also include a transfection facilitating agent such as lipids, liposomes, including lecithin liposomes or other liposomes known in the art, as a DNA-liposome mixture (see for example WO9324640), calcium ions, viral proteins, polyanions, polycations, or nanoparticles, or other known transfection facilitating agents. Preferably, the transfection facilitating agent is a polyanion, polycation, including poly-L-glutamate (LGS), or lipid.

In some preferred embodiments, the DNA plasmids are delivered with genes for proteins which further enhance the immune response. Examples of such genes are those which encode other cytokines and lymphokines such as alpha-interferon, gamma-interferon, platelet derived growth factor (PDGF), TNF α, TNFβ, GM-CSF, epidermal growth factor (EGF), IL-1, IL-2, IL-4, IL-5, IL-6, IL-10, IL-12, IL-18, WIC, CD80, CD86 and IL-15 including IL-15 having the signal sequence deleted and optionally including the signal peptide from IgE. Other genes which may be useful include those encoding: MCP-1, MIP-1α, MIP-1p, IL-8, RANTES, L-selectin, P-selectin, E-selectin, CD34, GlyCAM-1, MadCAM-1, LFA-1, VLA-1, Mac-1, p150.95, PECAM, ICAM-1, ICAM-2, ICAM-3, CD2, LFA-3, M-CSF, G-CSF, IL-4, mutant forms of IL-18, CD40, CD40L, vascular growth factor, fibroblast growth factor, IL-7, nerve growth factor, vascular endothelial growth factor, Fas, TNF receptor, Fit, Apo-1, p55, WSL-1, DR3, TRAMP, Apo-3, AIR, LARD, NGRF, DR4, DR5, KILLER, TRAIL-R2, TRICK2, DR6, Caspase ICE, Fos, c-jun, Sp-1, Ap-1, Ap-2, p38, p65Rel, MyD88, IRAK, TRAF6, IkB, Inactive NIK, SAP K, SAP-1, JNK, interferon response genes, NFkB, Bax, TRAIL, TRAILrec, TRAILrecDRC5, TRAIL-R3, TRAIL-R4, RANK, RANK LIGAND, Ox40, Ox40 LIGAND, NKG2D, MICA, MICB, NKG2A, NKG2B, NKG2C, NKG2E, NKG2F, TAP1, TAP2 and functional fragments thereof.

When the agents described herein are administered as pharmaceuticals to humans or animals, they can be given per se or as a pharmaceutical composition containing active ingredient in combination with a pharmaceutically acceptable carrier, excipient, or diluent.

Actual dosage levels and time course of administration of the active ingredients in the pharmaceutical compositions of the invention can be varied so as to obtain an amount of the active ingredient which is effective to achieve the desired therapeutic response for a particular patient, composition, and mode of administration, without being toxic to the patient. Generally, agents or pharmaceutical compositions of the invention are administered in an amount sufficient to reduce or eliminate symptoms associated with viral infection and/or autoimmune disease.

The composition comprising one or a plurality of nucleic acid molecules described herein preferably comprise DNA quantities of from about 1 nanogram to 10 milligrams; about 1 microgram to about 10 milligrams; or preferably about 0.1 microgram to about 10 milligrams; or more preferably about 100 microgram to about 1 milligram. In some preferred embodiments, DNA plasmid vaccines according to the present invention comprise about 5 nanograms to about 1000 micrograms of DNA. In some preferred embodiments, the DNA plasmid vaccines contain about 10 nanograms to about 800 micrograms of DNA. In some preferred embodiments, the DNA plasmid vaccines contain about 0.1 to about 500 micrograms of DNA. In some preferred embodiments, the DNA plasmid vaccines contain about 1 to about 350 micrograms of DNA. In some preferred embodiments, the DNA plasmid vaccines contain about 25 to about 250 micrograms of DNA. In some preferred embodiments, the DNA plasmid vaccines contain about 100 microgram to about 1 milligram DNA.

The pharmaceutical compositions according to the present invention are formulated according to the mode of administration to be used. In cases where pharmaceutical compositions are injectable pharmaceutical compositions, they are sterile, pyrogen free and particulate free. An isotonic formulation is preferably used. Generally, additives for isotonicity can include sodium chloride, dextrose, mannitol, sorbitol and lactose. In some cases, isotonic solutions such as phosphate buffered saline are preferred. Stabilizers include gelatin and albumin. In some embodiments, a vasoconstriction agent is added to the formulation.

Preferably the DNA formulations for use with a muscle or skin EP device described herein have high DNA concentrations, preferably concentrations that include microgram to tens of milligram quantities, and preferably milligram quantities, of DNA in small volumes that are optimal for delivery to the skin, preferably small injection volume, ideally 25-200 microliters (μL). In some embodiments, the DNA formulations have high DNA concentrations, such as 1 mg/mL or greater (mg DNA/volume of formulation). More preferably, the DNA formulation has a DNA concentration that provides for gram quantities of DNA in 200 μL of formula, and more preferably gram quantities of DNA in 100 μL of formula.

The DNA plasmids for use with the electroporation devices of the present invention can be formulated or manufactured using a combination of known devices and techniques, but preferably they are manufactured using an optimized plasmid manufacturing technique that is described in U.S. Patent Application Publication No. 20090004716, incorporated by reference in its entirety herein. In some examples, the DNA plasmids used in these studies can be formulated at concentrations greater than or equal to 10 mg/mL. The manufacturing techniques also include or incorporate various devices and protocols that are commonly known to those of ordinary skill in the art, in addition to those described in U.S. Patent Application Publication No. 20090004716 and those described in U.S. Pat. No. 7,238,522, incorporated by reference in their entireties herein. The high concentrations of plasmids used with the skin electroporation devices and delivery techniques described herein allow for administration of plasmids into the ID/SC space in a reasonably low volume and aids in enhancing expression and immunization effects.

Preferred unit dosage formulations are those containing a daily dose or unit, daily sub-dose, as hereinabove recited, or an appropriate fraction thereof, of the administered ingredient.

The dosage regimen for treating a disorder or a disease with the tumor specific neo-antigenic peptides of this invention and/or compositions of this invention is based on a variety of factors, including the type of disease, the age, weight, sex, medical condition of the patient, the severity of the condition, the route of administration, and the particular compound employed. Thus, the dosage regimen may vary widely, but can be determined routinely using standard methods.

The amounts and dosage regimens administered to a subject will depend on a number of factors, such as the mode of administration, the nature of the condition being treated, the body weight of the subject being treated and the judgment of the prescribing physician.

The quantity of DNA included within therapeutically active formulations according to the present invention is an effective amount for treating the disease or condition. Determination of an effective amount is well within the capability of those skilled in the art, especially in light of the detailed disclosure provided herein. Generally, an efficacious or effective amount of an agent is determined by first administering a low dose of the agent(s) and then incrementally increasing the administered dose or dosages until a desired effect (e.g., reduce or eliminate symptoms associated with viral infection or autoimmune disease) is observed in the treated subject, with minimal or acceptable toxic side effects. Applicable methods for determining an appropriate dose and dosing schedule for administration of a pharmaceutical composition of the present invention are described, for example, in Goodman and Gilman's The Pharmacological Basis of Therapeutics, Goodman et al., eds., 11th Edition, McGraw-Hill 2005, and Remington: The Science and Practice of Pharmacy, 20th and 21st Editions, Gennaro and University of the Sciences in Philadelphia, Eds., Lippencott Williams & Wilkins (2003 and 2005), each of which is hereby incorporated by reference.

In certain embodiments, the pharmaceutical composition is administered once daily; in other embodiments, the pharmaceutical composition is administered twice daily; in yet other embodiments, the pharmaceutical composition is administered once every two days, once every three days, once every four days, once every five days, once every six days, once every seven days, once every two weeks, once every three weeks, once every four weeks, once every two months, once every six months, or once per year. The dosing interval can be adjusted according to the needs of individual patients. For longer intervals of administration, extended release or depot formulations can be used.

In some embodiments, several divided dosages, as well as staggered dosages, can be administered daily or sequentially, or the dose can be continuously infused, or can be a bolus injection. Further, the dosages of the compound(s) of the disclosure can be proportionally increased or decreased as indicated by the exigencies of the therapeutic or prophylactic situation.

In some embodiments, the present disclosure also relates to methods for administration of the pharmaceutical compositions described herein using a prime-boost regimen. The term of "prime-boost" refers to the successive administrations of two different immunogenic or immunological composition types having at least one immunogen in common. The priming administration (priming) is the administration of a first immunogenic or immunological composition type and may comprise one, two or more administrations. The boost administration is the administration of a second immunogenic or immunological composition type and may comprise one, two or more administrations, and, for instance, may comprise or consist essentially of annual administrations. The "boost" may be administered from about 2 weeks to about 32 weeks after the "priming", or from about 4 to about 30 weeks after the priming, or from about 8 to about 28 weeks after the priming, advantageously from about 16 to about 24 weeks after the priming, and more advantageously, about 24 weeks after the priming.

The pharmaceutical compositions described herein can be used to treat diseases and disease conditions that are acute, and may also be used for treatment of chronic conditions. In certain embodiments, the pharmaceutical composition of the invention are administered for time periods exceeding two weeks, three weeks, one month, two months, three months, four months, five months, six months, one year, two years, three years, four years, or five years, ten years, or fifteen years; or for example, any time period range in days, months or years in which the low end of the range is any time period between 14 days and 15 years and the upper end of the range is between 15 days and 20 years (e.g., 4 weeks and 15 years, 6 months and 20 years). In some cases, it may be advantageous for the pharmaceutical composition of the invention to be administered for the remainder of the patient's life. In preferred embodiments, the patient is monitored to check the progression of the disease or disorder, and the dose is adjusted accordingly. In preferred embodiments, treatment according to the invention is effective for at least two weeks, three weeks, one month, two months, three months, four months, five months, six months, one year, two years, three years, four years, or five years, ten years, fifteen years, twenty years, or for the remainder of the subject's life.

Combination Therapy

According to embodiments of the disclosure, the pharmaceutical compositions described herein may be administered with one or more additional therapeutic agents. Various combination therapies contemplated by the present invention are described throughout.

In certain embodiments, any of the additional therapeutic agents is administered chronologically after or simultaneously with the DNA vaccine. In certain embodiments, the additional therapeutic agent is administered 1 hour, 2 hours, 3 hours, 4 hours, 5 hours, 6 hours, 7 hours, 8 hours, 9 hours, 10 hours, 11 hours, 12 hours, 1 day, 2 days, 3 days, 4 days, 5 days, 6 days, 7 days, 8 days, 9, days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 1 month, or any combination thereof, before the DNA vaccine or immunogenic compositions is administered. In certain embodiments, the additional therapeutic agent is administered 1 hour, 2 hours, 3 hours, 4 hours, 5 hours, 6 hours, 7 hours, 8 hours, 9 hours, 10 hours, 11 hours, 12 hours, 1 day, 2 days, 3 days, 4 days, 5 days, 6 days, 7 days, 8 days, 9, days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 1 month, or any combination thereof, after the DNA vaccine or immunogenic compositions is administered.

Adjuvants

In a further embodiment, the method further comprises administering an adjuvant to the subject. Administration may be either prior to, simultaneously with, or after treatment with the DNA vaccine or immunogenic compositions described herein.

Effective vaccine or immunogenic compositions described herein may include a strong adjuvant to initiate an immune response.

In certain embodiments, the adjuvant is selected from the group consisting of poly-ICLC, 1018 ISS, aluminum salts, Amplivax. AS15, BCG, CP-870,893, CpG7909, CyaA, GM-CSF, IC30, IC31, Imiquimod, ImuFact 1MP321, IS Patch, ISS, ISCOMATRIX, JuvImmune, LipoVac, monophosphoryf lipid A, Montanide IMS 1312, Montanide ISA 206, Montanide ISA 50V, Montanide ISA-51, OK-432, OM-174, OM-197-MP-EC, ONTAK, PEPTEL, vector system, PLGA microparticles, resiquimod, S L172, Virosomes and other Virus-like particles, YF-17D, VEGF trap, R848, beta-gluean, Pam3Cys, acrylic or methacrylic polymers, copolymers of maleic anhydride and Aquila's QS21 stimulon As described herein, poly-ICLC, an agonist of TLR3 and the RNA helicase-domains of MDA5 and RIG3, has shown several desirable properties for a vaccine or immunogenic composition adjuvant. These properties include the induction of local and systemic activation of immune cells in vivo, production of stimulatory chemokines and cytokines, and stimulation of antigen-presentation by DCs. Furthermore, poly-ICLC can induce durable CD4+ and CD 8+ responses in humans. Importantly, striking similarities in the upregulation of transcriptional and signal transduction pathways were seen in subjects vaccinated with poly-ICLC and in volunteers who had received the highly effective, replication-competent yellow fever vaccine. Furthermore, >90% of ovarian carcinoma patients immunized with poly-ICLC in combination with a NY-ESO-1 peptide vaccine (in addition to Montanide) showed induction of CD4+ and CD8+ T cell, as well as antibody responses to the peptide in a recent phase 1 study. At the same time, poly-ICLC has been extensively tested in more than 25 clinical trials to date and exhibited a relatively benign toxicity profile. In addition to a powerful and specific immunogen the neoantigen vaccines of the present disclosure may be combined with an adjuvant (e.g., poly-ICLC). Without being bound by theory, these neoantigens are expected to bypass central thymic tolerance (thus allowing stronger anti-tumor T cell response), while reducing the potential for autoimmunity (e.g., by avoiding targeting of normal self-antigens). An effective immune response advantageously includes a strong adjuvant to activate the immune system (Speiser and Romero, Molecularly defined vaccines for cancer immunotherapy, and protective T cell immunity Seminars in Immunol 22: 144 (2010)). For example, Toll-like receptors (TLRs) have emerged as powerful sensors of microbial and viral pathogen "danger signals", effectively inducing the innate immune system, and in turn, the adaptive immune system (Bhardwaj and Gnjatic, Cancer J. 16:382-391 (2010)). Among the TLR agonists, poly-ICLC (a synthetic double-stranded RNA mimic) is one of the most potent activators of myeloid-derived dendritic cells. In a human volunteer study, poly-ICLC has been shown to be safe and to induce a gene expression profile in peripheral blood cells comparable to that induced by one of the most potent live attenuated viral vaccines, the yellow fever vaccine YF-17D (Caskey et al, Synthetic double-stranded RNA induces innate immune responses similar to a live viral vaccine in humans J Exp Med 208:2357 (2011)). In other embodiments, other adjuvants described herein are envisioned. For instance oil-in-water, water-in-oil or multiphasic W/O/W; see, e.g., U.S. Pat. No. 7,608,279 and Aucouturier et al, Vaccine 19 (2001), 2666-2672, and documents cited therein.

A combination of any one or more (e.g. 1, 2, 3, 4, 5 or more) adjuvants can be used in combination with the DNA vaccine or immunogenic compositions described herein.

In some embodiments, the pharmaceutical composition comprising a first plasmid encoding one or a plurality of neoantigens and a second and/or third and/or fourth plasmid, each second, third or fourth plasmid comprising a nucleic acid sequence encoding a cytokine or functional fragment thereof.

Checkpoint Inhibitors

In a further embodiment, the method further comprises administering a checkpoint inhibitor to the subject. Administration may be either prior to, simultaneously with, or after treatment with the DNA vaccine or immunogenic compositions described herein.

Immune checkpoints regulate T cell function in the immune system. T cells play a central role in cell-mediated immunity. Checkpoint proteins interact with specific ligands which send a signal into the T cell and essentially switch off or inhibit T cell function. Cancer cells take advantage of this system by driving high levels of expression of checkpoint proteins on their surface which results in control of the T cells expressing checkpoint proteins on the surface of T cells that enter the tumor microenvironment, thus suppressing the anticancer immune response. As such, inhibition of checkpoint proteins would result in restoration of T cell function and an immune response to the cancer cells.

Checkpoint inhibitors include any agent that blocks or inhibits the inhibitory pathways of the immune system. Such inhibitors may include small molecule inhibitors or may include antibodies, or antigen binding fragments thereof, that bind to and block or inhibit immune checkpoint receptors or antibodies that bind to and block or inhibit immune checkpoint receptor ligands. Illustrative checkpoint molecules that may be targeted for blocking or inhibition include, but are not limited to, CTLA-4, PDL1, PDL2, PD1, B7-H3, B7-H4, BTLA, HVEM, GAL9, LAG3, TIM3, VISTA, KIR, 2B4 (belongs to the CD2 family of molecules and is expressed on all NK, γδ, and memory CD8+ (αβ) T cells), CD160 (also referred to as BY55), CGEN-15049, CHK 1 and CHK2 kinases, A2aR and various B-7 family ligands. B7 family ligands include, but are not limited to, B7-1, B7-2, B7-DC, B7-H1, B7-H2, B7-H3, B7-H4, B7-H5, B7-H6 and B7-H7. Checkpoint inhibitors include antibodies, or antigen binding fragments thereof, other binding proteins, biologic therapeutics or small molecules, that bind to and block or inhibit the activity of one or more of CTLA-4, PDL1, PDL2, PD1, BTLA, HVEM, TIM3, GAL9, LAG3, VISTA, KIR, 2B4, CD 160 and CGEN-15049. Illustrative immune checkpoint inhibitors include Tremelimumab (CTLA-4 blocking antibody), anti-OX40, PD-L1 monoclonal Antibody (Anti-B7-H1; MEDI4736), MK-3475 (PD-1 blocker), Nivolumab (anti-PD1 antibody), CT-011 (anti-PD1 antibody), BY55 monoclonal antibody, AMP224 (anti-PDL1 antibody), BMS-936559 (anti-PDL1 antibody), MPLDL3280A (anti-PDL1 antibody), MSB0010718C (anti-PDL1 antibody) and Yervoy®/ipilimumab (anti-CTLA-4 checkpoint inhibitor). Checkpoint protein ligands include, but are not limited to PD-L1, PD-L2, B7-H3, B7-H4, CD28, CD86 and TIM-3.

In some embodiments, the present disclosure covers the use of a specific class of checkpoint inhibitor are drugs that block the interaction between immune checkpoint receptor programmed cell death protein 1 (PD-1) and its ligand PDL-1. See A. Mullard, "New checkpoint inhibitors ride the immunotherapy tsunami," Nature Reviews: Drug Discovery (2013), 12:489-492. PD-1 is expressed on and regulates the activity of T-cells. Specifically, when PD-1 is unbound to PDL-1, the T-cells can engage and kill target cells. However, when PD-1 is bound to PDL-1 it causes the T-cells to cease engaging and killing target cells. Furthermore, unlike other checkpoints, PD-1 acts proximately such the PDLs are overexpresseed directly on cancer cells which leads to increased binding to the PD-1 expressing T-cells.

One aspect of the present disclosure provides checkpoint inhibitors which are antibodies that can act as agonists of PD-1, thereby modulating immune responses regulated by PD-1. In some embodiments, the anti-PD-1 antibodies can be antigen-binding fragments. Anti-PD-1 antibodies disclosed herein are able to bind to human PD-1 and agonize the activity of PD-1, thereby inhibiting the function of immune cells expressing PD-1.

In some embodiments, the present disclosure covers the use of a specific class of checkpoint inhibitor are drugs that inhibit CTLA-4. Suitable anti-CTLA4 antagonist agents for use in the methods of the invention, include, without limitation, anti-CTLA4 antibodies, human anti-CTLA4 antibodies, mouse anti-CTLA4 antibodies, mammalian anti-CTLA4 antibodies, humanized anti-CTLA4 antibodies, monoclonal anti-CTLA4 antibodies, polyclonal anti-CTLA4 antibodies, chimeric anti-CTLA4 antibodies, MDX-010 (ipilimumab), tremelimumab, anti-CD28 antibodies, anti-CTLA4 adnectins, anti-CTLA4 domain antibodies, single chain anti-CTLA4 fragments, heavy chain anti-CTLA4 fragments, light chain anti-CTLA4 fragments, inhibitors of CTLA4 that agonize the co-stimulatory pathway, the antibodies disclosed in PCT Publication No. WO 2001/014424, the antibodies disclosed in PCT Publication No. WO 2004/035607, the antibodies disclosed in U.S. Publication No. 2005/0201994, and the antibodies disclosed in granted European Patent No. EP 1212422 B1. Additional CTLA-4 antibodies are described in U.S. Pat. Nos. 5,811,097, 5,855,887, 6,051,227, and 6,984,720; in PCT Publication Nos. WO 01/14424 and WO 00/37504; and in U.S. Publication Nos. 2002/0039581 and 2002/086014. Other anti-CTLA-4 antibodies that can be used in a method of the present invention include, for example, those disclosed in: WO 98/42752; U.S. Pat. Nos. 6,682,736 and 6,207,156; Hurwitz et al, Proc. Natl. Acad. Sci. USA, 95(17):10067-10071 (1998); Camacho et al, J. Clin. Oncology, 22(145): Abstract No. 2505 (2004) (antibody CP-675206); Mokyr et al, Cancer Res., 58:5301-5304 (1998), and U.S. Pat. Nos. 5,977,318, 6,682,736, 7,109,003, and 7,132,281.

Additional anti-CTLA4 antagonists include, but are not limited to, the following: any inhibitor that is capable of disrupting the ability of CD28 antigen to bind to its cognate ligand, to inhibit the ability of CTLA4 to bind to its cognate ligand, to augment T cell responses via the co-stimulatory pathway, to disrupt the ability of B7 to bind to CD28 and/or CTLA4, to disrupt the ability of B7 to activate the co-stimulatory pathway, to disrupt the ability of CD80 to bind to CD28 and/or CTLA4, to disrupt the ability of CD80 to activate the co-stimulatory pathway, to disrupt the ability of CD86 to bind to CD28 and/or CTLA4, to disrupt the ability of CD86 to activate the co-stimulatory pathway, and to disrupt the co-stimulatory pathway, in general from being activated. This necessarily includes small molecule inhibitors of CD28, CD80, CD86, CTLA4, among other members of the co-stimulatory pathway; antibodies directed to CD28, CD80, CD86, CTLA4, among other members of the co-stimulatory pathway; antisense molecules directed against CD28, CD80, CD86, CTLA4, among other members of the co-stimulatory pathway; adnectins directed against CD28, CD80, CD86, CTLA4, among other members of the co-stimulatory pathway, RNAi inhibitors (both single and double stranded) of CD28, CD80, CD86, CTLA4, among other members of the co-stimulatory pathway, among other anti-CTLA4 antagonists.

In some embodiments, the present disclosure covers the use of a specific class of checkpoint inhibitor drugs that inhibit TIM-3. Blocking the activation of TΓM-3 by a ligand, results in an increase in Th1 cell activation. Furthermore, TIM-3 has been identified as an important inhibitory receptor expressed by exhausted CD8+ T cells. TIM-3 has also been reported as a key regulator of nucleic acid mediated antitumor immunity. In one example, TIM-3 has been shown to be upregulated on tumor-associated dendritic cells (TADCs).

The combination of a check point inhibitor and DNA vaccine or immunogenic composition described herein can be more effective in treating cancer in some subjects and/or can initiate, enable, increase, enhance or prolong the activity and/or number of immune cells (including T cells, B cells, NK cells and/or others) or convey a medically beneficial response by a tumor (including regression, necrosis or elimination thereof).

A combination of any one or more (e.g. 1, 2, 3, 4, 5 or more) checkpoint inhibitors can be used in combination with the DNA vaccine or immunogenic compositions described herein.

Immunostimulatory Agents

In a further embodiment, the method further comprises administering one or more immunostimulatory agents to the subject. Administration may be either prior to, simultaneously with, or after treatment with the DNA vaccine or immunogenic compositions described herein.

In some embodiments, the present invention is directed to the use of immunostimulatory agents, including T cell growth factors and interleukins. Immunostimulatory agents are substances (drugs and nutrients) that stimulate the immune system by inducing activation or increasing activity of any of its components. Immunostimulants include bacterial vaccines, colony stimulating factors, interferons, interleukins, other immunostimulants, therapeutic vaccines, vaccine combinations and viral vaccines.

T cell growth factors are proteins which stimulate the proliferation of T cells. Examples of T cell growth factors include 11-2, IL-7, IL-15, IL-17, IL-21 and IL-33.

Interleukins are a group of cytokines that were first seen to be expressed by white blood cells. The function of the immune system depends in a large part on interleukins, and rare deficiencies of a number of them have been described, all featuring autoimmune diseases or immune deficiency. The majority of interleukins are synthesized by helper CD4 T lymphocytes, as well as through monocytes, macrophages, and endothelial cells. They promote the development and differentiation of T and B lymphocytes, and hematopoietic cells. Examples of interleukins include IL-1, IL-2, IL-3, IL-4, IL-5, IL-6, IL-7, IL-8, IL-9, IL-10, IL-11, IL-12, IL-13, IL-14, IL-15 and IL-17.

In some embodiments, the interleukin is IL-12.

In some embodiments, the DNA plasmids are delivered with immunostimulatory agents that are genes for proteins which further enhance the immune response against such target proteins. Examples of such genes are those which encode other cytokines and lymphokines such as alpha-interferon, gamma-interferon, platelet derived growth factor (PDGF), TNF α, TNFβ, GM-CSF, epidermal growth factor (EGF), IL-1, IL-2, IL-4, IL-5, IL-6, IL-10, IL-12, IL-18, MEW, CD80, CD86 and IL-15 including IL-15 having the signal sequence deleted and optionally including the signal peptide from IgE. Other genes which may be useful include those encoding: MCP-1, MIP-1α, MIP-1p, IL-8, RANTES, L-selectin, P-selectin, E-selectin, CD34, GlyCAM-1, MadCAM-1, LFA-1, VLA-1, Mac-1, p150.95, PECAM, ICAM-1, ICAM-2, ICAM-3, CD2, LFA-3, M-CSF, G-CSF, IL-4, mutant forms of IL-18, CD40, CD40L, vascular growth factor, fibroblast growth factor, IL-7, nerve growth factor, vascular endothelial growth factor, Fas, TNF receptor, Fit, Apo-1, p55, WSL-1, DR3, TRAMP, Apo-3, AIR, LARD, NGRF, DR4, DR5, KILLER, TRAIL-R2, TRICK2, DR6, Caspase ICE, Fos, c-jun, Sp-1, Ap-1, Ap-2, p38, p65Rel, MyD88, IRAK, TRAF6, IkB, Inactive NIK, SAP K, SAP-1, JNK, interferon response genes, NFkB, Bax, TRAIL, TRAILrec, TRAILrecDRC5, TRAIL-R3, TRAIL-R4, RANK, RANK LIGAND, Ox40, Ox40 LIGAND, NKG2D, MICA, MICB, NKG2A, NKG2B, NKG2C, NKG2E, NKG2F, TAP1, TAP2 and functional fragments thereof.

A combination of any one or more (e.g. 1, 2, 3, 4, 5 or more) immunostimulatory agents can be used in combination with the DNA vaccine or immunogenic compositions described herein.

Chemotherapeutic Agents

In a further embodiment, the method further comprises administering a chemotherapeutic agent, targeted therapy or radiation to the subject. Administration may be either prior to, simultaneously with, or after treatment with the DNA vaccine or immunogenic compositions described herein.

Examples of cancer therapeutic agents or chemotherapeutic agents include alkylating agents such as thiotepa and cyclophosphamide (CYTOXAN); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; antimetabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK.R™; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxoids, e.g. paclitaxel (TAXOL™, Bristol-Myers Squibb Oncology, Princeton, N.J.) and doxetaxel (TAXOTEPvE™, Pvhne-Poulenc Rorer, Antony, France); chlorambucil; gemcitabine; 6-thioguanine; mercaptopurine; methotrexate; platinum analogs such as cisplatin and carboplatin; vinblastine; trastuzumab, docetaxel, platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylomithine (DMFO); retinoic acid derivatives such as Targretin™ (bexarotene), Panretin™ (alitretinoin); ONTAKT™ (denileukin diftitox); esperamicins; capecitabine; and pharmaceutically acceptable salts, acids or derivatives of any of the above. Also included in this definition are anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY 1 17018, onapristone, and toremifene (Fareston); and anti-androgens such as flutamide, nilutamide, bicalutamide, leuprolide, and goserelin; and pharmaceutically acceptable salts, acids or derivatives of any of the above. Further cancer therapeutic agents include sorafenib and other protein kinase inhibitors such as afatinib, axitinib, bevacizumab, cetuximab, crizotinib, dasatinib, erlotinib, fostamatinib, gefitinib, imatinib, lapatinib, lenvatinib, mubritinib, nilotinib, panitumumab, pazopanib, pegaptanib, ranibizumab, ruxolitinib, trastuzumab, vandetanib, vemurafenib, and sunitinib; sirolimus (rapamycin), everolimus and other mTOR inhibitors.

Examples of additional chemotherapeutic agents include topoisomerase I inhibitors (e.g., irinotecan, topotecan, camptothecin and analogs or metabolites thereof, and doxorubicin); topoisomerase II inhibitors (e.g., etoposide, teniposide, and daunorubicin); alkylating agents (e.g., melphalan, chlorambucil, busulfan, thiotepa, ifosfamide, carmustine, lomustine, semustine, streptozocin, decarbazine, methotrexate, mitomycin C, and cyclophosphamide); DNA intercalators (e.g., cisplatin, oxaliplatin, and carboplatin); DNA intercalators and free radical generators such as bleomycin; and nucleoside mimetics (e.g., 5-fluorouracil, capecitibine, gemcitabine, fludarabine, cytarabine, mercaptopurine, thioguanine, pentostatin, and hydroxyurea). Moreover, exemplary chemotherapeutic agents that disrupt cell replication include: paclitaxel, docetaxel, and related analogs; vincristine, vinblastin, and related analogs; thalidomide, lenalidomide, and related analogs (e.g., CC-5013 and CC-4047); protein tyrosine kinase inhibitors (e.g., imatinib mesylate and gefitinib); proteasome inhibitors (e.g., bortezomib); NF-κB inhibitors, including inhibitors of IκB kinase; antibodies which bind to proteins overexpressed in cancers and other inhibitors of proteins or enzymes known to be upregulated, over-expressed or activated in cancers, the inhibition of which downregulates cell replication.

A combination of any one or more (e.g. 1, 2, 3, 4, 5 or more) chemotherapeutic agents can be used in combination with the DNA vaccine or immunogenic compositions described herein.

In certain embodiments, the subject nucleic acid molecules, and compositions comprising the nucleic acid molecules, of the disclosure can be used alone.

Vaccines

In an exemplary embodiment, the present invention is directed to an immunogenic composition, e.g., a vaccine, composition comprising the nucleic acid molecules described herein, capable of raising an immune response, and in particular a specific T-cell response.

DNA vaccines are described in U.S. Pat. Nos. 5,593,972, 5,739,118, 5,817,637, 5,830,876, 5,962,428, 5,981,505, 5,580,859, 5,703,055, 5,676,594, and the priority applications cited therein, which are each incorporated herein by reference. In addition to the delivery protocols described in those applications, alternative methods of delivering DNA are described in U.S. Pat. Nos. 4,945,050 and 5,036,006, which are both incorporated herein by reference.

In certain embodiments, the vaccine composition comprises mutant neo-antigenic nucleic acid molecules as described herein (e.g. comprising a nucleic acid sequence comprising the formula: [(antigen expression domain 1)-(linker)-(antigen expression domain 2)-(linker)] n), corresponding to tumor specific neo-antigens identified by the methods described herein. A suitable vaccine will preferably contain a plurality of tumor specific neo-antigenic nucleic acid molecules. In an embodiment, the vaccine will include between about 1 to about 200 nucleic acid molecules, between about 2 to about 100 nucleic acid molecules, between about 2 to about 58 nucleic acid molecules, between about 2 to about 29 nucleic acid molecules. In certain embodiments, the vaccine will include about 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 nucleic acid molecules. In certain embodiments, the vaccine will include about 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 nucleic acid molecules. In certain embodiments, the vaccine will include about 41, 42, 43, 44, 45, 46, 47, 48, 49, 50, 51, 52, 53, 54, 55, 56, 57, 58, 59, 60, 61, 62, 63, 64, 65, 66, 67, 68, 69 or 70 nucleic acid molecules. In certain embodiments, the vaccine will include about 61, 62, 63, 64, 65, 66, 67, 68, 69, 70, 71, 72, 73, 74, 75, 76, 77, 78, 79, 80, 81, 82, 83, 84, 85, 86, 87, 88, 89 or 90 nucleic acid molecules. In certain embodiments, the vaccine will include about 81, 82, 83, 84, 85, 86, 87, 88, 89, 90, 91, 92, 93, 94, 95, 96, 97, 98, 99 or 100 nucleic acid molecules.

In certain embodiments, the vaccine composition is capable of enhancing a CD8+ T cell immune response in a subject. In some embodiments, enhancing the CD8+ T cell immune response comprises activating CD8+ T cells. In another embodiment, enhancing the CD8+ T cell immune response comprises expanding CD8+ T cells. In other embodiments, the vaccine composition is capable of raising a specific cytotoxic T-cells response and/or a specific helper T-cell response.

The vaccine composition can further comprise an adjuvant and/or a carrier.

Adjuvants are described herein, and are any substance whose admixture into the vaccine composition increases or otherwise modifies the immune response to the mutant peptide. Carriers are scaffold structures, for example a polypeptide or a polysaccharide, to which the neo-antigenic peptides, is capable of being associated. Optionally, adjuvants are conjugated covalently or non-covalently to the peptides or polypeptides of the invention.

The ability of an adjuvant to increase the immune response to an antigen is typically manifested by a significant increase in immune-mediated reaction, or reduction in disease symptoms. For example, an increase in humoral immunity is typically manifested by a significant increase in the titer of antibodies raised to the antigen, and an increase in T-cell activity is typically manifested in increased cell proliferation, or cellular cytotoxicity, or cytokine secretion. An adjuvant may also alter an immune response, for example, by changing a primarily humoral or Th2 response into a primarily cellular, or Th1 response. Suitable adjuvants are described herein.

A vaccine composition according to the present invention may comprise more than one different adjuvant. Furthermore, the invention encompasses a therapeutic composition comprising any adjuvant substance including any of the above or combinations thereof. It is also contemplated that the nucleic acid molecule, and the adjuvant can be administered separately in any appropriate sequence.

Cytotoxic T-cells (CTLs) recognize an antigen in the form of a peptide bound to an MHC molecule rather than the intact foreign antigen itself. The MHC molecule itself is located at the cell surface of an antigen presenting cell. Thus, an activation of CTLs is only possible if a trimeric complex of peptide antigen, MHC molecule, and APC is present. Therefore, in some embodiments the vaccine composition according to the present invention additionally contains at least one antigen presenting cell.

The antigen-presenting cell (or stimulator cell) typically has an MHC class I or II molecule on its surface, and In some embodiments is substantially incapable of itself loading the MHC class I or II molecule with the selected antigen.

Preferably, the antigen presenting cells are dendritic cells. In some embodiments, the dendritic cells are autologous to a subject. In some embodiments of the present invention the antigen presenting cell comprises an expression construct comprising the nucleic acid molecules of the present invention. The nucleic acid molecules are capable of transducing the dendritic cell, thus resulting in the presentation of a peptide and induction of immunity.

In one aspect, the disclosure features a method of making an individualized cancer vaccine for a subject suspected of having or diagnosed with a cancer, comprising identifying a plurality of mutations in a sample from the subject; analyzing the plurality of mutations to identify one or more neoantigen mutations; and producing, based on the identified subset, a personalized cancer vaccine.

In some embodiments, identifying comprises sequencing the cancer. Methods for carrying out sequencing are described herein.

In some embodiments, identifying comprises sequencing the cancer.

In another embodiment, analyzing further comprises determining one or more binding characteristics associated with the neoantigen mutation, the binding characteristics selected from the group consisting of binding of the subject-specific peptides to T-cell receptor, binding of the subject-specific peptides to a HLA protein of the subject and binding of the subject-specific peptides to transporter associated with antigen processing (TAP); and ranking, based on the determined characteristics, each of the neo-antigenic mutations.

In some embodiments, the method further comprises cloning nucleic acid sequences encoding the one or plurality of neoantigen mutations into a nucleic acid molecule.

In some embodiments, the nucleic acid molecule is a plasmid. In another embodiment, the nucleic acid molecule comprises a nucleic acid sequence of Formula I that is positioned within the multiple cloning site of a plasmid selected from the group consisting of selected from the group consisting of pGX4501, pGX4503, pGX 4504, pGX4505, and pGX4506. In some embodiments, the nucleic acid sequence of Formula I is positioned with the multiple cloning site of pGX4501. In some embodiments, the nucleic acid sequence of Formula I is positioned with the multiple cloning site of a plasmid selected from the group consisting of pGX4503. In some embodiments, the nucleic acid sequence of Formula I is positioned with the multiple cloning site of a plasmid selected from the group consisting of ppGX 4504. In some embodiments, the nucleic acid sequence of Formula I is positioned with the multiple cloning site of a plasmid selected from the group consisting of pGX4505. In some embodiments, the nucleic acid sequence of Formula I is positioned with the multiple cloning site of a plasmid selected from the group consisting of pGX4506. In some embodiments, the plasmid is pGX4505. In some embodiments, the plasmid comprises the backbone and linker sequence of pGX4505 with at least two or more AED nucleotide sequence encoding one or more neoantigens from a subject.

Kits

The present disclosure provides a kit comprising a pharmaceutical composition comprising one or a plurality of nucleic acid molecules as described herein. The components of the kit are preferably formulated in pharmaceutically acceptable carriers.

Also included in the kit are instructions for use in methods of treating cancer in a subject or enhancing a CD8+ T cell immune response in a subject.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Wei, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

Other embodiments are described in the following non-limiting Examples.

EXAMPLES

Example 1. Materials and Methods

The experiments carried out in the following Examples were performed using, but not limited to, the following materials and methods.

Animals and Cell Lines

C57Bl/6 mice were purchased from Jackson labs. TC1 and LLC tumors were generated by injecting 100,000 cells subcutaneously. ID8 tumors were generated by injecting 2 million cells intraperitoneally. Mice were treated by injecting 25 μg of DNA resuspended in 30 μL of water into the tibialis anterior muscle followed by electroporation with the CELLECTRA-3P device (Inovio Pharmaceuticals). For each immunization, mice were delivered two 0.1 Amp electric constant current square-wave pulses.

DNA and RNA Sequencing

The mouse exome and RNA sequencing were performed on Illumina HiSeq-2500 platform. The SureSelect Mouse All Exon Kit (Agilent Technologies, USA) was used. All samples generated greater 13 Gb of data, with greater than 98% of the exomes covered at ≥150×. Overall, 99% of the reads aligned to the mouse reference genome. Mapping quality for 80% of the aligned reads was ≥Q60. Duplicate % was low 4-6%. Somatic variant calling was performed using Strelka program v1.0.14. The identified somatic variants were further filtered and only passed and on-target variants were considered for further analysis.

The RNA sequencing was performed using TrueSeq RNA library prep kit v2 (Illumina, USA). All samples generated >100 million reads. Reads mapping to ribosomal and mitochondrial genome were removed before performing alignment. The reads were aligned using STAR (2.4.1) aligner. Overall 96-98% of the total pre-processed reads mapped to the reference gene model/genome. The gene expression was estimated using Cufflinks v2.2.1.

Neoepitopes were prioritized from non-synonymous coding missense and frameshift mutants, where the mutant allele expression >1 FPKM. MHC class I binding analysis was performed for all coding missense and frameshift mutations. For this 9-mer peptides were processed using NetMHCons v1.1 on the C57Bl/6 MHC alleles (H-2-Kb,H-2-Db). Peptides were further prioritized based on lower proteasomal processing score using NetChop3.1 (IEDB). Peptides showing a score ≥0.7 were selected. Peptides were scored for TAP binding and peptides having binding affinity <0.5 were prioritized.

Design of Neoantigen Vaccines

Figure 28:
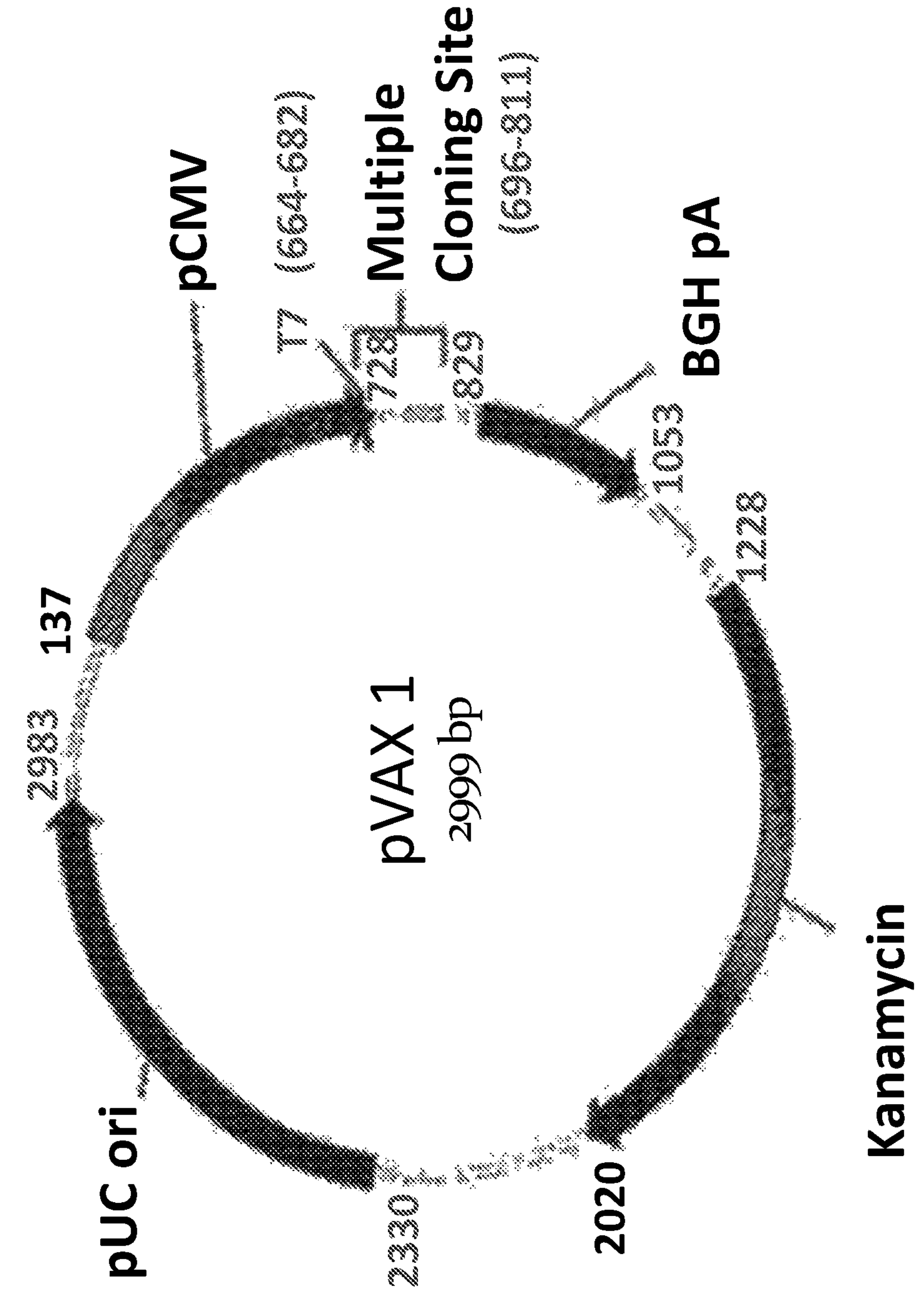
FIG. 28 is a map of the 2999 basepair backbone vector plasmid pVAX1 (Invitrogen, Carlsbad Calif.). The CMV promoter is located at bases 137-724. The T7 promoter/priming site is at bases 664-683. Multiple cloning sites are at bases 696-811. Bovine GH polyadenylation signal is at bases 829-1053. The Kanamycin resistance gene is at bases 1226-2020. The pUC origin is at bases 2320-2993.
Figure 29:
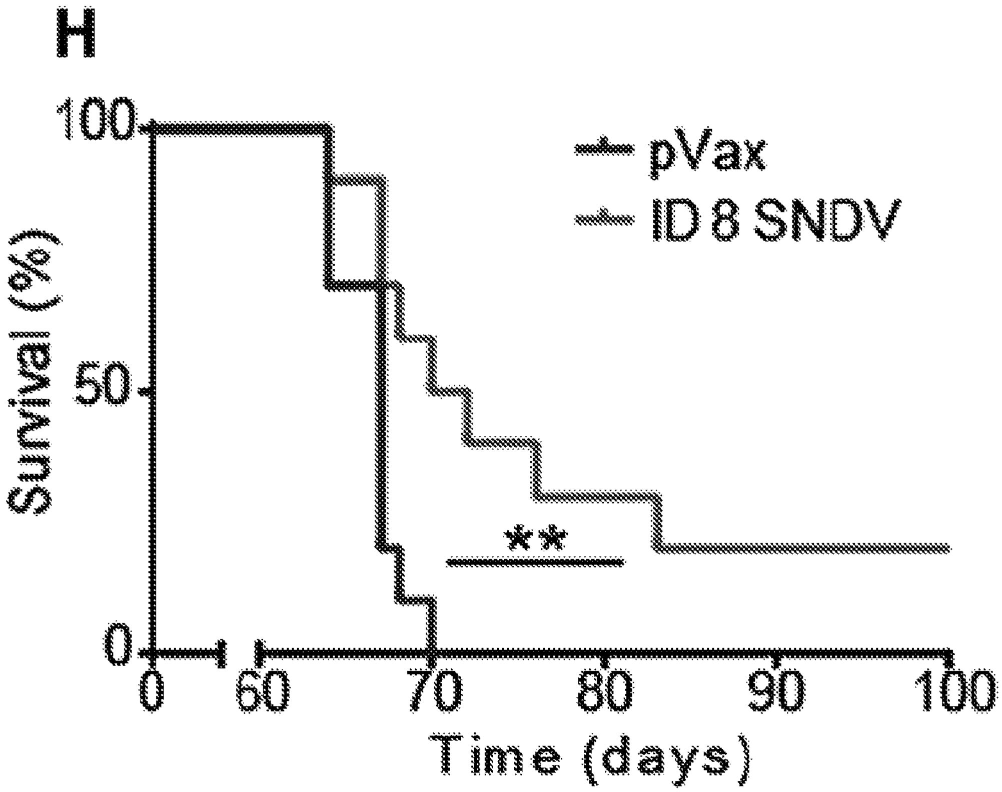
FIG. 29 depicts how the DNA neoantigen vaccine affects tumor growth. C57Bl/6 Mice were immunized three time at 3 week intervals with about 25 micrograms of ID8 plasmids 1 and 2 or pVAX without an insert and challenged with 2×106 ID8 tumor cells injected intraperitoneally 1 week following the final immunization.

Neoantigen vaccines were designed by selecting the predicted neoantigens from the DNA and RNA sequencing data obtained from the TC1, LLC and ID8 established tumors. Twelve epitopes were included, defined as the predicted sequence that would bind to H2-K(b) or H2-D(b), keeping the mutated amino acid in the central position and keeping 12 non-mutated amino acids flanking on each side. Twelve 33-mers were concatenated with furin cleavage sites and each construct was subcloned into the pVax1 plasmid (GenScript). FIG. 28 is a map of the 2999 basepair backbone vector plasmid pVAX1 (Invitrogen, Carlsbad Calif.). The CMV promoter is located at bases 137-724. The T7 promoter/priming site is at bases 664-683. Multiple cloning sites are at bases 696-811. Bovine GH polyadenylation signal is at bases 829-1053. The Kanamycin resistance gene is at bases 1226-2020. The pUC origin is at bases 2320-2993.

Flow Cytometry

BD LSRII flow cytometer (BD Biosciences) was used. Anti-mouse antibodies used were directly fluorochrome conjugated. The following antibodies were used: CD3e (17A2), CD4 (RM4-5), CD8b (YTS156.7.7), Interferon-γ (XMG1.2), TNFα (MP6-XT22), Interleukin-2 (JES6-5H4), and T-bet (4B10), all from Biolegend. Live/dead exclusion was done with Violet viability kit (Invitrogen). For the determination of intracellular cytokine production, 2 million splenocytes were cultured in the presence of peptides (5 μg/mL) derived from the corresponding wild-type or mutated neoantigen, Golgi-stop protein transport inhibitor (BD biosciences) and CD107a antibody (1D4B) for 4-5 hours prior to surface and intracellular staining. The neoantigen peptides consisted of 15mer peptides overlapping by 9 amino acids. These peptides spanned the entire 33mer used for immunization.

ELISPOT

Splenocytes were harvested and coincubated with each neoantigen derived peptide pool comprising 15-mers overlapping by 9 amino acids. After a 24 hour incubation, mouse interferon-γ ELISPOT was performed according to the manufacturer's instructions (Mabtech). Spots were read using an ImmunoSpot CTL reader, and spot forming units (SFU) were calculated by subtracting media alone wells from stimulated wells. Concanavalin A was used as a positive control (not shown) to ensure spot development.

T-Cell Expansion and Activation

Splenocytes were harvested from vaccinated mice and pulsed with 5 ug/ml of neoantigen specific peptides and 30 UI/ml of IL-2. Peptides and IL-2 (Peprotech) were refreshed with irradiated (4000 rad) splenocytes from naïve mice (1:3-10 T-cell:splenocyte ratio) once a week. 4-6 weeks after initiating the T-cell expansion, splenocytes were cocultured with the tumor cells for performing in vitro cytotoxicity experiments.

In Vitro Cytotoxicity 10,000 luciferase transduced TC1 or ID8 cells were plated per well in a 96-well plate. 18 hours later, the cells were coincubated for 24 hours with 10 or 50,000 in vitro expanded T-cells. Cytotoxicity was measured using CYTO-TOX-GLO Cytotoxicity Assay (Promega), according to the manufacturer's instructions. Cytotoxicity was reported as a ratio of luciferase expression in the T cell containing study wells divided by luciferase expression in the wells with tumor cells only (no T cells).

Statistical Analysis

Differences between the means of experimental groups were calculated using a two-tailed unpaired Student's t test. Comparisons between two groups with repeated measures were done using Two-way ANOVA. Error bars represent standard error of the mean. For mouse survival analysis, significance was determined using a Gehan-Brelow-Wilcoxon test. All statistical analyses were done using Graph Pad Prism 7.0. $p<0.05$ was considered statistically significant.

Figure 5:
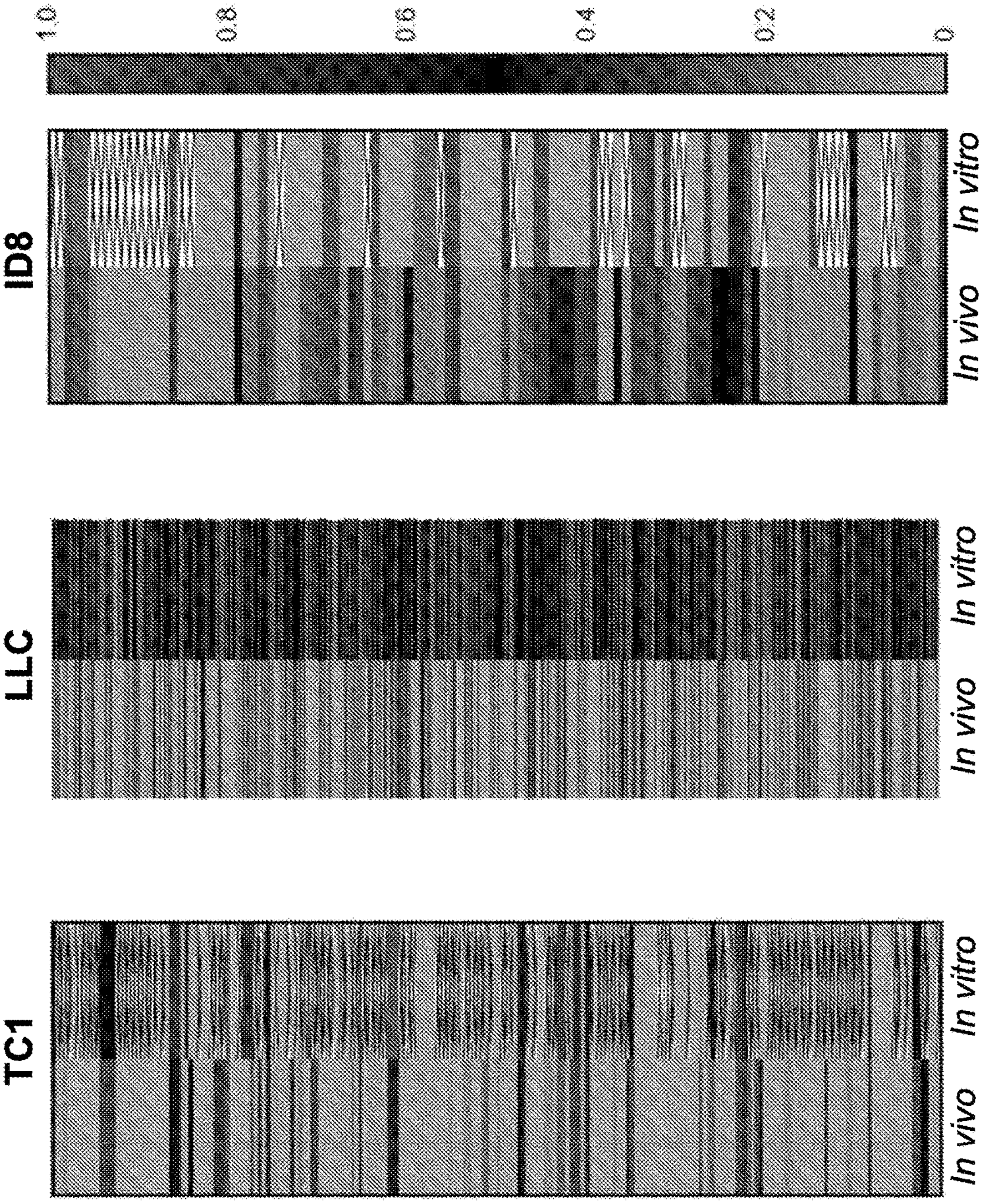
FIG. 5 shows allele frequency of neoantigen gene expression in tumor cell lines in vivo vs in vitro. Allele frequency of mutated genes in TC1, ID8 and LLC tumor cell lines growing in vivo (forming tumors in C57Bl/6) or in vitro (growing in 2D in cell culture flasks).
Figure 6A:
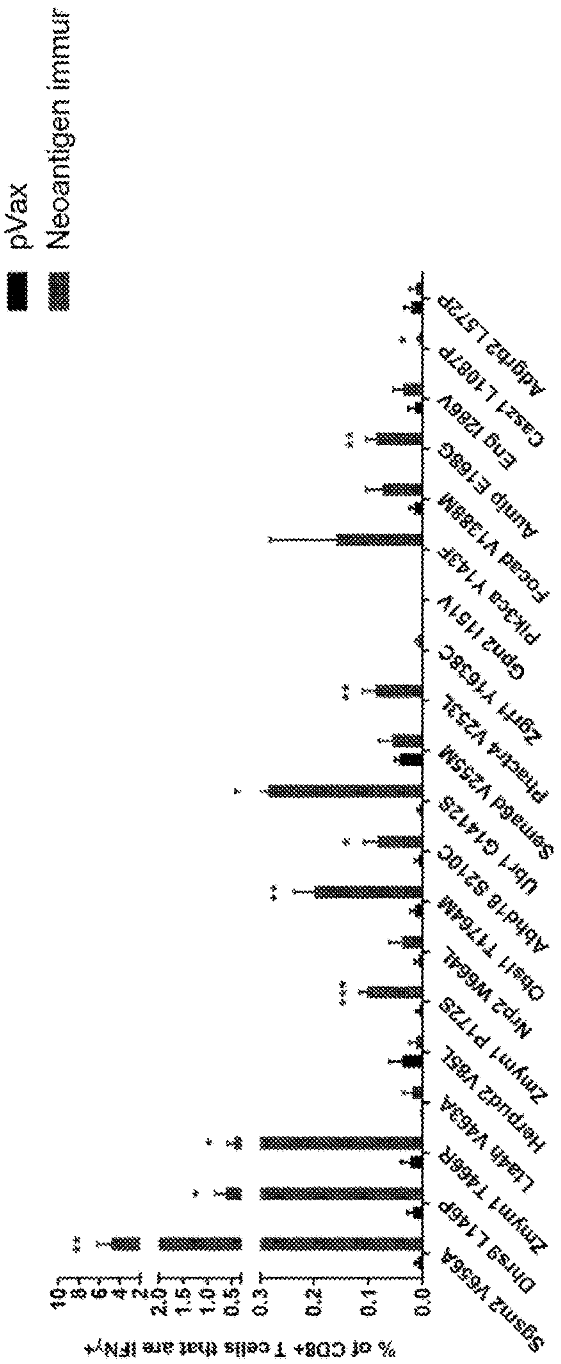
FIG. 6A-F shows CD4 and CD8 T cell responses to neoantigens.
Figure 6B:
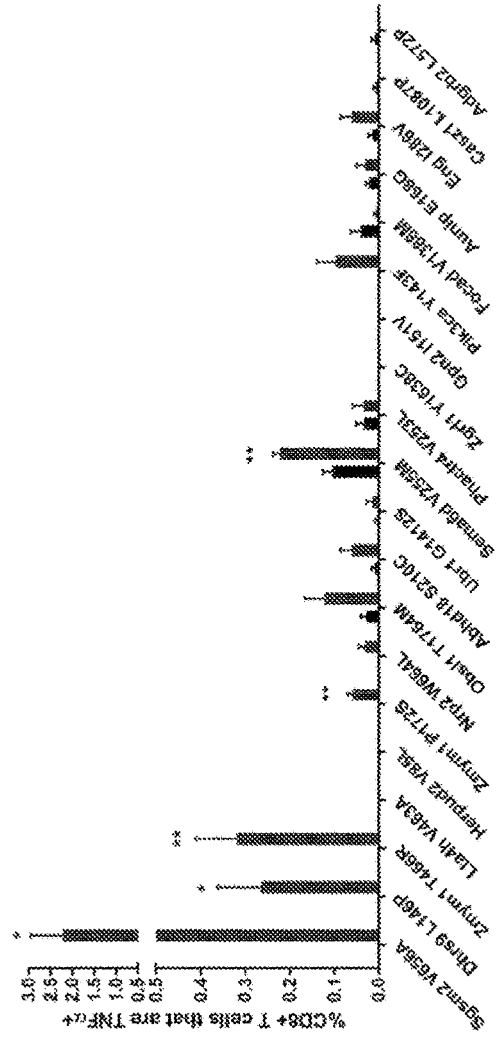
Figures 6C, 6D:
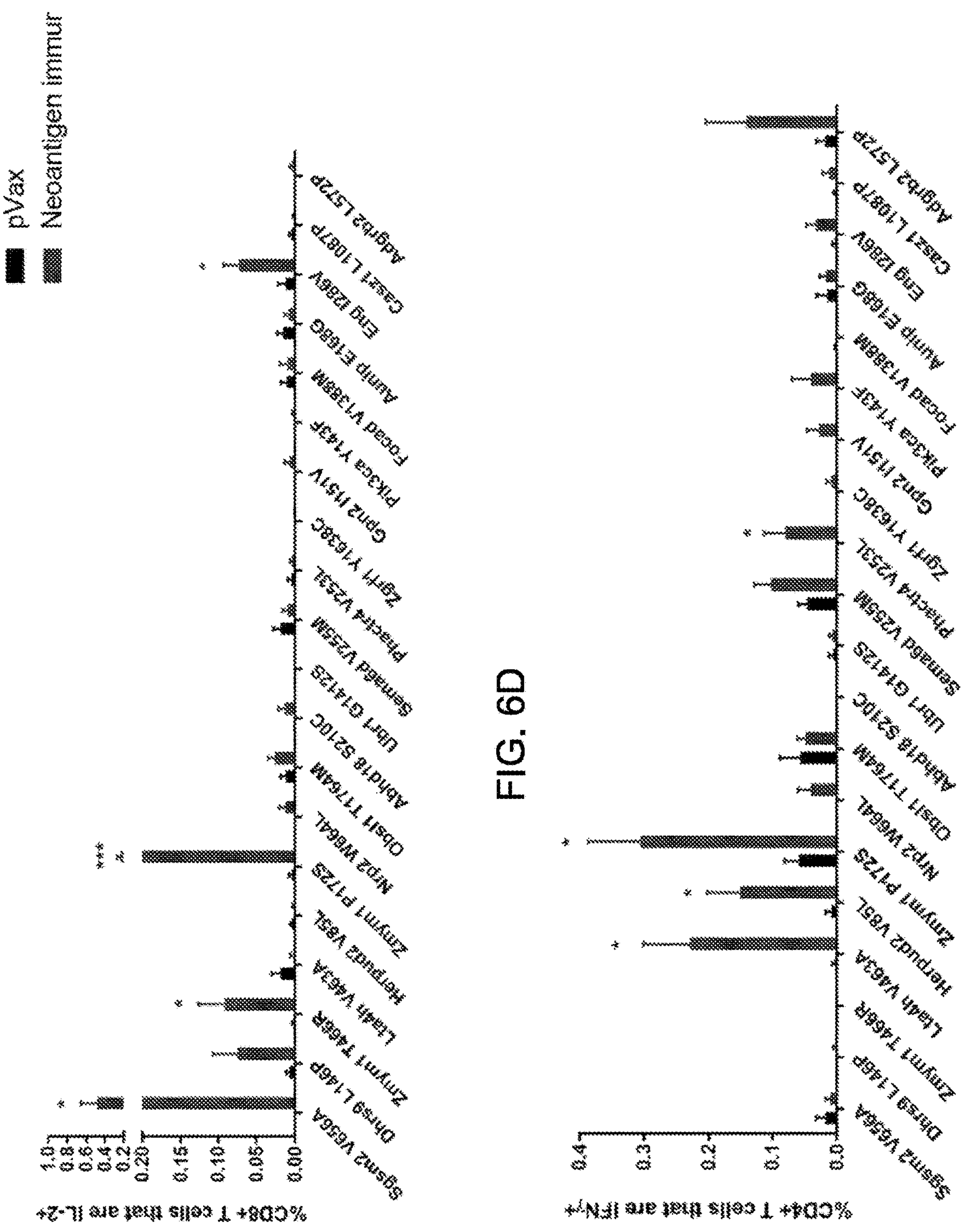
Figure 6E:
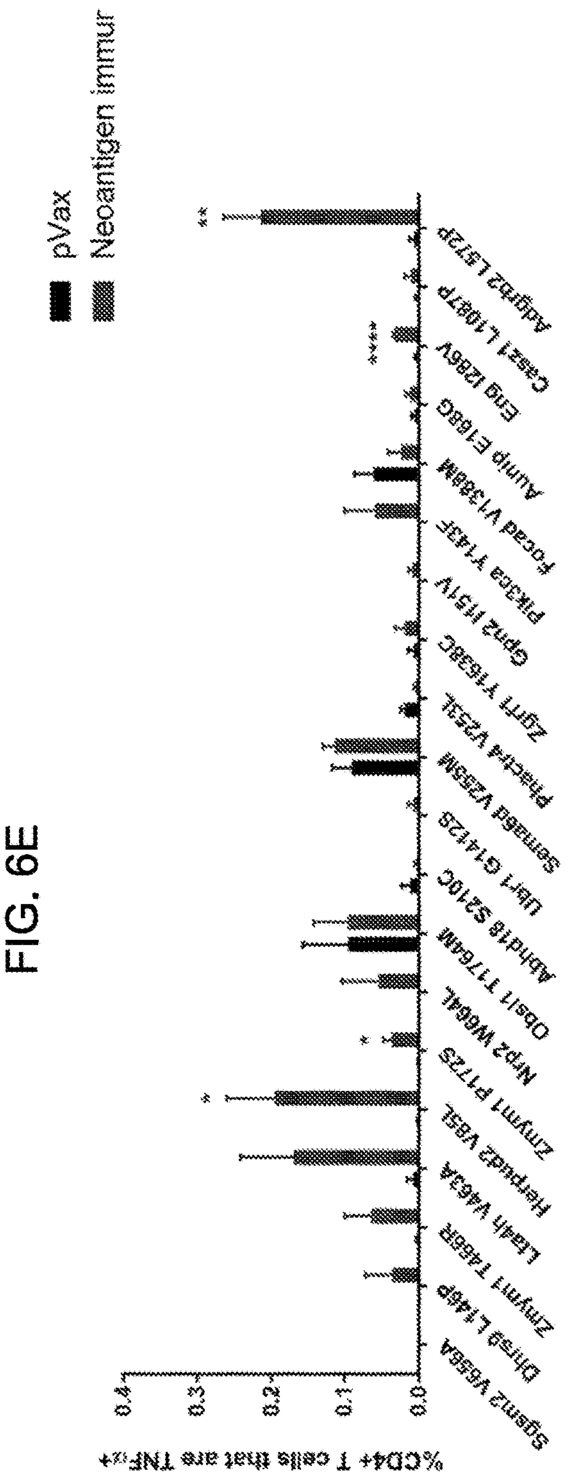
Figure 6F:
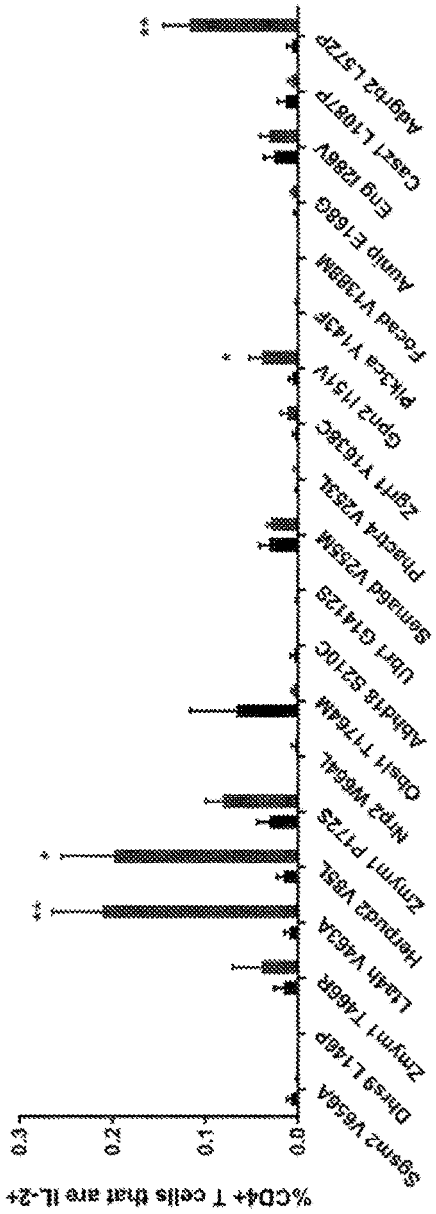

Example 2. DNA Vaccine Neo-Epitope Dodecamers Induce Frequent Immune Responses in Mice C57Bl/6 mice were implanted with three different tumor types: LLC and TC1, mouse lung tumor models, as well as ID8, a mouse ovarian tumor model. LLC and TC1 tumor cells were injected subcutaneously, and ID8 tumor cells into the peritoneum. After 3 weeks, tumors were harvested and DNA and RNA isolation was performed, as well as exome and RNA sequencing (FIG. 1A). DNA and RNA sequencing of cell lines cultured in vitro to the same cell lines implanted into mice (FIG. 5). Mutations that were expressed with an Alt allele depth in RNA-seq ≥1, a proteasomal cleavage score of ≥10, and a TAP processing score ≤0.5 (see methods for more detail) were included. As previously reported (13), a substantial proportion of mutations were differently expressed in tumors compared to cell lines, indicating differential expression of these genes in the context of the three-dimensional tumor microenvironment (FIG. 5).

Figure 1B:
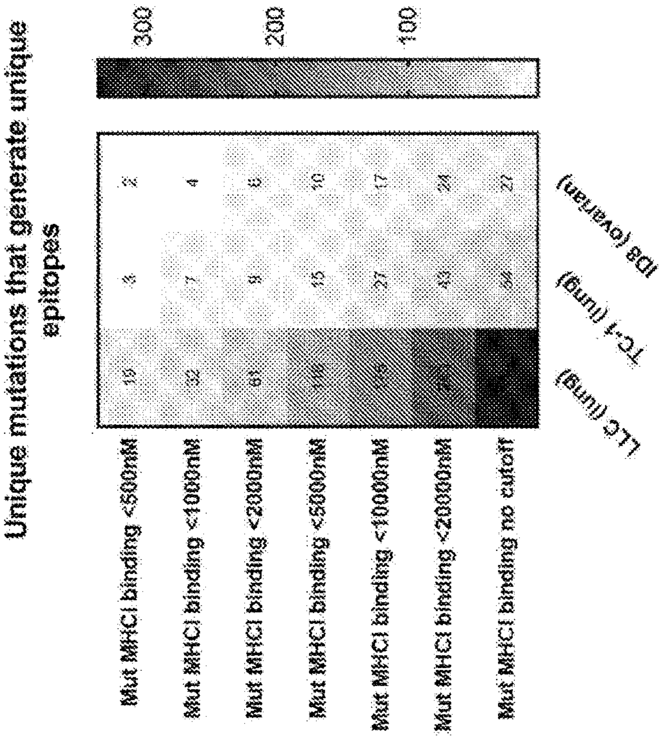
Figure 1C:
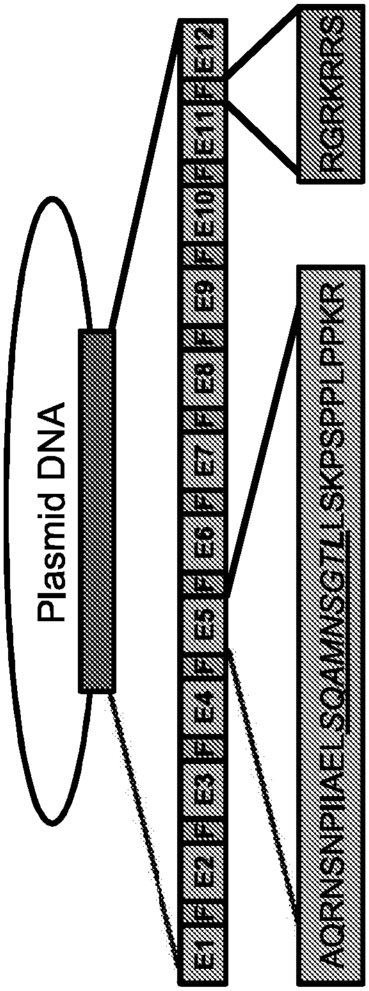

There were a total of 334, 54, and 27 non-synonymous, expressed mutations that generate unique neoepitopes in the LLC, TC1 and ID8 tumor models, respectively (FIG. 1B). Only 19, 3 and 2 epitopes from LLC, TC1 and ID8, respectively, had less than 500 nM binding affinity to H2-K(b) or H2-D(b), predicted using NetMHCons v1.1 (FIG. 1B). 36 epitopes were chosen from LLC, 24 epitopes were chosen from TC1 and 24 epitopes were chosen from ID8 to test for immunogenicity using a DNA vaccine platform. All of the highest affinity epitopes (<500 nM) were included, as well as some low affinity epitopes to assess the value of the MHCI prediction programs. 7 total DNA vaccine neo-epitope dodecamers were designed, which included 12 total 33-mer epitopes per plasmid, linked together with furin cleavage sites (FIG. 1C). The 33-mer epitopes were designed to include the predicted immunogenic 9mer surrounded by 12 amino acids on either side, in order to supply potential $CD4^+$ T cell responses for the epitope (FIG. 1C).

The seven plasmids are as follows:

(1) LLC Plasmid #1 is shown in FIG. 2A (nucleotide sequence) and FIG. 2B (amino acid sequence).

(2) LLC Plasmid #2 is shown in FIG. 2C (nucleotide sequence) and FIG. 2D (amino acid sequence).

(3) LLC Plasmid #3 is shown in FIG. 2E (nucleotide sequence) and FIG. 2F (amino acid sequence). LL Plasmid #3 binds to HLA proteins with an IC50 of less than about 500 nM.

(4) TC1 Plasmid #1 is shown in FIG. 3A (nucleotide sequence) and FIG. 3B (amino acid sequence).

(5) TC1 Plasmid #2 is shown in FIG. 3C (nucleotide sequence) and FIG. 3D (amino acid sequence).

(6) ID8 Plasmid #1 is shown in FIG. 4A (nucleotide sequence) and FIG. 4B (amino acid sequence).

(7) ID8 Plasmid #2 is shown in FIG. 4C (nucleotide sequence) and FIG. 4D (amino acid sequence).

Figure 1D:
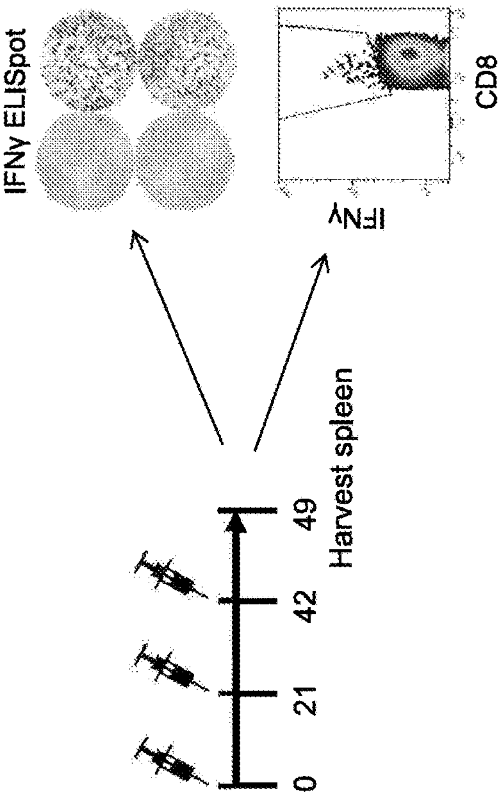
Figure 1E:
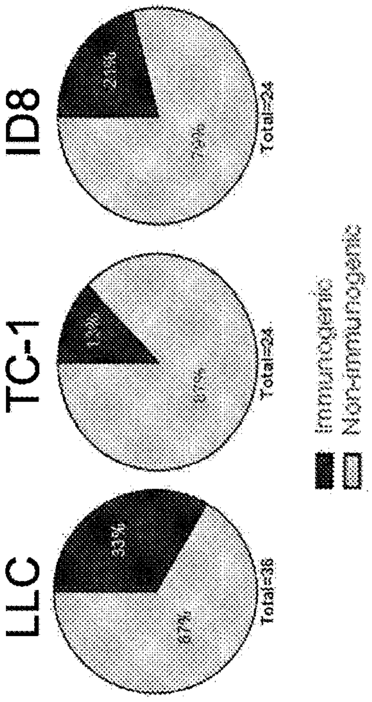

These 7 plasmids, containing 84 neo-epitopes total, were tested by immunizing C57Bl/6 mice with 25 μg of DNA followed by electroporation with the CELLECTRA-3P device, at 3-week intervals for a total of three immunizations (FIG. 1D). Mice were sacrificed one week following the final immunization, and spleens were harvested for both IFNγ ELISpot analysis, as well as intracellular cytokine staining to identify $CD4^+$ versus $CD8^+$ reactive epitopes (FIG. 1D). The threshold for immunoreactivity was set to be ≥30 spot forming units per million splenocytes by IFNγ ELISpot against the peptides corresponding to the mutated peptide. In addition, epitopes classified as immunogenic required responses to the mutant peptide that were statistically significantly higher than those induced by mice immunized with control pVax plasmid. Using these criteria, 12/36 epitopes were identified from the LLC model, 3/24 epitopes were identified from the TC1 tumor model, and 5/24 epitopes were identified from the ID8 model that were immunogenic when delivered using DNA vaccines (FIG. 1E). Overall, 24% (20/84) of epitopes generated immune responses, which is similar to what has been reported for RNA and SLP vaccines in pre-clinical studies without selection for high affinity MHCI binding.

Figure 7A:
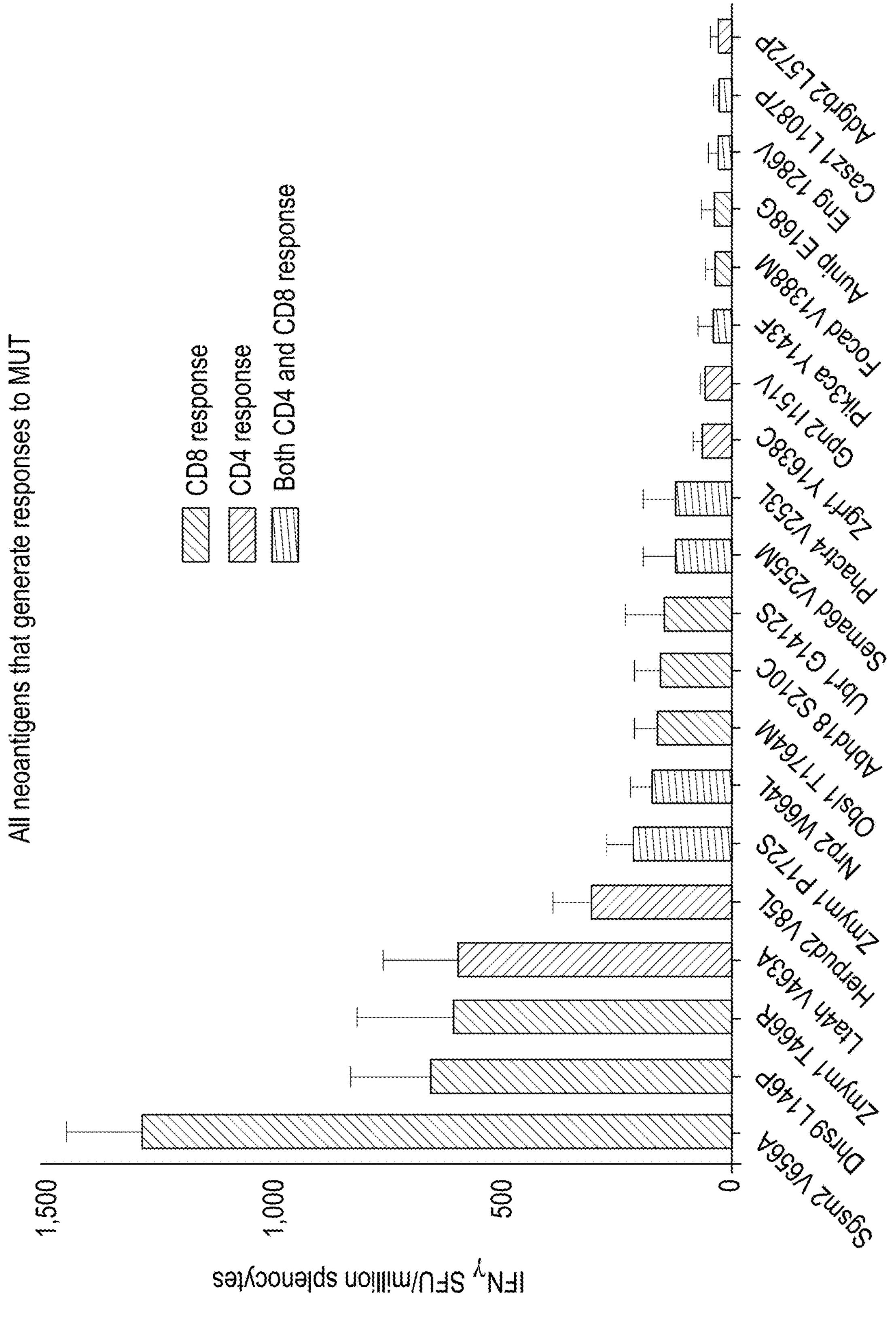
FIG. 7A-FIG. 7E shows DNA vaccines generate predominantly CD8 T cell responses to neoantigens.
Figure 7B:
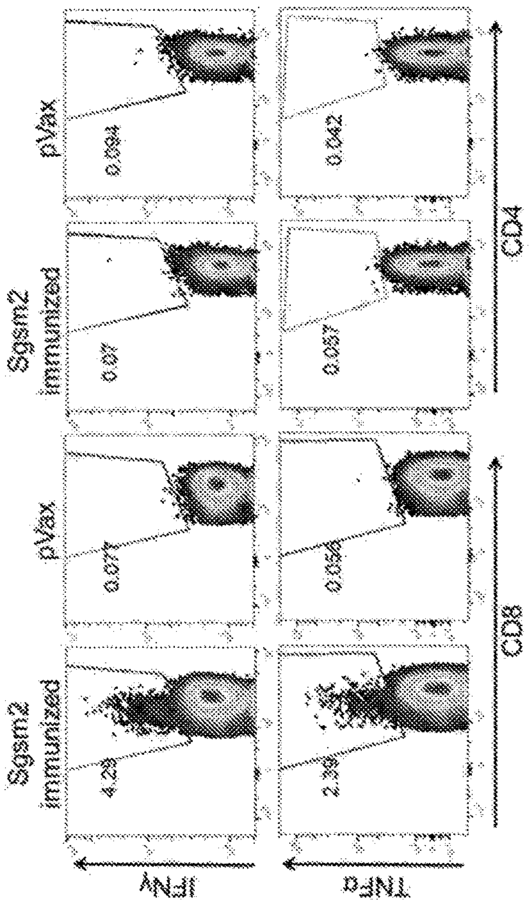
Figure 7C:
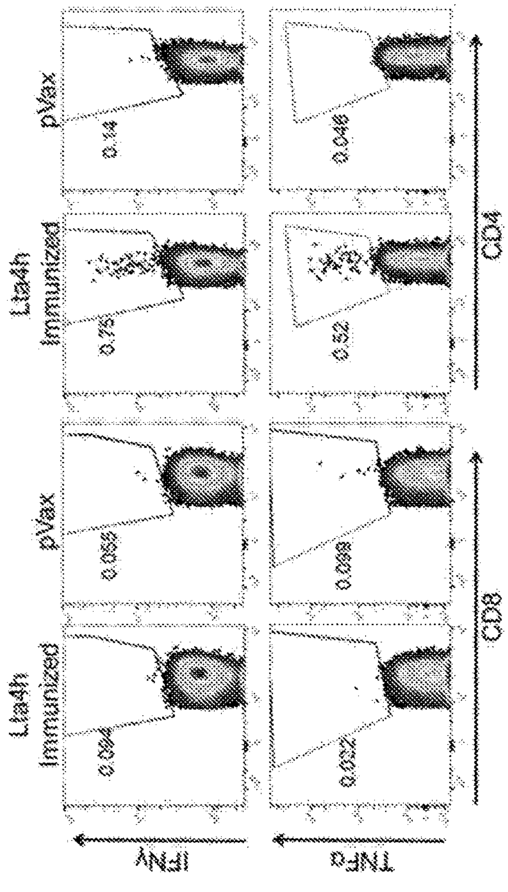

Example 3. DNA Vaccines Generate Predominantly $CD8^+$ T Cell Responses to Neoantigens Intracellular staining and flow cytometry were performed to determine which of these epitopes generated $CD8^+$ T cell responses, $CD4^+$ T cell responses, or both (FIG. 6A-F). Strikingly, 40% of the responses generated were mediated by $CD8^+$ T cells, 35% of the responses were mediated by both $CD8^+$ and $CD4^+$ T cells, and only 25% of responses were mediated by $CD4^+$ T cells alone (FIG. 7A, FIG. 6A-F). There was a wide range in individual epitope immune responses, ranging from a mean of 36-1286.5 SFU (FIG. 2A). The strongest $CD8^+$ (Sgsm2) and $CD4^+$ (Lta4h) T cell epitopes generated both IFNγ and TNFα cytokine production exclusively in $CD8^+$ and $CD4^+$ T cells, respectively (FIG. 7B and FIG. 7C). Many other epitopes generated polyfunctional responses as well, with expression of multiple cytokines (IFNγ, TNFα and IL-2) simultaneously, in addition to expression of T-bet and CD107a, indicating cytolytic potential (FIG. 8A-F).

Figure 7D:
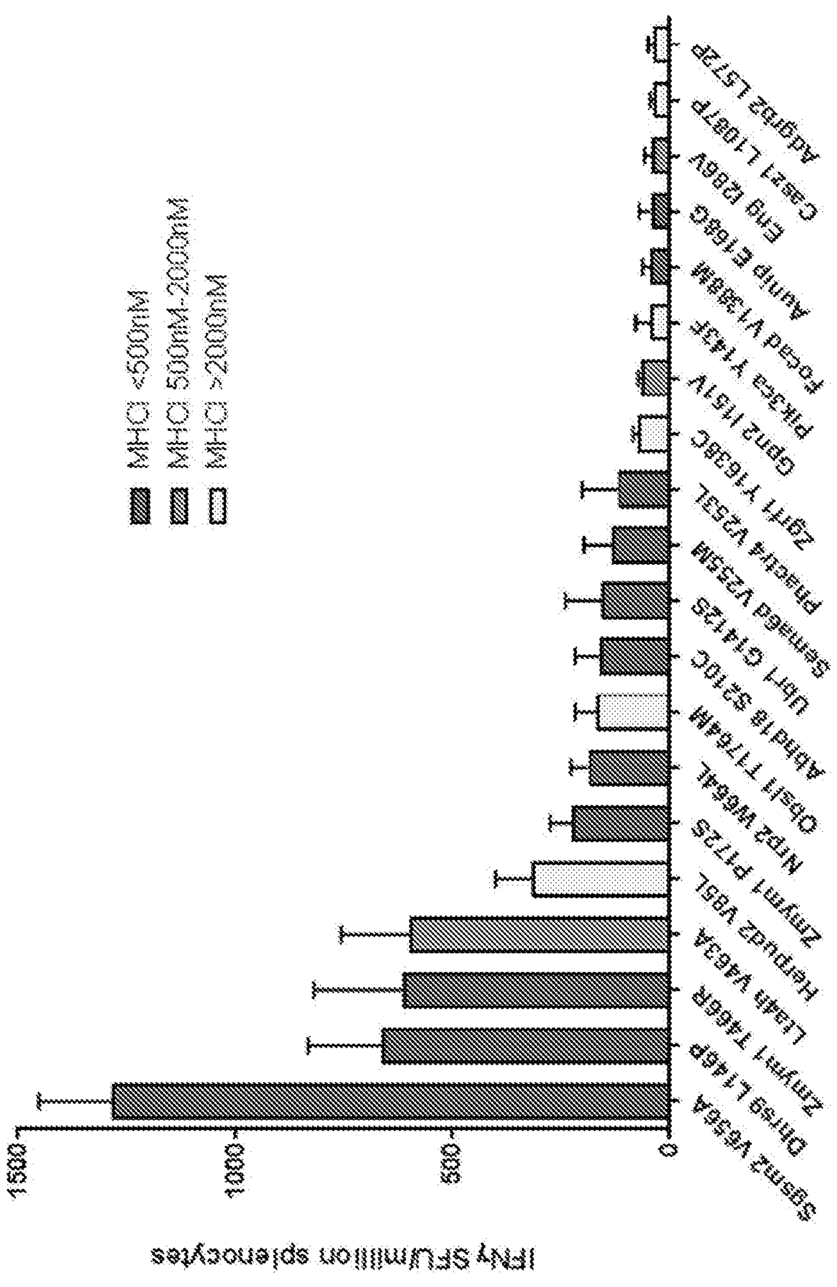
Figure 7E:
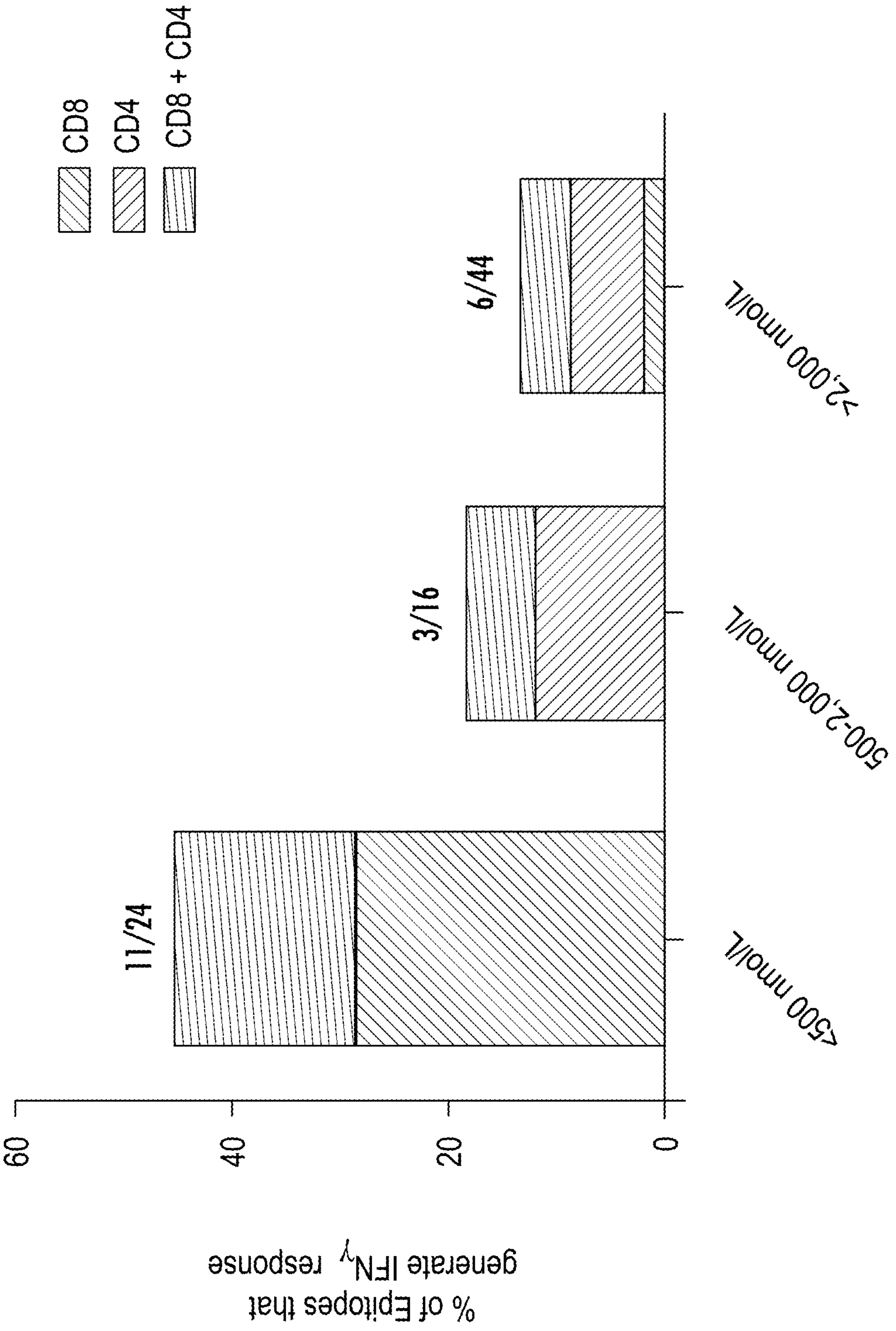
Figure 8A:
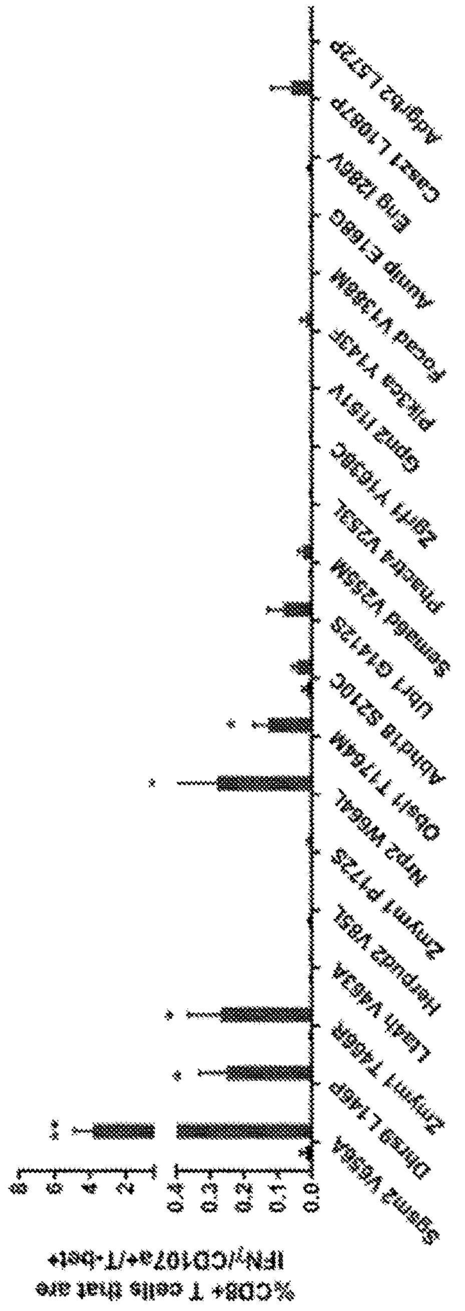
FIG. 8A-FIG. 8F shows polyfunctional T cell responses to neoantigens.
Figure 8B:
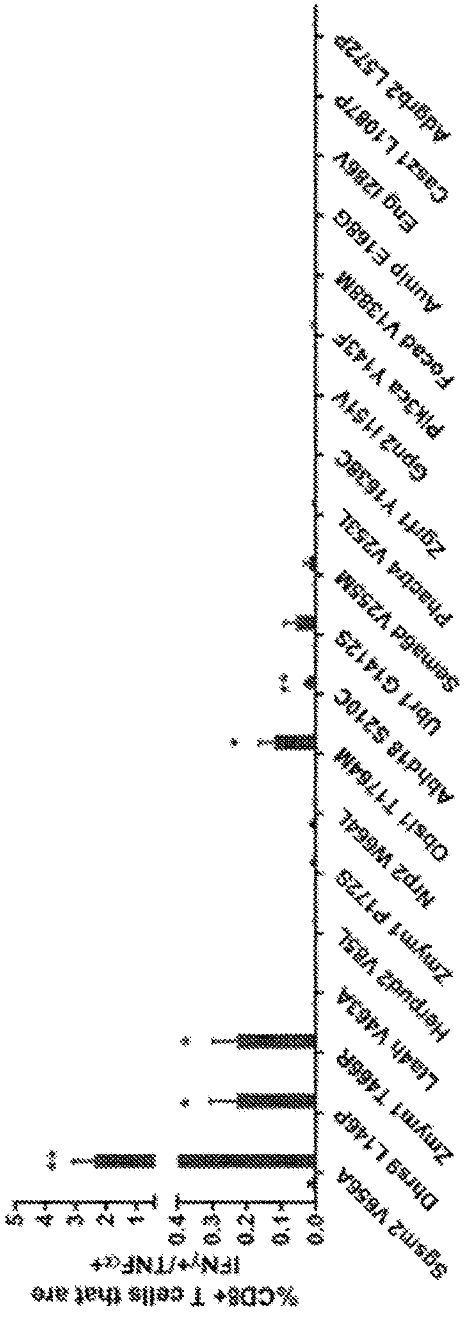
Figure 8C:
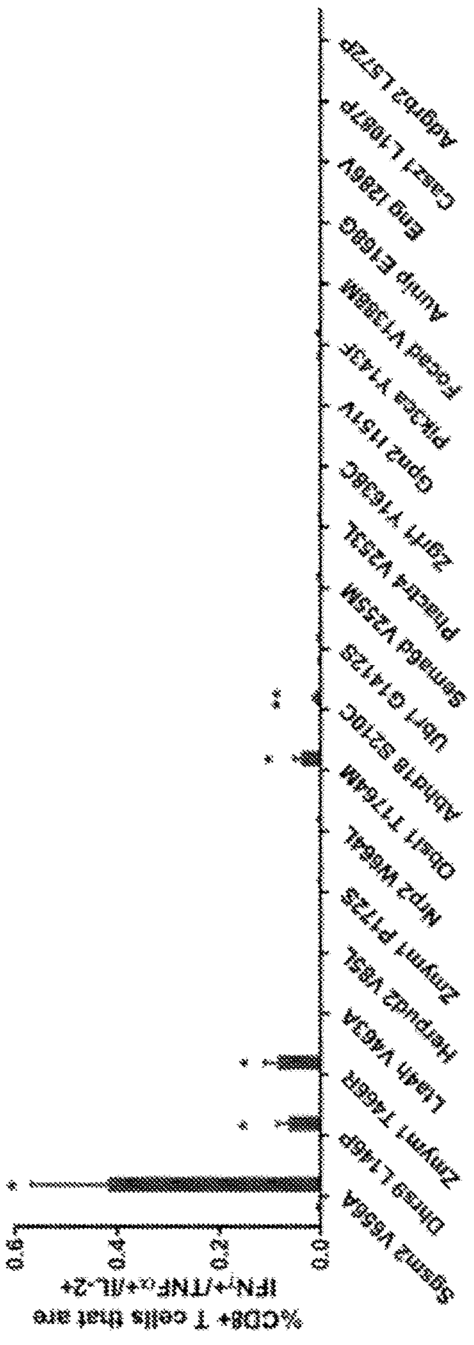
Figure 8D:
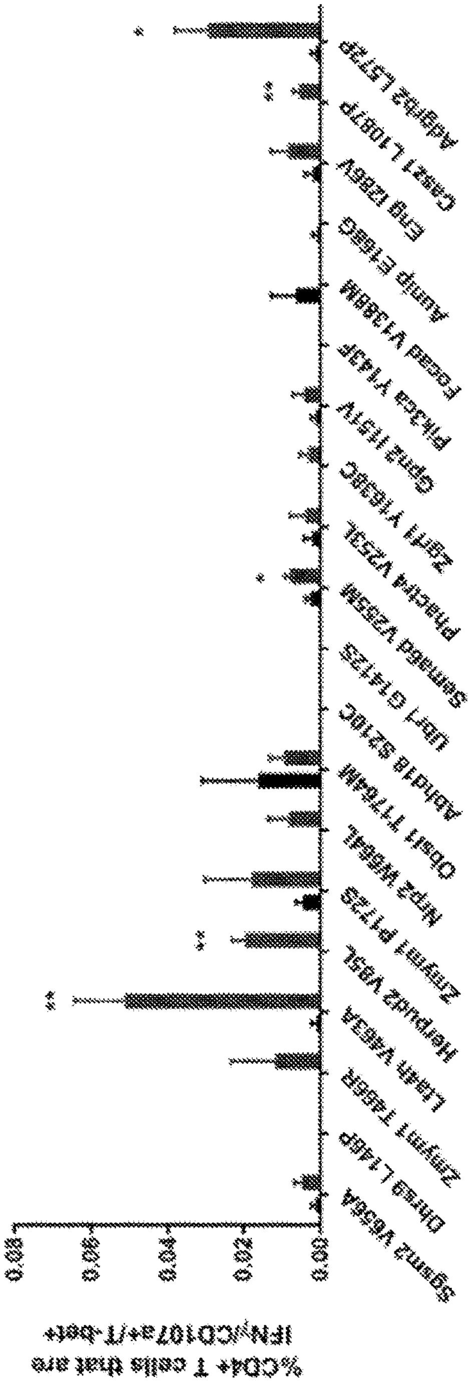
Figure 8E:
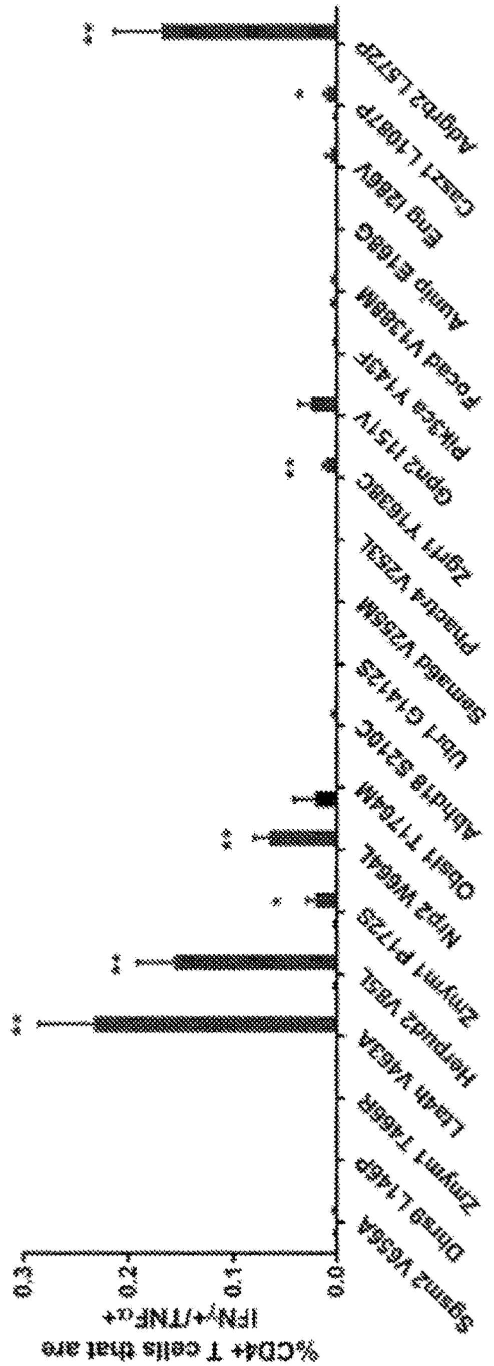
Figure 8F:
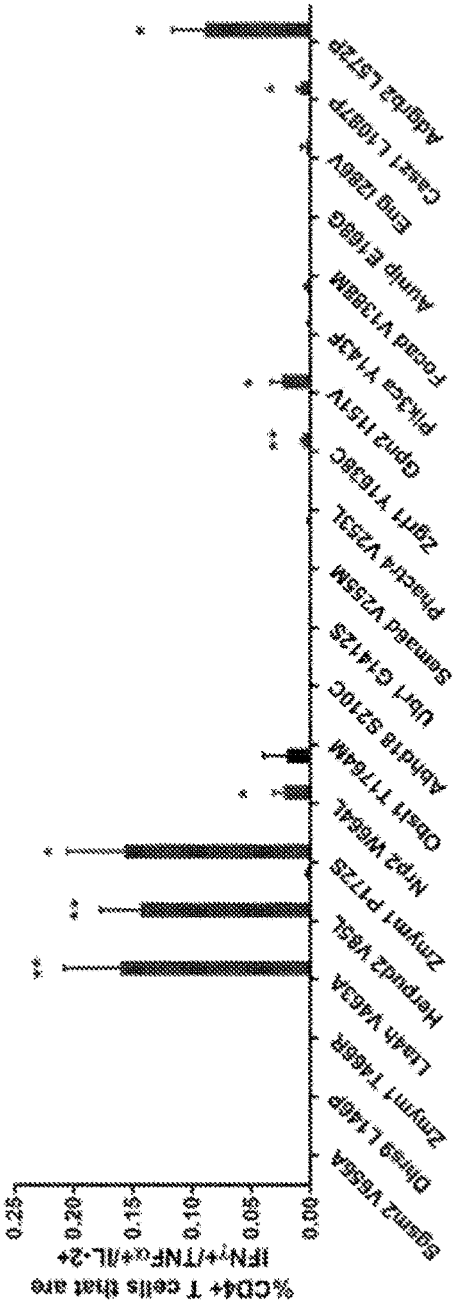

Next, the ability of the MHC class I binding affinity to predict immunogenic epitopes was assessed. NetMHCcons v1.1 were found to have some prediction power, and epitopes that were immunogenic were selected for (FIG. 7D and FIG. 7E). In fact, 46% of the epitopes that had <500 nM binding affinity generated immune responses, which is superior to the 24% of immunogenic epitopes without MHC class I affinity selection (FIG. 1E, FIG. 7E). Strikingly, 100% of the high affinity epitopes generated either $CD8^+$ or $CD8^+/CD4^+$ T cell responses (FIG. 7E). These data suggest that the type of response elicited by the neoantigen may depend on the immunization platform, and that DNA vaccines are capable of inducing robust $CD8^+$ T cell responses to neoantigens as opposed to other modes of vaccination that elicit minimal CD8+ T cell responses.

Figure 9A:
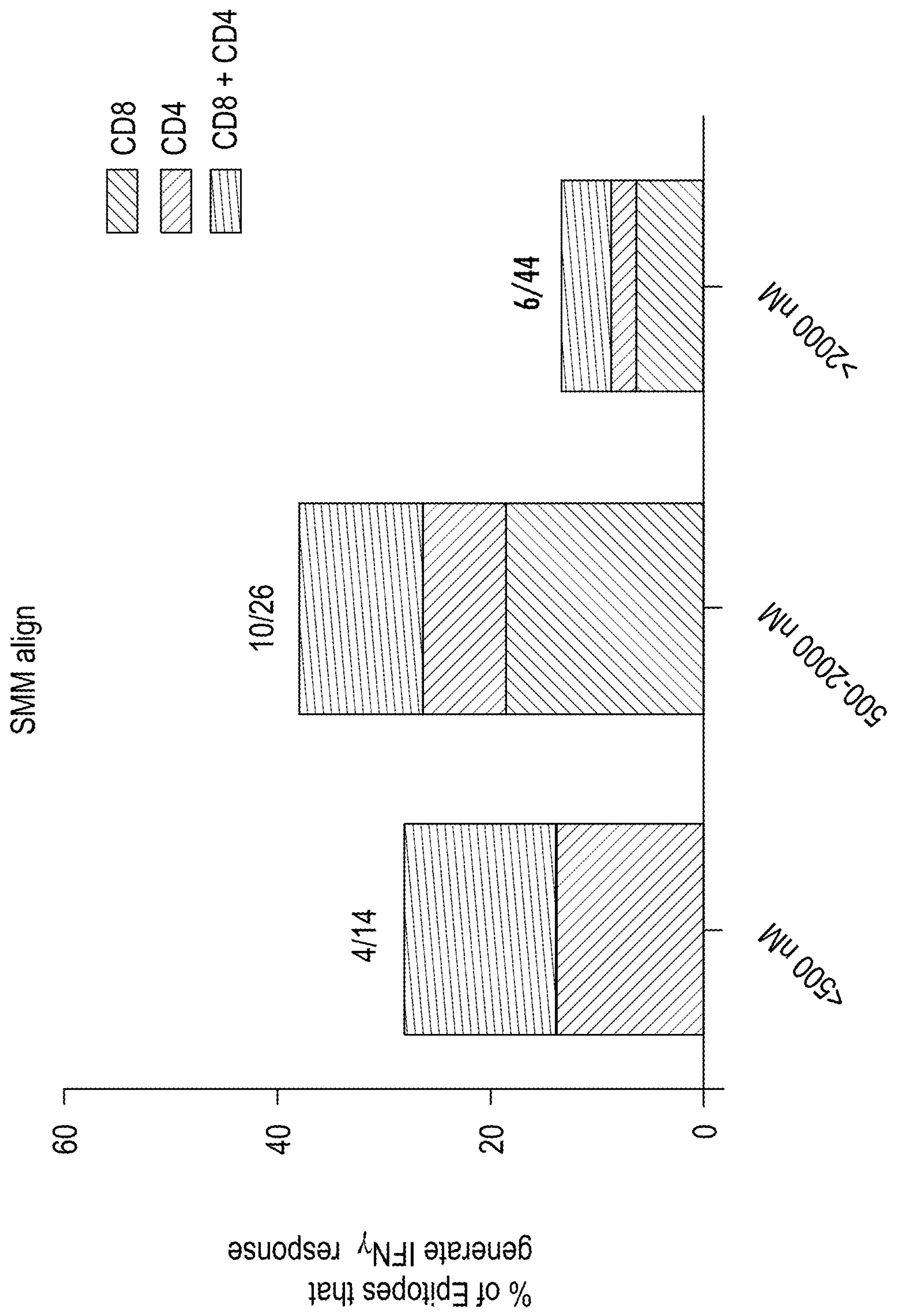
FIG. 9A and FIG. 9B shows MHCII prediction of neoantigen responses. Percentage of epitopes that generate CD4 versus CD8 T cell responses, organized according to MHC class II affinity, predicted using the SMM align method (netMHCII-1.1, FIG. 9A) or the NN align method (netMHCII-2.2, FIG. 9B).
Figure 9B:
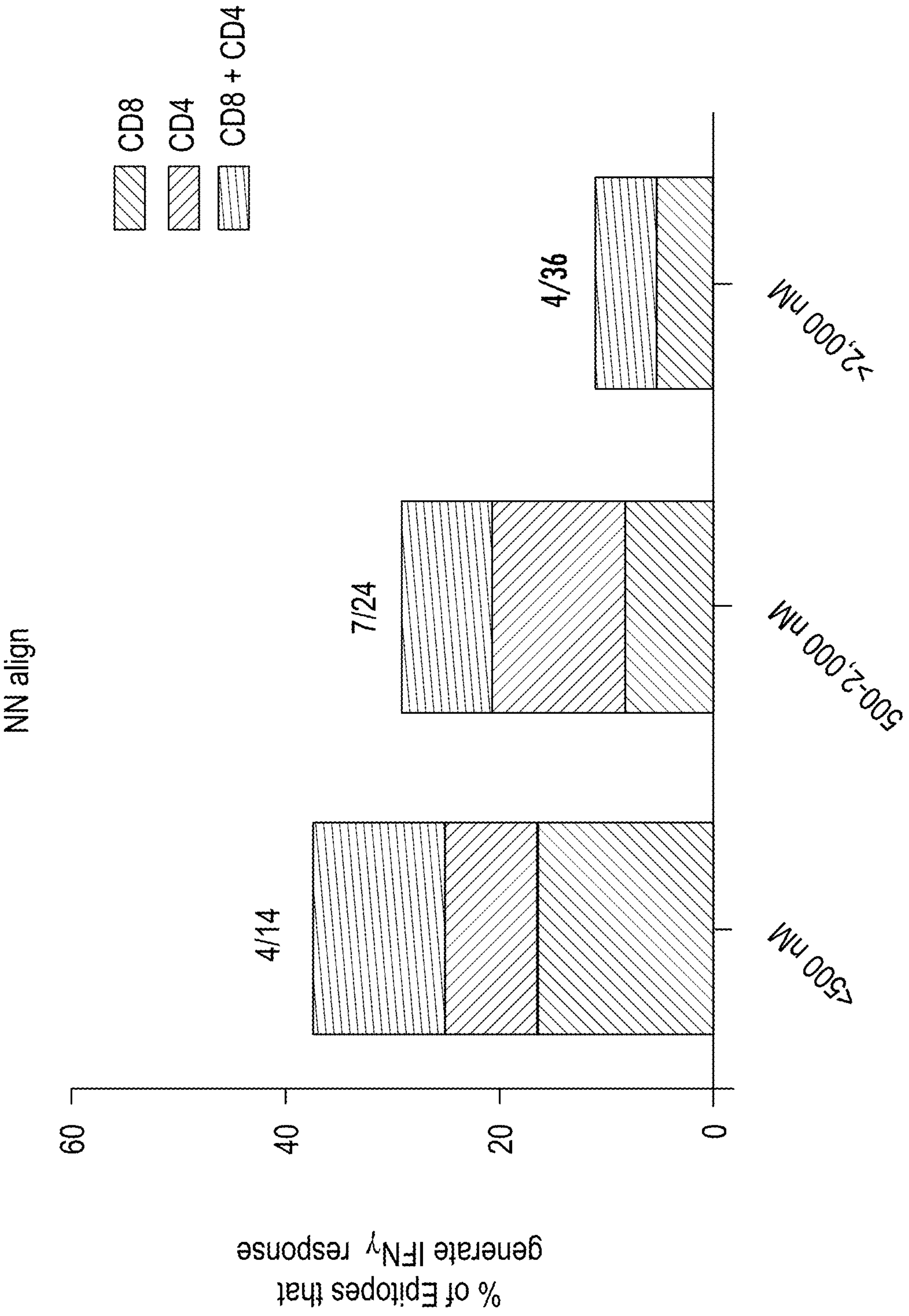

Next, the ability of MHC class II binding affinity to predict immunogenic epitopes was tested (FIG. 9A and FIG. 9B). Both netMHCII-1.1 (SMM align) and netMHCII-2.2 (NN align) prediction programs were tested, and it was found that neither program had demonstrable power to specifically predict $CD4^+$ T cell epitopes. The SMM align prediction program did not predict immunogenic epitopes (28.6% of the epitopes with <500 nM binding affinity generated immune responses, FIG. 9A). While the NN align program did select for immunogenic epitopes (37.5% of epitopes with <500 nM binding affinity generated immune responses), this program did not specifically select for $CD4^+$ T cell responses (FIG. 9B). Therefore, as reported by others (Lin et al. BMC Bioinformatics. 2008; 9 Suppl 12:S22), these MHC class II prediction programs have limited power to predict $CD4^+$ T cell epitopes.

Example 4. DNA Vaccine Primed T Cells Selectively Kill Mutated Cells

Figure 10A:
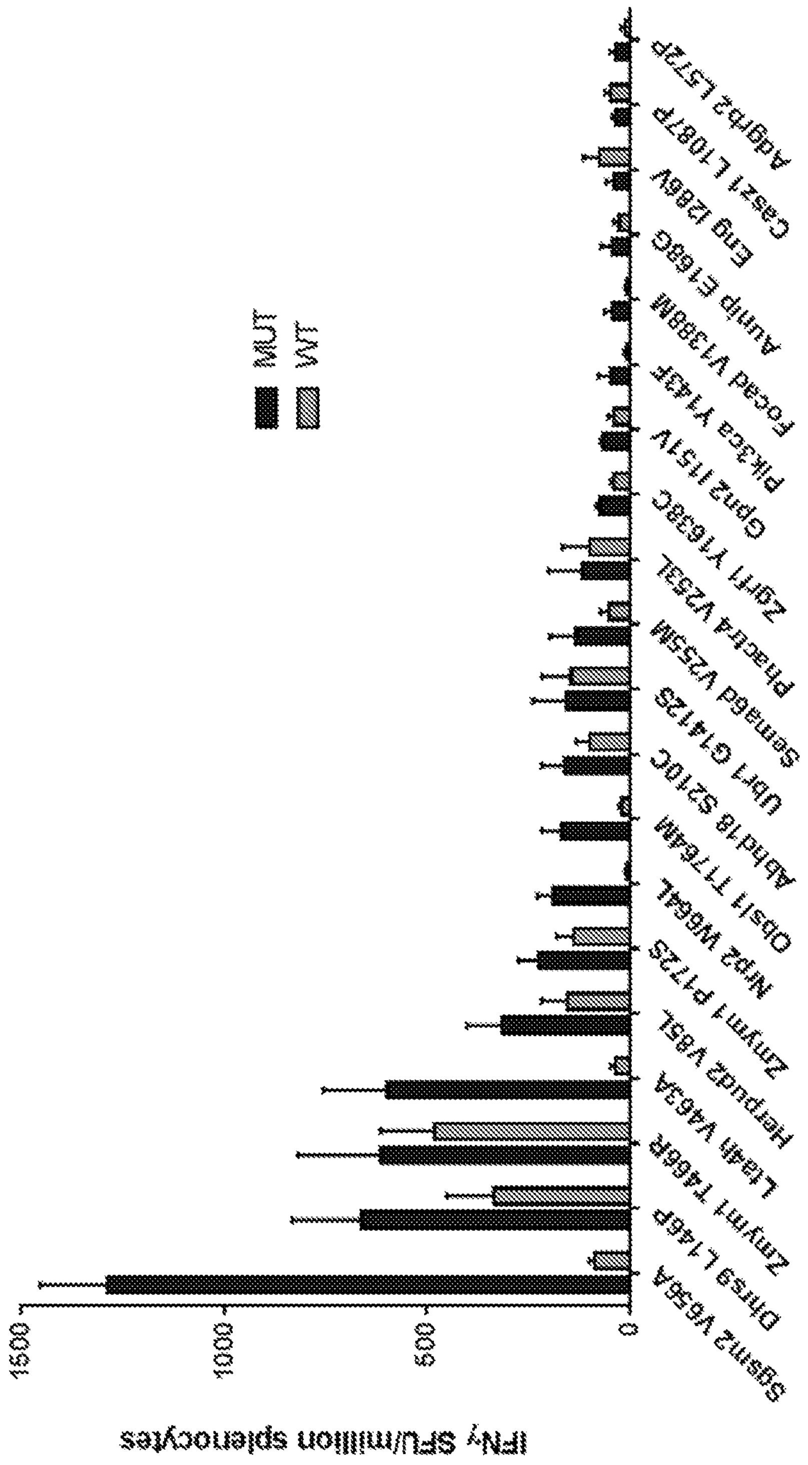
FIG. 10A and FIG. 10B shows most neoantigen responses are specific to the mutant peptide rather than the wild-type peptide.
Figure 10B:
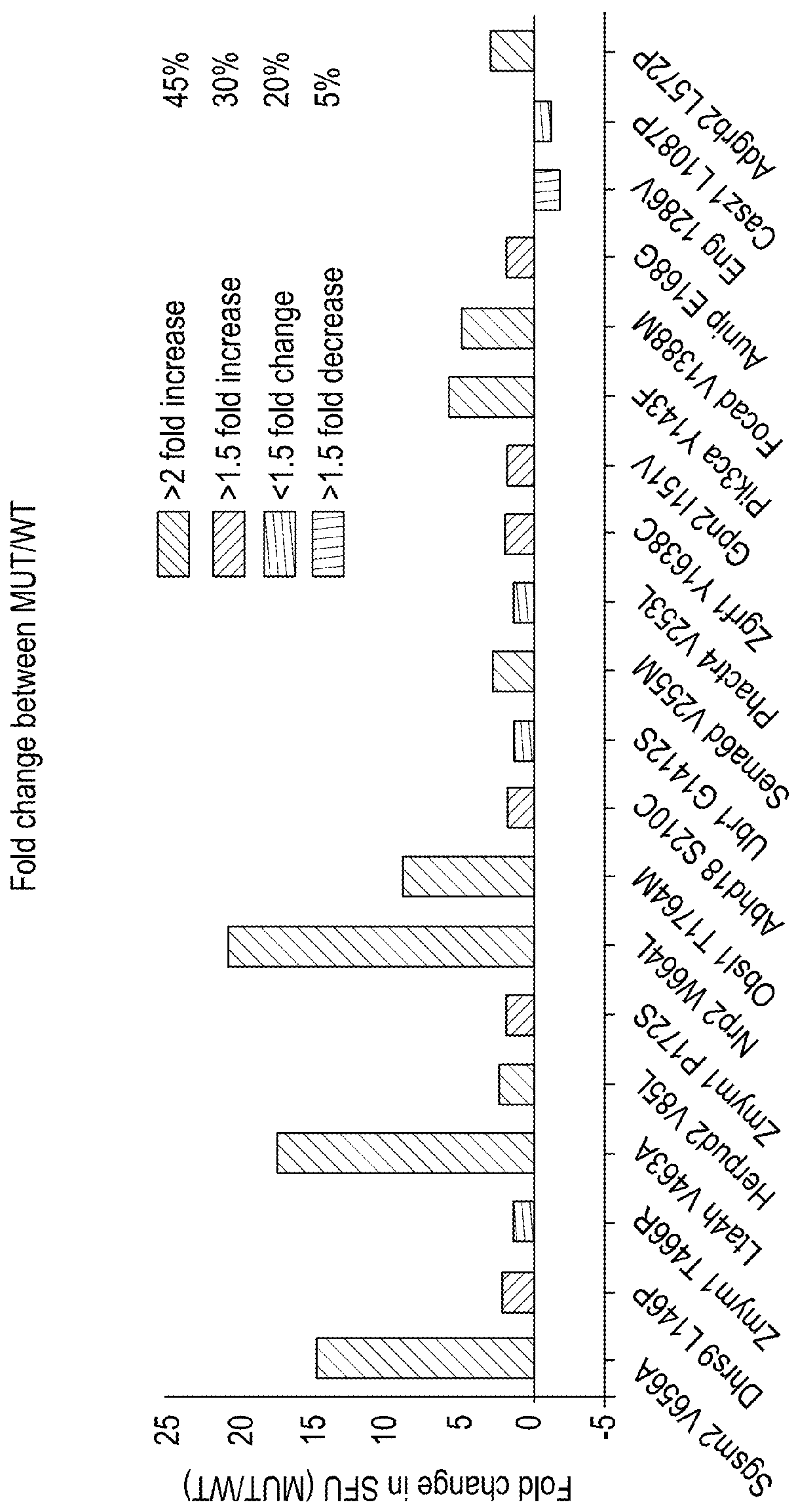

Immune responses generated from the immunized mice against the corresponding wild-type (non-mutated) neoantigen epitope were compared. It was found that the majority of immune responses are specific to the mutated epitope rather than the wild-type epitope (FIG. 10A and FIG. 10B). 75% of immune responses generated were at least 1.5 fold higher for the mutated epitope compared to the wild-type epitope. The remaining 25% of immune responses were similar when comparing mutant versus wild-type epitopes (FIG. 10B). These results are similar to what has been previously reported for neoantigen SLP vaccines, in which 68.8% of responses were specific to the mutated epitope (Castle et al. American Association for Cancer Research; 2012; 72:1081-91).

Figure 11A:
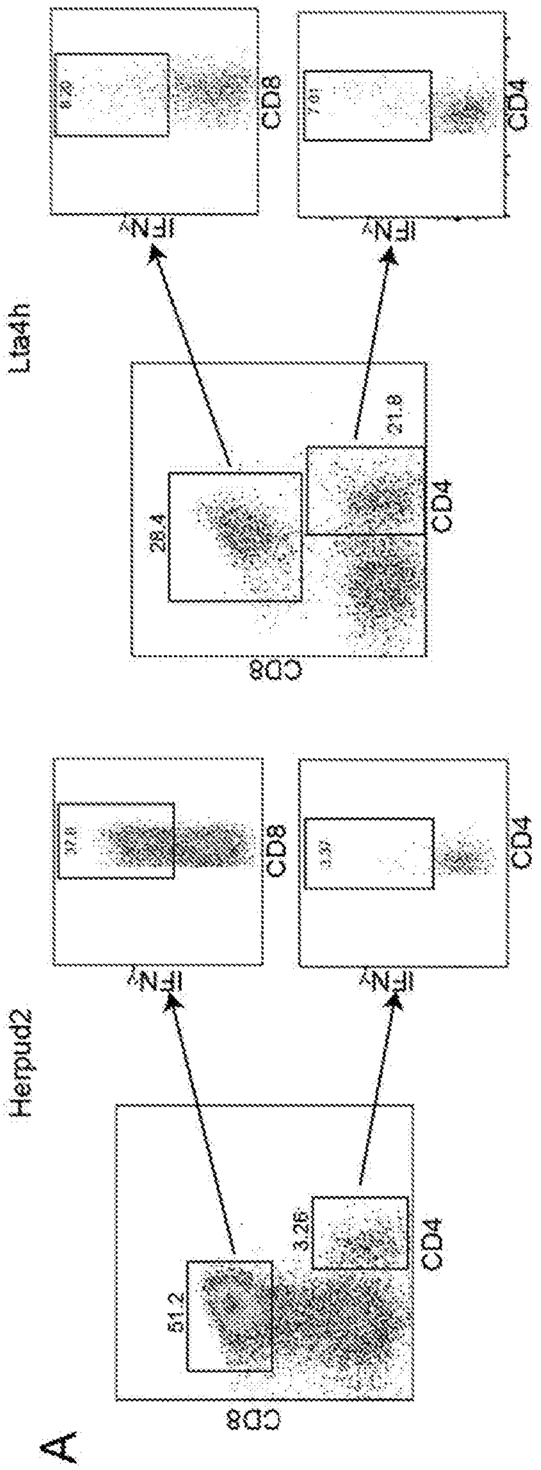
FIG. 11A-FIG. 11F shows DNA vaccine primed T cells selectively kill mutated cells.

To determine the cytotoxic functionality and specificity of the T cells primed by our neoantigen DNA vaccines, the best responding T cells to the different TC1 neoantigens (Sgsm2, Herpud2 and Lta4h) were expanded ex vivo. Interestingly, after ex vivo expansion the majority of T cells expanded with the Herpud2 and Lta4h peptides (originally $CD4^+$) were in fact $CD8^+$ T cells (FIG. 11A), indicating that these epitopes can generate a $CD8^+$ T cell response in mice in addition to the $CD4^+$ T cell response.

Figure 11B:
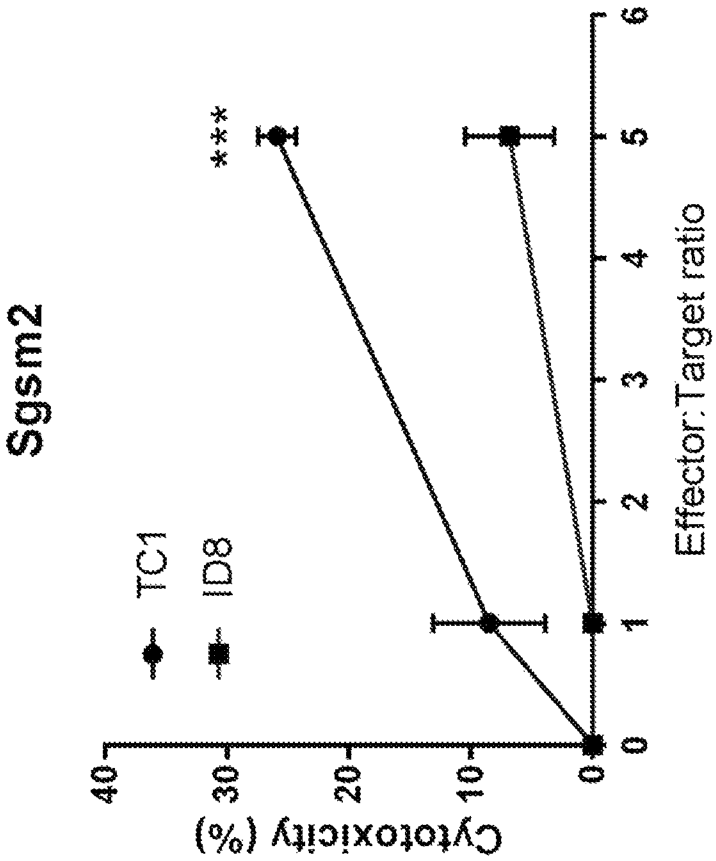
Figure 11C:
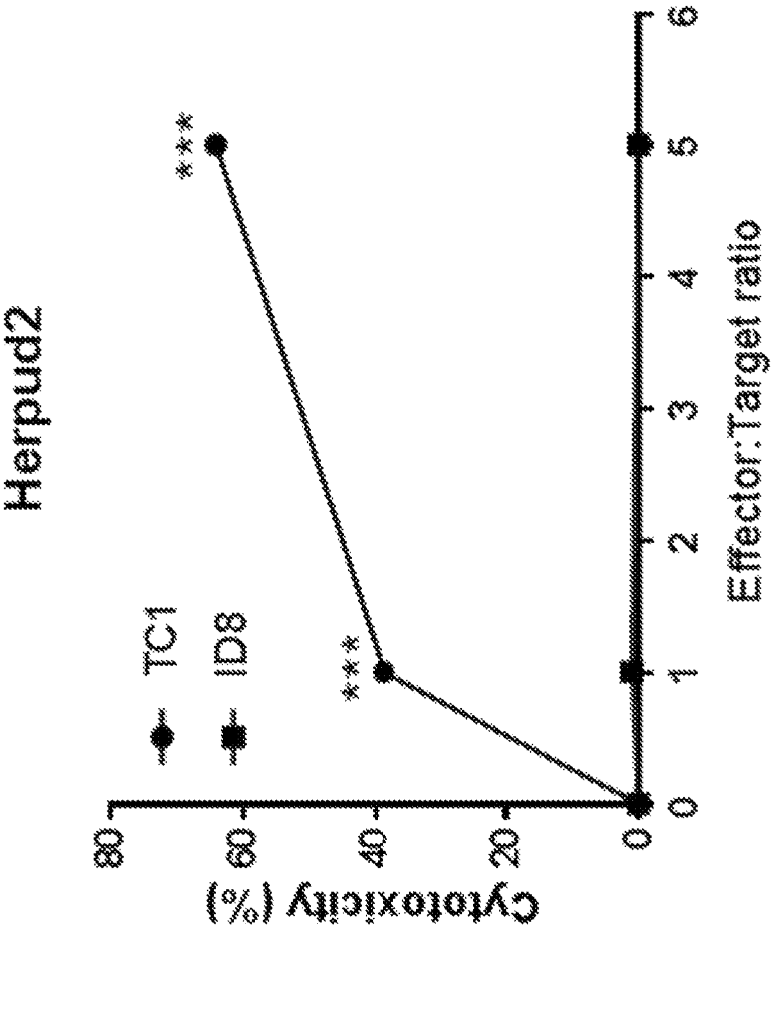
Figure 11D:
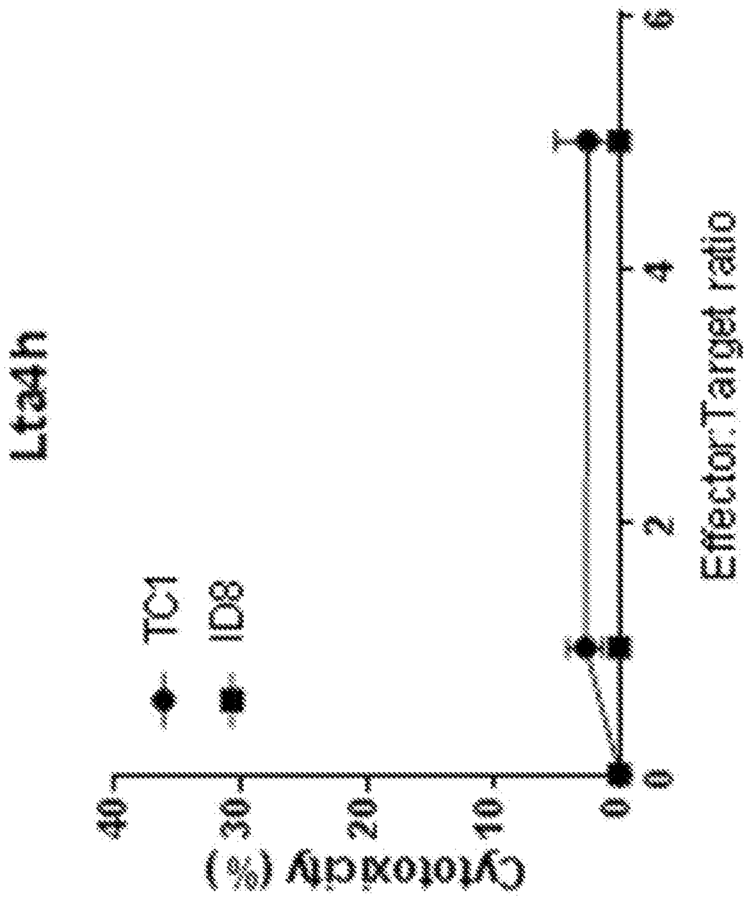

These expanded T cells were cocultured with TC1 cells or ID8 cells, which did not carry the neoantigen mutations in the selected genes. Co-incubation of the T cells with the tumor cells showed specific cytotoxicity of the TC1 neoantigen T cells against TC1 in the cases of Herpud2 and Sgsm2 (FIG. 11B and FIG. 11C). However, no cytotoxic activity of Lta4h restricted T cells against TC1 was found (FIG. 11C). One hypothesis to explain this result is that TC1 cells may not express Lta4h in vitro. The RNA sequencing data generated from the TC1 cultured cells and tumor were examined (FIG. 5), and it was found that Lta4h is only expressed at the RNA level in vivo in tumor tissue, and is not expressed in cultured TC1 cells (FIG. 11D).

Although physiological expression of MHC class II is restricted to antigen presenting cells, some tumors in both humans and mice express this presenting protein complex, allowing for $CD4^+$ direct recognition. To determine if there was potential direct recognition and potential cytotoxicity by $CD4^+$ T cells, MHC class II was measured in the tumor cells. It was found that, unlike B16 melanoma or ID8, TC1 and LLC cells did not have MHC class II expression upon incubation with various doses of IFNγ (FIG. 11E and FIG. 12), and therefore tumor killing must occur through an MHC class I restricted mechanism.

Figure 13A:
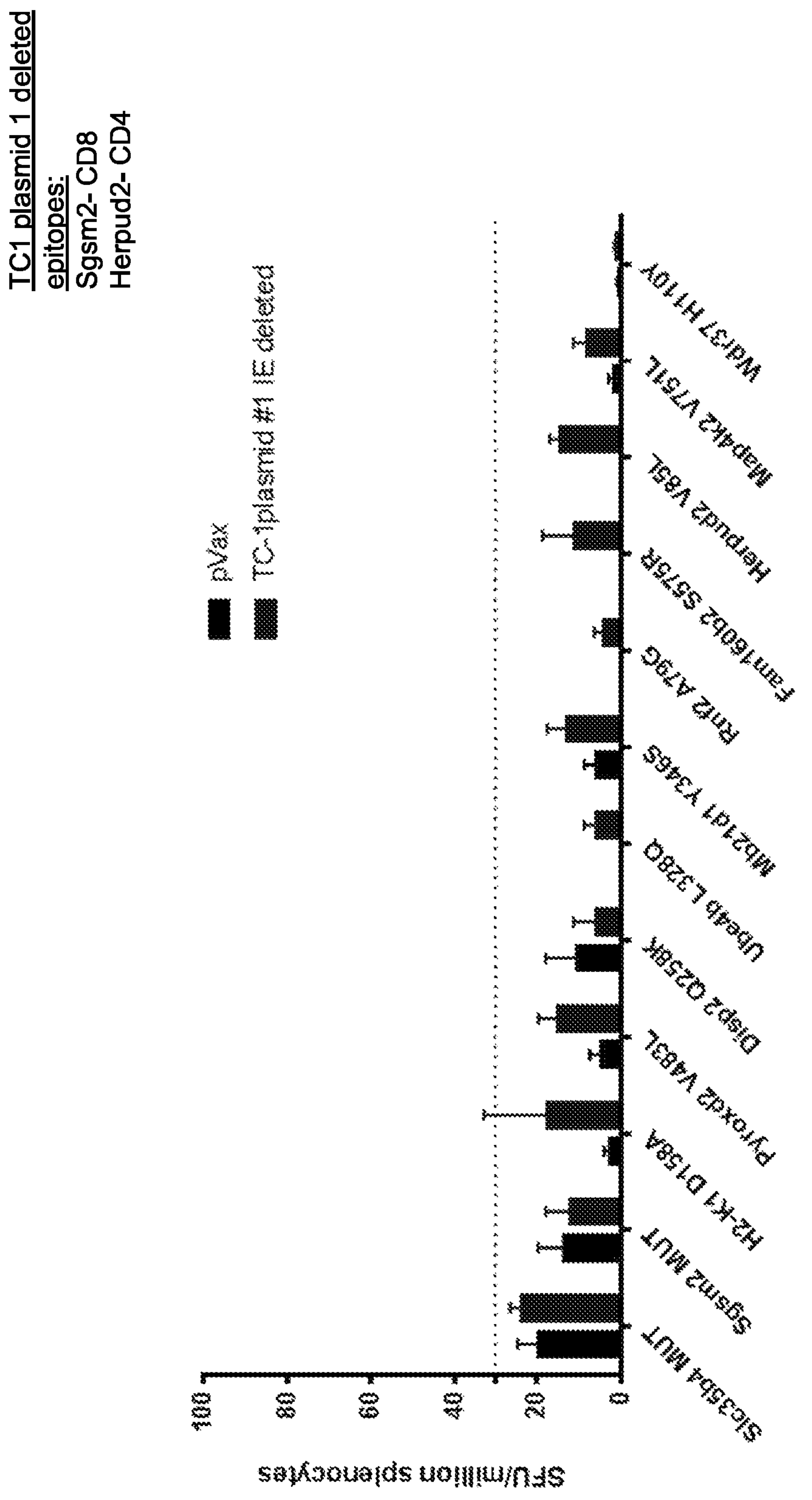
FIG. 13A and FIG. 13B shows deletion of immunodominant epitopes in TC1 plasmids does not result in improved immunogenicity of sub-dominant epitopes. IFNγ ELISpot responses from mice immunized with a control plasmid (pVax), compared to mice immunized with the TC1 plasmid #1 in which Sgsm2 and Herpud2 immunodominant epitopes were deleted (FIG. 13A), or with the TC1 plasmid #2 in which the Lta4h immunodominant epitope was deleted (FIG. 13B). N=5 mice per group. Error bars indicate ±SEM.
Figure 13B:
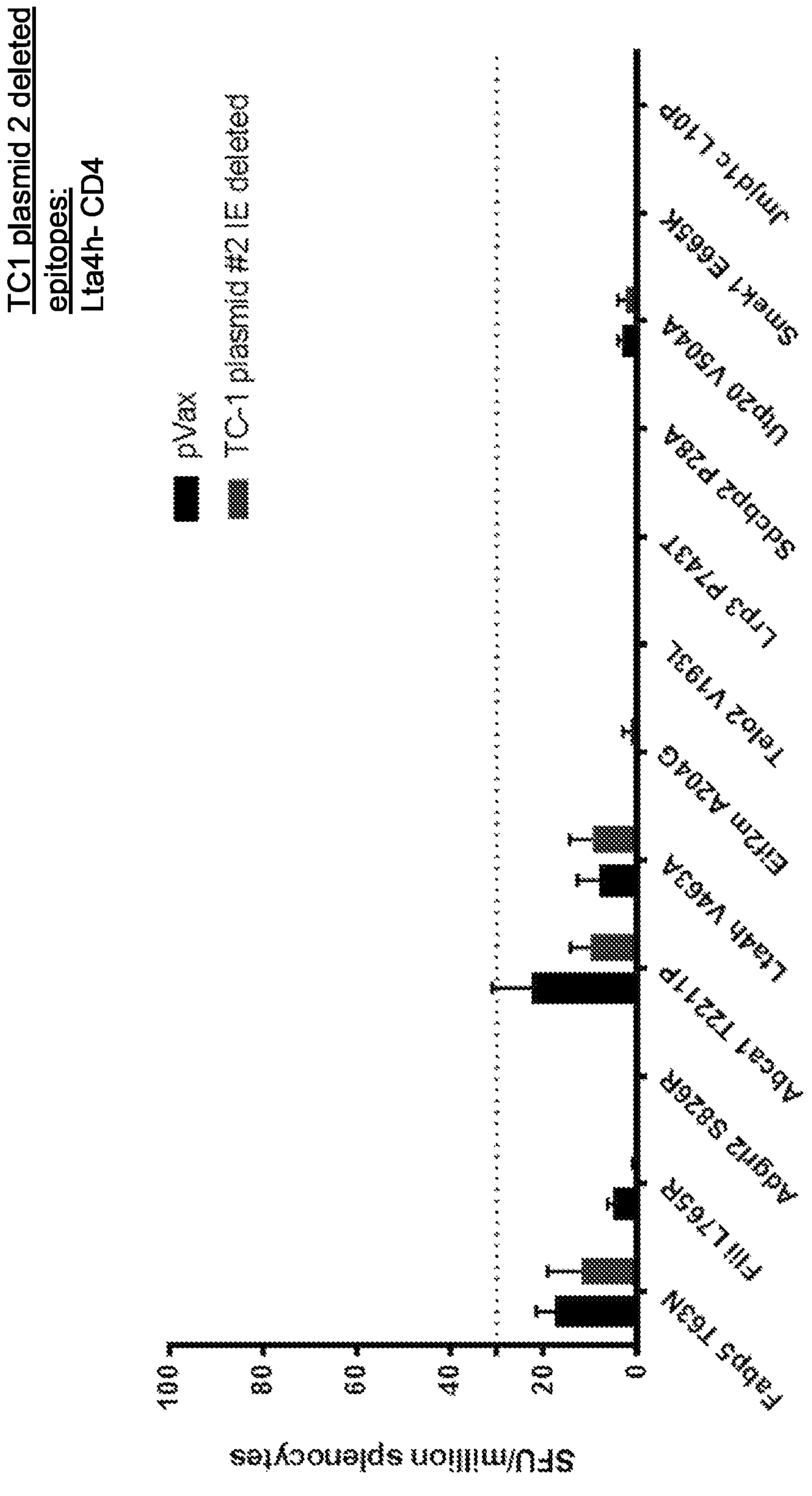

Next, the hierarchy of immunodominance for the epitopes within the TC1 neoantigen plasmids was examined. It was tested if the strong responses observed for the Sgsm2, Herpud2 and Lta4h epitopes could be masking potential sub-dominant immune responses from other epitopes within the same plasmid by deleting the immunodominant epitopes from each plasmid (FIG. 13A and FIG. 13B). It was found that, for each plasmid, deleting the immunodominant epitopes did not result in generation of immune responses from sub-dominant epitopes (FIG. 13A and FIG. 13B).

Example 5. DNA Neoantigen Vaccines Delay Tumor Progression

Figure 11E:
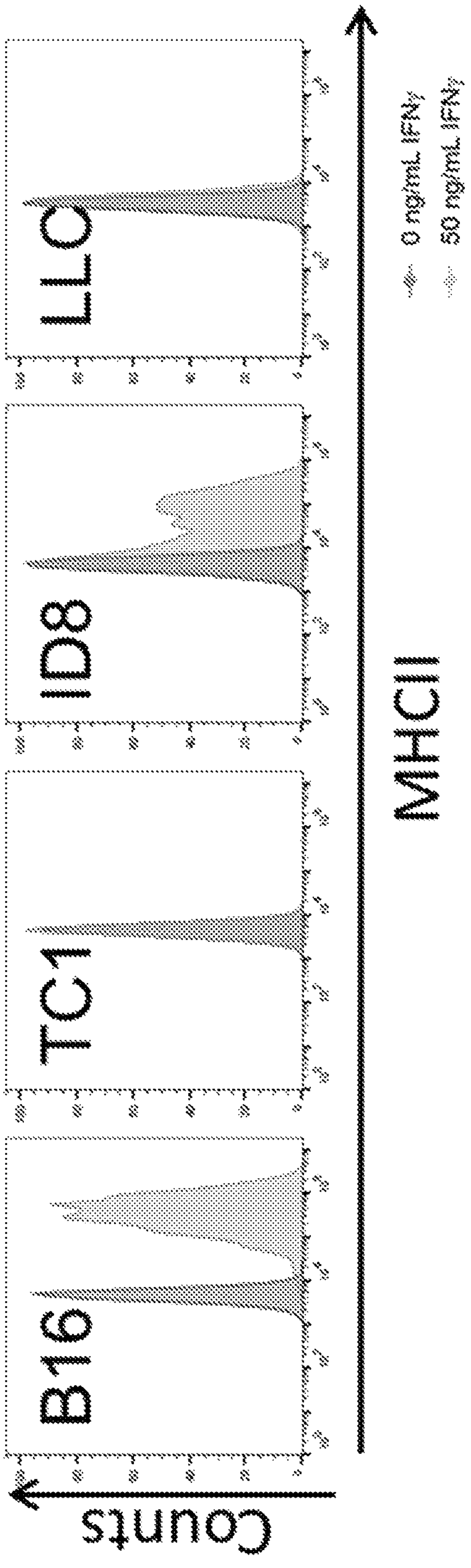
Figure 11F:
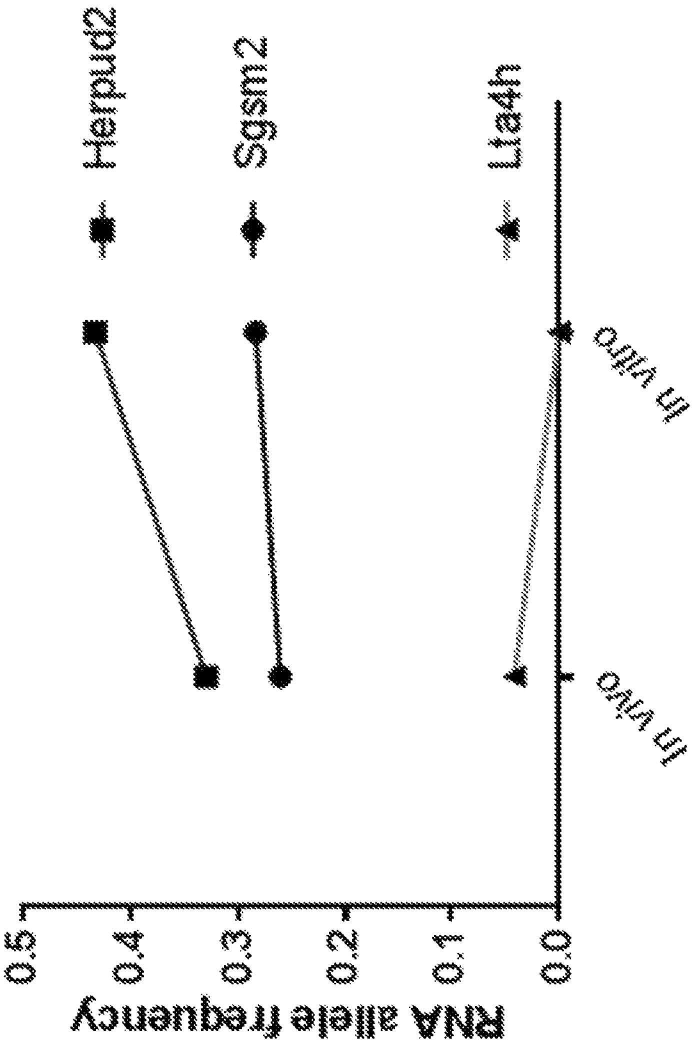
Figure 12:
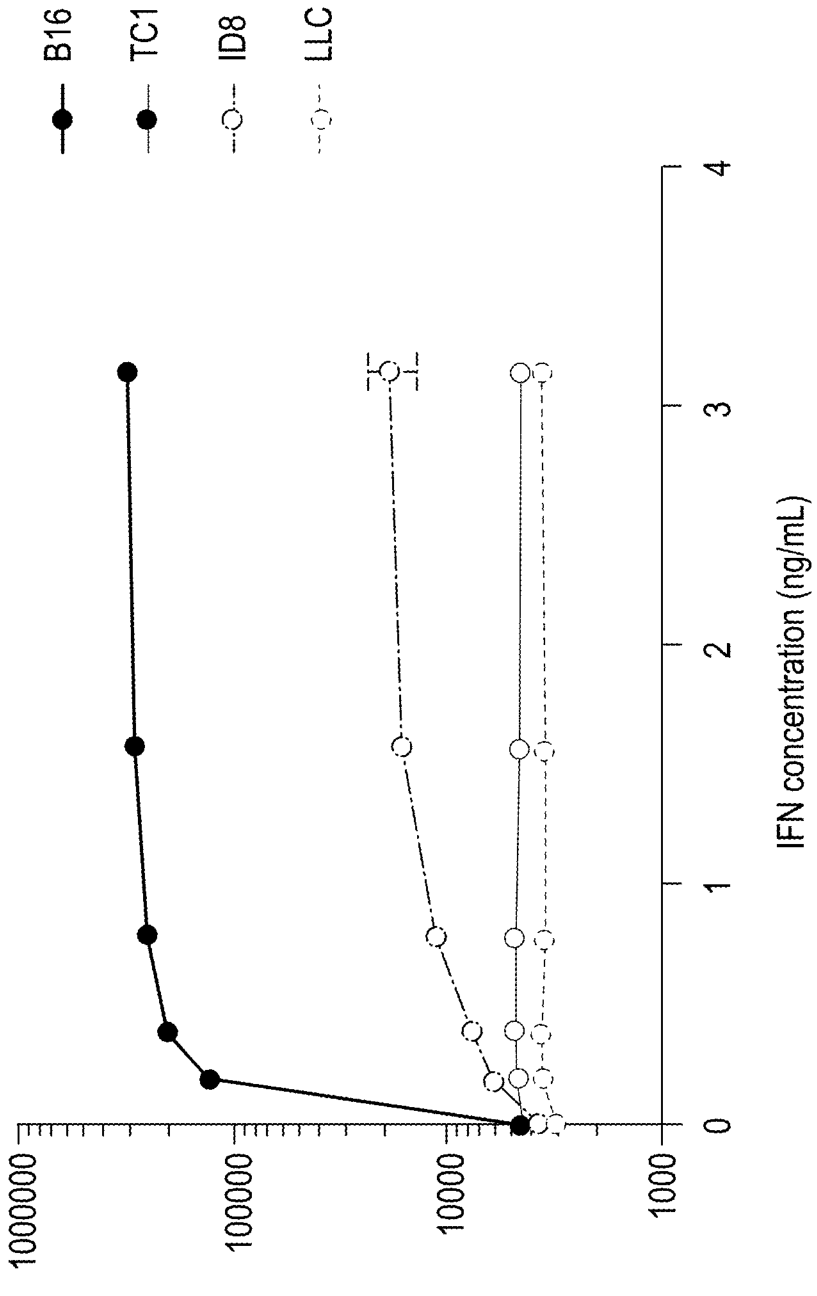
FIG. 12. Surface expression of MHC class II on tumor cells. Flow cytometric quantification of MHC class II surface expression in B16 melanoma, TC1, ID8 and LLC tumor cell lines upon exposure to different concentrations of interferon gamma (measured as mean fluorescent intensity, triplicates). Error bars indicate ±SEM.
Figure 14A:
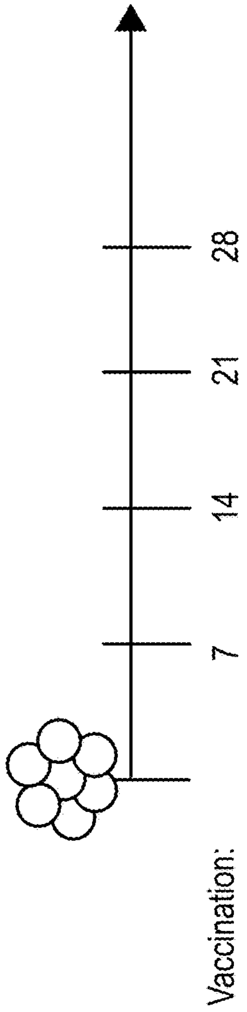
FIG. 14A-FIG. 14C shows DNA neoantigen vaccines delay tumor progression.
Figure 14B:
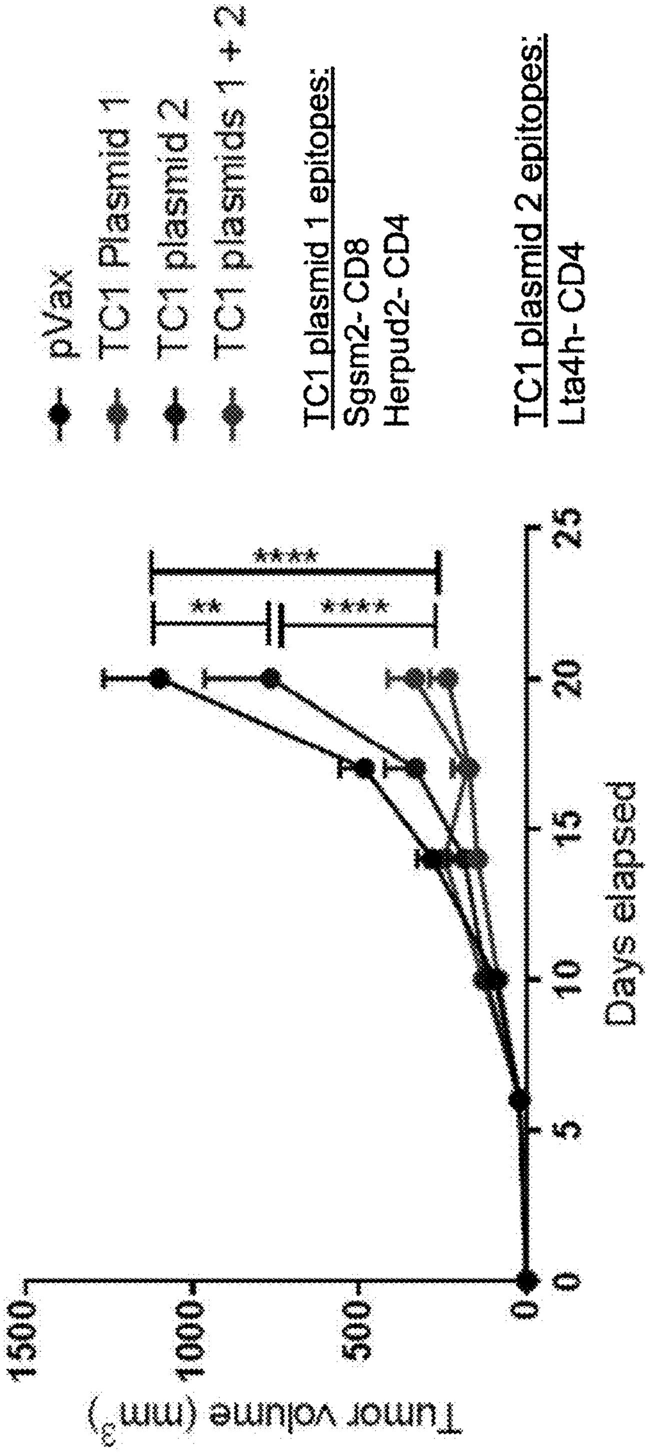
Figure 14C:
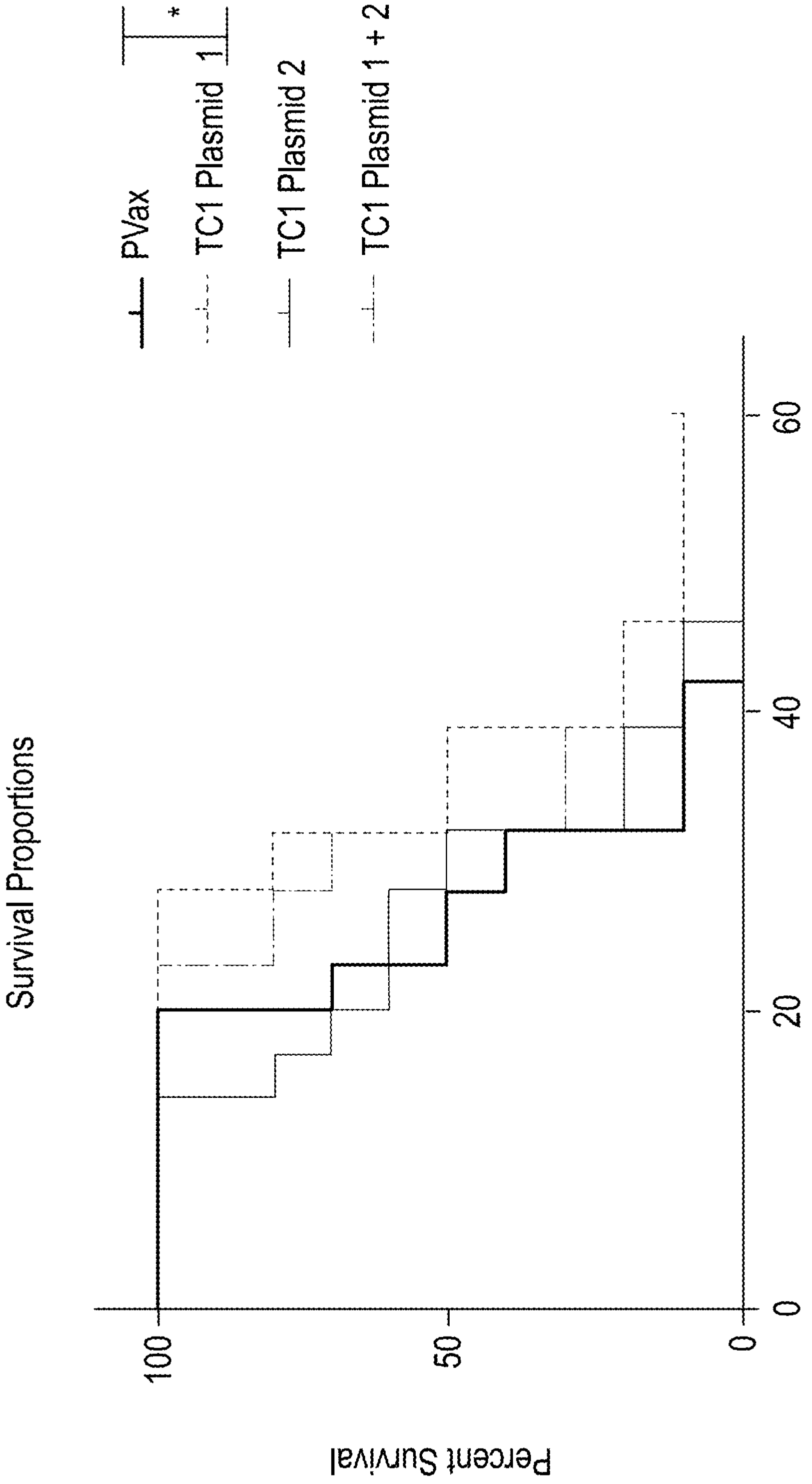

The in vivo anti-tumor effect of the TC1 vaccine was examined. To do this, mice were implanted with the TC1 cell line, and 7 days later the mice were vaccinated with weekly doses of the dodecamer vaccine Plasmid 1 (containing the immunogenic neoantigens Sgsm2 and Herpud2), Plasmid 2 (containing the immunogenic neoantigen Lta4h), both or the empty pVax vector (FIG. 14A). A profound delay in tumor progression associated with a longer survival was found when the mice were treated with the Plasmid 1 alone or the combination (FIG. 14B). A significant, although less intense, tumor delay was found with Plasmid 2 (FIG. 14B). FIG. 14C Survival curve of mice bearing TC1 treated TC1 plasmid 1, 2, both or pVax (n=10 mice per group). While the Lta4h epitope was highly immunogenic, it generated primarily $CD4^+$ T cell responses (FIG. 7A). These neoantigen-specific $CD4^+$ T cells were likely not as effective at delaying tumor progression in this TC1 tumor model, because the TC1 cells do not express MHC class II (FIG. 11E). In addition, the level of expression of the Lta4h neoantigen was relatively low (FIG. 11D) compared to the neoantigens present in Plasmid 1.

Examples 1-5 describe for the first time the possibility of generating effective anti-tumor immune responses against cancer neoantigens using DNA based vaccines. The DNA vaccine platform has several a priori advantages over other assayed platforms for generating effective anti-tumor neoantigen vaccines such as speed of vaccine production, vaccine stability and manufacturing cost. Time is a critical factor in cancer treatment. Even patients with surgically resectable tumors are at risk for development of micrometastases with potentially immune suppressive microenvironments. Therefore, the speed in which a personalized vaccine can be manufactured is of paramount importance. DNA vaccine production is more rapid than other platforms because it does not require complex peptide synthesis or RNA in vitro transcription. Furthermore, DNA is stable at room temperature, and, unlike RNA and peptide vaccines, does not require a cold chain. This ease of manufacturing and transport contributes to the much lower cost of DNA vaccines, making it an ideal technology for personalized patient specific therapeutic applications.

$CD8^+$ T cells are thought to be the major mediators of anti-tumor T cell responses. As we have previously shown in preclinical and clinical studies (Trimble et al. Lancet (London, England). 2015; Duperret et al. Cell. 2017). DNA vaccines are able to generate robust $CD8^+$ T cell responses. Examples 1-5 show that, as expected, DNA encoded neoantigens predicted for high MHCI binding generated $CD8^+$ or $CD8^+$/$CD4^+$ neoantigen specific immune responses. RNA and peptide-based vaccines generated based on predicted MHCI restricted responses have surprisingly resulted in MHCII-restricted responses (Ott et al. 2017; Sahin et al. 2017). MHCI presentation of epitopes requires intracellular protein synthesis and proteasomal degradation (Rock et al. Trends Immunol. 2017). Synthetic long peptides are injected directly into tissues, and therefore are primarily engulfed and presented by antigen presenting cells, which will skew them towards a class II presentation. In the case of RNA and DNA, peptide synthesis occurs in the cell and can be cleaved as necessary by the proteasome and enter the MHC class I pathway. The strong $CD4^+$ bias from RNA vaccines could be due to the pro-inflammatory properties of RNA. RNA is sensed by multiple innate immune receptors such as TLR3, 7,8 and RIG-I like receptors which promote pro-inflammatory cytokine production (for instance, IL-6 or TNFα) (Pardi et al. Nat Rev Drug Discov. 2018). This inflammatory response can be detrimental to $CD8^+$ activation and cytokine production (Wu et al. Sci Rep. 2015), and can additionally inhibit mRNA replication, stall translation and result in RNA degradation (Pardi et al. 2018; J Virol. 2012; 86:2900-10).

It has been shown that $CD4^+$ T cells can generate anti-tumor cytotoxicity. $CD4^+$ T cells can exert direct cytotoxicity based on granule exocytosis or Fas-Fas ligand pathway upon recognition of MHC class II-peptide complex (Fang et al. Proc Natl Acad Sci USA. 201; 109:9983-8; Janssens et al. J Immunol. 2003; 171:4604-12). However, it is not common for solid tumors to express MHCII (41% in melanoma, 0% in small cell lung cancer) (He et al. Lung Cancer. 2017; 112:75-80; Johnson et al. Nat Commun. 2016; 7:10582). $CD4^+$ T cells have also been suggested to induce killing of tumor cells that do not express MHC class II by activating macrophage killing of tumor cells (Laurtizen et al. Cell Immunol. 1993; 148:177-88).

The number of neoantigens in cancer varies widely according to the tumor type but has been defined to be approximately between 33 and 163 expressed, non-synonymous mutations (Vogelstein 2013). Using the described DNA platform to generate neoantigen based vaccines allows the encoding of a high number of neoantigens in each plasmid. Considering the insert size (33aa) and the linker (7aa), a vaccine with 50 neoantigens would only require an insert of 6150 bp. This would permit possible immunization of all identified neoantigens in most cancer patients using only one plasmid. For those with very high mutation loads, all neoantigens could be included using 2 or 3 plasmids. This strategy would increase exponentially the ability to generate a wide range of anti-tumor T-cell responses. Because driver mutations are rarely immunogenic, and immunogenic neoantigens typically occur as passenger mutations, immunizing against a larger number of neoantigens per tumor would prevent or delay tumor immune escape. This approach of immunizing against all potential neoantigens also eliminates the need to validate experimentally the real (vs predicted) value of each individual epitope, shortening valuable time before the vaccine can be produced and administered to the patient. In addition, because humans have 6 different MHC class I molecules (more than the 2 different molecules present in inbred mice), it is likely that a higher proportion of epitopes will be able to bind to human HLA and generate responses to the vaccine.

In conclusion, Examples 1-5 show for the first time that DNA vaccines against tumor neoantigens are able to generate $CD8^+$ T-cell anti-tumor specific responses and delay tumor progression. This promising technology possesses advantages such as rapid manufacturing time, lower manufacturing costs, higher stability and the ability to target most, if not all, of the neoantigens present in each patient.

Example 6. Design of Poly-Neoepitope DNA Vaccine Against B16 Model

Design of Neoantigen Vaccines

We designed the pGX4501, pGX4503, pGX4504, pGX4505, and pGX4506 vaccines by encoding the previously identified 27mer B16 and CT26 neoantigens (M27, M30, and M33 for B16, and M19, M20 and M26 for CT26) (Kreiter et al. 2015). We separated each epitope with no linker, a furin cleavage site or a furin cleavage site separating 2 epitopes and a P2A cleavage site separating 2 epitopes. These sequences were subcloned into the pVax1 plasmid (GenScript).

The methods of designing the vAED portion of the vector were identical to the methods performed in above Example 1 except that the peptides were 15mers overlapping by 11 (instead of 15mers overlapping by 9 as indicated above).

Figure 15:
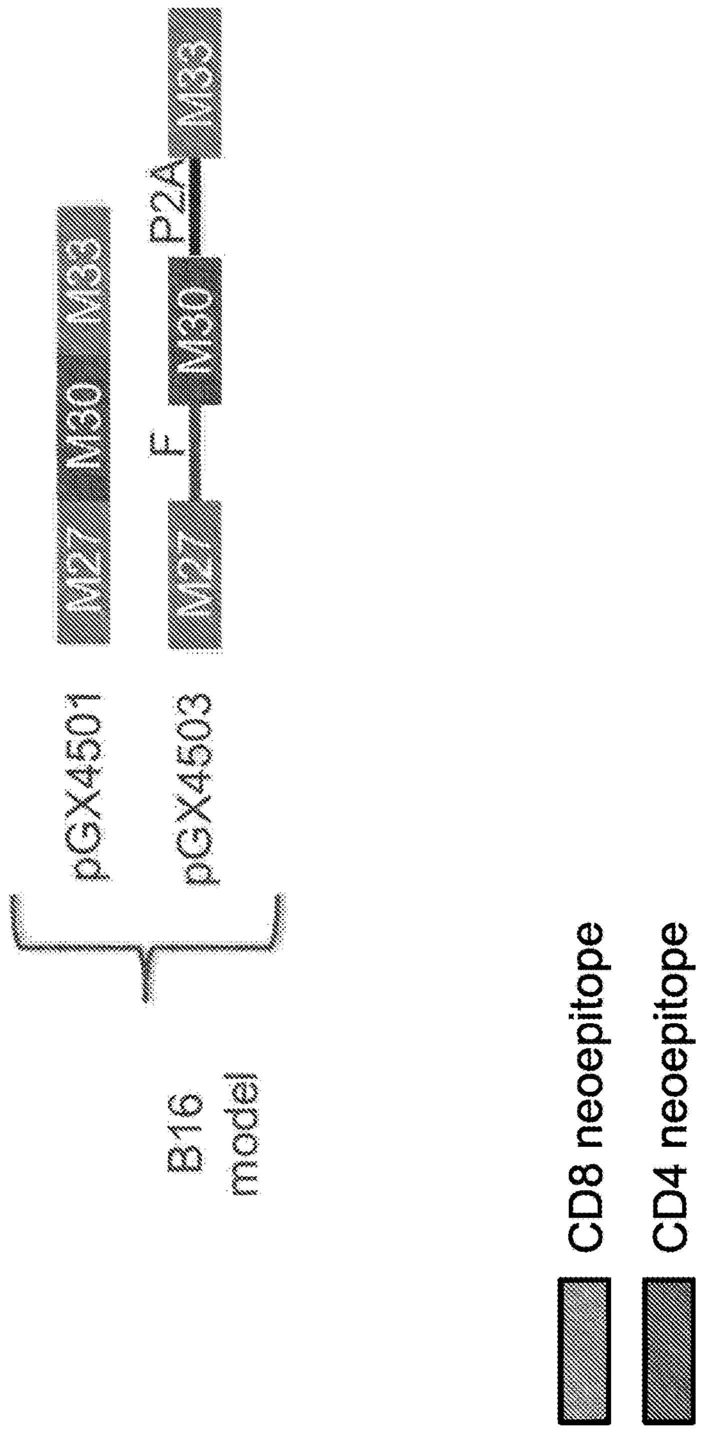
FIG. 15 shows a schematic of the design of poly-neoepitope DNA vaccine against B16 model. pGX4501 and pGX4503 plasmids were used. F indicates a furin cleavage site, encoded by a linker region. P2A indicates a porcine teschovirus-1 cleavage site, encoded by the linker.

FIG. 15 shows a schematic of the design of poly-neoepitope DNA vaccine against B16 model. pGX4501 and pGX4503 plasmids were used. F indicates a furin cleavage site, or linker. P2A indicates a porcine teschovirus-1 cleavage site, or linker.

Figure 16:
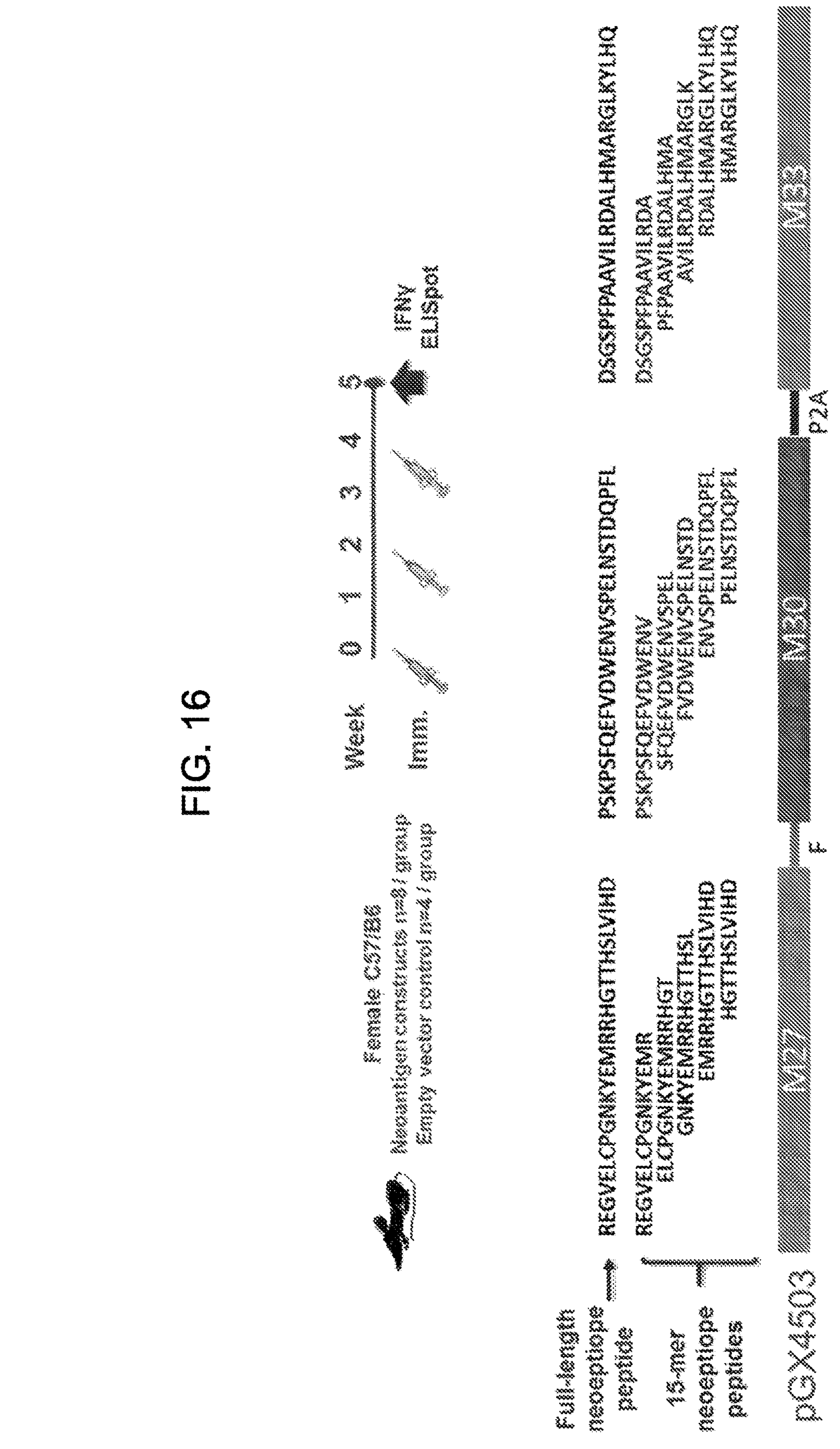
FIG. 16 shows the strategy for assessment of immune responses induced by a DNA vaccine against B16. Female C57/B6 mice were immunized with neoantigen constructs (n=8/group) or empty vector control (n=4). Immunization was carried out at weeks 0, 2, and 4. Splenic lymphocytes were stimulated for 18 hours with peptides for the full neoeptiope sequence (MHC II) (from left to right, SEQ ID NOS: 70, 76, and 82) or 15-mer peptides overlapping by 11 amino acids (MHC I) (left from top to bottom, SEQ ID NOS: 71, 72, 73, 74, and 75; center from top to bottom, SEQ ID NOS: 77, 78, 79, 80, and 81; right from top to bottom, SEQ ID NOS: 83, 84, 85, 86, and 87). Peptides were designed not to include cleavage sites. IFNγ ELISpot assay was carried out at week 5.

FIG. 16 shows the strategy for assessment of immune responses induced by a DNA vaccine against B16. Female C57/B6 mice were immunized with neoantigen constructs (n=8/group) or empty vector control (n=4). Immunization was carried out at weeks 0, 2, and 4. Splenic lymphocytes were stimulated for 18 hours with peptides for the full neoeptiope sequence (MHC II) or 15-mer peptides overlapping by 11 amino acids (MHC I). Peptides were design to not include cleavage sites. IFNγ ELISpot assay was carried out at week 5.

Figure 17:
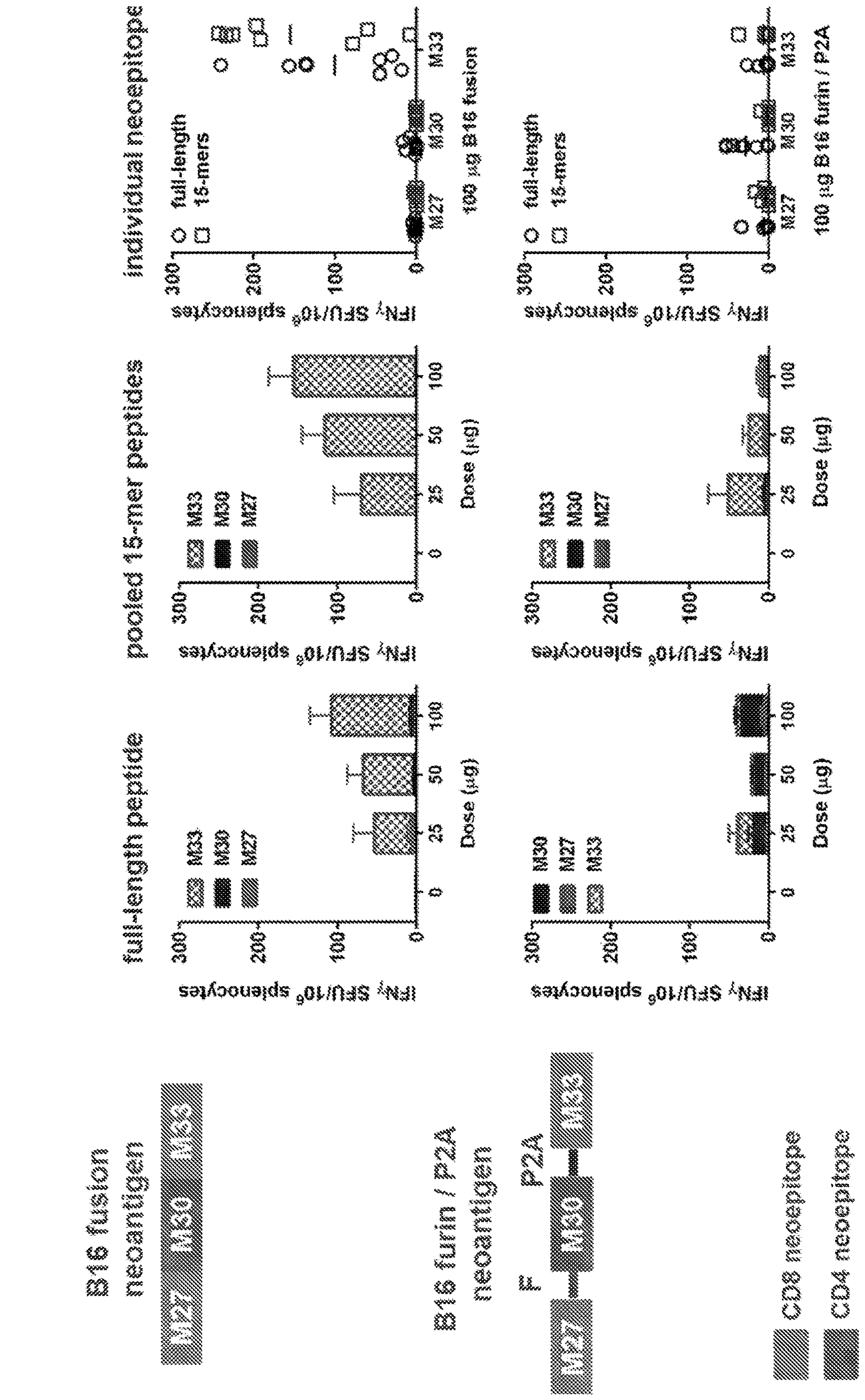
FIG. 17 shows a panel of graphs that show the results from the ELISpot assay, measuring the amount of IFNγ SFU/10e6 splenocytes, corresponding to T cell activation, for the tested full length peptide, pooled 15-mer peptides and individual neoepitopes. The B16 fusion neoantigen construct (top) and the B16 furin/P2A neoantigen construct (bottom) were tested.

FIG. 17 shows a panel of graphs that show the results from the ELISpot assay, measuring the amount of IFNγ SFU/10e6 splenocytes, which corresponds to T cell activation, in response to the full length peptide, pooled 15-mer peptides and individual neoepitopes. As shown in FIG. 17, the individual neoepitopes presented in the B16 fusion neoantigen generated the strongest response. The B16 fusion neoantigen construct (top) and the B16 furin/P2A neoantigen construct (bottom) were tested.

Figure 18:
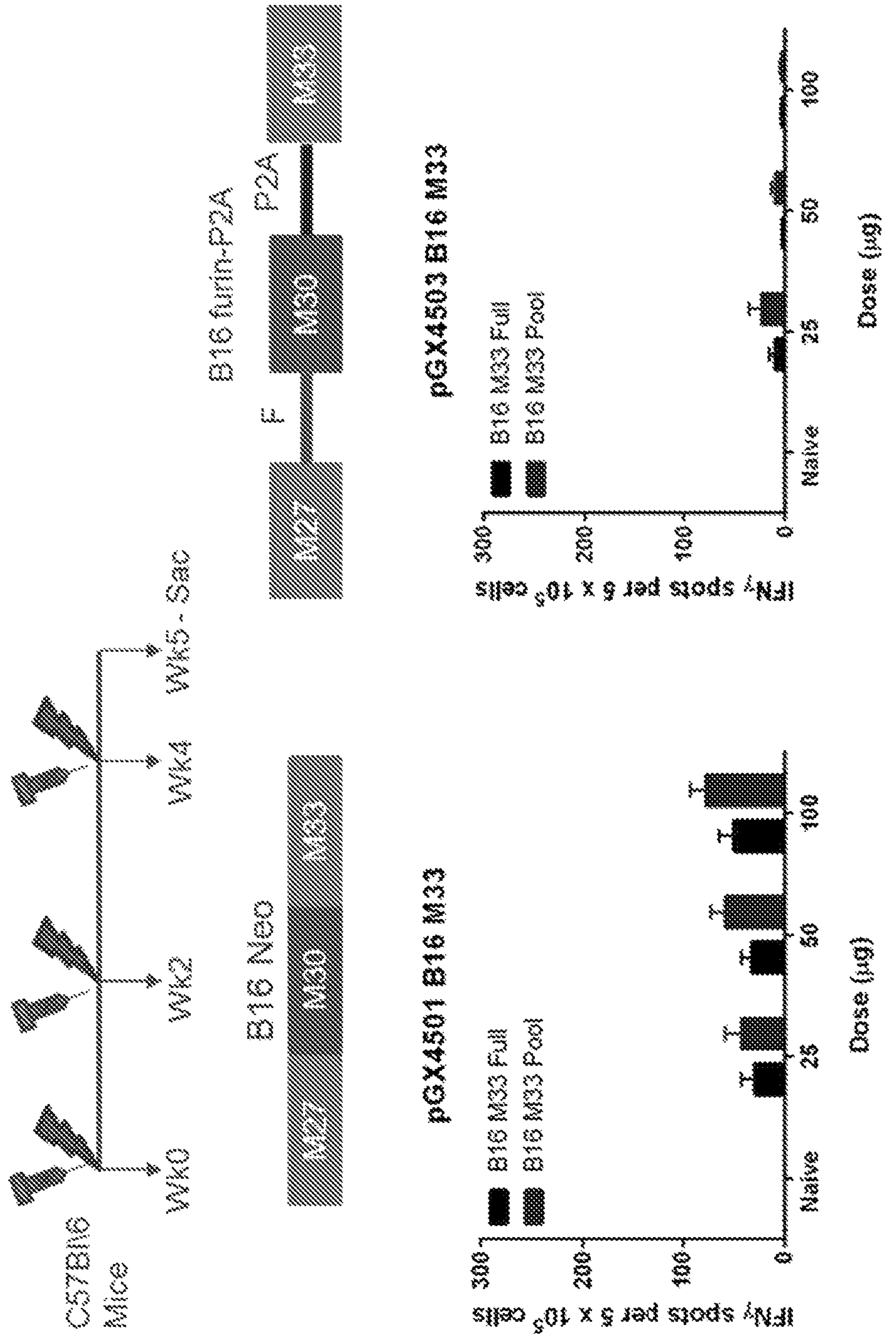
FIG. 18 shows proof of concept neoantigen studies: B16 neoantigens. In the absence of an adjuvant, pGX4501 can induce an immune response in mice, particularly in the M33 region, which is a CD8 epitope.

FIG. 18 shows proof of concept neoantigen studies: B16 neoantigens. In the absence of an adjuvant, pGX4501 can induce an immune response in mice, particularly in the M33 region, which is a CD8 epitope.

Example 7. Design of Poly-Neoepitope DNA Vaccine Against CT26 Model

Figure 19:
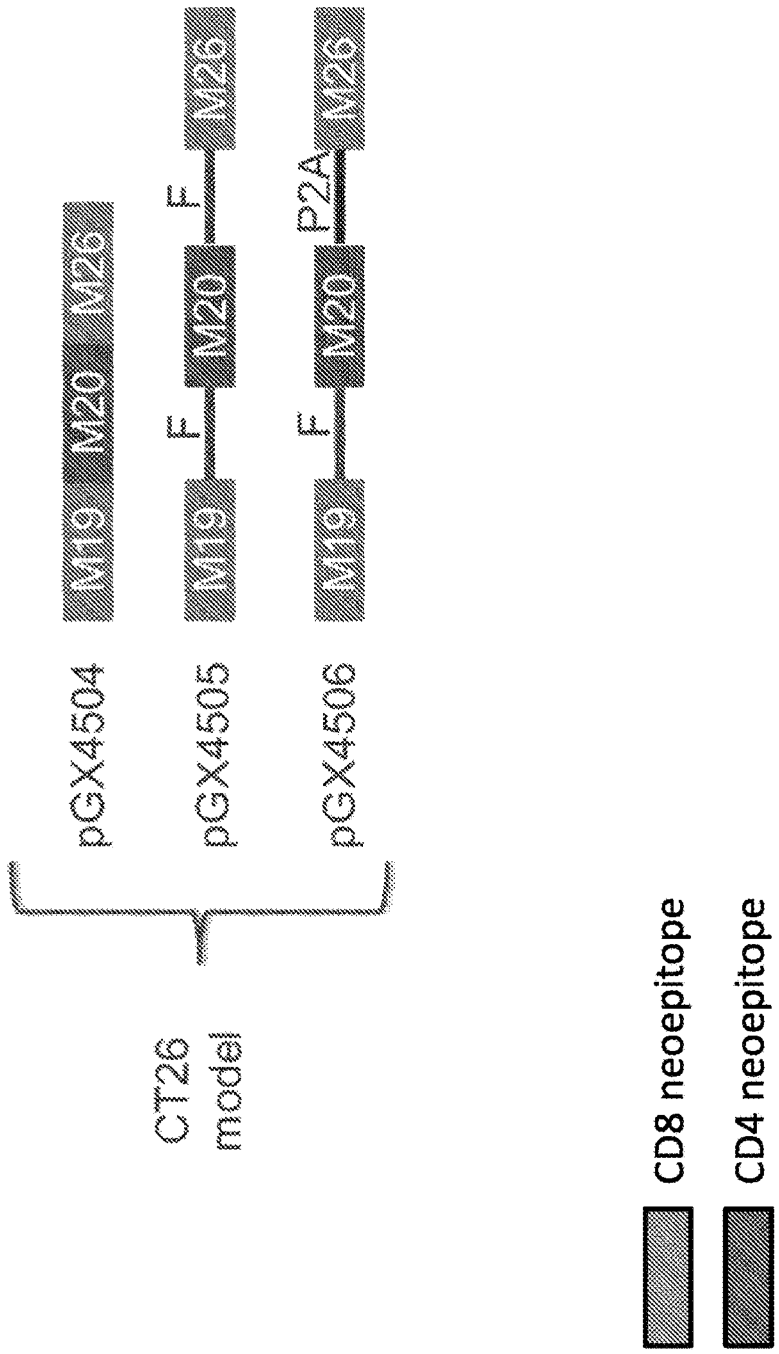
FIG. 19 shows a schematic of the design of poly-neoepitope DNA vaccine against B16 model. pGX4504, pGX5405 and pGX4506 plasmids were used. F indicates a furin cleavage site, encoded by the linker. P2A indicates a porcine teschovirus-1 cleavage site, encoded by the linker.

FIG. 19 shows a schematic of the design of poly-neoepitope DNA vaccine against B16 model. pGX4504, pGX5405 and pGC4506 plasmids were used. F indicates a furin linker. P2A indicates a porcine teschovirus-1 linker.

Figure 20:
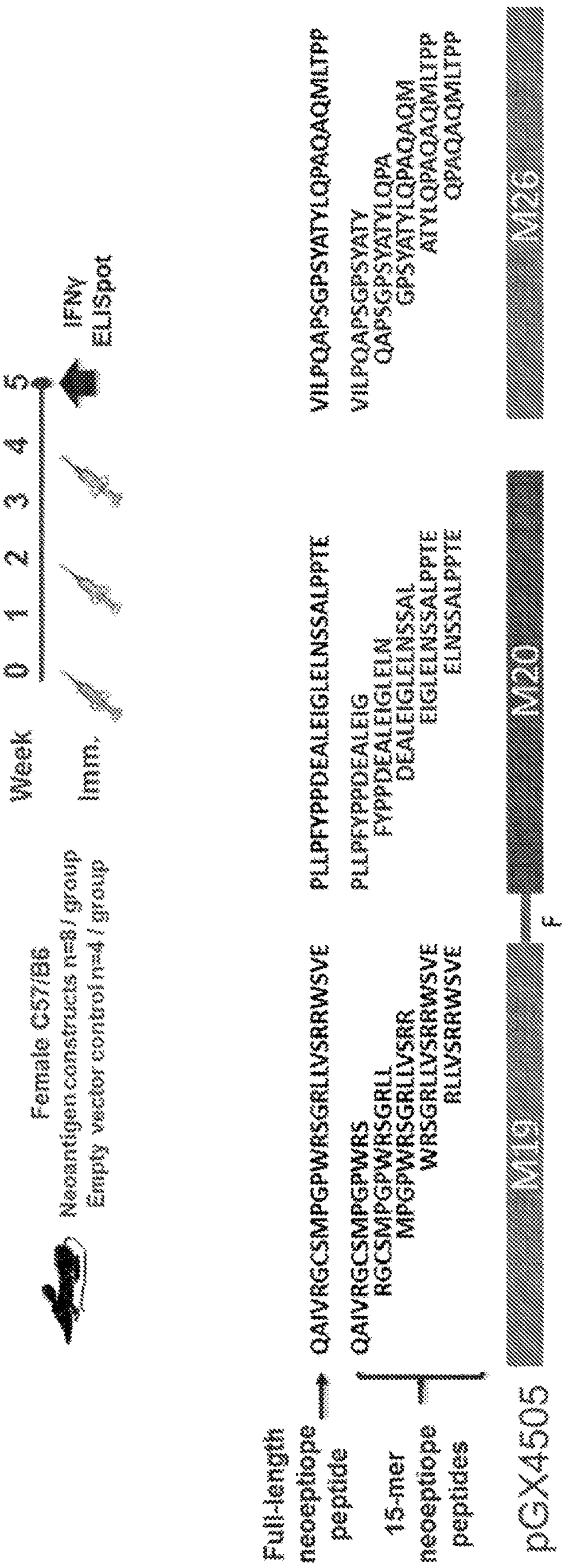
FIG. 20 shows the strategy for assessment of immune responses induced by a DNA vaccine against B16. Female C57/B6 mice were immunized with neoantigen constructs (n=8/group) or empty vector control (n=4). Immunization was carried out at weeks 0, 2, and 4. Splenic lymphocytes were stimulated for 18 hours with peptides for the full neoeptiope sequence (MHC II) (from left to right, SEQ ID NOS: 88, 94, and 100) or 15-mer peptides overlapping by 11 amino acids (MHC I) (left from top to bottom, SEQ ID NOS: 89, 90, 91, 92, and 93; center from top to bottom, SEQ ID NOS: 95, 96, 97, 98, and 99); right from top to bottom, SEQ ID NOS: 101, 102, 103, 104, and 105). Peptides were designed not to include cleavage sites. IFNγ ELISpot assay was carried out at week 5.

FIG. 20 shows the strategy for assessment of immune responses induced by a DNA vaccine against B16. Female C57/B6 mice were immunized with neoantigen constructs (n=8/group) or empty vector control (n=4). Immunization was carried out at weeks 0, 2, and 4. Splenic lymphocytes were stimulated for 18 hours with peptides for the full neoeptiope sequence (MHC II) or 15-mer peptides overlapping by 11 amino acids (MHC I). Peptides were design to not include cleavage sites. IFNγ ELISpot assay was carried out at week 5.

Figure 21:
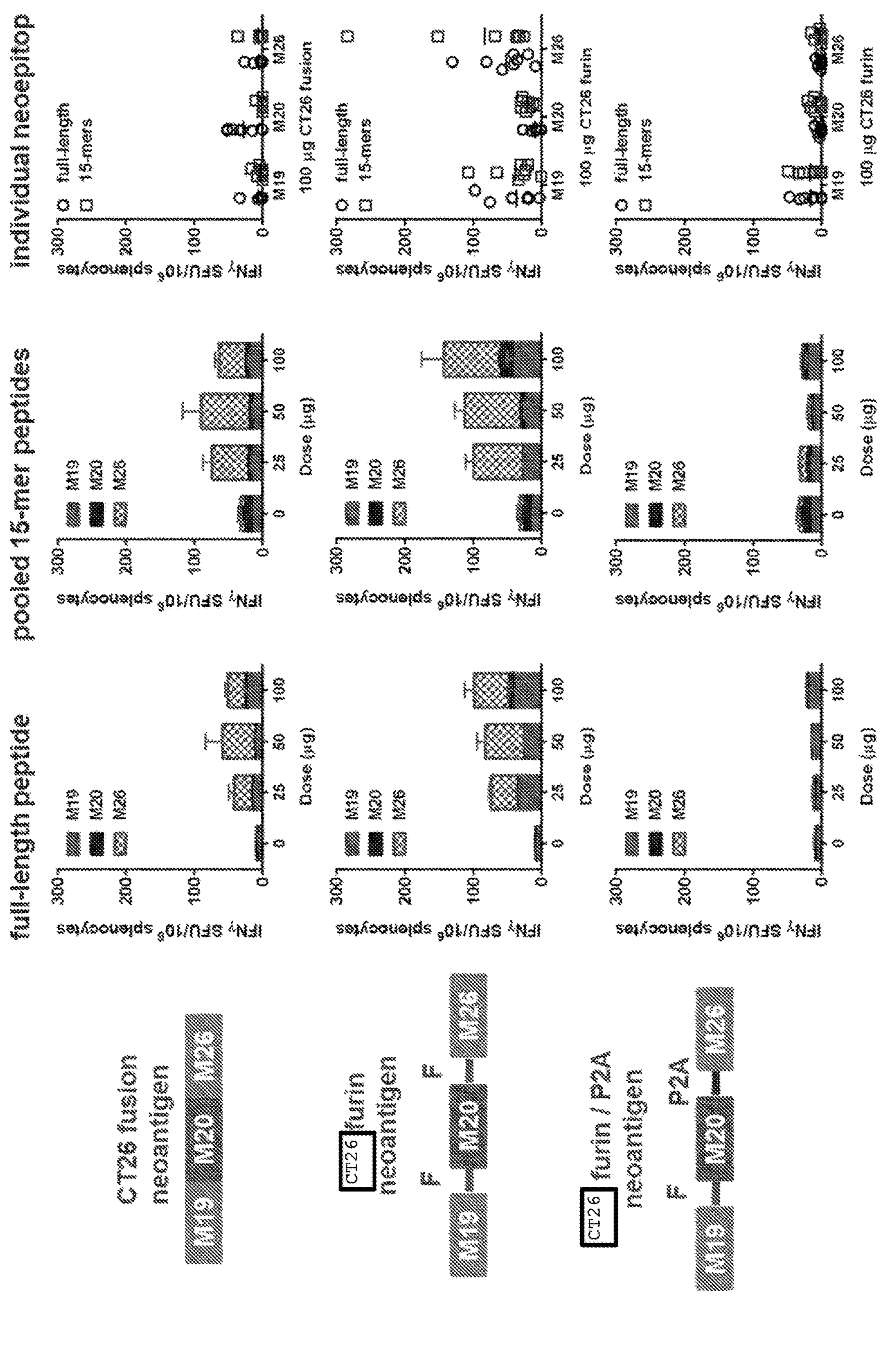
FIG. 21 shows a panel of results from the ELISpot assay, measuring the amount of IFNγ SFU/10e6 splenocytes, corresponding to T cell activation, for the tested full length peptide, pooled 15-mer peptides and individual neoepitopes. The CT26 fusion neoantigen construct (top), the CT26 furin neoantigen (middle) and the CT26 furin/P2A neoantigen construct (bottom) were tested.

FIG. 21 shows a panel of graphs that show the results from the ELISpot assay, measuring the amount of IFNγ SFU/10e6 splenocytes, corresponding to T cell activation, for the tested full length peptide, pooled 15-mer peptides and individual neoepitopes. As shown in FIG. 21, the individual neoepitopes presented in the CT26 furin neoantigen generated the strongest response. The CT26 fusion neoantigen construct (top), the CT26 furin neoantigen (middle) and the CT26 furin/P2A neoantigen construct (bottom) were tested.

Figure 22:
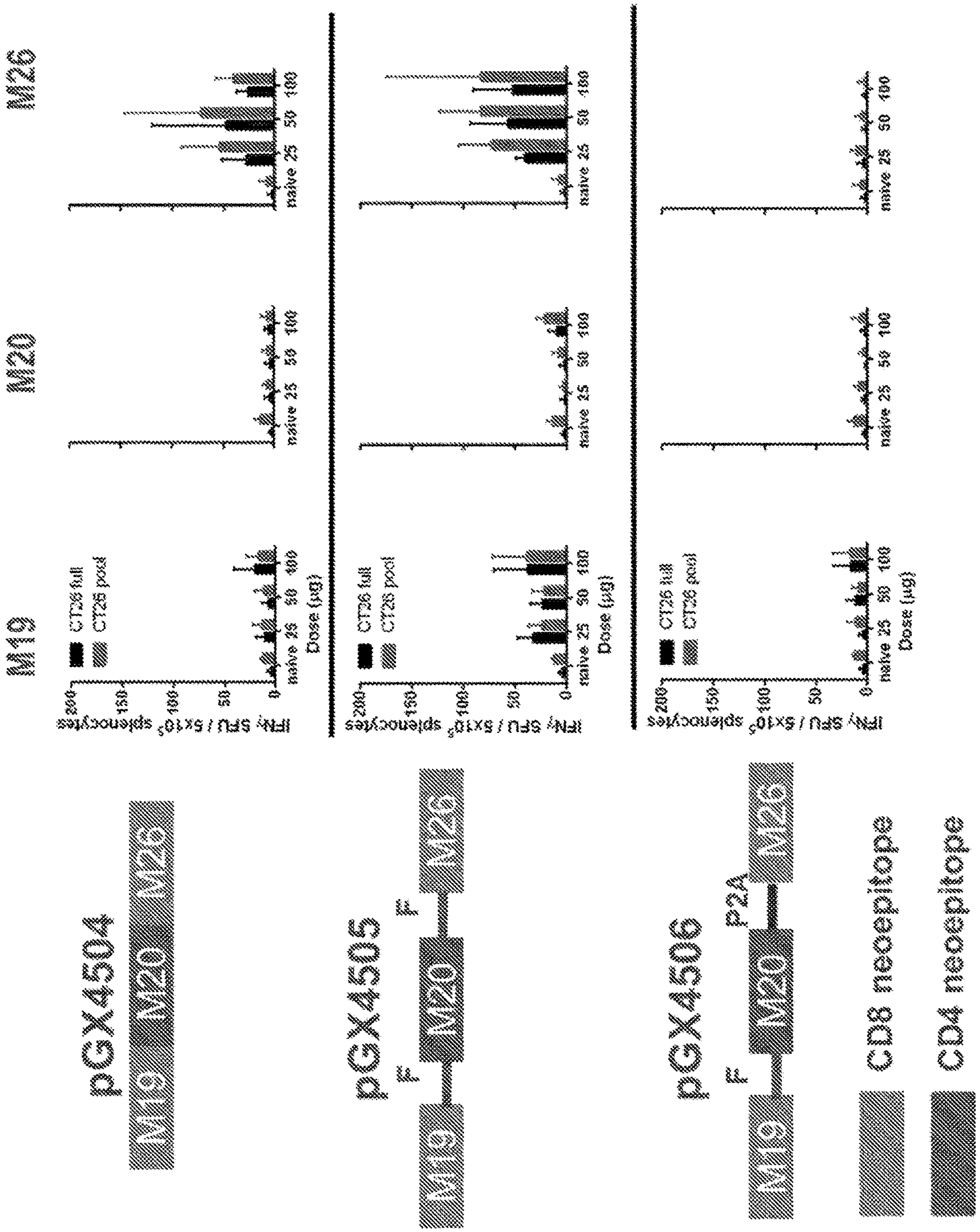
FIG. 22 shows proof of concept neoantigen studies: CT26 neoantigens.
Figure 23B:
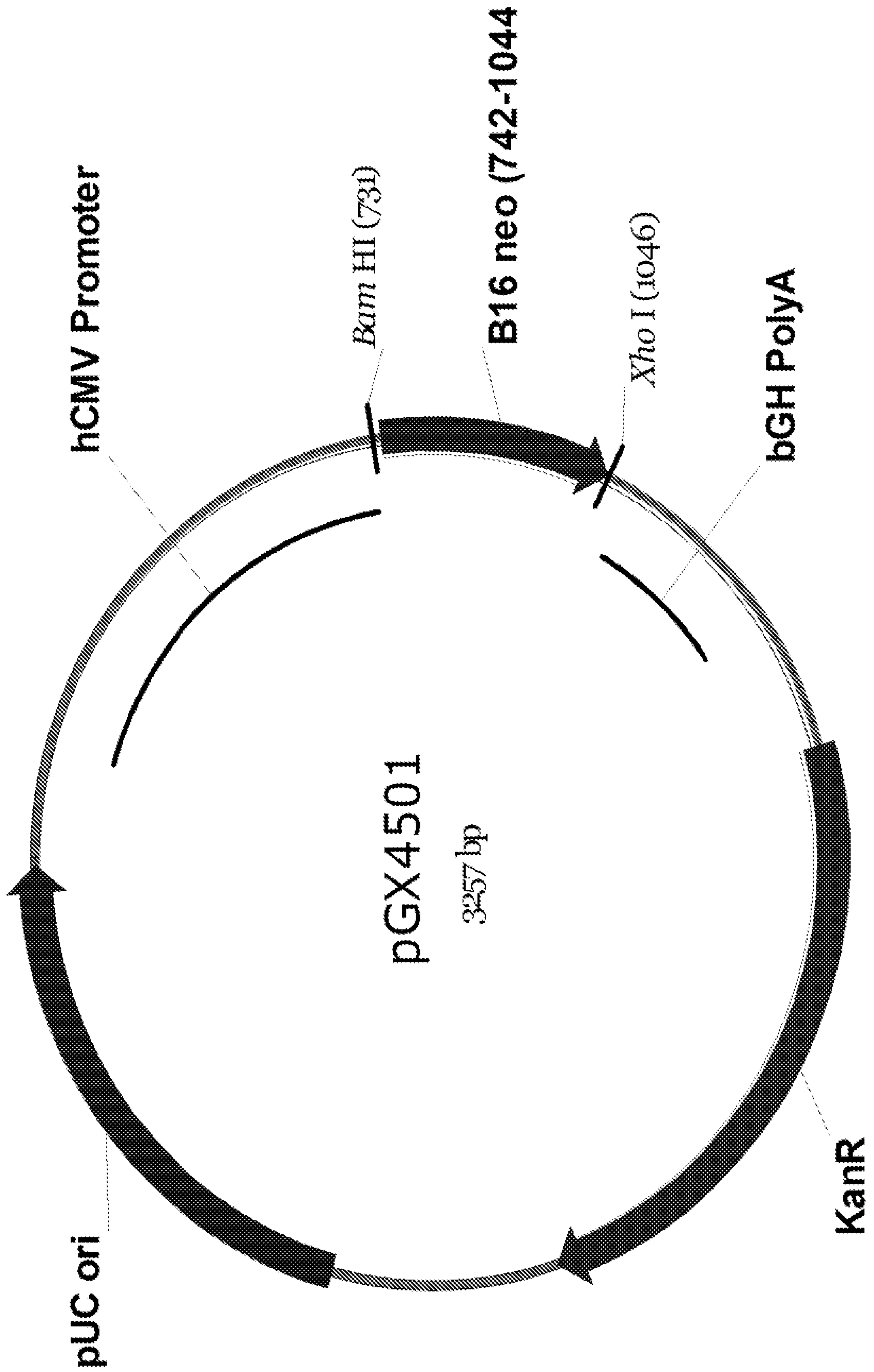
Figure 24B:
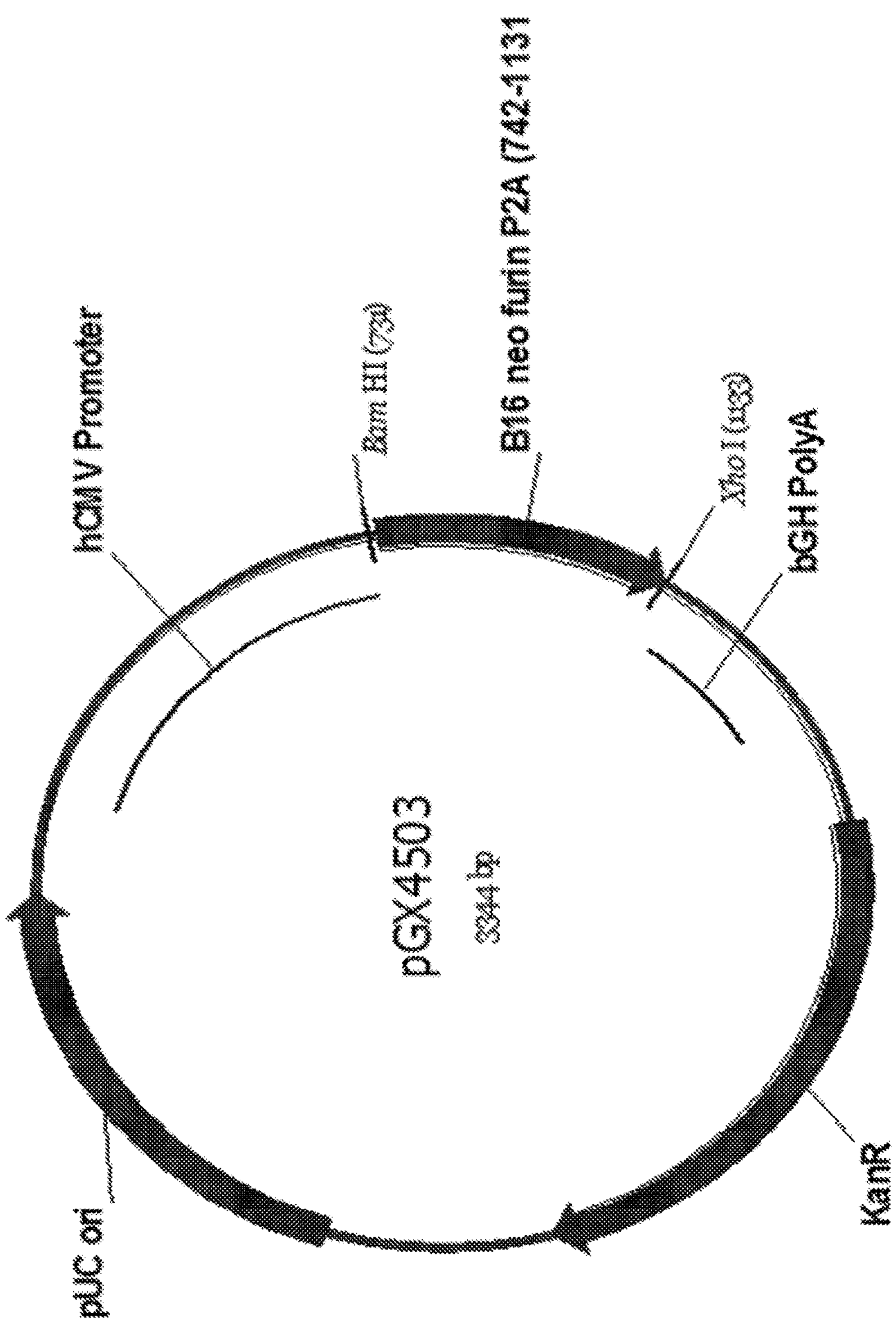
Figure 25B:
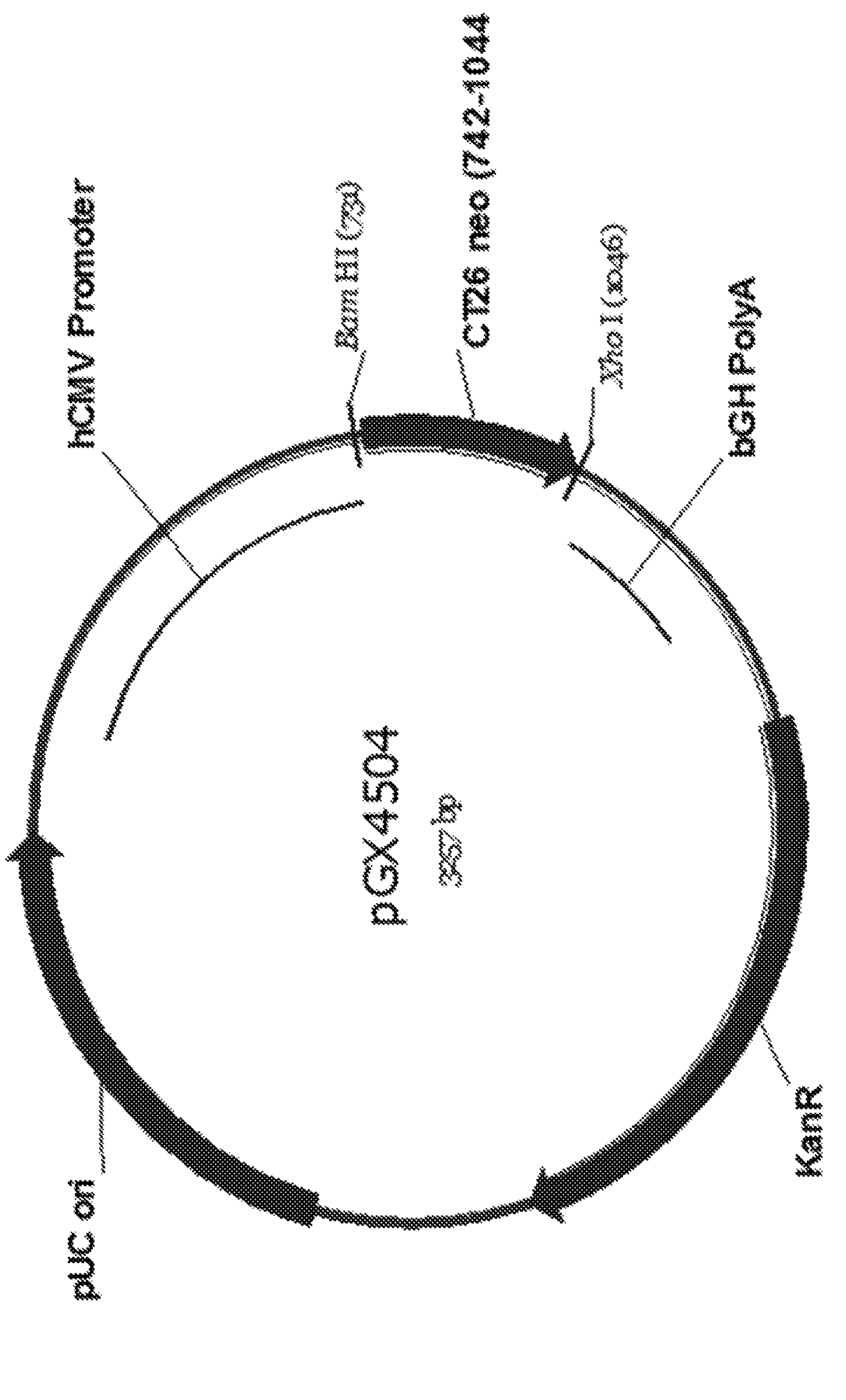
Figure 26B:
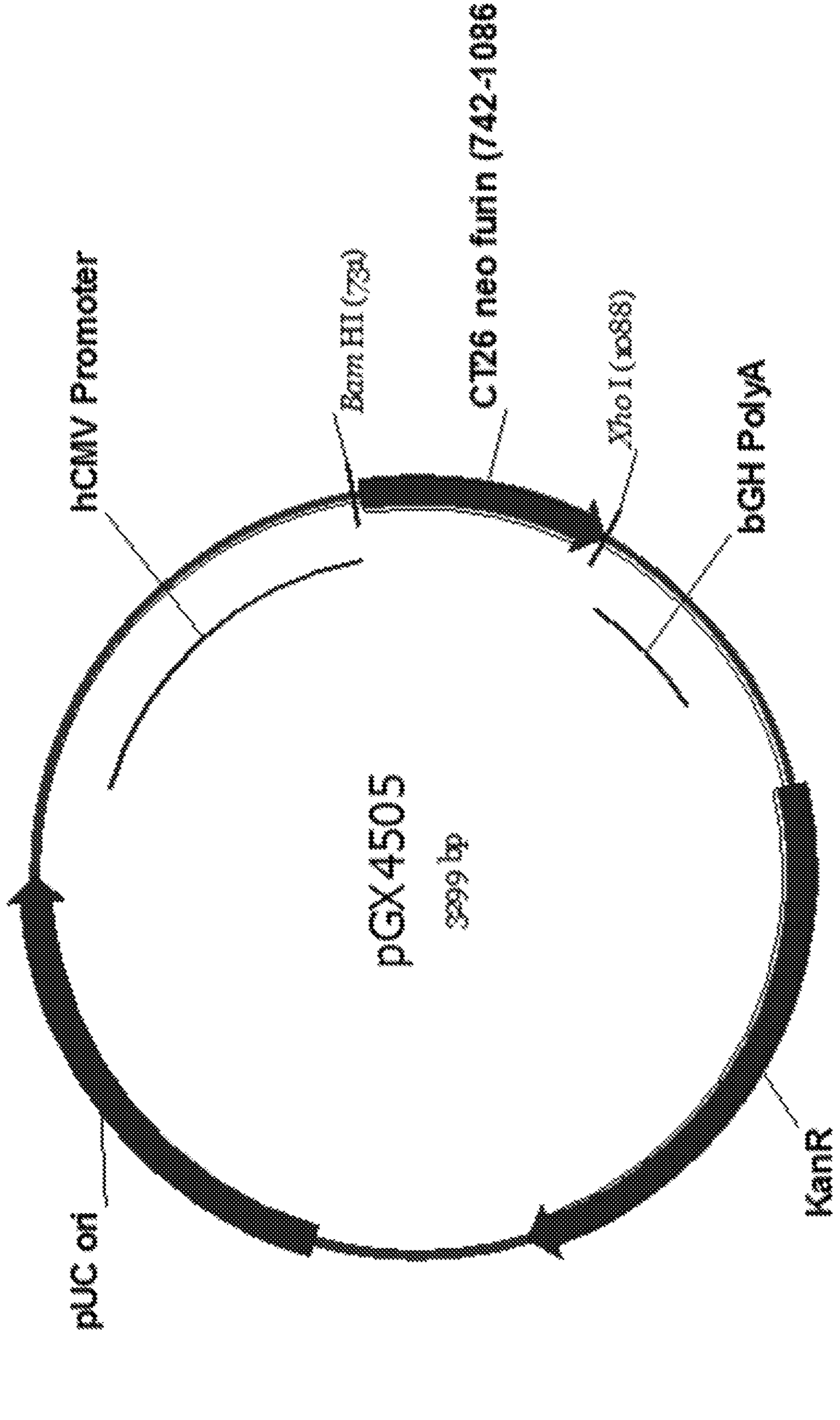
Figure 27B:
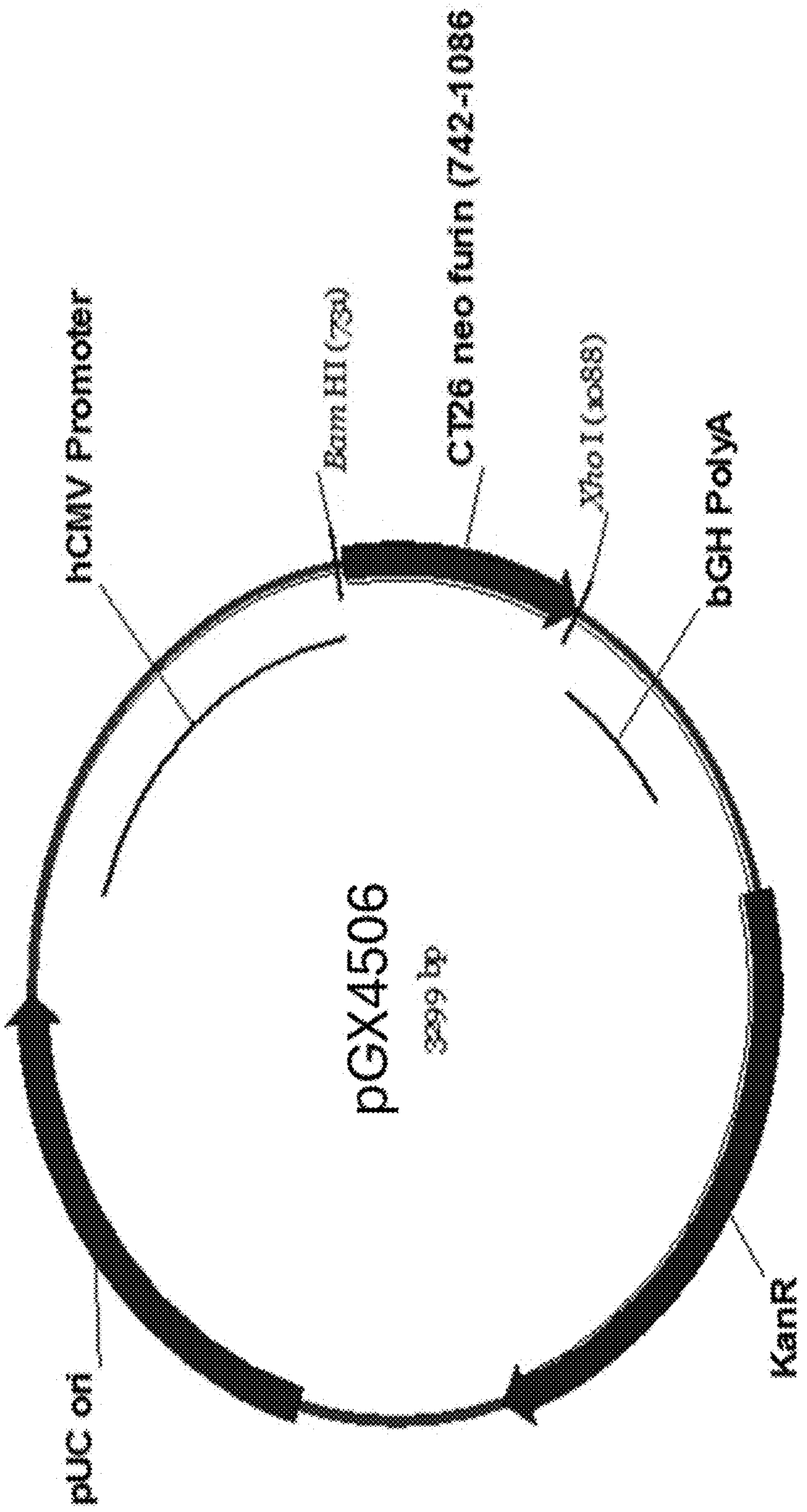

FIG. 22 shows proof of concept neoantigen studies: CT26 neoantigens.

Example 8. Expression of DNA Vaccines for Ex Vivo Priming Using Dendritic Cells Neoantigen DNA vaccines can also be used to prime T cells against neoantigens ex vivo. Dendritic cells are differentiated from the host, and are transfected with the DNA plasmids. T cells are added to the culture to obtain a selective expansion of T cells that can detect the neoantigen MHC-peptide complex.

Briefly, the procedure is as follows:

Thaw or Isolate bone marrow BM (get one female B6, flush bone marrow cells, lyse red blood cells, plate 2.5 million per well in 10 cm dish and add 10 ml RPMI, add 40 ng/ml of GMCSF. At day 3 refresh GMCSF by adding 10 ml of RPMI with 40 ng/ml of GMCSF.

At day 6, refresh GMCSF by spinning down 10 ml of RPMI and resuspend in 10 ml of fresh RPMI with 40 ng/ml of GMCSF.

On day 7: collect expanded dendritic cells and plate 0.5 million in a 6 well plate. Following, transfect neoantigen vaccine plasmids using lipofectamine reagent.

On day 8: plate T-cells at 10 (Tcells):1(BMDC) ratio (so 5 million per well) with 20 IU IL-2/ml and 1 ng/ml IL7.

Refresh transfected dendritic cell culture weekly for 4-6 weeks and use T cells in desired experiments.

Example 9: Delivery of a Plurality of Epitopes in One Formulation and Effect on Tumor Challenge Efficacy The purpose of this study is to demonstrate the ability to deliver 60 epitopes in one formulation (5 plasmids), and to demonstrate that delivery of more epitopes does not impact tumor challenge efficacy.

For this study, 5 groups of mice are implanted with tumors (TC1 tumors specifically) and are delivered the following vaccine combinations:

1. pVax (25 ug)
2. TC1 Plasmid #1 alone (25 ug)
3. 3 LLC Plasmids (25 ug per plasmid)+pVax (50 ug)
4. 2 TC1 plasmids (25 ug per plasmid)+pVax (75 ug)
5. 3 LLC Plasmids (25 ug per plasmid)+2 TC1 Plasmids (25 ug per plasmid)

In this study, it is expected that group #2, group #4 and group #5 will have similar anti-tumor activity, and that group #1 and group #3 will have no anti-tumor activity.

This study will demonstrate that adding irrelevant immunogenic epitopes from the LLC tumors does not impact the ability of the TC1 plasmids to generate anti-tumor immunity to TC1 tumors.

Full-length pVAX sequence is as follows:

```
                                                (SEQ ID NO: 68)
gctgcttcgcgatgtacgggccagatatacgcgttgacattgattattgac

tagttattaatagtaatcaattacggggtcattagttcatagcccatatat

ggagttccgcgttacataacttacggtaaatggcccgcctggctgaccgcc

caacgacccccgcccattgacgtcaataatgacgtatgttcccatagtaac

gccaatagggactttccattgacgtcaatgggtggagtatttacggtaaac

tgcccacttggcagtacatcaagtgtatcatatgccaagtacgccccctat

tgacgtcaatgacggtaaatggcccgcctggcattatgcccagtacatgac

cttatgggactttcctacttggcagtacatctacgtattagtcatcgctat

taccatggtgatgcggttttggcagtacatcaatgggcgtggatagcggtt

tgactcacggggatttccaagtctccaccccattgacgtcaatgggagttt

gttttggcaccaaaatcaacgggactttccaaaatgtcgtaacaactccgc

cccattgacgcaaatgggcggtaggcgtgtacggtgggaggtctatataag

cagagctctctggctaactagagaacccactgcttactggcttatcgaaat

taatacgactcactatagggagacccaagctggctagcgtttaaacttaag

cttggtaccgagctcggatccactagtccagtgtggtggaattctgcagat

atccagcacagtggcggccgctcgagtctagagggcccgtttaaacccgct

gatcagcctcgactgtgccttctagttgccagccatctgttgtttgcccct

cccccgtgccttccttgaccctggaaggtgccactcccactgtcctttcct

aataaaatgaggaaattgcatcgcattgtctgagtaggtgtcattctattc

tggggggtggggtggggcaggacagcaagggggaggattgggaagacaata

gcaggcatgctggggatgcggtgggctctatggcttctactgggcggtttt

atggacagcaagcgaaccggaattgccagctggggcgccctctggtaaggt
```

-continued

```
tgggaagccctgcaaagtaaactggatggctttcttgccgccaaggatctg

atggcgcaggggatcaagctctgatcaagagacaggatgaggatcgtttcg

catgattgaacaagatggattgcacgcaggttctccggccgcttgggtgga

gaggctattcggctatgactgggcacaacagacaatcggctgctctgatgc

cgccgtgttccggctgtcagcgcaggggcgcccggttctttttgtcaagac

cgacctgtccggtgccctgaatgaactgcaagacgaggcagcgcggctatc

gtggctggccacgacgggcgttccttgcgcagctgtgctcgacgttgtcac

ctgaagcgggaagggactggctgctattgggcgaagtgcggggcaggatct

cctgtcatctcaccttgctcctgccgagaaagtatccatcatggctgatgc

aatgcggcggctgcatacgcttgatccggctacctgcccattcgaccacca

agcgaaacatcgcatcgagcgagcacgtactcggatggaagccggtcttgt

gcgatcaggatgatctggacgaagagcatcaggctcgcgccagccgaact

gttcgccaggctcaaggcgagcatgcccgacggcgaggatctcgtcgtgac

accatggcgatgcctgcttgccgaatatctggtggaaaatggccgcttttc

tggattcatcgactgtggccggctgggtgtggcggaccgctatcaggacat

agcgttggctacccgtgatattgctgaagagcttggcggcgaatgggctga

ccgcttcctcgtgctttacggtatcgccgctcccgattcgcagcgcatcgc

cttctatcgccttcttgacgagttcttctgaattattaacgcttacaattt

cctgatgcggtattttctccttacgcatctgtgcggtatttcacaccgcat

caggtggcacttttcggggaaatgtgcgcggaacccctatttgtttatttt

tctaaatacattcaaatatgtatccgctcatgagacaataaccctgataaa

tgcttcaataatagcacgtgctaaaacttcatttttaatttaaaaggatct

aggtgaagatcctttttgataatctcatgaccaaaatcccttaacgtgagt

tttcgttccactgagcgtcagaccccgtagaaaagatcaaaggatcttctt

gagatcctttttttctgcgcgtaatctgctgcttgcaaacaaaaaaaccac

ccgctaccagcggtggtttgtttgccggatcaagagctaccaatctttttc

cgaaggtaactggcttcagcagagcgcagataccaaatactgttcttctag

tgtagccgtagttaggccaccacttcaagaactctgtagcaccgcctacat

acctcgctctgctaatcctgttaccagtggctgctgccagtggcgataagt

cgtgtcttaccgggttggactcaagacgatagttaccggataaggcgcagc

ggtcgggctgaacggggggttcgtgcacacagcccagcttggagcgaacga
```

-continued

```
cctacaccgaactgagatacctacagcgtgagctatgagaaagcgccacgc

ttcccgaagggagaaaggcggacaggtatccggtaagcggcagggtcggaa

caggagagcgcacgagggagcttccagggggaaacgcctggtatctttata

gtcctgtcgggtttcgccacctctgacttgagcgtcgatttttgtgatgct

cgtcaggggggcggagcctatggaaaaacgccagcaacgcggcctttttac

ggttcctggccttttgctggccttttgctcacatgttctt
```

Figure 30:
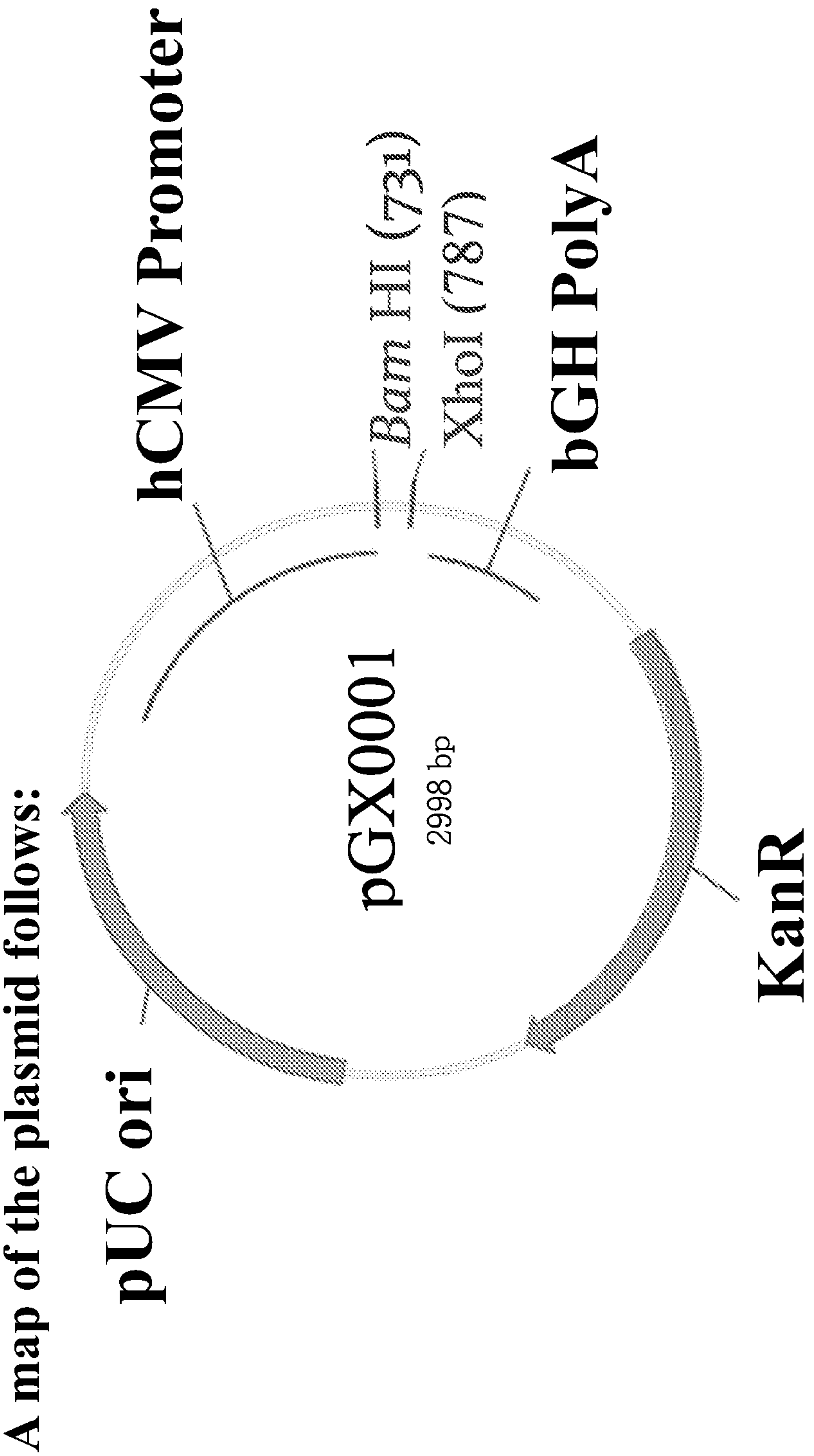
FIG. 30 is a restriction map of the pVAX plasmid.

A map of the plasmid is depicted in FIG. 30.

Example 10

Here are the studies that we have currently ongoing:

1. We are testing whether or not the IL-12 immune plasmid adjuvant can boost immune responses generated by LLC Plasmid #3.
2. We are testing the relative contributions of CD4 and CD8 T cells for the anti-tumor impact of the TC1 Plasmid #1 vaccine through immune depletion studies.
3. We are testing the anti-tumor activity of the 3 LLC plasmids in the LLC tumor model.
4. We are testing the anti-tumor activity of the 2 ID8 Plasmids either alone or in combination with immune checkpoint inhibitors targeting CTLA4 and PD1 in the ID8 ovarian tumor model.
5. We are looking for neo-antigen competition in the TC1 tumor model by delivering non-TC1 targeted neo-epitope plasmids (from LLC) in combination with the TC1 Plasmids and comparing to TC1 Plasmid #1 alone.

Example 11—40 Antigen Plasmid Construction and Vaccination

Purpose #1: Compare the efficacy of a 12-epitope plasmid versus 24-epitope plasmid versus 40-epitope plasmid.

Purpose #2: Alter the position of Sgsm2 within each plasmid to determine if that has an impact.

Figure 31:
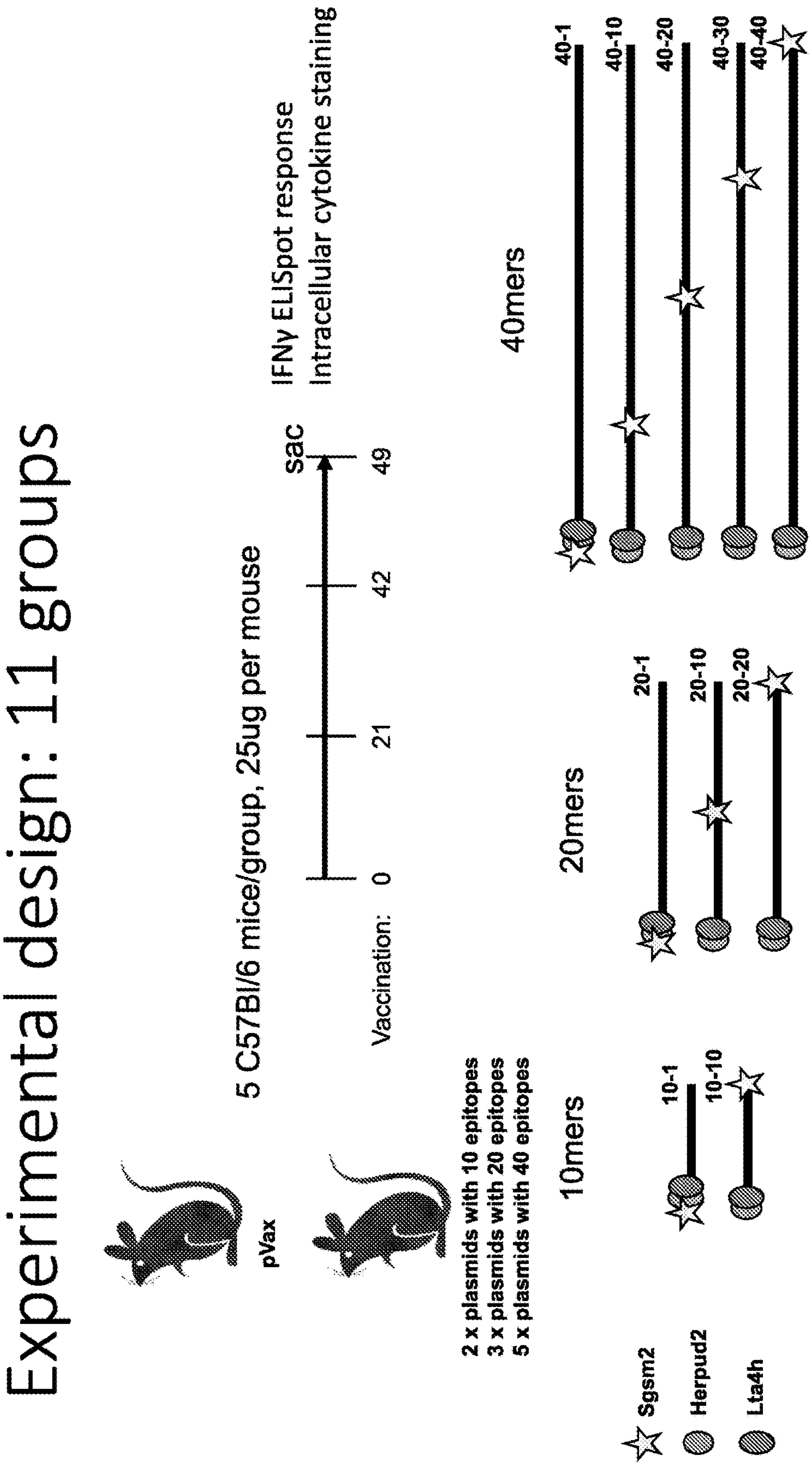
FIG. 31 depicts a both a vaccination protocol of an experiment performed with plasmids and the structure of plasmids in graphic form.
Figure 32:
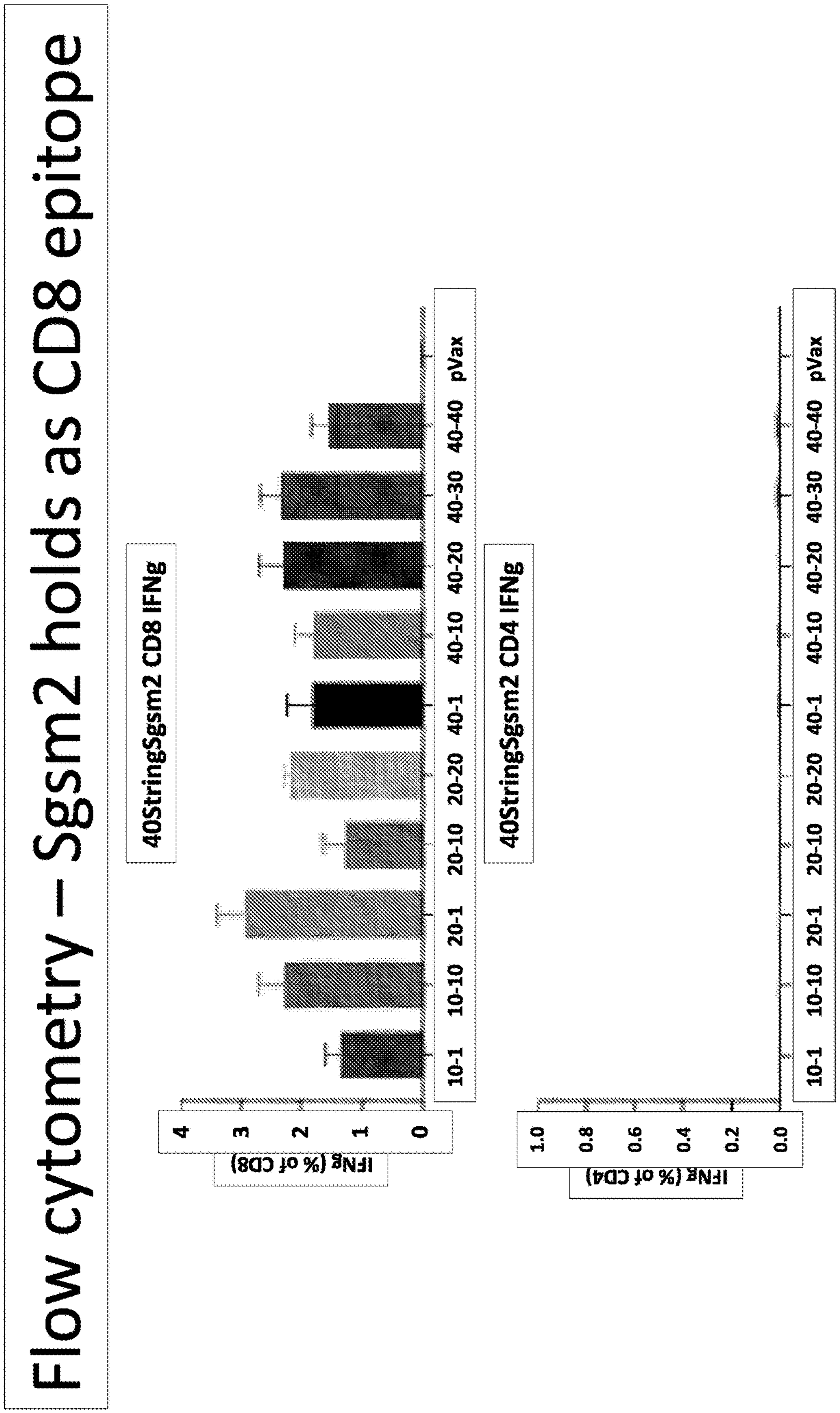
FIG. 32 depicts results of the experiment of Example 11 using the plasmids identified in FIG. 31.

Plasmid sequences of pVAX1 were created comprising nucleic acid constructs that encode the epitopes below. As indicated nucleic acid sequences encoding the amino acid sequence provided were cloned into the pVAX1 vector multiple cloning site with 10 antigens, 20 antigens or 40 antigens. Animals were vaccinated using the protocol depicted in FIG. 31. The labels of each plasmid depict the number and order in which antigens are presented within the plasmid. After vaccination, ELISPOT assays with the protocol identified in Example 1 above were performed and CD8+ cells as well as CD4+ cells were isolated using the above flow cytometry protocol of Example 1. Results of the how many IFN-gamma producing cells of those particular subsets were calculated and depicted in FIG. 32.

All immunogenic epitopes:

1. Sgsm2 V656A:

(SEQ ID NO: 1)

SHVQRLVHRDSTISNDAFISVDDLEPSGPQDLE

2. Herpud2 V85L:

(SEQ ID NO: 2)

DHLQLKDILRKQDEYHMVHLLCASRSPPSSPKS

3. Lta4h V463A:

(SEQ ID NO: 3)

WNTWLYAPGLPPVKPNYDATLTNACIALSQRWV

4. Phactr4 V253L:

(SEQ ID NO: 4)

AQRNSNPIIAELSQAMNSGTLLSKPSPPLPPKR

-continued

5. Aunip E168G:

(SEQ ID NO: 5)

GESKGPLDSSFSQYLGRSCLLDQREAKRKGEGL

6. Pik3ca Y143F:

(SEQ ID NO: 6)

QGKYILKVCGCDEYFLEKFPLSQYKYIRSCIML

7. Gpn2 I151V:

(SEQ ID NO: 7)

KFISVLCTSLATMLHVELPHVNLLSKMDLIEHY

8. Eng I286V:

(SEQ ID NO: 8)

LRPSTLSQEVYKTVSMRLNVVSPDLSGKGLVLP

9. Zmym1 P172S:

(SEQ ID NO: 9)

ACSSSYNSAVMESSSVNVSMVHSSSKENLCPKK

10. Sema6d V255M:

(SEQ ID NO: 10)

REIAVEHNNLGKAVYSRMARICKNDMGGSQRVL

11. Ubr1 G1412S:

(SEQ ID NO: 11)

PGLLSVDLFHVLVSAVLAFPSLYWDDTVDLQPS

12. Zgrf1 Y1638C:

(SEQ ID NO: 12)

LCLMGHKPVLLRTQCRCHPAISAIANDLFYEGS

13. Casz1 L1087P:

(SEQ ID NO: 13)

TSAAETKPPLAPSSPPAPPGTMVAGSSLEGPAP

14. Adgrb2 L572P:

(SEQ ID NO: 14)

RSLQELLARRTYYSGDPLFSVDILRNVTDTFKR

15. ObsI1 T1764M:

(SEQ ID NO: 15)

GGHVCWMREGVELCPGNKYEMRRHGTTHSLVIH

16. Dhrs9 L146P:

(SEQ ID NO: 16)

EPIEVNLFGLINVTPNMLPLVKKARGRVINVSS

17. Zmym1 T466R:

(SEQ ID NO: 17)

VDFNKICGQAYDSATNFRVKLNEVVAEFKKEEP

18. Nrp2 W664L:

(SEQ ID NO: 18)

NCNFDFPEETCGWVYDHAKLLRSTWISSANPND

19. Abhd18 S210C:

(SEQ ID NO: 19)

ISMGGHMASLAVCNWPKPMPLIPCLSWSTASGV

20. Focad V1388M:

(SEQ ID NO: 20)

GLSLNIKKYLLVSMPLWAKHMSDEQIQGFVENL (SEQ ID NO: 41)

RGRKRRS - furin cleavage site 10-epitope plasmid:
1. Sgsm2 V656A:

(SEQ ID NO: 1)

SHVQRLVHRDSTISNDAFISVDDLEPSGPQDLE

2. Herpud2 V85L:

(SEQ ID NO: 2)

DHLQLKDILRKQDEYHMVHLLCASRSPPSSPKS

3. Lta4h V463A:

(SEQ ID NO: 3)

WNTWLYAPGLPPVKPNYDATLTNACIALSQRWV

-continued

9. Zmym1 P172S:

(SEQ ID NO: 9)

ACSSSYNSAVMESSSVNVSMVHSSSKENLCPKK

11. Ubr1 G1412S:

(SEQ ID NO: 11)

PGLLSVDLFHVLVSAVLAFPSLYWDDTVDLQPS

15. ObsI1 T1764M:

(SEQ ID NO: 15)

GGHVCWMREGVELCPGNKYEMRRHGTTHSLVIH

16. Dhrs9 L146P:

(SEQ ID NO: 16)

EPIEVNLFGLINVTPNMLPLVKKARGRVINVSS

17. Zmym1 T466R:

(SEQ ID NO: 17)

VDFNKICGQAYDSATNFRVKLNEVVAEFKKEEP

18. Nrp2 W664L:

(SEQ ID NO: 18)

NCNFDFPEETCGWVYDHAKLLRSTWISSANPND

19. Abhd18 S210C:

(SEQ ID NO: 19)

ISMGGHMASLAVCNWPKPMPLIPCLSWSTASGV 20-epitope plasmid:

1. Sgsm2 V656A:

(SEQ ID NO: 1)

SHVQRLVHRDSTISNDAFISVDDLEPSGPQDLE

2. Herpud2 V85L:

(SEQ ID NO: 2)

DHLQLKDILRKQDEYHMVHLLCASRSPPSSPKS

3. Lta4h V463A:

(SEQ ID NO: 3)

WNTWLYAPGLPPVKPNYDATLTNACIALSQRWV

4. Phactr4 V253L:

(SEQ ID NO: 4)

AQRNSNPIIAELSQAMNSGTLLSKPSPPLPPKR

5. Aunip E168G:

(SEQ ID NO: 5)

GESKGPLDSSFSQYLGRSCLLDQREAKRKGEGL

6. Pik3ca Y143F:

(SEQ ID NO: 6)

QGKYILKVCGCDEYFLEKFPLSQYKYIRSCIML

7. Gpn2 I151V:

(SEQ ID NO: 7)

KFISVLCTSLATMLHVELPHVNLLSKMDLIEHY

8. Eng I286V:

(SEQ ID NO: 8)

LRPSTLSQEVYKTVSMRLNVVSPDLSGKGLVLP

9. Zmym1 P172S:

(SEQ ID NO: 9)

ACSSSYNSAVMESSSVNVSMVHSSSKENLCPKK

10. Sema6d V255M:

(SEQ ID NO: 10)

REIAVEHNNLGKAVYSRMARICKNDMGGSQRVL

11. Ubr1 G1412S:

(SEQ ID NO: 11)

PGLLSVDLFHVLVSAVLAFPSLYWDDTVDLQPS

12. Zgrf1 Y1638C:

(SEQ ID NO: 12)

LCLMGHKPVLLRTQCRCHPAISAIANDLFYEGS

13. Casz1 L1087P:

(SEQ ID NO: 13)

TSAAETKPPLAPSSPPAPPGTMVAGSSLEGPAP

-continued

14. Adgrb2 L572P:

(SEQ ID NO: 14)
RSLQELLARRTYYSGDPLFSVDILRNVTDTFKR

15. ObsI1 T1764M:

(SEQ ID NO: 15)
GGHVCWMREGVELCPGNKYEMRRHGTTHSLVIH

16. Dhrs9 L146P:

(SEQ ID NO: 16)
EPIEVNLFGLINVTPNMLPLVKKARGRVINVSS

17. Zmym1 T466R:

(SEQ ID NO: 17)
VDFNKICGQAYDSATNFRVKLNEVVAEFKKEEP

18. Nrp2 W664L:

(SEQ ID NO: 18)
NCNFDFPEETCGWVYDHAKLLRSTWISSANPND

19. Abhd18 S210C:

(SEQ ID NO: 19)
ISMGGHMASLAVCNWPKPMPLIPCLSWSTASGV

20. Focad VI 388M:

(SEQ ID NO: 20)
GLSLNIKKYLLVSMPLWAKHMSDEQIQGFVENL 40-epitope plasmid:
20 immunogenic epitopes + 20 non-immunogenic epitopes
1. Sgsm2 V656A:

(SEQ ID NO: 1)
SHVQRLVHRDSTISNDAFISVDDLEPSGPQDLE

2. Herpud2 V85L:

(SEQ ID NO: 2)
DHLQLKDILRKQDEYHMVHLLCASRSPPSSPKS

3. Lta4h V463A:

(SEQ ID NO: 3)
WNTWLYAPGLPPVKPNYDATLTNACIALSQRWV

4. Phactr4 V253L:

(SEQ ID NO: 4)
AQRNSNPIIAELSQAMNSGTLLSKPSPPLPPKR

5. Aunip E168G:

(SEQ ID NO: 5)
GESKGPLDSSFSQYLGRSCLLDQREAKRKGEGL

6. Pik3ca Y143F:

(SEQ ID NO: 6)
QGKYILKVCGCDEYFLEKFPLSQYKYIRSCIML

7. Gpn2 I151V:

(SEQ ID NO: 7)
KFISVLCTSLATMLHVELPHVNLLSKMDLIEHY

8. Eng I286V:

(SEQ ID NO: 8)
LRPSTLSQEVYKTVSMRLNVVSPDLSGKGLVLP

9. Zmym1 P172S:

(SEQ ID NO: 9)
ACSSSYNSAVMESSSVNVSMVHSSSKENLCPKK

10. Sema6d V255M:

(SEQ ID NO: 10)
REIAVEHNNLGKAVYSRMARICKNDMGGSQRVL

11. Ubr1 G1412S:

(SEQ ID NO: 11)
PGLLSVDLFHVLVSAVLAFPSLYWDDTVDLQPS

12. Zgrf1 Y1638C:

(SEQ ID NO: 12)
LCLMGHKPVLLRTQCRCHPAISAIANDLFYEGS

13. Casz1 L1087P:

(SEQ ID NO: 13)
TSAAETKPPLAPSSPPAPPGTMVAGSSLEGPAP

-continued

14. Adgrb2 L572P:
(SEQ ID NO: 14)
RSLQELLARRTYYSGDPLFSVDILRNVTDTFKR

15. ObsI1 T1764M:
(SEQ ID NO: 15)
GGHVCWMREGVELCPGNKYEMRRHGTTHSLVIH

16. Dhrs9 L146P:
(SEQ ID NO: 16)
EPIEVNLFGLINVTPNMLPLVKKARGRVINVSS

17. Zmym1 T466R:
(SEQ ID NO: 17)
VDFNKICGQAYDSATNFRVKLNEVVAEFKKEEP

18. Nrp2 W664L:
(SEQ ID NO: 18)
NCNFDFPEETCGWVYDHAKLLRSTWISSANPND

19. Abhd18 S210C:
(SEQ ID NO: 19)
ISMGGHMASLAVCNWPKPMPLIPCLSWSTASGV

20. Focad V1388M:
(SEQ ID NO: 20)
GLSLNIKKYLLVSMPLWAKHMSDEQIQGFVENL

Non-immunogenic epitopes:

1. Hdac4 W1020C:
(SEQ ID NO: 21)
ANAVHSMEKVMDIHSKYCRCLQRLSSTVGHSLI

2. Gmppa H24Y:
(SEQ ID NO: 22)
EVPKPLFPVAGVPMIQYHIEACAQVPGMQEILL

3. Fras1 L3135P:
(SEQ ID NO: 23)
SNEDREWHESFSLVLGPDDPVEAVLGDVTTATV

4. Padi3 L193P:
(SEQ ID NO: 24)
MSVMVLRTQGPEAPFEDHRLILHTSSCDAERAR

5. Pdia3 Y264C:
(SEQ ID NO: 25)
CPHMTEDNKDLIQGKDLLTACYDVDYEKNAKGS

6. Pnisr R476G:
(SEQ ID NO: 26)
TRGLAYLHTELPQGDHYKPAISHRDLNSRNVLV

7. Capg F167L:
(SEQ ID NO: 27)
IHREQNSLSLLEASEADGDAVNDKKRTPNEAPS

8. Spen N2066S:
(SEQ ID NO: 28)
EPKRDRRDPSTDKSGPDTFPVEVLERKPPEKTY

9. Usp21 V229M:
(SEQ ID NO: 29)
SGHVGLRNLGNTLPQCFLNAMLQCLSSTRPLRD

10. Clspn A101V:
(SEQ ID NO: 30)
AEDTQENLHSGKSQSRSFPKVLADSDESDMEET

11. Nckap1 K344T:
(SEQ ID NO: 31)
ECKEAAVSHAGSMHRERRTFLRSALKELATVLS

12. Map7d1 R577W:
(SEQ ID NO: 32)
RMREEQLAREAEAWAEREAEARRREEQEAREKA

13. C77080 S770A:
(SEQ ID NO: 33)
LSQTPPPAPPPSAGSEPLARLPQKDSVGKHSGA

-continued

14. Stard9 R1686M:

(SEQ ID NO: 34)
NTQIQKLTGSPFRSREYVQTMESESEHSYPPPG

15. Wdr37 H110Y:

(SEQ ID NO: 35)
TTTSRAICQLVKEYIGYRDGIWDVSVTRTQPIV

16. Fam160b2 S575R:

(SEQ ID NO: 36)
NGYDTYVHDAYGLFQECRSRVAHWGWPLGPAPL

17. Mb21d1 Y346S:

(SEQ ID NO: 37)
IQGWLGTKVRTNLRREPFSLVPKNAKDGNSFQG

18. Pyroxd2 V483L:

(SEQ ID NO: 38)
GGKVWNEQEKNTYADKLFDCIEAYAPGFKRSVL

19. Jmjd1c L1715P:

(SEQ ID NO: 39)
WMKCVKGQPHDHKHLMPTQIIPGSVLTDLLDAM

20. Smek1 E665K:

(SEQ ID NO: 40)
SILRNHRYRRDARTLEDKEEMWFNTDEDDMEDG

The entire length of encoded amino acid seqeunce in the plasmids is presented below.
 indicates stop codon and should not be included in each sequence identifier even if SEQ ID number appears after the ""

10-epitope Sgsm2 pos 1:

(SEQ ID NO: 42)
MSHVQRLVHRDSTISNDAFISVDDLEPSGPQDLERGRKRRSDHLQLKDILRKQDEYHMVHLLC

ASRSPPSSPKSRGRKRRSWNTWLYAPGLPPVKPNYDATLTNACIALSQRWVRGRKRRSACSS

SYNSAVMESSSVNVSMVHSSSKENLCPKKRGRKRRSPGLLSVDLFHVLVSAVLAFPSLYWDD

TVDLQPSRGRKRRSGGHVCWMREGVELCPGNKYEMRRHGTTHSLVIHRGRKRRSEPIEVNLF

GLINVTPNMLPLVKKARGRVINVSSRGRKRRSVDFNKICGQAYDSATNFRVKLNEVVAEFKKEE

PRGRKRRSNCNFDFPEETCGWVYDHAKLLRSTWISSANPNDRGRKRRSISMGGHMASLAVC

NWPKPMPLIPCLSWSTASGV**

10-epitope Sgsm2 pos 10:

(SEQ ID NO: 43)
MDHLQLKDILRKQDEYHMVHLLCASRSPPSSPKSRGRKRRSWNTWLYAPGLPPVKPNYDATL

TNACIALSQRWVRGRKRRSACSSSYNSAVMESSSVNVSMVHSSSKENLCPKKRGRKRRSPG

LLSVDLFHVLVSAVLAFPSLYWDDTVDLQPSRGRKRRSGGHVCWMREGVELCPGNKYEMRR

HGTTHSLVIHRGRKRRSEPIEVNLFGLINVTPNMLPLVKKARGRVINVSSRGRKRRSVDFNKICG

QAYDSATNFRVKLNEVVAEFKKEEPRGRKRRSNCNFDFPEETCGWVYDHAKLLRSTWISSAN

PNDRGRKRRSISMGGHMASLAVCNWPKPMPLIPCLSWSTASGVRGRKRRSSHVQRLVHRDS

TISNDAFISVDDLEPSGPQDLE**

20-epitope Sgsm2 pos 1:

(SEQ ID NO: 44)
MSHVQRLVHRDSTISNDAFISVDDLEPSGPQDLERGRKRRSDHLQLKDILRKQDEYHMVHLLC

ASRSPPSSPKSRGRKRRSWNTWLYAPGLPPVKPNYDATLTNACIALSQRWVRGRKRRSAQR

NSNPIIAELSQAMNSGTLLSKPSPPLPPKRRGRKRRSGESKGPLDSSFSQYLGRSCLLDQREA

KRKGEGLRGRKRRSQGKYILKVCGCDEYFLEKFPLSQYKYIRSCIMLRGRKRRSKFISVLCTSL

ATMLHVELPHVNLLSKMDLIEHYRGRKRRSLRPSTLSQEVYKTVSMRLNVVSPDLSGKGLVLP

RGRKRRSACSSSYNSAVMESSSVNVSMVHSSSKENLCPKKRGRKRRSREIAVEHNNLGKAVY

SRMARICKNDMGGSQRVLRGRKRRSPGLLSVDLFHVLVSAVLAFPSLYWDDTVDLQPSRGRK

-continued

RRSLCLMGHKPVLLRTQCRCHPAISAIANDLFYEGSRGRKRRSTSAAETKPPLAPSSPPAPPGT

MVAGSSLEGPAPRGRKRRSRSLQELLARRTYYSGDPLFSVDILRNVTDTFKRRGRKRRSGGH

VCWMREGVELCPGNKYEMRRHGTTHSLVIHRGRKRRSEPIEVNLFGLINVTPNMLPLVKKARG

RVINVSSRGRKRRSVDFNKICGQAYDSATNFRVKLNEVVAEFKKEEPRGRKRRSNCNFDFPEE

TCGWVYDHAKLLRSTWISSANPNDRGRKRRSISMGGHMASLAVCNWPKPMPLIPCLSWSTAS

GVRGRKRRSGLSLNIKKYLLVSMPLWAKHMSDEQIQGFVENL**

20-epitope Sgsm2 pos 10:

(SEQ ID NO: 45)

MHLQLKDILRKQDEYHMVHLLCASRSPPSSPKSRGRKRRSWNTWLYAPGLPPVKPNYDATL

TNACIALSQRWVRGRKRRSAQRNSNPIIAELSQAMNSGTLLSKPSPPLPPKRRGRKRRSGESK

GPLDSSFSQYLGRSCLLDQREAKRKGEGLRGRKRRSQGKYILKVCGCDEYFLEKFPLSQYKYI

RSCIMLRGRKRRSKFISVLCTSLATMLHVELPHVNLLSKMDLIEHYRGRKRRSLRPSTLSQEVY

KTVSMRLNVVSPDLSGKGLVLPRGRKRRSACSSSYNSAVMESSSVNVSMVHSSSKENLCPKK

RGRKRRSREIAVEHNNLGKAVYSRMARICKNDMGGSQRVLRGRKRRSSHVQRLVHRDSTISN

DAFISVDDLEPSGPQDLERGRKRRSPGLLSVDLFHVLVSAVLAFPSLYWDDTVDLQPSRGRKR

RSLCLMGHKPVLLRTQCRCHPAISAIANDLFYEGSRGRKRRSTSAAETKPPLAPSSPPAPPGT

MVAGSSLEGPAPRGRKRRSRSLQELLARRTYYSGDPLFSVDILRNVTDTFKRRGRKRRSGGH

VCWMREGVELCPGNKYEMRRHGTTHSLVIHRGRKRRSEPIEVNLFGLINVTPNMLPLVKKARG

RVINVSSRGRKRRSVDFNKICGQAYDSATNFRVKLNEVVAEFKKEEPRGRKRRSNCNFDFPEE

TCGWVYDHAKLLRSTWISSANPNDRGRKRRSISMGGHMASLAVCNWPKPMPLIPCLSWSTAS

GVRGRKRRSGLSLNIKKYLLVSMPLWAKHMSDEQIQGFVENL**

20-epitope Sgsm2 pos 20:

(SEQ ID NO: 46)

MDHLQLKDILRKQDEYHMVHLLCASRSPPSSPKSRGRKRRSWNTWLYAPGLPPVKPNYDATL

TNACIALSQRWVRGRKRRSAQRNSNPIIAELSQAMNSGTLLSKPSPPLPPKRRGRKRRSGESK

GPLDSSFSQYLGRSCLLDQREAKRKGEGLRGRKRRSQGKYILKVCGCDEYFLEKFPLSQYKYI

RSCIMLRGRKRRSKFISVLCTSLATMLHVELPHVNLLSKMDLIEHYRGRKRRSLRPSTLSQEVY

KTVSMRLNVVSPDLSGKGLVLPRGRKRRSACSSSYNSAVMESSSVNVSMVHSSSKENLCPKK

RGRKRRSREIAVEHNNLGKAVYSRMARICKNDMGGSQRVLRGRKRRSPGLLSVDLFHVLVSA

VLAFPSLYVVDDTVDLQPSRGRKRRSLCLMGHKPVLLRTQCRCHPAISAIANDLFYEGSRGRKR

RSTSAAETKPPLAPSSPPAPPGTMVAGSSLEGPAPRGRKRRSRSLQELLARRTYYSGDPLFSV

DILRNVTDTFKRRGRKRRSGGHVCWMREGVELCPGNKYEMRRHGTTHSLVIHRGRKRRSEPI

EVNLFGLINVTPNMLPLVKKARGRVINVSSRGRKRRSVDFNKICGQAYDSATNFRVKLNEVVAE

FKKEEPRGRKRRSNCNFDFPEETCGWVYDHAKLLRSTWISSANPNDRGRKRRSISMGGHMA

SLAVCNWPKPMPLIPCLSWSTASGVRGRKRRSGLSLNIKKYLLVSMPLWAKHMSDEQIQGFVE

NLRGRKRRSSHVQRLVHRDSTISNDAFISVDDLEPSGPQDLE**

40-epitope Sgsm2 pos 1:

(SEQ ID NO: 47)

MSHVQRLVHRDSTISNDAFISVDDLEPSGPQDLERGRKRRSANAVHSMEKVMDIHSKYCRCLQ

RLSSTVGHSLIRGRKRRSDHLQLKDILRKQDEYHMVHLLCASRSPPSSPKSRGRKRRSEVPKP

LFPVAGVPMIQYHIEACAQVPGMQEILLRGRKRRSWNTWLYAPGLPPVKPNYDATLTNACIALS

QRVVVRGRKRRSSNEDREWHESFSLVLGPDDPVEAVLGDVTTATVRGRKRRSAQRNSNPIIAE

LSQAMNSGTLLSKPSPPLPPKRRGRKRRSMSVMVLRTQGPEAPFEDHRLILHTSSCDAERAR

-continued

RGRKRRSGESKGPLDSSFSQYLGRSCLLDQREAKRKGEGLRGRKRRSCPHMTEDNKDLIQG

KDLLTACYDVDYEKNAKGSRGRKRRSQGKYILKVCGCDEYFLEKFPLSQYKYIRSCIMLRGRK

RRSTRGLAYLHTELPQGDHYKPAISHRDLNSRNVLVRGRKRRSKFISVLCTSLATMLHVELPHV

NLLSKMDLIEHYRGRKRRSIHREQNSLSLLEASEADGDAVNDKKRTPNEAPSRGRKRRSLRPS

TLSQEVYKTVSMRLNVVSPDLSGKGLVLPRGRKRRSEPKRDRRDPSTDKSGPDTFPVEVLER

KPPEKTYRGRKRRSACSSSYNSAVMESSSVNVSMVHSSSKENLCPKKRGRKRRSSGHVGLR

NLGNTLPQCFLNAMLQCLSSTRPLRDRGRKRRSREIAVEHNNLGKAVYSRMARICKNDMGGS

QRVLRGRKRRSAEDTQENLHSGKSQSRSFPKVLADSDESDMEETRGRKRRSPGLLSVDLFHV

LVSAVLAFPSLYWDDTVDLQPSRGRKRRSECKEAAVSHAGSMHRERRTFLRSALKELATVLSR

GRKRRSLCLMGHKPVLLRTQCRCHPAISAIANDLFYEGSRGRKRRSRMREEQLAREAEAWAE

REAEARRREEQEAREKARGRKRRSTSAAETKPPLAPSSPPAPPGTMVAGSSLEGPAPRGRKR

RSLSQTPPPAPPPSAGSEPLARLPQKDSVGKHSGARGRKRRSRSLQELLARRTYYSGDPLFS

VDILRNVTDTFKRRGRKRRSNTQIQKLTGSPFRSREYVQTMESESEHSYPPPGRGRKRRSGG

HVCWMREGVELCPGNKYEMRRHGTTHSLVIHRGRKRRSTTTSRAICQLVKEYIGYRDGIWDV

SVTRTQPIVRGRKRRSEPIEVNLFGLINVTPNMLPLVKKARGRVINVSSRGRKRRSNGYDTYVH

DAYGLFQECRSRVAHWGWPLGPAPLRGRKRRSVDFNKICGQAYDSATNFRVKLNEVVAEFKK

EEPRGRKRRSIQGWLGTKVRTNLRREPFSLVPKNAKDGNSFQGRGRKRRSNCNFDFPEETC

GVVVYDHAKLLRSTWISSANPNDRGRKRRSGGKVWNEQEKNTYADKLFDCIEAYAPGFKRSVL

RGRKRRSISMGGHMASLAVCNWPKPMPLIPCLSWSTASGVRGRKRRSWMKCVKGQPHDHK

HLMPTQIIPGSVLTDLLDAMRGRKRRSGLSLNIKKYLLVSMPLWAKHMSDEQIQGFVENLRGRK

RRSSILRNHRYRRDARTLEDKEEMWFNTDEDDMEDG**

40-epitope Sgsm2 pos 10:

(SEQ ID NO: 48)

MANAVHSMEKVMDIHSKYCRCLQRLSSTVGHSLIRGRKRRSDHLQLKDILRKQDEYHMVHLLC

ASRSPPSSPKSRGRKRRSEVPKPLFPVAGVPMIQYHIEACAQVPGMQEILLRGRKRRSWNTW

LYAPGLPPVKPNYDATLTNACIALSQRWVRGRKRRSSNEDREWHESFSLVLGPDDPVEAVLG

DVTTATVRGRKRRSAQRNSNPIIAELSQAMNSGTLLSKPSPPLPPKRRGRKRRSMSVMVLRTQ

GPEAPFEDHRLILHTSSCDAERARRGRKRRSGESKGPLDSSFSQYLGRSCLLDQREAKRKGE

GLRGRKRRSCPHMTEDNKDLIQGKDLLTACYDVDYEKNAKGSRGRKRRSSHVQRLVHRDSTI

SNDAFISVDDLEPSGPQDLERGRKRRSQGKYILKVCGCDEYFLEKFPLSQYKYIRSCIMLRGRK

RRSTRGLAYLHTELPQGDHYKPAISHRDLNSRNVLVRGRKRRSKFISVLCTSLATMLHVELPHV

NLLSKMDLIEHYRGRKRRSIHREQNSLSLLEASEADGDAVNDKKRTPNEAPSRGRKRRSLRPS

TLSQEVYKTVSMRLNVVSPDLSGKGLVLPRGRKRRSEPKRDRRDPSTDKSGPDTFPVEVLER

KPPEKTYRGRKRRSACSSSYNSAVMESSSVNVSMVHSSSKENLCPKKRGRKRRSSGHVGLR

NLGNTLPQCFLNAMLQCLSSTRPLRDRGRKRRSREIAVEHNNLGKAVYSRMARICKNDMGGS

QRVLRGRKRRSAEDTQENLHSGKSQSRSFPKVLADSDESDMEETRGRKRRSPGLLSVDLFHV

LVSAVLAFPSLYWDDTVDLQPSRGRKRRSECKEAAVSHAGSMHRERRTFLRSALKELATVLSR

GRKRRSLCLMGHKPVLLRTQCRCHPAISAIANDLFYEGSRGRKRRSRMREEQLAREAEAWAE

REAEARRREEQEAREKARGRKRRSTSAAETKPPLAPSSPPAPPGTMVAGSSLEGPAPRGRKR

RSLSQTPPPAPPPSAGSEPLARLPQKDSVGKHSGARGRKRRSRSLQELLARRTYYSGDPLFS

VDILRNVTDTFKRRGRKRRSNTQIQKLTGSPFRSREYVQTMESESEHSYPPPGRGRKRRSGG

HVCWMREGVELCPGNKYEMRRHGTTHSLVIHRGRKRRSTTTSRAICQLVKEYIGYRDGIWDV

-continued

SVTRTQPIVRGRKRRSEPIEVNLFGLINVTPNMLPLVKKARGRVINVSSRGRKRRSNGYDTYVH
DAYGLFQECRSRVAHWGWPLGPAPLRGRKRRSVDFNKICGQAYDSATNFRVKLNEVVAEFKK
EEPRGRKRRSIQGWLGTKVRTNLRREPFSLVPKNAKDGNSFQGRGRKRRSNCNFDFPEETC
GWVYDHAKLLRSTWISSANPNDRGRKRRSGGKVWNEQEKNTYADKLFDCIEAYAPGFKRSVL
RGRKRRSISMGGHMASLAVCNWPKPMPLIPCLSWSTASGVRGRKRRSWMKCVKGQPHDHK
HLMPTQIIPGSVLTDLLDAMRGRKRRSGLSLNIKKYLLVSMPLWAKHMSDEQIQGFVENLRGRK
RRSSILRNHRYRRDARTLEDKEEMWFNTDEDDMEDG**

40-epitope Sgsm2 pos 20:

(SEQ ID NO: 49)

MANAVHSMEKVMDIHSKYCRCLQRLSSTVGHSLIRGRKRRSDHLQLKDILRKQDEYHMVHLLC
ASRSPPSSPKSRGRKRRSEVPKPLFPVAGVPMIQYHIEACAQVPGMQEILLRGRKRRSWNTW
LYAPGLPPVKPNYDATLTNACIALSQRWVRGRKRRSSNEDREWHESFSLVLGPDDPVEAVLG
DVTTATVRGRKRRSAQRNSNPIIAELSQAMNSGTLLSKPSPPLPPKRRGRKRRSMSVMVLRTQ
GPEAPFEDHRLILHTSSCDAERARRGRKRRSGESKGPLDSSFSQYLGRSCLLDQREAKRKGE
GLRGRKRRSCPHMTEDNKDLIQGKDLLTACYDVDYEKNAKGSRGRKRRSQGKYILKVCGCDE
YFLEKFPLSQYKYIRSCIMLRGRKRRSTRGLAYLHTELPQGDHYKPAISHRDLNSRNVLVRGRK
RRSKFISVLCTSLATMLHVELPHVNLLSKMDLIEHYRGRKRRSIHREQNSLSLLEASEADGDAV
NDKKRTPNEAPSRGRKRRSLRPSTLSQEVYKTVSMRLNVVSPDLSGKGLVLPRGRKRRSEPK
RDRRDPSTDKSGPDTFPVEVLERKPPEKTYRGRKRRSACSSSYNSAVMESSSVNVSMVHSSS
KENLCPKKRGRKRRSSGHVGLRNLGNTLPQCFLNAMLQCLSSTRPLRDRGRKRRSREIAVEH
NNLGKAVYSRMARICKNDMGGSQRVLRGRKRRSAEDTQENLHSGKSQSRSFPKVLADSDES
DMEETRGRKRRSSHVQRLVHRDSTISNDAFISVDDLEPSGPQDLERGRKRRSPGLLSVDLFHV
LVSAVLAFPSLYWDDTVDLQPSRGRKRRSECKEAAVSHAGSMHRERRTFLRSALKELATVLSR
GRKRRSLCLMGHKPVLLRTQCRCHPAISAIANDLFYEGSRGRKRRSRMREEQLAREAEAWAE
REAEARRREEQEAREKARGRKRRSTSAAETKPPLAPSSPPAPPGTMVAGSSLEGPAPRGRKR
RSLSQTPPPAPPPSAGSEPLARLPQKDSVGKHSGARGRKRRSRSLQELLARRTYYSGDPLFS
VDILRNVTDTFKRRGRKRRSNTQIQKLTGSPFRSREYVQTMESESEHSYPPPGRGRKRRSGG
HVCWMREGVELCPGNKYEMRRHGTTHSLVIHRGRKRRSTTTSRAICQLVKEYIGYRDGIWDV
SVTRTQPIVRGRKRRSEPIEVNLFGLINVTPNMLPLVKKARGRVINVSSRGRKRRSNGYDTYVH
DAYGLFQECRSRVAHWGWPLGPAPLRGRKRRSVDFNKICGQAYDSATNFRVKLNEVVAEFKK
EEPRGRKRRSIQGWLGTKVRTNLRREPFSLVPKNAKDGNSFQGRGRKRRSNCNFDFPEETC
GWVYDHAKLLRSTWISSANPNDRGRKRRSGGKVWNEQEKNTYADKLFDCIEAYAPGFKRSVL
RGRKRRSISMGGHMASLAVCNWPKPMPLIPCLSWSTASGVRGRKRRSWMKCVKGQPHDHK
HLMPTQIIPGSVLTDLLDAMRGRKRRSGLSLNIKKYLLVSMPLWAKHMSDEQIQGFVENLRGRK
RRSSILRNHRYRRDARTLEDKEEMWFNTDEDDMEDG**

40-epitope Sgsm2 pos 30:

(SEQ ID NO: 50)

MANAVHSMEKVMDIHSKYCRCLQRLSSTVGHSLIRGRKRRSDHLQLKDILRKQDEYHMVHLLC
ASRSPPSSPKSRGRKRRSEVPKPLFPVAGVPMIQYHIEACAQVPGMQEILLRGRKRRSWNTW
LYAPGLPPVKPNYDATLTNACIALSQRWVRGRKRRSSNEDREWHESFSLVLGPDDPVEAVLG
DVTTATVRGRKRRSAQRNSNPIIAELSQAMNSGTLLSKPSPPLPPKRRGRKRRSMSVMVLRTQ
GPEAPFEDHRLILHTSSCDAERARRGRKRRSGESKGPLDSSFSQYLGRSCLLDQREAKRKGE

-continued

GLRGRKRRSCPHMTEDNKDLIQGKDLLTACYDVDYEKNAKGSRGRKRRSQGKYILKVCGCDE

YFLEKFPLSQYKYIRSCIMLRGRKRRSTRGLAYLHTELPQGDHYKPAISHRDLNSRNVLVRGRK

RRSKFISVLCTSLATMLHVELPHVNLLSKMDLIEHYRGRKRRSIHREQNSLSLLEASEADGDAV

NDKKRTPNEAPSRGRKRRSLRPSTLSQEVYKTVSMRLNVVSPDLSGKGLVLPRGRKRRSEPK

RDRRDPSTDKSGPDTFPVEVLERKPPEKTYRGRKRRSACSSSYNSAVMESSSVNVSMVHSSS

KENLCPKKRGRKRRSSGHVGLRNLGNTLPQCFLNAMLQCLSSTRPLRDRGRKRRSREIAVEH

NNLGKAVYSRMARICKNDMGGSQRVLRGRKRRSAEDTQENLHSGKSQSRSFPKVLADSDES

DMEETRGRKRRSPGLLSVDLFHVLVSAVLAFPSLYVVDDTVDLQPSRGRKRRSECKEAAVSHA

GSMHRERRTFLRSALKELATVLSRGRKRRSLCLMGHKPVLLRTQCRCHPAISAIANDLFYEGS

RGRKRRSRMREEQLAREAEAWAEREAEARRREEQEAREKARGRKRRSTSAAETKPPLAPSS

PPAPPGTMVAGSSLEGPAPRGRKRRSLSQTPPPAPPPSAGSEPLARLPQKDSVGKHSGARG

RKRRSRSLQELLARRTYYSGDPLFSVDILRNVTDTFKRRGRKRRSNTQIQKLTGSPFRSREYV

QTMESESEHSYPPPGRGRKRRSGGHVCWMREGVELCPGNKYEMRRHGTTHSLVIHRGRKR

RSTTTSRAICQLVKEYIGYRDGIWDVSVTRTQPIVRGRKRRSSHVQRLVHRDSTISNDAFISVDD

LEPSGPQDLERGRKRRSEPIEVNLFGLINVTPNMLPLVKKARGRVINVSSRGRKRRSNGYDTY

VHDAYGLFQECRSRVAHWGWPLGPAPLRGRKRRSVDFNKICGQAYDSATNFRVKLNEVVAEF

KKEEPRGRKRRSIQGWLGTKVRTNLRREPFSLVPKNAKDGNSFQGRGRKRRSNCNFDFPEET

CGWVYDHAKLLRSTWISSANPNDRGRKRRSGGKVWNEQEKNTYADKLFDCIEAYAPGFKRSV

LRGRKRRSISMGGHMASLAVCNWPKPMPLIPCLSWSTASGVRGRKRRSWMKCVKGQPHDH

KHLMPTQIIPGSVLTDLLDAMRGRKRRSGLSLNIKKYLLVSMPLWAKHMSDEQIQGFVENLRGR

KRRSSILRNHRYRRDARTLEDKEEMWFNTDEDDMEDG**

40-epitope Sgsm2 pos 40:

(SEQ ID NO: 51)

MANAVHSMEKVMDIHSKYCRCLQRLSSTVGHSLIRGRKRRSDHLQLKDILRKQDEYHMVHLLC

ASRSPPSSPKSRGRKRRSEVPKPLFPVAGVPMIQYHIEACAQVPGMQEILLRGRKRRSWNTW

LYAPGLPPVKPNYDATLTNACIALSQRWVRGRKRRSSNEDREWHESFSLVLGPDDPVEAVLG

DVTTATVRGRKRRSAQRNSNPIIAELSQAMNSGTLLSKPSPPLPPKRRGRKRRSMSVMVLRTQ

GPEAPFEDHRLILHTSSCDAERARRGRKRRSGESKGPLDSSFSQYLGRSCLLDQREAKRKGE

GLRGRKRRSCPHMTEDNKDLIQGKDLLTACYDVDYEKNAKGSRGRKRRSQGKYILKVCGCDE

YFLEKFPLSQYKYIRSCIMLRGRKRRSTRGLAYLHTELPQGDHYKPAISHRDLNSRNVLVRGRK

RRSKFISVLCTSLATMLHVELPHVNLLSKMDLIEHYRGRKRRSIHREQNSLSLLEASEADGDAV

NDKKRTPNEAPSRGRKRRSLRPSTLSQEVYKTVSMRLNVVSPDLSGKGLVLPRGRKRRSEPK

RDRRDPSTDKSGPDTFPVEVLERKPPEKTYRGRKRRSACSSSYNSAVMESSSVNVSMVHSSS

KENLCPKKRGRKRRSSGHVGLRNLGNTLPQCFLNAMLQCLSSTRPLRDRGRKRRSREIAVEH

NNLGKAVYSRMARICKNDMGGSQRVLRGRKRRSAEDTQENLHSGKSQSRSFPKVLADSDES

DMEETRGRKRRSPGLLSVDLFHVLVSAVLAFPSLYVVDDTVDLQPSRGRKRRSECKEAAVSHA

GSMHRERRTFLRSALKELATVLSRGRKRRSLCLMGHKPVLLRTQCRCHPAISAIANDLFYEGS

RGRKRRSRMREEQLAREAEAWAEREAEARRREEQEAREKARGRKRRSTSAAETKPPLAPSS

PPAPPGTMVAGSSLEGPAPRGRKRRSLSQTPPPAPPPSAGSEPLARLPQKDSVGKHSGARG

RKRRSRSLQELLARRTYYSGDPLFSVDILRNVTDTFKRRGRKRRSNTQIQKLTGSPFRSREYV

QTMESESEHSYPPPGRGRKRRSGGHVCWMREGVELCPGNKYEMRRHGTTHSLVIHRGRKR

RSTTTSRAICQLVKEYIGYRDGIWDVSVTRTQPIVRGRKRRSEPIEVNLFGLINVTPNMLPLVKK

-continued

ARGRVINVSSRGRKRRSNGYDTYVHDAYGLFQECRSRVAHWGWPLGPAPLRGRKRRSVDFN

KICGQAYDSATNFRVKLNEVVAEFKKEEPRGRKRRSIQGWLGTKVRTNLRREPFSLVPKNAKD

GNSFQGRGRKRRSNCNFDFPEETCGVVVYDHAKLLRSTWISSANPNDRGRKRRSGGKVWNE

QEKNTYADKLFDCIEAYAPGFKRSVLRGRKRRSISMGGHMASLAVCNWPKPMPLIPCLSWSTA

SGVRGRKRRSWMKCVKGQPHDHKHLMPTQIIPGSVLTDLLDAMRGRKRRSGLSLNIKKYLLVS

MPLWAKHMSDEQIQGFVENLRGRKRRSSILRNHRYRRDARTLEDKEEMWFNTDEDDMEDGR

GRKRRSSHVQRLVHRDSTISNDAFISVDDLEPSGPQDLE**

Follow-up study #2:
Determine if the epitopes can be repeated (without cloning issues), and if this can allow for higher immunogenicity for patients with only a few epitopes.

*1st 5 from the previous study

1. Sgsm2 V656A:

(SEQ ID NO: 1)
SHVQRLVHRDSTISNDAFISVDDLEPSGPQDLE

2. Herpud2 V85L:

(SEQ ID NO: 2)
DHLQLKDILRKQDEYHMVHLLCASRSPPSSPKS

3. Lta4h V463A:

(SEQ ID NO: 3)
WNTWLYAPGLPPVKPNYDATLTNACIALSQRWV

4. Phactr4 V253L:

(SEQ ID NO: 4)
AQRNSNPIIAELSQAMNSGTLLSKPSPPLPPKR

5. Aunip E168G:

(SEQ ID NO: 5)
GESKGPLDSSFSQYLGRSCLLDQREAKRKGEGL 5-epitope Sgsm2 pos 1:

(SEQ ID NO: 52)
MSHVQRLVHRDSTISNDAFISVDDLEPSGPQDLERGRKRRSDHLQLKDILRKQDEYHMVHLLC

ASRSPPSSPKSRGRKRRSWNTWLYAPGLPPVKPNYDATLTNACIALSQRWVRGRKRRSAQR

NSNPIIAELSQAMNSGTLLSKPSPPLPPKRRGRKRRSGESKGPLDSSFSQYLGRSCLLDQREA

KRKGEGL**

40-epitope repeat:

(SEQ ID NO: 53)
MSHVQRLVHRDSTISNDAFISVDDLEPSGPQDLERGRKRRSDHLQLKDILRKQDEYHMVHLLC

ASRSPPSSPKSRGRKRRSWNTWLYAPGLPPVKPNYDATLTNACIALSQRWVRGRKRRSAQR

NSNPIIAELSQAMNSGTLLSKPSPPLPPKRRGRKRRSGESKGPLDSSFSQYLGRSCLLDQREA

KRKGEGLRGRKRRSSHVQRLVHRDSTISNDAFISVDDLEPSGPQDLERGRKRRSDHLQLKDIL

RKQDEYHMVHLLCASRSPPSSPKSRGRKRRSWNTWLYAPGLPPVKPNYDATLTNACIALSQR

WVRGRKRRSAQRNSNPIIAELSQAMNSGTLLSKPSPPLPPKRRGRKRRSGESKGPLDSSFSQ

YLGRSCLLDQREAKRKGEGLRGRKRRSSHVQRLVHRDSTISNDAFISVDDLEPSGPQDLERGR

KRRSDHLQLKDILRKQDEYHMVHLLCASRSPPSSPKSRGRKRRSWNTWLYAPGLPPVKPNYD

ATLTNACIALSQRWVRGRKRRSAQRNSNPIIAELSQAMNSGTLLSKPSPPLPPKRRGRKRRSG

ESKGPLDSSFSQYLGRSCLLDQREAKRKGEGLRGRKRRSSHVQRLVHRDSTISNDAFISVDDL

EPSGPQDLERGRKRRSDHLQLKDILRKQDEYHMVHLLCASRSPPSSPKSRGRKRRSWNTWL

YAPGLPPVKPNYDATLTNACIALSQRWVRGRKRRSAQRNSNPIIAELSQAMNSGTLLSKPSPPL

PPKRRGRKRRSGESKGPLDSSFSQYLGRSCLLDQREAKRKGEGLRGRKRRSSHVQRLVHRD

STISNDAFISVDDLEPSGPQDLERGRKRRSDHLQLKDILRKQDEYHMVHLLCASRSPPSSPKSR

GRKRRSWNTWLYAPGLPPVKPNYDATLTNACIALSQRWVRGRKRRSAQRNSNPIIAELSQAM

NSGTLLSKPSPPLPPKRRGRKRRSGESKGPLDSSFSQYLGRSOLLDQREAKRKGEGL**

We claim:

1. A method of treating cancer in a subject having cancer, the method comprising administering to the subject a nucleic acid molecule, wherein the nucleic acid molecule comprises:

(i) a DNA backbone region, and (ii) an expressible nucleic acid sequence operably linked to a regulatory sequence;

wherein the expressible nucleic acid sequence is a DNA comprising Formula I that encodes a chimeric polypeptide comprising a concatemer of a linked series of neoantigens or antigenic determinants thereof from the cancer, Formula I comprising independently selected, non-repetitive antigen expression domains (AED):

$$(AED_1)\text{-}(linker)_1\text{-}(AED_2)\text{-}(linker)_2\text{-}(AED_3)\text{-}(linker)_3 \ldots (AED_n)\text{-}(linker)_n\text{-}[AED_{n+1}],$$

wherein each AED encodes one of the neoantigens or antigenic determinants thereof, each linker has a length independently selectable from about 15 to about 300 nucleotides and encodes a furin cleavage site, the length of each AED is independently selectable from about 90 to about 250 nucleotides, n is any positive integer from about 19 to about 58, and the DNA backbone region comprises SEQ ID NO:68 or a functional fragment thereof comprising about 90% sequence identity to SEQ ID NO:68, and wherein the sequence of SEQ ID NO: 68 or the functional fragment thereof comprises the regulatory sequence and a multiple cloning site, and the expressible nucleic acid sequence is positioned within the multiple cloning site.

2. The method of claim 1, wherein the administering comprises administering a therapeutically effective amount of the nucleic acid molecule that is effective to achieve:

(i) a clinical outcome selected from the group consisting of tumor regression, tumor shrinkage, tumor necrosis, anti-tumor response by the immune system, prevention or delay of tumor recurrence, prevention of tumor growth, prevention of tumor spread and/or induce tumor elimination, or a combination thereof;

(ii) an increase, enhancement or prolongation of anti-tumor activity by T cells;

(iii) an increase in the number of anti-tumor T cells or activated T cells as compared with the number prior to treatment; or (iv) a combination thereof.

3. The method of claim 1, wherein the administering comprises electroporation.

4. The method of claim 1, wherein the length of each AED is independently selectable from about 90 to about 100 nucleotides.

5. The method of claim 1, wherein each linker has a length independently selectable from about 18 to about 30 natural or non-natural nucleotides.

6. The method of claim 1, wherein the length of each AED is independently selectable from about 90 to about 100 nucleotides, each linker has a length independently selectable from about 18 to about 30 nucleotides, and the backbone region comprises the sequence of SEQ ID NO:68 or a functional fragment thereof comprising 95% sequence identity to SEQ ID NO:68.

7. The method of claim 1 further comprising administering to the subject one or more immunostimulatory agent, wherein the one or more immunostimulatory agent comprises a nucleic acid sequence encoding IL-12.

8. The method of claim 1 further comprising administering to the subject an inhibitor of the programmed death-I (PD-I) pathway.

9. The method of claim 1, wherein the administering comprises intradermal injection.

10. The method of claim 1, wherein the administering comprises administering a dose of about 1 mg of the nucleic acid molecule.

11. The method of claim 1, wherein the administering comprises administering a dose of from about 0.1 mg to about 10 mg of the nucleic acid molecule.

12. The method of claim 1, wherein the DNA that encodes the chimeric polypeptide consists of the concatemer of linked series of AEDs.

13. The method of claim 1, wherein the DNA backbone region comprises SEQ ID NO: 68.

14. The method of claim 1, wherein the length of each AED is about 100 nucleotides, each linker is about 21 nucleotides, the DNA backbone region comprises SEQ ID NO: 68, and the method further comprises administering to the subject a nucleic acid sequence encoding IL-12.

15. The method of claim 1, wherein the cancer is hepatocellular cancer.

16. A method of enhancing an immune response against a plurality of heterogeneous hyperproliferative cells expressing neoantigens or antigen determinants thereof in a subject having the plurality of heterogenous hyperproliferative cells, the method comprising administering to the subject a therapeutically effective amount of a nucleic acid molecule; wherein the therapeutically effective amount is effective to enhance the immune response of the subject to the plurality of heterogeneous hyperproliferative cells relative to an immune response elicited by administration of a control nucleic acid molecule free of a nucleic acid sequence encoding a neoantigen to the subject, and wherein the nucleic acid molecule comprises:

(i) a DNA backbone region, and (ii) an expressible nucleic acid sequence operably linked to a regulatory sequence; wherein the expressible nucleic acid sequence is a DNA that encodes a chimeric polypeptide comprising a concatemer of a linked series of the neoantigens or antigenic determinants thereof, and comprises Formula I, comprising independently selected non-repetitive antigen expression domains (AED):

$$(AED_1)\text{-}(linker)_1\text{-}(AED_2)\text{-}(linker)]_2\text{-}(AED_3)\text{-}(linker)_3 \ldots (AED_n)\text{-}(linker)_n\text{-}[AED_{n+1}],$$

wherein each AED independently encodes one of the neoantigens or antigenic determinants thereof, wherein each linker has a length independently selectable from about 15 to about 300 nucleotides and encodes a furin protease cleavage site;

wherein the length of each AED is independently selectable from about 90 to about 250 nucleotides, wherein n is any positive integer from about 19 to about 100, wherein the DNA backbone region comprises the sequence of SEQ ID NO:68 or a functional fragment thereof comprising about 90% sequence identity to SEQ ID NO: 68, and wherein the sequence of SEQ ID NO: 68 or the functional fragment thereof comprises the regulatory sequence and a multiple cloning site, and the expressible nucleic acid sequence is positioned within the multiple cloning site, and the neoantigen or antigenic determinant thereof expressed by the heterogeneous hyperproliferative cells is one of the neoantigens or antigenic determinants of the chimeric polypeptide.

17. The method of claim 16, wherein the subject has a tumor, and wherein the administering comprises administering a therapeutically effective amount of the nucleic acid sufficient to induce an immune response of a sufficient magnitude or efficacy to inhibit or retard tumor growth, induce tumor cell death, induce tumor regression, prevent or delay tumor recurrence, prevent tumor growth, prevent tumor spread and/or induce tumor elimination.

18. The method of claim 16, further comprising administration of one or more therapeutic agents.

19. The method of claim 18, wherein the therapeutic agent is a biologic therapeutic or a small molecule.

20. The method of claim 19, wherein the therapeutic agent is:

(i) a checkpoint inhibitor or functional fragment thereof or a nucleic acid molecule encoding a checkpoint inhibitor or a functional fragment thereof;

(ii) an adjuvant;

(iii) an immunostimulatory agent; or (iv) a chemotherapeutic agent.

21. The method of claim 20, wherein:

the checkpoint inhibitor inhibits a checkpoint protein selected from the group consisting of CTLA-4, PDL1, PDL2, PD1, B7-H3, B7-H4, BTLA, HVEM, TIM3, GAL9, LAG3, VISTA, KIR, 2B4, CD160, CGEN-15049, CHK 1, CHK2, A2aR, B-7 family ligands, and IDO inhibitors, or a combination thereof.

22. The method of claim 20, wherein:

the checkpoint inhibitor is an inhibitor of the programmed death-I (PD-I) pathway.

23. The method of claim 20, wherein:

the immunostimulatory agent is an interleukin or functional fragment thereof.

24. The method of claim 16, wherein the length of each AED is independently selectable from about 90 to about 100 nucleotides, each linker has a length independently selectable from about 18 to about 30 nucleotides, and the backbone region comprises the sequence of SEQ ID NO:68 or a functional fragment thereof comprising 95% sequence identity to SEQ ID NO:68.

25. The method of claim 16, wherein the length of each AED is about 100 nucleotides, each linker is about 21 nucleotides, the DNA backbone region comprises SEQ ID NO: 68, and the method further comprises administering to the subject a nucleic acid sequence encoding IL-12.

* * * * *

SEQUENCE LISTING

<160> NUMBER OF SEQ ID NOS: 130

<210> SEQ ID NO 1
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Ser His Val Gln Arg Leu Val His Arg Asp Ser Thr Ile Ser Asn Asp
1               5                   10                  15

Ala Phe Ile Ser Val Asp Asp Leu Glu Pro Ser Gly Pro Gln Asp Leu
            20                  25                  30

Glu

<210> SEQ ID NO 2
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Asp His Leu Gln Leu Lys Asp Ile Leu Arg Lys Gln Asp Glu Tyr His
1               5                   10                  15

Met Val His Leu Leu Cys Ala Ser Arg Ser Pro Pro Ser Ser Pro Lys
            20                  25                  30

Ser

<210> SEQ ID NO 3
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Trp Asn Thr Trp Leu Tyr Ala Pro Gly Leu Pro Pro Val Lys Pro Asn
1               5                   10                  15

Tyr Asp Ala Thr Leu Thr Asn Ala Cys Ile Ala Leu Ser Gln Arg Trp
            20                  25                  30

Val

<210> SEQ ID NO 4
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Ala Gln Arg Asn Ser Asn Pro Ile Ile Ala Glu Leu Ser Gln Ala Met 1 5 10 15

Asn Ser Gly Thr Leu Leu Ser Lys Pro Ser Pro Pro Leu Pro Pro Lys
20 25 30

Arg

<210> SEQ ID NO 5
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 5

Gly Glu Ser Lys Gly Pro Leu Asp Ser Ser Phe Ser Gln Tyr Leu Gly
1 5 10 15

Arg Ser Cys Leu Leu Asp Gln Arg Glu Ala Lys Arg Lys Gly Glu Gly
20 25 30

Leu

<210> SEQ ID NO 6
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 6

Gln Gly Lys Tyr Ile Leu Lys Val Cys Gly Cys Asp Glu Tyr Phe Leu
1 5 10 15

Glu Lys Phe Pro Leu Ser Gln Tyr Lys Tyr Ile Arg Ser Cys Ile Met
20 25 30

Leu

<210> SEQ ID NO 7
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 7

Lys Phe Ile Ser Val Leu Cys Thr Ser Leu Ala Thr Met Leu His Val
1 5 10 15

Glu Leu Pro His Val Asn Leu Leu Ser Lys Met Asp Leu Ile Glu His
20 25 30

Tyr

<210> SEQ ID NO 8
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 8

Leu Arg Pro Ser Thr Leu Ser Gln Glu Val Tyr Lys Thr Val Ser Met
1 5 10 15

Arg Leu Asn Val Val Ser Pro Asp Leu Ser Gly Lys Gly Leu Val Leu

```
            20                  25                  30

Pro


<210> SEQ ID NO 9
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Ala Cys Ser Ser Ser Tyr Asn Ser Ala Val Met Glu Ser Ser Ser Val
1               5                   10                  15

Asn Val Ser Met Val His Ser Ser Ser Lys Glu Asn Leu Cys Pro Lys
            20                  25                  30

Lys


<210> SEQ ID NO 10
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Arg Glu Ile Ala Val Glu His Asn Asn Leu Gly Lys Ala Val Tyr Ser
1               5                   10                  15

Arg Met Ala Arg Ile Cys Lys Asn Asp Met Gly Gly Ser Gln Arg Val
            20                  25                  30

Leu


<210> SEQ ID NO 11
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Pro Gly Leu Leu Ser Val Asp Leu Phe His Val Leu Val Ser Ala Val
1               5                   10                  15

Leu Ala Phe Pro Ser Leu Tyr Trp Asp Asp Thr Val Asp Leu Gln Pro
            20                  25                  30

Ser


<210> SEQ ID NO 12
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Leu Cys Leu Met Gly His Lys Pro Val Leu Leu Arg Thr Gln Cys Arg
1               5                   10                  15

Cys His Pro Ala Ile Ser Ala Ile Ala Asn Asp Leu Phe Tyr Glu Gly
            20                  25                  30

Ser
```

<210> SEQ ID NO 13
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 13

```
Thr Ser Ala Ala Glu Thr Lys Pro Pro Leu Ala Pro Ser Ser Pro Pro
1               5                   10                  15

Ala Pro Pro Gly Thr Met Val Ala Gly Ser Ser Leu Glu Gly Pro Ala
            20                  25                  30

Pro
```

<210> SEQ ID NO 14
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 14

```
Arg Ser Leu Gln Glu Leu Leu Ala Arg Arg Thr Tyr Tyr Ser Gly Asp
1               5                   10                  15

Pro Leu Phe Ser Val Asp Ile Leu Arg Asn Val Thr Asp Thr Phe Lys
            20                  25                  30

Arg
```

<210> SEQ ID NO 15
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 15

```
Gly Gly His Val Cys Trp Met Arg Glu Gly Val Glu Leu Cys Pro Gly
1               5                   10                  15

Asn Lys Tyr Glu Met Arg Arg His Gly Thr Thr His Ser Leu Val Ile
            20                  25                  30

His
```

<210> SEQ ID NO 16
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 16

```
Glu Pro Ile Glu Val Asn Leu Phe Gly Leu Ile Asn Val Thr Pro Asn
1               5                   10                  15

Met Leu Pro Leu Val Lys Lys Ala Arg Gly Arg Val Ile Asn Val Ser
            20                  25                  30

Ser
```

<210> SEQ ID NO 17

<211> LENGTH: 33
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 17

Val Asp Phe Asn Lys Ile Cys Gly Gln Ala Tyr Asp Ser Ala Thr Asn
1 5 10 15

Phe Arg Val Lys Leu Asn Glu Val Val Ala Glu Phe Lys Lys Glu Glu
20 25 30

Pro

<210> SEQ ID NO 18
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 18

Asn Cys Asn Phe Asp Phe Pro Glu Glu Thr Cys Gly Trp Val Tyr Asp
1 5 10 15

His Ala Lys Leu Leu Arg Ser Thr Trp Ile Ser Ser Ala Asn Pro Asn
20 25 30

Asp

<210> SEQ ID NO 19
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 19

Ile Ser Met Gly Gly His Met Ala Ser Leu Ala Val Cys Asn Trp Pro
1 5 10 15

Lys Pro Met Pro Leu Ile Pro Cys Leu Ser Trp Ser Thr Ala Ser Gly
20 25 30

Val

<210> SEQ ID NO 20
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 20

Gly Leu Ser Leu Asn Ile Lys Lys Tyr Leu Leu Val Ser Met Pro Leu
1 5 10 15

Trp Ala Lys His Met Ser Asp Glu Gln Ile Gln Gly Phe Val Glu Asn
20 25 30

Leu

<210> SEQ ID NO 21
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 21

Ala Asn Ala Val His Ser Met Glu Lys Val Met Asp Ile His Ser Lys
1 5 10 15

Tyr Cys Arg Cys Leu Gln Arg Leu Ser Ser Thr Val Gly His Ser Leu
20 25 30

Ile

<210> SEQ ID NO 22
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 22

Glu Val Pro Lys Pro Leu Phe Pro Val Ala Gly Val Pro Met Ile Gln
1 5 10 15

Tyr His Ile Glu Ala Cys Ala Gln Val Pro Gly Met Gln Glu Ile Leu
20 25 30

Leu

<210> SEQ ID NO 23
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 23

Ser Asn Glu Asp Arg Glu Trp His Glu Ser Phe Ser Leu Val Leu Gly
1 5 10 15

Pro Asp Asp Pro Val Glu Ala Val Leu Gly Asp Val Thr Thr Ala Thr
20 25 30

Val

<210> SEQ ID NO 24
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 24

Met Ser Val Met Val Leu Arg Thr Gln Gly Pro Glu Ala Pro Phe Glu
1 5 10 15

Asp His Arg Leu Ile Leu His Thr Ser Ser Cys Asp Ala Glu Arg Ala
20 25 30

Arg

<210> SEQ ID NO 25
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 25

Cys Pro His Met Thr Glu Asp Asn Lys Asp Leu Ile Gln Gly Lys Asp
1 5 10 15

Leu Leu Thr Ala Cys Tyr Asp Val Asp Tyr Glu Lys Asn Ala Lys Gly
20 25 30

Ser

<210> SEQ ID NO 26
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 26

Thr Arg Gly Leu Ala Tyr Leu His Thr Glu Leu Pro Gln Gly Asp His
1 5 10 15

Tyr Lys Pro Ala Ile Ser His Arg Asp Leu Asn Ser Arg Asn Val Leu
20 25 30

Val

<210> SEQ ID NO 27
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 27

Ile His Arg Glu Gln Asn Ser Leu Ser Leu Leu Glu Ala Ser Glu Ala
1 5 10 15

Asp Gly Asp Ala Val Asn Asp Lys Lys Arg Thr Pro Asn Glu Ala Pro
20 25 30

Ser

<210> SEQ ID NO 28
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 28

Glu Pro Lys Arg Asp Arg Arg Asp Pro Ser Thr Asp Lys Ser Gly Pro
1 5 10 15

Asp Thr Phe Pro Val Glu Val Leu Glu Arg Lys Pro Pro Glu Lys Thr
20 25 30

Tyr

<210> SEQ ID NO 29
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 29

Ser Gly His Val Gly Leu Arg Asn Leu Gly Asn Thr Leu Pro Gln Cys
1 5 10 15

Phe Leu Asn Ala Met Leu Gln Cys Leu Ser Ser Thr Arg Pro Leu Arg
20 25 30

Asp

<210> SEQ ID NO 30
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 30

Ala Glu Asp Thr Gln Glu Asn Leu His Ser Gly Lys Ser Gln Ser Arg
1 5 10 15

Ser Phe Pro Lys Val Leu Ala Asp Ser Asp Glu Ser Asp Met Glu Glu
20 25 30

Thr

<210> SEQ ID NO 31
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 31

Glu Cys Lys Glu Ala Ala Val Ser His Ala Gly Ser Met His Arg Glu
1 5 10 15

Arg Arg Thr Phe Leu Arg Ser Ala Leu Lys Glu Leu Ala Thr Val Leu
20 25 30

Ser

<210> SEQ ID NO 32
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 32

Arg Met Arg Glu Glu Gln Leu Ala Arg Glu Ala Glu Ala Trp Ala Glu
1 5 10 15

Arg Glu Ala Glu Ala Arg Arg Arg Glu Glu Gln Glu Ala Arg Glu Lys
20 25 30

Ala

<210> SEQ ID NO 33
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 33

Leu Ser Gln Thr Pro Pro Pro Ala Pro Pro Pro Ser Ala Gly Ser Glu
1 5 10 15

Pro Leu Ala Arg Leu Pro Gln Lys Asp Ser Val Gly Lys His Ser Gly
            20                  25                  30

Ala

<210> SEQ ID NO 34
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Asn Thr Gln Ile Gln Lys Leu Thr Gly Ser Pro Phe Arg Ser Arg Glu
1               5                   10                  15

Tyr Val Gln Thr Met Glu Ser Glu Ser Glu His Ser Tyr Pro Pro Pro
            20                  25                  30

Gly

<210> SEQ ID NO 35
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Thr Thr Thr Ser Arg Ala Ile Cys Gln Leu Val Lys Glu Tyr Ile Gly
1               5                   10                  15

Tyr Arg Asp Gly Ile Trp Asp Val Ser Val Thr Arg Thr Gln Pro Ile
            20                  25                  30

Val

<210> SEQ ID NO 36
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Asn Gly Tyr Asp Thr Tyr Val His Asp Ala Tyr Gly Leu Phe Gln Glu
1               5                   10                  15

Cys Arg Ser Arg Val Ala His Trp Gly Trp Pro Leu Gly Pro Ala Pro
            20                  25                  30

Leu

<210> SEQ ID NO 37
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Ile Gln Gly Trp Leu Gly Thr Lys Val Arg Thr Asn Leu Arg Arg Glu
1               5                   10                  15

Pro Phe Ser Leu Val Pro Lys Asn Ala Lys Asp Gly Asn Ser Phe Gln
            20                  25                  30

Gly

<210> SEQ ID NO 38
<211> LENGTH: 33
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 38

Gly Gly Lys Val Trp Asn Glu Gln Glu Lys Asn Thr Tyr Ala Asp Lys
1 5 10 15

Leu Phe Asp Cys Ile Glu Ala Tyr Ala Pro Gly Phe Lys Arg Ser Val
20 25 30

Leu

<210> SEQ ID NO 39
<211> LENGTH: 33
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 39

Trp Met Lys Cys Val Lys Gly Gln Pro His Asp His Lys His Leu Met
1 5 10 15

Pro Thr Gln Ile Ile Pro Gly Ser Val Leu Thr Asp Leu Leu Asp Ala
20 25 30

Met

<210> SEQ ID NO 40
<211> LENGTH: 33
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 40

Ser Ile Leu Arg Asn His Arg Tyr Arg Arg Asp Ala Arg Thr Leu Glu
1 5 10 15

Asp Lys Glu Glu Met Trp Phe Asn Thr Asp Glu Asp Asp Met Glu Asp
20 25 30

Gly

<210> SEQ ID NO 41
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 41

Arg Gly Arg Lys Arg Arg Ser
1 5

<210> SEQ ID NO 42
<211> LENGTH: 394
<212> TYPE: PRT
<213> ORGANISM: Artificial Sequence
<220> FEATURE:

<223> OTHER INFORMATION: Description of Artificial Sequence: Synthetic
polypeptide

<400> SEQUENCE: 42

Met Ser His Val Gln Arg Leu Val His Arg Asp Ser Thr Ile Ser Asn
1 5 10 15

Asp Ala Phe Ile Ser Val Asp Asp Leu Glu Pro Ser Gly Pro Gln Asp
20 25 30

Leu Glu Arg Gly Arg Lys Arg Arg Ser Asp His Leu Gln Leu Lys Asp
35 40 45

Ile Leu Arg Lys Gln Asp Glu Tyr His Met Val His Leu Leu Cys Ala
50 55 60

Ser Arg Ser Pro Pro Ser Ser Pro Lys Ser Arg Gly Arg Lys Arg Arg
65 70 75 80

Ser Trp Asn Thr Trp Leu Tyr Ala Pro Gly Leu Pro Pro Val Lys Pro
85 90 95

Asn Tyr Asp Ala Thr Leu Thr Asn Ala Cys Ile Ala Leu Ser Gln Arg
100 105 110

Trp Val Arg Gly Arg Lys Arg Arg Ser Ala Cys Ser Ser Ser Tyr Asn
115 120 125

Ser Ala Val Met Glu Ser Ser Ser Val Asn Val Ser Met Val His Ser
130 135 140

Ser Ser Lys Glu Asn Leu Cys Pro Lys Lys Arg Gly Arg Lys Arg Arg
145 150 155 160

Ser Pro Gly Leu Leu Ser Val Asp Leu Phe His Val Leu Val Ser Ala
165 170 175

Val Leu Ala Phe Pro Ser Leu Tyr Trp Asp Asp Thr Val Asp Leu Gln
180 185 190

Pro Ser Arg Gly Arg Lys Arg Arg Ser Gly Gly His Val Cys Trp Met
195 200 205

Arg Glu Gly Val Glu Leu Cys Pro Gly Asn Lys Tyr Glu Met Arg Arg
210 215 220

His Gly Thr Thr His Ser Leu Val Ile His Arg Gly Arg Lys Arg Arg
225 230 235 240

Ser Glu Pro Ile Glu Val Asn Leu Phe Gly Leu Ile Asn Val Thr Pro
245 250 255

Asn Met Leu Pro Leu Val Lys Lys Ala Arg Gly Arg Val Ile Asn Val
260 265 270

Ser Ser Arg Gly Arg Lys Arg Arg Ser Val Asp Phe Asn Lys Ile Cys
275 280 285

Gly Gln Ala Tyr Asp Ser Ala Thr Asn Phe Arg Val Lys Leu Asn Glu
290 295 300

Val Val Ala Glu Phe Lys Lys Glu Glu Pro Arg Gly Arg Lys Arg Arg
305 310 315 320

Ser Asn Cys Asn Phe Asp Phe Pro Glu Glu Thr Cys Gly Trp Val Tyr
325 330 335

Asp His Ala Lys Leu Leu Arg Ser Thr Trp Ile Ser Ser Ala Asn Pro
340 345 350

Asn Asp Arg Gly Arg Lys Arg Arg Ser Ile Ser Met Gly Gly His Met
355 360 365

Ala Ser Leu Ala Val Cys Asn Trp Pro Lys Pro Met Pro Leu Ile Pro
370 375 380

Cys Leu Ser Trp Ser Thr Ala Ser Gly Val
385 390

<210> SEQ ID NO 43
<211> LENGTH: 394
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 43

Met Asp His Leu Gln Leu Lys Asp Ile Leu Arg Lys Gln Asp Glu Tyr
1 5 10 15

His Met Val His Leu Leu Cys Ala Ser Arg Ser Pro Pro Ser Ser Pro
20 25 30

Lys Ser Arg Gly Arg Lys Arg Arg Ser Trp Asn Thr Trp Leu Tyr Ala
35 40 45

Pro Gly Leu Pro Pro Val Lys Pro Asn Tyr Asp Ala Thr Leu Thr Asn
50 55 60

Ala Cys Ile Ala Leu Ser Gln Arg Trp Val Arg Gly Arg Lys Arg Arg
65 70 75 80

Ser Ala Cys Ser Ser Ser Tyr Asn Ser Ala Val Met Glu Ser Ser Ser
85 90 95

Val Asn Val Ser Met Val His Ser Ser Ser Lys Glu Asn Leu Cys Pro
100 105 110

Lys Lys Arg Gly Arg Lys Arg Arg Ser Pro Gly Leu Leu Ser Val Asp
115 120 125

Leu Phe His Val Leu Val Ser Ala Val Leu Ala Phe Pro Ser Leu Tyr
130 135 140

Trp Asp Asp Thr Val Asp Leu Gln Pro Ser Arg Gly Arg Lys Arg Arg
145 150 155 160

Ser Gly Gly His Val Cys Trp Met Arg Glu Gly Val Glu Leu Cys Pro
165 170 175

Gly Asn Lys Tyr Glu Met Arg Arg His Gly Thr Thr His Ser Leu Val
180 185 190

Ile His Arg Gly Arg Lys Arg Arg Ser Glu Pro Ile Glu Val Asn Leu
195 200 205

Phe Gly Leu Ile Asn Val Thr Pro Asn Met Leu Pro Leu Val Lys Lys
210 215 220

Ala Arg Gly Arg Val Ile Asn Val Ser Ser Arg Gly Arg Lys Arg Arg
225 230 235 240

Ser Val Asp Phe Asn Lys Ile Cys Gly Gln Ala Tyr Asp Ser Ala Thr
245 250 255

Asn Phe Arg Val Lys Leu Asn Glu Val Val Ala Glu Phe Lys Lys Glu
260 265 270

Glu Pro Arg Gly Arg Lys Arg Arg Ser Asn Cys Asn Phe Asp Phe Pro
275 280 285

Glu Glu Thr Cys Gly Trp Val Tyr Asp His Ala Lys Leu Leu Arg Ser
290 295 300

Thr Trp Ile Ser Ser Ala Asn Pro Asn Asp Arg Gly Arg Lys Arg Arg
305 310 315 320

Ser Ile Ser Met Gly Gly His Met Ala Ser Leu Ala Val Cys Asn Trp
325 330 335

Pro Lys Pro Met Pro Leu Ile Pro Cys Leu Ser Trp Ser Thr Ala Ser
340 345 350

Gly Val Arg Gly Arg Lys Arg Arg Ser Ser His Val Gln Arg Leu Val

```
        355                 360                 365

His Arg Asp Ser Thr Ile Ser Asn Asp Ala Phe Ile Ser Val Asp Asp
    370                 375                 380

Leu Glu Pro Ser Gly Pro Gln Asp Leu Glu
385                 390


<210> SEQ ID NO 44
<211> LENGTH: 794
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Met Ser His Val Gln Arg Leu Val His Arg Asp Ser Thr Ile Ser Asn
1               5                   10                  15

Asp Ala Phe Ile Ser Val Asp Asp Leu Glu Pro Ser Gly Pro Gln Asp
            20                  25                  30

Leu Glu Arg Gly Arg Lys Arg Arg Ser Asp His Leu Gln Leu Lys Asp
        35                  40                  45

Ile Leu Arg Lys Gln Asp Glu Tyr His Met Val His Leu Leu Cys Ala
    50                  55                  60

Ser Arg Ser Pro Pro Ser Ser Pro Lys Ser Arg Gly Arg Lys Arg Arg
65                  70                  75                  80

Ser Trp Asn Thr Trp Leu Tyr Ala Pro Gly Leu Pro Pro Val Lys Pro
                85                  90                  95

Asn Tyr Asp Ala Thr Leu Thr Asn Ala Cys Ile Ala Leu Ser Gln Arg
            100                 105                 110

Trp Val Arg Gly Arg Lys Arg Arg Ser Ala Gln Arg Asn Ser Asn Pro
        115                 120                 125

Ile Ile Ala Glu Leu Ser Gln Ala Met Asn Ser Gly Thr Leu Leu Ser
    130                 135                 140

Lys Pro Ser Pro Pro Leu Pro Pro Lys Arg Arg Gly Arg Lys Arg Arg
145                 150                 155                 160

Ser Gly Glu Ser Lys Gly Pro Leu Asp Ser Ser Phe Ser Gln Tyr Leu
                165                 170                 175

Gly Arg Ser Cys Leu Leu Asp Gln Arg Glu Ala Lys Arg Lys Gly Glu
            180                 185                 190

Gly Leu Arg Gly Arg Lys Arg Arg Ser Gln Gly Lys Tyr Ile Leu Lys
        195                 200                 205

Val Cys Gly Cys Asp Glu Tyr Phe Leu Glu Lys Phe Pro Leu Ser Gln
    210                 215                 220

Tyr Lys Tyr Ile Arg Ser Cys Ile Met Leu Arg Gly Arg Lys Arg Arg
225                 230                 235                 240

Ser Lys Phe Ile Ser Val Leu Cys Thr Ser Leu Ala Thr Met Leu His
                245                 250                 255

Val Glu Leu Pro His Val Asn Leu Leu Ser Lys Met Asp Leu Ile Glu
            260                 265                 270

His Tyr Arg Gly Arg Lys Arg Arg Ser Leu Arg Pro Ser Thr Leu Ser
        275                 280                 285

Gln Glu Val Tyr Lys Thr Val Ser Met Arg Leu Asn Val Val Ser Pro
    290                 295                 300

Asp Leu Ser Gly Lys Gly Leu Val Leu Pro Arg Gly Arg Lys Arg Arg
305                 310                 315                 320
```

```
Ser Ala Cys Ser Ser Ser Tyr Asn Ser Ala Val Met Glu Ser Ser Ser
                325                 330                 335

Val Asn Val Ser Met Val His Ser Ser Ser Lys Glu Asn Leu Cys Pro
            340                 345                 350

Lys Lys Arg Gly Arg Lys Arg Arg Ser Arg Glu Ile Ala Val Glu His
        355                 360                 365

Asn Asn Leu Gly Lys Ala Val Tyr Ser Arg Met Ala Arg Ile Cys Lys
    370                 375                 380

Asn Asp Met Gly Gly Ser Gln Arg Val Leu Arg Gly Arg Lys Arg Arg
385                 390                 395                 400

Ser Pro Gly Leu Leu Ser Val Asp Leu Phe His Val Leu Val Ser Ala
                405                 410                 415

Val Leu Ala Phe Pro Ser Leu Tyr Trp Asp Asp Thr Val Asp Leu Gln
            420                 425                 430

Pro Ser Arg Gly Arg Lys Arg Arg Ser Leu Cys Leu Met Gly His Lys
        435                 440                 445

Pro Val Leu Leu Arg Thr Gln Cys Arg Cys His Pro Ala Ile Ser Ala
    450                 455                 460

Ile Ala Asn Asp Leu Phe Tyr Glu Gly Ser Arg Gly Arg Lys Arg Arg
465                 470                 475                 480

Ser Thr Ser Ala Ala Glu Thr Lys Pro Pro Leu Ala Pro Ser Ser Pro
                485                 490                 495

Pro Ala Pro Pro Gly Thr Met Val Ala Gly Ser Ser Leu Glu Gly Pro
            500                 505                 510

Ala Pro Arg Gly Arg Lys Arg Arg Ser Arg Ser Leu Gln Glu Leu Leu
        515                 520                 525

Ala Arg Arg Thr Tyr Tyr Ser Gly Asp Pro Leu Phe Ser Val Asp Ile
    530                 535                 540

Leu Arg Asn Val Thr Asp Thr Phe Lys Arg Arg Gly Arg Lys Arg Arg
545                 550                 555                 560

Ser Gly Gly His Val Cys Trp Met Arg Glu Gly Val Glu Leu Cys Pro
                565                 570                 575

Gly Asn Lys Tyr Glu Met Arg Arg His Gly Thr Thr His Ser Leu Val
            580                 585                 590

Ile His Arg Gly Arg Lys Arg Arg Ser Glu Pro Ile Glu Val Asn Leu
        595                 600                 605

Phe Gly Leu Ile Asn Val Thr Pro Asn Met Leu Pro Leu Val Lys Lys
    610                 615                 620

Ala Arg Gly Arg Val Ile Asn Val Ser Ser Arg Gly Arg Lys Arg Arg
625                 630                 635                 640

Ser Val Asp Phe Asn Lys Ile Cys Gly Gln Ala Tyr Asp Ser Ala Thr
                645                 650                 655

Asn Phe Arg Val Lys Leu Asn Glu Val Val Ala Glu Phe Lys Lys Glu
            660                 665                 670

Glu Pro Arg Gly Arg Lys Arg Arg Ser Asn Cys Asn Phe Asp Phe Pro
        675                 680                 685

Glu Glu Thr Cys Gly Trp Val Tyr Asp His Ala Lys Leu Leu Arg Ser
    690                 695                 700

Thr Trp Ile Ser Ser Ala Asn Pro Asn Asp Arg Gly Arg Lys Arg Arg
705                 710                 715                 720

Ser Ile Ser Met Gly Gly His Met Ala Ser Leu Ala Val Cys Asn Trp
                725                 730                 735

Pro Lys Pro Met Pro Leu Ile Pro Cys Leu Ser Trp Ser Thr Ala Ser
```

```
            740                 745                 750

Gly Val Arg Gly Arg Lys Arg Arg Ser Gly Leu Ser Leu Asn Ile Lys
        755                 760                 765

Lys Tyr Leu Leu Val Ser Met Pro Leu Trp Ala Lys His Met Ser Asp
    770                 775                 780

Glu Gln Ile Gln Gly Phe Val Glu Asn Leu
785                 790


<210> SEQ ID NO 45
<211> LENGTH: 794
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Met Asp His Leu Gln Leu Lys Asp Ile Leu Arg Lys Gln Asp Glu Tyr
1               5                   10                  15

His Met Val His Leu Leu Cys Ala Ser Arg Ser Pro Pro Ser Ser Pro
            20                  25                  30

Lys Ser Arg Gly Arg Lys Arg Arg Ser Trp Asn Thr Trp Leu Tyr Ala
        35                  40                  45

Pro Gly Leu Pro Pro Val Lys Pro Asn Tyr Asp Ala Thr Leu Thr Asn
    50                  55                  60

Ala Cys Ile Ala Leu Ser Gln Arg Trp Val Arg Gly Arg Lys Arg Arg
65                  70                  75                  80

Ser Ala Gln Arg Asn Ser Asn Pro Ile Ile Ala Glu Leu Ser Gln Ala
                85                  90                  95

Met Asn Ser Gly Thr Leu Leu Ser Lys Pro Ser Pro Pro Leu Pro Pro
            100                 105                 110

Lys Arg Arg Gly Arg Lys Arg Arg Ser Gly Glu Ser Lys Gly Pro Leu
        115                 120                 125

Asp Ser Ser Phe Ser Gln Tyr Leu Gly Arg Ser Cys Leu Leu Asp Gln
    130                 135                 140

Arg Glu Ala Lys Arg Lys Gly Glu Gly Leu Arg Gly Arg Lys Arg Arg
145                 150                 155                 160

Ser Gln Gly Lys Tyr Ile Leu Lys Val Cys Gly Cys Asp Glu Tyr Phe
                165                 170                 175

Leu Glu Lys Phe Pro Leu Ser Gln Tyr Lys Tyr Ile Arg Ser Cys Ile
            180                 185                 190

Met Leu Arg Gly Arg Lys Arg Arg Ser Lys Phe Ile Ser Val Leu Cys
        195                 200                 205

Thr Ser Leu Ala Thr Met Leu His Val Glu Leu Pro His Val Asn Leu
    210                 215                 220

Leu Ser Lys Met Asp Leu Ile Glu His Tyr Arg Gly Arg Lys Arg Arg
225                 230                 235                 240

Ser Leu Arg Pro Ser Thr Leu Ser Gln Glu Val Tyr Lys Thr Val Ser
                245                 250                 255

Met Arg Leu Asn Val Val Ser Pro Asp Leu Ser Gly Lys Gly Leu Val
            260                 265                 270

Leu Pro Arg Gly Arg Lys Arg Arg Ser Ala Cys Ser Ser Ser Tyr Asn
        275                 280                 285

Ser Ala Val Met Glu Ser Ser Ser Val Asn Val Ser Met Val His Ser
    290                 295                 300
```

-continued

```
Ser Ser Lys Glu Asn Leu Cys Pro Lys Lys Arg Gly Arg Lys Arg Arg
305                 310                 315                 320

Ser Arg Glu Ile Ala Val Glu His Asn Asn Leu Gly Lys Ala Val Tyr
                325                 330                 335

Ser Arg Met Ala Arg Ile Cys Lys Asn Asp Met Gly Gly Ser Gln Arg
            340                 345                 350

Val Leu Arg Gly Arg Lys Arg Arg Ser Ser His Val Gln Arg Leu Val
        355                 360                 365

His Arg Asp Ser Thr Ile Ser Asn Asp Ala Phe Ile Ser Val Asp Asp
    370                 375                 380

Leu Glu Pro Ser Gly Pro Gln Asp Leu Glu Arg Gly Arg Lys Arg Arg
385                 390                 395                 400

Ser Pro Gly Leu Leu Ser Val Asp Leu Phe His Val Leu Val Ser Ala
                405                 410                 415

Val Leu Ala Phe Pro Ser Leu Tyr Trp Asp Asp Thr Val Asp Leu Gln
            420                 425                 430

Pro Ser Arg Gly Arg Lys Arg Arg Ser Leu Cys Leu Met Gly His Lys
        435                 440                 445

Pro Val Leu Leu Arg Thr Gln Cys Arg Cys His Pro Ala Ile Ser Ala
    450                 455                 460

Ile Ala Asn Asp Leu Phe Tyr Glu Gly Ser Arg Gly Arg Lys Arg Arg
465                 470                 475                 480

Ser Thr Ser Ala Ala Glu Thr Lys Pro Pro Leu Ala Pro Ser Ser Pro
                485                 490                 495

Pro Ala Pro Pro Gly Thr Met Val Ala Gly Ser Ser Leu Glu Gly Pro
            500                 505                 510

Ala Pro Arg Gly Arg Lys Arg Arg Ser Arg Ser Leu Gln Glu Leu Leu
        515                 520                 525

Ala Arg Arg Thr Tyr Tyr Ser Gly Asp Pro Leu Phe Ser Val Asp Ile
    530                 535                 540

Leu Arg Asn Val Thr Asp Thr Phe Lys Arg Arg Gly Arg Lys Arg Arg
545                 550                 555                 560

Ser Gly Gly His Val Cys Trp Met Arg Glu Gly Val Glu Leu Cys Pro
                565                 570                 575

Gly Asn Lys Tyr Glu Met Arg Arg His Gly Thr Thr His Ser Leu Val
            580                 585                 590

Ile His Arg Gly Arg Lys Arg Arg Ser Glu Pro Ile Glu Val Asn Leu
        595                 600                 605

Phe Gly Leu Ile Asn Val Thr Pro Asn Met Leu Pro Leu Val Lys Lys
    610                 615                 620

Ala Arg Gly Arg Val Ile Asn Val Ser Ser Arg Gly Arg Lys Arg Arg
625                 630                 635                 640

Ser Val Asp Phe Asn Lys Ile Cys Gly Gln Ala Tyr Asp Ser Ala Thr
                645                 650                 655

Asn Phe Arg Val Lys Leu Asn Glu Val Val Ala Glu Phe Lys Lys Glu
            660                 665                 670

Glu Pro Arg Gly Arg Lys Arg Arg Ser Asn Cys Asn Phe Asp Phe Pro
        675                 680                 685

Glu Glu Thr Cys Gly Trp Val Tyr Asp His Ala Lys Leu Leu Arg Ser
    690                 695                 700

Thr Trp Ile Ser Ser Ala Asn Pro Asn Asp Arg Gly Arg Lys Arg Arg
705                 710                 715                 720

Ser Ile Ser Met Gly Gly His Met Ala Ser Leu Ala Val Cys Asn Trp
```

```
                725                 730                 735

Pro Lys Pro Met Pro Leu Ile Pro Cys Leu Ser Trp Ser Thr Ala Ser
            740                 745                 750

Gly Val Arg Gly Arg Lys Arg Arg Ser Gly Leu Ser Leu Asn Ile Lys
        755                 760                 765

Lys Tyr Leu Leu Val Ser Met Pro Leu Trp Ala Lys His Met Ser Asp
    770                 775                 780

Glu Gln Ile Gln Gly Phe Val Glu Asn Leu
785                 790


<210> SEQ ID NO 46
<211> LENGTH: 794
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Met Asp His Leu Gln Leu Lys Asp Ile Leu Arg Lys Gln Asp Glu Tyr
1               5                   10                  15

His Met Val His Leu Leu Cys Ala Ser Arg Ser Pro Pro Ser Ser Pro
            20                  25                  30

Lys Ser Arg Gly Arg Lys Arg Arg Ser Trp Asn Thr Trp Leu Tyr Ala
        35                  40                  45

Pro Gly Leu Pro Pro Val Lys Pro Asn Tyr Asp Ala Thr Leu Thr Asn
    50                  55                  60

Ala Cys Ile Ala Leu Ser Gln Arg Trp Val Arg Gly Arg Lys Arg Arg
65                  70                  75                  80

Ser Ala Gln Arg Asn Ser Asn Pro Ile Ile Ala Glu Leu Ser Gln Ala
                85                  90                  95

Met Asn Ser Gly Thr Leu Leu Ser Lys Pro Ser Pro Pro Leu Pro Pro
            100                 105                 110

Lys Arg Arg Gly Arg Lys Arg Arg Ser Gly Glu Ser Lys Gly Pro Leu
        115                 120                 125

Asp Ser Ser Phe Ser Gln Tyr Leu Gly Arg Ser Cys Leu Leu Asp Gln
    130                 135                 140

Arg Glu Ala Lys Arg Lys Gly Glu Gly Leu Arg Gly Arg Lys Arg Arg
145                 150                 155                 160

Ser Gln Gly Lys Tyr Ile Leu Lys Val Cys Gly Cys Asp Glu Tyr Phe
                165                 170                 175

Leu Glu Lys Phe Pro Leu Ser Gln Tyr Lys Tyr Ile Arg Ser Cys Ile
            180                 185                 190

Met Leu Arg Gly Arg Lys Arg Arg Ser Lys Phe Ile Ser Val Leu Cys
        195                 200                 205

Thr Ser Leu Ala Thr Met Leu His Val Glu Leu Pro His Val Asn Leu
    210                 215                 220

Leu Ser Lys Met Asp Leu Ile Glu His Tyr Arg Gly Arg Lys Arg Arg
225                 230                 235                 240

Ser Leu Arg Pro Ser Thr Leu Ser Gln Glu Val Tyr Lys Thr Val Ser
                245                 250                 255

Met Arg Leu Asn Val Val Ser Pro Asp Leu Ser Gly Lys Gly Leu Val
            260                 265                 270

Leu Pro Arg Gly Arg Lys Arg Arg Ser Ala Cys Ser Ser Ser Tyr Asn
        275                 280                 285
```

```
Ser Ala Val Met Glu Ser Ser Ser Val Asn Val Ser Met Val His Ser
    290                 295                 300

Ser Ser Lys Glu Asn Leu Cys Pro Lys Lys Arg Gly Arg Lys Arg Arg
305                 310                 315                 320

Ser Arg Glu Ile Ala Val Glu His Asn Asn Leu Gly Lys Ala Val Tyr
                325                 330                 335

Ser Arg Met Ala Arg Ile Cys Lys Asn Asp Met Gly Gly Ser Gln Arg
                340                 345                 350

Val Leu Arg Gly Arg Lys Arg Arg Ser Pro Gly Leu Leu Ser Val Asp
        355                 360                 365

Leu Phe His Val Leu Val Ser Ala Val Leu Ala Phe Pro Ser Leu Tyr
    370                 375                 380

Trp Asp Asp Thr Val Asp Leu Gln Pro Ser Arg Gly Arg Lys Arg Arg
385                 390                 395                 400

Ser Leu Cys Leu Met Gly His Lys Pro Val Leu Leu Arg Thr Gln Cys
                405                 410                 415

Arg Cys His Pro Ala Ile Ser Ala Ile Ala Asn Asp Leu Phe Tyr Glu
            420                 425                 430

Gly Ser Arg Gly Arg Lys Arg Arg Ser Thr Ser Ala Ala Glu Thr Lys
        435                 440                 445

Pro Pro Leu Ala Pro Ser Ser Pro Pro Ala Pro Pro Gly Thr Met Val
    450                 455                 460

Ala Gly Ser Ser Leu Glu Gly Pro Ala Pro Arg Gly Arg Lys Arg Arg
465                 470                 475                 480

Ser Arg Ser Leu Gln Glu Leu Leu Ala Arg Arg Thr Tyr Tyr Ser Gly
                485                 490                 495

Asp Pro Leu Phe Ser Val Asp Ile Leu Arg Asn Val Thr Asp Thr Phe
            500                 505                 510

Lys Arg Arg Gly Arg Lys Arg Arg Ser Gly Gly His Val Cys Trp Met
        515                 520                 525

Arg Glu Gly Val Glu Leu Cys Pro Gly Asn Lys Tyr Glu Met Arg Arg
    530                 535                 540

His Gly Thr Thr His Ser Leu Val Ile His Arg Gly Arg Lys Arg Arg
545                 550                 555                 560

Ser Glu Pro Ile Glu Val Asn Leu Phe Gly Leu Ile Asn Val Thr Pro
                565                 570                 575

Asn Met Leu Pro Leu Val Lys Lys Ala Arg Gly Arg Val Ile Asn Val
            580                 585                 590

Ser Ser Arg Gly Arg Lys Arg Arg Ser Val Asp Phe Asn Lys Ile Cys
        595                 600                 605

Gly Gln Ala Tyr Asp Ser Ala Thr Asn Phe Arg Val Lys Leu Asn Glu
    610                 615                 620

Val Val Ala Glu Phe Lys Lys Glu Glu Pro Arg Gly Arg Lys Arg Arg
625                 630                 635                 640

Ser Asn Cys Asn Phe Asp Phe Pro Glu Glu Thr Cys Gly Trp Val Tyr
                645                 650                 655

Asp His Ala Lys Leu Leu Arg Ser Thr Trp Ile Ser Ser Ala Asn Pro
            660                 665                 670

Asn Asp Arg Gly Arg Lys Arg Arg Ser Ile Ser Met Gly Gly His Met
        675                 680                 685

Ala Ser Leu Ala Val Cys Asn Trp Pro Lys Pro Met Pro Leu Ile Pro
    690                 695                 700

Cys Leu Ser Trp Ser Thr Ala Ser Gly Val Arg Gly Arg Lys Arg Arg
```

705 710 715 720

Ser Gly Leu Ser Leu Asn Ile Lys Lys Tyr Leu Leu Val Ser Met Pro
725 730 735

Leu Trp Ala Lys His Met Ser Asp Glu Gln Ile Gln Gly Phe Val Glu
740 745 750

Asn Leu Arg Gly Arg Lys Arg Arg Ser Ser His Val Gln Arg Leu Val
755 760 765

His Arg Asp Ser Thr Ile Ser Asn Asp Ala Phe Ile Ser Val Asp Asp
770 775 780

Leu Glu Pro Ser Gly Pro Gln Asp Leu Glu
785 790

<210> SEQ ID NO 47
<211> LENGTH: 1594
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 47

Met Ser His Val Gln Arg Leu Val His Arg Asp Ser Thr Ile Ser Asn
1 5 10 15

Asp Ala Phe Ile Ser Val Asp Asp Leu Glu Pro Ser Gly Pro Gln Asp
20 25 30

Leu Glu Arg Gly Arg Lys Arg Arg Ser Ala Asn Ala Val His Ser Met
35 40 45

Glu Lys Val Met Asp Ile His Ser Lys Tyr Cys Arg Cys Leu Gln Arg
50 55 60

Leu Ser Ser Thr Val Gly His Ser Leu Ile Arg Gly Arg Lys Arg Arg
65 70 75 80

Ser Asp His Leu Gln Leu Lys Asp Ile Leu Arg Lys Gln Asp Glu Tyr
85 90 95

His Met Val His Leu Leu Cys Ala Ser Arg Ser Pro Pro Ser Ser Pro
100 105 110

Lys Ser Arg Gly Arg Lys Arg Arg Ser Glu Val Pro Lys Pro Leu Phe
115 120 125

Pro Val Ala Gly Val Pro Met Ile Gln Tyr His Ile Glu Ala Cys Ala
130 135 140

Gln Val Pro Gly Met Gln Glu Ile Leu Leu Arg Gly Arg Lys Arg Arg
145 150 155 160

Ser Trp Asn Thr Trp Leu Tyr Ala Pro Gly Leu Pro Pro Val Lys Pro
165 170 175

Asn Tyr Asp Ala Thr Leu Thr Asn Ala Cys Ile Ala Leu Ser Gln Arg
180 185 190

Trp Val Arg Gly Arg Lys Arg Arg Ser Ser Asn Glu Asp Arg Glu Trp
195 200 205

His Glu Ser Phe Ser Leu Val Leu Gly Pro Asp Asp Pro Val Glu Ala
210 215 220

Val Leu Gly Asp Val Thr Thr Ala Thr Val Arg Gly Arg Lys Arg Arg
225 230 235 240

Ser Ala Gln Arg Asn Ser Asn Pro Ile Ile Ala Glu Leu Ser Gln Ala
245 250 255

Met Asn Ser Gly Thr Leu Leu Ser Lys Pro Ser Pro Pro Leu Pro Pro
260 265 270

```
Lys Arg Arg Gly Arg Lys Arg Arg Ser Met Ser Val Met Val Leu Arg
        275                 280                 285

Thr Gln Gly Pro Glu Ala Pro Phe Glu Asp His Arg Leu Ile Leu His
    290                 295                 300

Thr Ser Ser Cys Asp Ala Glu Arg Ala Arg Arg Gly Arg Lys Arg Arg
305                 310                 315                 320

Ser Gly Glu Ser Lys Gly Pro Leu Asp Ser Ser Phe Ser Gln Tyr Leu
                325                 330                 335

Gly Arg Ser Cys Leu Leu Asp Gln Arg Glu Ala Lys Arg Lys Gly Glu
            340                 345                 350

Gly Leu Arg Gly Arg Lys Arg Arg Ser Cys Pro His Met Thr Glu Asp
        355                 360                 365

Asn Lys Asp Leu Ile Gln Gly Lys Asp Leu Leu Thr Ala Cys Tyr Asp
    370                 375                 380

Val Asp Tyr Glu Lys Asn Ala Lys Gly Ser Arg Gly Arg Lys Arg Arg
385                 390                 395                 400

Ser Gln Gly Lys Tyr Ile Leu Lys Val Cys Gly Cys Asp Glu Tyr Phe
                405                 410                 415

Leu Glu Lys Phe Pro Leu Ser Gln Tyr Lys Tyr Ile Arg Ser Cys Ile
            420                 425                 430

Met Leu Arg Gly Arg Lys Arg Arg Ser Thr Arg Gly Leu Ala Tyr Leu
        435                 440                 445

His Thr Glu Leu Pro Gln Gly Asp His Tyr Lys Pro Ala Ile Ser His
    450                 455                 460

Arg Asp Leu Asn Ser Arg Asn Val Leu Val Arg Gly Arg Lys Arg Arg
465                 470                 475                 480

Ser Lys Phe Ile Ser Val Leu Cys Thr Ser Leu Ala Thr Met Leu His
                485                 490                 495

Val Glu Leu Pro His Val Asn Leu Leu Ser Lys Met Asp Leu Ile Glu
            500                 505                 510

His Tyr Arg Gly Arg Lys Arg Arg Ser Ile His Arg Glu Gln Asn Ser
        515                 520                 525

Leu Ser Leu Leu Glu Ala Ser Glu Ala Asp Gly Asp Ala Val Asn Asp
    530                 535                 540

Lys Lys Arg Thr Pro Asn Glu Ala Pro Ser Arg Gly Arg Lys Arg Arg
545                 550                 555                 560

Ser Leu Arg Pro Ser Thr Leu Ser Gln Glu Val Tyr Lys Thr Val Ser
                565                 570                 575

Met Arg Leu Asn Val Val Ser Pro Asp Leu Ser Gly Lys Gly Leu Val
            580                 585                 590

Leu Pro Arg Gly Arg Lys Arg Arg Ser Glu Pro Lys Arg Asp Arg Arg
        595                 600                 605

Asp Pro Ser Thr Asp Lys Ser Gly Pro Asp Thr Phe Pro Val Glu Val
    610                 615                 620

Leu Glu Arg Lys Pro Pro Glu Lys Thr Tyr Arg Gly Arg Lys Arg Arg
625                 630                 635                 640

Ser Ala Cys Ser Ser Ser Tyr Asn Ser Ala Val Met Glu Ser Ser Ser
                645                 650                 655

Val Asn Val Ser Met Val His Ser Ser Ser Lys Glu Asn Leu Cys Pro
            660                 665                 670

Lys Lys Arg Gly Arg Lys Arg Arg Ser Ser Gly His Val Gly Leu Arg
        675                 680                 685

Asn Leu Gly Asn Thr Leu Pro Gln Cys Phe Leu Asn Ala Met Leu Gln
```

```
    690                 695                 700

Cys Leu Ser Ser Thr Arg Pro Leu Arg Asp Arg Gly Arg Lys Arg Arg
705                 710                 715                 720

Ser Arg Glu Ile Ala Val Glu His Asn Asn Leu Gly Lys Ala Val Tyr
                725                 730                 735

Ser Arg Met Ala Arg Ile Cys Lys Asn Asp Met Gly Gly Ser Gln Arg
            740                 745                 750

Val Leu Arg Gly Arg Lys Arg Arg Ser Ala Glu Asp Thr Gln Glu Asn
        755                 760                 765

Leu His Ser Gly Lys Ser Gln Ser Arg Ser Phe Pro Lys Val Leu Ala
    770                 775                 780

Asp Ser Asp Glu Ser Asp Met Glu Glu Thr Arg Gly Arg Lys Arg Arg
785                 790                 795                 800

Ser Pro Gly Leu Leu Ser Val Asp Leu Phe His Val Leu Val Ser Ala
                805                 810                 815

Val Leu Ala Phe Pro Ser Leu Tyr Trp Asp Asp Thr Val Asp Leu Gln
            820                 825                 830

Pro Ser Arg Gly Arg Lys Arg Arg Ser Glu Cys Lys Glu Ala Ala Val
        835                 840                 845

Ser His Ala Gly Ser Met His Arg Glu Arg Arg Thr Phe Leu Arg Ser
    850                 855                 860

Ala Leu Lys Glu Leu Ala Thr Val Leu Ser Arg Gly Arg Lys Arg Arg
865                 870                 875                 880

Ser Leu Cys Leu Met Gly His Lys Pro Val Leu Leu Arg Thr Gln Cys
                885                 890                 895

Arg Cys His Pro Ala Ile Ser Ala Ile Ala Asn Asp Leu Phe Tyr Glu
            900                 905                 910

Gly Ser Arg Gly Arg Lys Arg Arg Ser Arg Met Arg Glu Glu Gln Leu
        915                 920                 925

Ala Arg Glu Ala Glu Ala Trp Ala Glu Arg Glu Ala Glu Ala Arg Arg
    930                 935                 940

Arg Glu Glu Gln Glu Ala Arg Glu Lys Ala Arg Gly Arg Lys Arg Arg
945                 950                 955                 960

Ser Thr Ser Ala Ala Glu Thr Lys Pro Pro Leu Ala Pro Ser Ser Pro
                965                 970                 975

Pro Ala Pro Pro Gly Thr Met Val Ala Gly Ser Ser Leu Glu Gly Pro
            980                 985                 990

Ala Pro Arg Gly Arg Lys Arg Arg  Ser Leu Ser Gln Thr  Pro Pro Pro
        995                 1000                1005

Ala Pro  Pro Pro Ser Ala Gly  Ser Glu Pro Leu Ala  Arg Leu Pro
    1010                1015                1020

Gln Lys  Asp Ser Val Gly Lys  His Ser Gly Ala Arg  Gly Arg Lys
    1025                1030                1035

Arg Arg  Ser Arg Ser Leu Gln  Glu Leu Leu Ala Arg  Arg Thr Tyr
    1040                1045                1050

Tyr Ser  Gly Asp Pro Leu Phe  Ser Val Asp Ile Leu  Arg Asn Val
    1055                1060                1065

Thr Asp  Thr Phe Lys Arg Arg  Gly Arg Lys Arg Arg  Ser Asn Thr
    1070                1075                1080

Gln Ile  Gln Lys Leu Thr Gly  Ser Pro Phe Arg Ser  Arg Glu Tyr
    1085                1090                1095

Val Gln  Thr Met Glu Ser Glu  Ser Glu His Ser Tyr  Pro Pro Pro
    1100                1105                1110
```

```
Gly Arg  Gly Arg Lys Arg Arg  Ser Gly Gly His Val  Cys Trp Met
    1115                 1120                 1125

Arg Glu  Gly Val Glu Leu Cys  Pro Gly Asn Lys Tyr  Glu Met Arg
    1130                 1135                 1140

Arg His  Gly Thr Thr His Ser  Leu Val Ile His Arg  Gly Arg Lys
    1145                 1150                 1155

Arg Arg  Ser Thr Thr Thr Ser  Arg Ala Ile Cys Gln  Leu Val Lys
    1160                 1165                 1170

Glu Tyr  Ile Gly Tyr Arg Asp  Gly Ile Trp Asp Val  Ser Val Thr
    1175                 1180                 1185

Arg Thr  Gln Pro Ile Val Arg  Gly Arg Lys Arg Arg  Ser Glu Pro
    1190                 1195                 1200

Ile Glu  Val Asn Leu Phe Gly  Leu Ile Asn Val Thr  Pro Asn Met
    1205                 1210                 1215

Leu Pro  Leu Val Lys Lys Ala  Arg Gly Arg Val Ile  Asn Val Ser
    1220                 1225                 1230

Ser Arg  Gly Arg Lys Arg Arg  Ser Asn Gly Tyr Asp  Thr Tyr Val
    1235                 1240                 1245

His Asp  Ala Tyr Gly Leu Phe  Gln Glu Cys Arg Ser  Arg Val Ala
    1250                 1255                 1260

His Trp  Gly Trp Pro Leu Gly  Pro Ala Pro Leu Arg  Gly Arg Lys
    1265                 1270                 1275

Arg Arg  Ser Val Asp Phe Asn  Lys Ile Cys Gly Gln  Ala Tyr Asp
    1280                 1285                 1290

Ser Ala  Thr Asn Phe Arg Val  Lys Leu Asn Glu Val  Val Ala Glu
    1295                 1300                 1305

Phe Lys  Lys Glu Glu Pro Arg  Gly Arg Lys Arg Arg  Ser Ile Gln
    1310                 1315                 1320

Gly Trp  Leu Gly Thr Lys Val  Arg Thr Asn Leu Arg  Arg Glu Pro
    1325                 1330                 1335

Phe Ser  Leu Val Pro Lys Asn  Ala Lys Asp Gly Asn  Ser Phe Gln
    1340                 1345                 1350

Gly Arg  Gly Arg Lys Arg Arg  Ser Asn Cys Asn Phe  Asp Phe Pro
    1355                 1360                 1365

Glu Glu  Thr Cys Gly Trp Val  Tyr Asp His Ala Lys  Leu Leu Arg
    1370                 1375                 1380

Ser Thr  Trp Ile Ser Ser Ala  Asn Pro Asn Asp Arg  Gly Arg Lys
    1385                 1390                 1395

Arg Arg  Ser Gly Gly Lys Val  Trp Asn Glu Gln Glu  Lys Asn Thr
    1400                 1405                 1410

Tyr Ala  Asp Lys Leu Phe Asp  Cys Ile Glu Ala Tyr  Ala Pro Gly
    1415                 1420                 1425

Phe Lys  Arg Ser Val Leu Arg  Gly Arg Lys Arg Arg  Ser Ile Ser
    1430                 1435                 1440

Met Gly  Gly His Met Ala Ser  Leu Ala Val Cys Asn  Trp Pro Lys
    1445                 1450                 1455

Pro Met  Pro Leu Ile Pro Cys  Leu Ser Trp Ser Thr  Ala Ser Gly
    1460                 1465                 1470

Val Arg  Gly Arg Lys Arg Arg  Ser Trp Met Lys Cys  Val Lys Gly
    1475                 1480                 1485

Gln Pro  His Asp His Lys His  Leu Met Pro Thr Gln  Ile Ile Pro
    1490                 1495                 1500
```

Gly Ser Val Leu Thr Asp Leu Leu Asp Ala Met Arg Gly Arg Lys
1505 1510 1515

Arg Arg Ser Gly Leu Ser Leu Asn Ile Lys Lys Tyr Leu Leu Val
1520 1525 1530

Ser Met Pro Leu Trp Ala Lys His Met Ser Asp Glu Gln Ile Gln
1535 1540 1545

Gly Phe Val Glu Asn Leu Arg Gly Arg Lys Arg Arg Ser Ser Ile
1550 1555 1560

Leu Arg Asn His Arg Tyr Arg Arg Asp Ala Arg Thr Leu Glu Asp
1565 1570 1575

Lys Glu Glu Met Trp Phe Asn Thr Asp Glu Asp Asp Met Glu Asp
1580 1585 1590

Gly

<210> SEQ ID NO 48
<211> LENGTH: 1594
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 48

Met Ala Asn Ala Val His Ser Met Glu Lys Val Met Asp Ile His Ser
1 5 10 15

Lys Tyr Cys Arg Cys Leu Gln Arg Leu Ser Ser Thr Val Gly His Ser
20 25 30

Leu Ile Arg Gly Arg Lys Arg Arg Ser Asp His Leu Gln Leu Lys Asp
35 40 45

Ile Leu Arg Lys Gln Asp Glu Tyr His Met Val His Leu Leu Cys Ala
50 55 60

Ser Arg Ser Pro Pro Ser Ser Pro Lys Ser Arg Gly Arg Lys Arg Arg
65 70 75 80

Ser Glu Val Pro Lys Pro Leu Phe Pro Val Ala Gly Val Pro Met Ile
85 90 95

Gln Tyr His Ile Glu Ala Cys Ala Gln Val Pro Gly Met Gln Glu Ile
100 105 110

Leu Leu Arg Gly Arg Lys Arg Arg Ser Trp Asn Thr Trp Leu Tyr Ala
115 120 125

Pro Gly Leu Pro Pro Val Lys Pro Asn Tyr Asp Ala Thr Leu Thr Asn
130 135 140

Ala Cys Ile Ala Leu Ser Gln Arg Trp Val Arg Gly Arg Lys Arg Arg
145 150 155 160

Ser Ser Asn Glu Asp Arg Glu Trp His Glu Ser Phe Ser Leu Val Leu
165 170 175

Gly Pro Asp Asp Pro Val Glu Ala Val Leu Gly Asp Val Thr Thr Ala
180 185 190

Thr Val Arg Gly Arg Lys Arg Arg Ser Ala Gln Arg Asn Ser Asn Pro
195 200 205

Ile Ile Ala Glu Leu Ser Gln Ala Met Asn Ser Gly Thr Leu Leu Ser
210 215 220

Lys Pro Ser Pro Pro Leu Pro Pro Lys Arg Arg Gly Arg Lys Arg Arg
225 230 235 240

Ser Met Ser Val Met Val Leu Arg Thr Gln Gly Pro Glu Ala Pro Phe
245 250 255

-continued

```
Glu Asp His Arg Leu Ile Leu His Thr Ser Ser Cys Asp Ala Glu Arg
            260                 265                 270

Ala Arg Arg Gly Arg Lys Arg Arg Ser Gly Glu Ser Lys Gly Pro Leu
        275                 280                 285

Asp Ser Ser Phe Ser Gln Tyr Leu Gly Arg Ser Cys Leu Leu Asp Gln
    290                 295                 300

Arg Glu Ala Lys Arg Lys Gly Glu Gly Leu Arg Gly Arg Lys Arg Arg
305                 310                 315                 320

Ser Cys Pro His Met Thr Glu Asp Asn Lys Asp Leu Ile Gln Gly Lys
                325                 330                 335

Asp Leu Leu Thr Ala Cys Tyr Asp Val Asp Tyr Glu Lys Asn Ala Lys
            340                 345                 350

Gly Ser Arg Gly Arg Lys Arg Arg Ser Ser His Val Gln Arg Leu Val
        355                 360                 365

His Arg Asp Ser Thr Ile Ser Asn Asp Ala Phe Ile Ser Val Asp Asp
    370                 375                 380

Leu Glu Pro Ser Gly Pro Gln Asp Leu Glu Arg Gly Arg Lys Arg Arg
385                 390                 395                 400

Ser Gln Gly Lys Tyr Ile Leu Lys Val Cys Gly Cys Asp Glu Tyr Phe
                405                 410                 415

Leu Glu Lys Phe Pro Leu Ser Gln Tyr Lys Tyr Ile Arg Ser Cys Ile
            420                 425                 430

Met Leu Arg Gly Arg Lys Arg Arg Ser Thr Arg Gly Leu Ala Tyr Leu
        435                 440                 445

His Thr Glu Leu Pro Gln Gly Asp His Tyr Lys Pro Ala Ile Ser His
    450                 455                 460

Arg Asp Leu Asn Ser Arg Asn Val Leu Val Arg Gly Arg Lys Arg Arg
465                 470                 475                 480

Ser Lys Phe Ile Ser Val Leu Cys Thr Ser Leu Ala Thr Met Leu His
                485                 490                 495

Val Glu Leu Pro His Val Asn Leu Leu Ser Lys Met Asp Leu Ile Glu
            500                 505                 510

His Tyr Arg Gly Arg Lys Arg Arg Ser Ile His Arg Glu Gln Asn Ser
        515                 520                 525

Leu Ser Leu Leu Glu Ala Ser Glu Ala Asp Gly Asp Ala Val Asn Asp
    530                 535                 540

Lys Lys Arg Thr Pro Asn Glu Ala Pro Ser Arg Gly Arg Lys Arg Arg
545                 550                 555                 560

Ser Leu Arg Pro Ser Thr Leu Ser Gln Glu Val Tyr Lys Thr Val Ser
                565                 570                 575

Met Arg Leu Asn Val Val Ser Pro Asp Leu Ser Gly Lys Gly Leu Val
            580                 585                 590

Leu Pro Arg Gly Arg Lys Arg Arg Ser Glu Pro Lys Arg Asp Arg Arg
        595                 600                 605

Asp Pro Ser Thr Asp Lys Ser Gly Pro Asp Thr Phe Pro Val Glu Val
    610                 615                 620

Leu Glu Arg Lys Pro Pro Glu Lys Thr Tyr Arg Gly Arg Lys Arg Arg
625                 630                 635                 640

Ser Ala Cys Ser Ser Ser Tyr Asn Ser Ala Val Met Glu Ser Ser Ser
                645                 650                 655

Val Asn Val Ser Met Val His Ser Ser Ser Lys Glu Asn Leu Cys Pro
            660                 665                 670

Lys Lys Arg Gly Arg Lys Arg Arg Ser Ser Gly His Val Gly Leu Arg
```

```
        675                 680                 685

Asn Leu Gly Asn Thr Leu Pro Gln Cys Phe Leu Asn Ala Met Leu Gln
    690                 695                 700

Cys Leu Ser Ser Thr Arg Pro Leu Arg Asp Arg Gly Arg Lys Arg Arg
705                 710                 715                 720

Ser Arg Glu Ile Ala Val Glu His Asn Asn Leu Gly Lys Ala Val Tyr
                725                 730                 735

Ser Arg Met Ala Arg Ile Cys Lys Asn Asp Met Gly Gly Ser Gln Arg
            740                 745                 750

Val Leu Arg Gly Arg Lys Arg Arg Ser Ala Glu Asp Thr Gln Glu Asn
        755                 760                 765

Leu His Ser Gly Lys Ser Gln Ser Arg Ser Phe Pro Lys Val Leu Ala
    770                 775                 780

Asp Ser Asp Glu Ser Asp Met Glu Glu Thr Arg Gly Arg Lys Arg Arg
785                 790                 795                 800

Ser Pro Gly Leu Leu Ser Val Asp Leu Phe His Val Leu Val Ser Ala
                805                 810                 815

Val Leu Ala Phe Pro Ser Leu Tyr Trp Asp Asp Thr Val Asp Leu Gln
            820                 825                 830

Pro Ser Arg Gly Arg Lys Arg Arg Ser Glu Cys Lys Glu Ala Ala Val
        835                 840                 845

Ser His Ala Gly Ser Met His Arg Glu Arg Arg Thr Phe Leu Arg Ser
    850                 855                 860

Ala Leu Lys Glu Leu Ala Thr Val Leu Ser Arg Gly Arg Lys Arg Arg
865                 870                 875                 880

Ser Leu Cys Leu Met Gly His Lys Pro Val Leu Leu Arg Thr Gln Cys
                885                 890                 895

Arg Cys His Pro Ala Ile Ser Ala Ile Ala Asn Asp Leu Phe Tyr Glu
            900                 905                 910

Gly Ser Arg Gly Arg Lys Arg Arg Ser Arg Met Arg Glu Glu Gln Leu
        915                 920                 925

Ala Arg Glu Ala Glu Ala Trp Ala Glu Arg Glu Ala Glu Ala Arg Arg
    930                 935                 940

Arg Glu Glu Gln Glu Ala Arg Glu Lys Ala Arg Gly Arg Lys Arg Arg
945                 950                 955                 960

Ser Thr Ser Ala Ala Glu Thr Lys Pro Pro Leu Ala Pro Ser Ser Pro
                965                 970                 975

Pro Ala Pro Pro Gly Thr Met Val Ala Gly Ser Ser Leu Glu Gly Pro
            980                 985                 990

Ala Pro Arg Gly Arg Lys Arg Arg  Ser Leu Ser Gln Thr  Pro Pro Pro
        995                 1000                1005

Ala Pro  Pro Pro Ser Ala Gly  Ser Glu Pro Leu Ala  Arg Leu Pro
    1010                1015                1020

Gln Lys  Asp Ser Val Gly Lys  His Ser Gly Ala Arg  Gly Arg Lys
    1025                1030                1035

Arg Arg  Ser Arg Ser Leu Gln  Glu Leu Leu Ala Arg  Arg Thr Tyr
    1040                1045                1050

Tyr Ser  Gly Asp Pro Leu Phe  Ser Val Asp Ile Leu  Arg Asn Val
    1055                1060                1065

Thr Asp  Thr Phe Lys Arg Arg  Gly Arg Lys Arg Arg  Ser Asn Thr
    1070                1075                1080

Gln Ile  Gln Lys Leu Thr Gly  Ser Pro Phe Arg Ser  Arg Glu Tyr
    1085                1090                1095
```

```
Val Gln  Thr Met Glu Ser Glu  Ser Glu His Ser Tyr  Pro Pro Pro
    1100                 1105                 1110

Gly Arg  Gly Arg Lys Arg Arg  Ser Gly Gly His Val  Cys Trp Met
    1115                 1120                 1125

Arg Glu  Gly Val Glu Leu Cys  Pro Gly Asn Lys Tyr  Glu Met Arg
    1130                 1135                 1140

Arg His  Gly Thr Thr His Ser  Leu Val Ile His Arg  Gly Arg Lys
    1145                 1150                 1155

Arg Arg  Ser Thr Thr Thr Ser  Arg Ala Ile Cys Gln  Leu Val Lys
    1160                 1165                 1170

Glu Tyr  Ile Gly Tyr Arg Asp  Gly Ile Trp Asp Val  Ser Val Thr
    1175                 1180                 1185

Arg Thr  Gln Pro Ile Val Arg  Gly Arg Lys Arg Arg  Ser Glu Pro
    1190                 1195                 1200

Ile Glu  Val Asn Leu Phe Gly  Leu Ile Asn Val Thr  Pro Asn Met
    1205                 1210                 1215

Leu Pro  Leu Val Lys Lys Ala  Arg Gly Arg Val Ile  Asn Val Ser
    1220                 1225                 1230

Ser Arg  Gly Arg Lys Arg Arg  Ser Asn Gly Tyr Asp  Thr Tyr Val
    1235                 1240                 1245

His Asp  Ala Tyr Gly Leu Phe  Gln Glu Cys Arg Ser  Arg Val Ala
    1250                 1255                 1260

His Trp  Gly Trp Pro Leu Gly  Pro Ala Pro Leu Arg  Gly Arg Lys
    1265                 1270                 1275

Arg Arg  Ser Val Asp Phe Asn  Lys Ile Cys Gly Gln  Ala Tyr Asp
    1280                 1285                 1290

Ser Ala  Thr Asn Phe Arg Val  Lys Leu Asn Glu Val  Val Ala Glu
    1295                 1300                 1305

Phe Lys  Lys Glu Glu Pro Arg  Gly Arg Lys Arg Arg  Ser Ile Gln
    1310                 1315                 1320

Gly Trp  Leu Gly Thr Lys Val  Arg Thr Asn Leu Arg  Arg Glu Pro
    1325                 1330                 1335

Phe Ser  Leu Val Pro Lys Asn  Ala Lys Asp Gly Asn  Ser Phe Gln
    1340                 1345                 1350

Gly Arg  Gly Arg Lys Arg Arg  Ser Asn Cys Asn Phe  Asp Phe Pro
    1355                 1360                 1365

Glu Glu  Thr Cys Gly Trp Val  Tyr Asp His Ala Lys  Leu Leu Arg
    1370                 1375                 1380

Ser Thr  Trp Ile Ser Ser Ala  Asn Pro Asn Asp Arg  Gly Arg Lys
    1385                 1390                 1395

Arg Arg  Ser Gly Gly Lys Val  Trp Asn Glu Gln Glu  Lys Asn Thr
    1400                 1405                 1410

Tyr Ala  Asp Lys Leu Phe Asp  Cys Ile Glu Ala Tyr  Ala Pro Gly
    1415                 1420                 1425

Phe Lys  Arg Ser Val Leu Arg  Gly Arg Lys Arg Arg  Ser Ile Ser
    1430                 1435                 1440

Met Gly  Gly His Met Ala Ser  Leu Ala Val Cys Asn  Trp Pro Lys
    1445                 1450                 1455

Pro Met  Pro Leu Ile Pro Cys  Leu Ser Trp Ser Thr  Ala Ser Gly
    1460                 1465                 1470

Val Arg  Gly Arg Lys Arg Arg  Ser Trp Met Lys Cys  Val Lys Gly
    1475                 1480                 1485
```

```
Gln Pro  His Asp His Lys His  Leu Met Pro Thr Gln  Ile Ile Pro
    1490                 1495                 1500

Gly Ser  Val Leu Thr Asp Leu  Leu Asp Ala Met Arg  Gly Arg Lys
    1505                 1510                 1515

Arg Arg  Ser Gly Leu Ser Leu  Asn Ile Lys Lys Tyr  Leu Leu Val
    1520                 1525                 1530

Ser Met  Pro Leu Trp Ala Lys  His Met Ser Asp Glu  Gln Ile Gln
    1535                 1540                 1545

Gly Phe  Val Glu Asn Leu Arg  Gly Arg Lys Arg Arg  Ser Ser Ile
    1550                 1555                 1560

Leu Arg  Asn His Arg Tyr Arg  Arg Asp Ala Arg Thr  Leu Glu Asp
    1565                 1570                 1575

Lys Glu  Glu Met Trp Phe Asn  Thr Asp Glu Asp Asp  Met Glu Asp
    1580                 1585                 1590

Gly


<210> SEQ ID NO 49
<211> LENGTH: 1594
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Met Ala Asn Ala Val His Ser Met Glu Lys Val Met Asp Ile His Ser
1               5                   10                  15

Lys Tyr Cys Arg Cys Leu Gln Arg Leu Ser Ser Thr Val Gly His Ser
            20                  25                  30

Leu Ile Arg Gly Arg Lys Arg Arg Ser Asp His Leu Gln Leu Lys Asp
        35                  40                  45

Ile Leu Arg Lys Gln Asp Glu Tyr His Met Val His Leu Leu Cys Ala
    50                  55                  60

Ser Arg Ser Pro Pro Ser Ser Pro Lys Ser Arg Gly Arg Lys Arg Arg
65                  70                  75                  80

Ser Glu Val Pro Lys Pro Leu Phe Pro Val Ala Gly Val Pro Met Ile
                85                  90                  95

Gln Tyr His Ile Glu Ala Cys Ala Gln Val Pro Gly Met Gln Glu Ile
            100                 105                 110

Leu Leu Arg Gly Arg Lys Arg Arg Ser Trp Asn Thr Trp Leu Tyr Ala
        115                 120                 125

Pro Gly Leu Pro Pro Val Lys Pro Asn Tyr Asp Ala Thr Leu Thr Asn
    130                 135                 140

Ala Cys Ile Ala Leu Ser Gln Arg Trp Val Arg Gly Arg Lys Arg Arg
145                 150                 155                 160

Ser Ser Asn Glu Asp Arg Glu Trp His Glu Ser Phe Ser Leu Val Leu
                165                 170                 175

Gly Pro Asp Asp Pro Val Glu Ala Val Leu Gly Asp Val Thr Thr Ala
            180                 185                 190

Thr Val Arg Gly Arg Lys Arg Arg Ser Ala Gln Arg Asn Ser Asn Pro
        195                 200                 205

Ile Ile Ala Glu Leu Ser Gln Ala Met Asn Ser Gly Thr Leu Leu Ser
    210                 215                 220

Lys Pro Ser Pro Pro Leu Pro Pro Lys Arg Arg Gly Arg Lys Arg Arg
225                 230                 235                 240
```

-continued

```
Ser Met Ser Val Met Val Leu Arg Thr Gln Gly Pro Glu Ala Pro Phe
                245                 250                 255

Glu Asp His Arg Leu Ile Leu His Thr Ser Ser Cys Asp Ala Glu Arg
            260                 265                 270

Ala Arg Arg Gly Arg Lys Arg Arg Ser Gly Glu Ser Lys Gly Pro Leu
        275                 280                 285

Asp Ser Ser Phe Ser Gln Tyr Leu Gly Arg Ser Cys Leu Leu Asp Gln
    290                 295                 300

Arg Glu Ala Lys Arg Lys Gly Glu Gly Leu Arg Gly Arg Lys Arg Arg
305                 310                 315                 320

Ser Cys Pro His Met Thr Glu Asp Asn Lys Asp Leu Ile Gln Gly Lys
                325                 330                 335

Asp Leu Leu Thr Ala Cys Tyr Asp Val Asp Tyr Glu Lys Asn Ala Lys
            340                 345                 350

Gly Ser Arg Gly Arg Lys Arg Arg Ser Gln Gly Lys Tyr Ile Leu Lys
        355                 360                 365

Val Cys Gly Cys Asp Glu Tyr Phe Leu Glu Lys Phe Pro Leu Ser Gln
    370                 375                 380

Tyr Lys Tyr Ile Arg Ser Cys Ile Met Leu Arg Gly Arg Lys Arg Arg
385                 390                 395                 400

Ser Thr Arg Gly Leu Ala Tyr Leu His Thr Glu Leu Pro Gln Gly Asp
                405                 410                 415

His Tyr Lys Pro Ala Ile Ser His Arg Asp Leu Asn Ser Arg Asn Val
            420                 425                 430

Leu Val Arg Gly Arg Lys Arg Arg Ser Lys Phe Ile Ser Val Leu Cys
        435                 440                 445

Thr Ser Leu Ala Thr Met Leu His Val Glu Leu Pro His Val Asn Leu
    450                 455                 460

Leu Ser Lys Met Asp Leu Ile Glu His Tyr Arg Gly Arg Lys Arg Arg
465                 470                 475                 480

Ser Ile His Arg Glu Gln Asn Ser Leu Ser Leu Leu Glu Ala Ser Glu
                485                 490                 495

Ala Asp Gly Asp Ala Val Asn Asp Lys Lys Arg Thr Pro Asn Glu Ala
            500                 505                 510

Pro Ser Arg Gly Arg Lys Arg Arg Ser Leu Arg Pro Ser Thr Leu Ser
        515                 520                 525

Gln Glu Val Tyr Lys Thr Val Ser Met Arg Leu Asn Val Val Ser Pro
    530                 535                 540

Asp Leu Ser Gly Lys Gly Leu Val Leu Pro Arg Gly Arg Lys Arg Arg
545                 550                 555                 560

Ser Glu Pro Lys Arg Asp Arg Arg Asp Pro Ser Thr Asp Lys Ser Gly
                565                 570                 575

Pro Asp Thr Phe Pro Val Glu Val Leu Glu Arg Lys Pro Pro Glu Lys
            580                 585                 590

Thr Tyr Arg Gly Arg Lys Arg Arg Ser Ala Cys Ser Ser Ser Tyr Asn
        595                 600                 605

Ser Ala Val Met Glu Ser Ser Ser Val Asn Val Ser Met Val His Ser
    610                 615                 620

Ser Ser Lys Glu Asn Leu Cys Pro Lys Lys Arg Gly Arg Lys Arg Arg
625                 630                 635                 640

Ser Ser Gly His Val Gly Leu Arg Asn Leu Gly Asn Thr Leu Pro Gln
                645                 650                 655

Cys Phe Leu Asn Ala Met Leu Gln Cys Leu Ser Ser Thr Arg Pro Leu
```

```
            660                 665                 670

Arg Asp Arg Gly Arg Lys Arg Arg Ser Arg Glu Ile Ala Val Glu His
        675                 680                 685

Asn Asn Leu Gly Lys Ala Val Tyr Ser Arg Met Ala Arg Ile Cys Lys
    690                 695                 700

Asn Asp Met Gly Gly Ser Gln Arg Val Leu Arg Gly Arg Lys Arg Arg
705                 710                 715                 720

Ser Ala Glu Asp Thr Gln Glu Asn Leu His Ser Gly Lys Ser Gln Ser
                725                 730                 735

Arg Ser Phe Pro Lys Val Leu Ala Asp Ser Asp Glu Ser Asp Met Glu
            740                 745                 750

Glu Thr Arg Gly Arg Lys Arg Arg Ser Ser His Val Gln Arg Leu Val
        755                 760                 765

His Arg Asp Ser Thr Ile Ser Asn Asp Ala Phe Ile Ser Val Asp Asp
    770                 775                 780

Leu Glu Pro Ser Gly Pro Gln Asp Leu Glu Arg Gly Arg Lys Arg Arg
785                 790                 795                 800

Ser Pro Gly Leu Leu Ser Val Asp Leu Phe His Val Leu Val Ser Ala
                805                 810                 815

Val Leu Ala Phe Pro Ser Leu Tyr Trp Asp Asp Thr Val Asp Leu Gln
            820                 825                 830

Pro Ser Arg Gly Arg Lys Arg Arg Ser Glu Cys Lys Glu Ala Ala Val
        835                 840                 845

Ser His Ala Gly Ser Met His Arg Glu Arg Arg Thr Phe Leu Arg Ser
    850                 855                 860

Ala Leu Lys Glu Leu Ala Thr Val Leu Ser Arg Gly Arg Lys Arg Arg
865                 870                 875                 880

Ser Leu Cys Leu Met Gly His Lys Pro Val Leu Leu Arg Thr Gln Cys
                885                 890                 895

Arg Cys His Pro Ala Ile Ser Ala Ile Ala Asn Asp Leu Phe Tyr Glu
            900                 905                 910

Gly Ser Arg Gly Arg Lys Arg Arg Ser Arg Met Arg Glu Glu Gln Leu
        915                 920                 925

Ala Arg Glu Ala Glu Ala Trp Ala Glu Arg Glu Ala Glu Ala Arg Arg
    930                 935                 940

Arg Glu Glu Gln Glu Ala Arg Glu Lys Ala Arg Gly Arg Lys Arg Arg
945                 950                 955                 960

Ser Thr Ser Ala Ala Glu Thr Lys Pro Pro Leu Ala Pro Ser Ser Pro
                965                 970                 975

Pro Ala Pro Pro Gly Thr Met Val Ala Gly Ser Ser Leu Glu Gly Pro
            980                 985                 990

Ala Pro Arg Gly Arg Lys Arg Arg  Ser Leu Ser Gln Thr  Pro Pro Pro
        995                 1000                1005

Ala Pro  Pro Pro Ser Ala Gly  Ser Glu Pro Leu Ala  Arg Leu Pro
    1010                1015                1020

Gln Lys  Asp Ser Val Gly Lys  His Ser Gly Ala Arg  Gly Arg Lys
    1025                1030                1035

Arg Arg  Ser Arg Ser Leu Gln  Glu Leu Leu Ala Arg  Arg Thr Tyr
    1040                1045                1050

Tyr Ser  Gly Asp Pro Leu Phe  Ser Val Asp Ile Leu  Arg Asn Val
    1055                1060                1065

Thr Asp  Thr Phe Lys Arg Arg  Gly Arg Lys Arg Arg  Ser Asn Thr
    1070                1075                1080
```

```
Gln Ile  Gln Lys Leu Thr Gly  Ser Pro Phe Arg Ser  Arg Glu Tyr
    1085                 1090                 1095

Val Gln  Thr Met Glu Ser Glu  Ser Glu His Ser Tyr  Pro Pro Pro
    1100                 1105                 1110

Gly Arg  Gly Arg Lys Arg Arg  Ser Gly Gly His Val  Cys Trp Met
    1115                 1120                 1125

Arg Glu  Gly Val Glu Leu Cys  Pro Gly Asn Lys Tyr  Glu Met Arg
    1130                 1135                 1140

Arg His  Gly Thr Thr His Ser  Leu Val Ile His Arg  Gly Arg Lys
    1145                 1150                 1155

Arg Arg  Ser Thr Thr Thr Ser  Arg Ala Ile Cys Gln  Leu Val Lys
    1160                 1165                 1170

Glu Tyr  Ile Gly Tyr Arg Asp  Gly Ile Trp Asp Val  Ser Val Thr
    1175                 1180                 1185

Arg Thr  Gln Pro Ile Val Arg  Gly Arg Lys Arg Arg  Ser Glu Pro
    1190                 1195                 1200

Ile Glu  Val Asn Leu Phe Gly  Leu Ile Asn Val Thr  Pro Asn Met
    1205                 1210                 1215

Leu Pro  Leu Val Lys Lys Ala  Arg Gly Arg Val Ile  Asn Val Ser
    1220                 1225                 1230

Ser Arg  Gly Arg Lys Arg Arg  Ser Asn Gly Tyr Asp  Thr Tyr Val
    1235                 1240                 1245

His Asp  Ala Tyr Gly Leu Phe  Gln Glu Cys Arg Ser  Arg Val Ala
    1250                 1255                 1260

His Trp  Gly Trp Pro Leu Gly  Pro Ala Pro Leu Arg  Gly Arg Lys
    1265                 1270                 1275

Arg Arg  Ser Val Asp Phe Asn  Lys Ile Cys Gly Gln  Ala Tyr Asp
    1280                 1285                 1290

Ser Ala  Thr Asn Phe Arg Val  Lys Leu Asn Glu Val  Val Ala Glu
    1295                 1300                 1305

Phe Lys  Lys Glu Glu Pro Arg  Gly Arg Lys Arg Arg  Ser Ile Gln
    1310                 1315                 1320

Gly Trp  Leu Gly Thr Lys Val  Arg Thr Asn Leu Arg  Arg Glu Pro
    1325                 1330                 1335

Phe Ser  Leu Val Pro Lys Asn  Ala Lys Asp Gly Asn  Ser Phe Gln
    1340                 1345                 1350

Gly Arg  Gly Arg Lys Arg Arg  Ser Asn Cys Asn Phe  Asp Phe Pro
    1355                 1360                 1365

Glu Glu  Thr Cys Gly Trp Val  Tyr Asp His Ala Lys  Leu Leu Arg
    1370                 1375                 1380

Ser Thr  Trp Ile Ser Ser Ala  Asn Pro Asn Asp Arg  Gly Arg Lys
    1385                 1390                 1395

Arg Arg  Ser Gly Gly Lys Val  Trp Asn Glu Gln Glu  Lys Asn Thr
    1400                 1405                 1410

Tyr Ala  Asp Lys Leu Phe Asp  Cys Ile Glu Ala Tyr  Ala Pro Gly
    1415                 1420                 1425

Phe Lys  Arg Ser Val Leu Arg  Gly Arg Lys Arg Arg  Ser Ile Ser
    1430                 1435                 1440

Met Gly  Gly His Met Ala Ser  Leu Ala Val Cys Asn  Trp Pro Lys
    1445                 1450                 1455

Pro Met  Pro Leu Ile Pro Cys  Leu Ser Trp Ser Thr  Ala Ser Gly
    1460                 1465                 1470
```

Val Arg Gly Arg Lys Arg Arg Ser Trp Met Lys Cys Val Lys Gly
1475 1480 1485

Gln Pro His Asp His Lys His Leu Met Pro Thr Gln Ile Ile Pro
1490 1495 1500

Gly Ser Val Leu Thr Asp Leu Leu Asp Ala Met Arg Gly Arg Lys
1505 1510 1515

Arg Arg Ser Gly Leu Ser Leu Asn Ile Lys Lys Tyr Leu Leu Val
1520 1525 1530

Ser Met Pro Leu Trp Ala Lys His Met Ser Asp Glu Gln Ile Gln
1535 1540 1545

Gly Phe Val Glu Asn Leu Arg Gly Arg Lys Arg Arg Ser Ser Ile
1550 1555 1560

Leu Arg Asn His Arg Tyr Arg Arg Asp Ala Arg Thr Leu Glu Asp
1565 1570 1575

Lys Glu Glu Met Trp Phe Asn Thr Asp Glu Asp Asp Met Glu Asp
1580 1585 1590

Gly

<210> SEQ ID NO 50
<211> LENGTH: 1594
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 50

Met Ala Asn Ala Val His Ser Met Glu Lys Val Met Asp Ile His Ser
1 5 10 15

Lys Tyr Cys Arg Cys Leu Gln Arg Leu Ser Ser Thr Val Gly His Ser
20 25 30

Leu Ile Arg Gly Arg Lys Arg Arg Ser Asp His Leu Gln Leu Lys Asp
35 40 45

Ile Leu Arg Lys Gln Asp Glu Tyr His Met Val His Leu Leu Cys Ala
50 55 60

Ser Arg Ser Pro Pro Ser Ser Pro Lys Ser Arg Gly Arg Lys Arg Arg
65 70 75 80

Ser Glu Val Pro Lys Pro Leu Phe Pro Val Ala Gly Val Pro Met Ile
85 90 95

Gln Tyr His Ile Glu Ala Cys Ala Gln Val Pro Gly Met Gln Glu Ile
100 105 110

Leu Leu Arg Gly Arg Lys Arg Arg Ser Trp Asn Thr Trp Leu Tyr Ala
115 120 125

Pro Gly Leu Pro Pro Val Lys Pro Asn Tyr Asp Ala Thr Leu Thr Asn
130 135 140

Ala Cys Ile Ala Leu Ser Gln Arg Trp Val Arg Gly Arg Lys Arg Arg
145 150 155 160

Ser Ser Asn Glu Asp Arg Glu Trp His Glu Ser Phe Ser Leu Val Leu
165 170 175

Gly Pro Asp Asp Pro Val Glu Ala Val Leu Gly Asp Val Thr Thr Ala
180 185 190

Thr Val Arg Gly Arg Lys Arg Arg Ser Ala Gln Arg Asn Ser Asn Pro
195 200 205

Ile Ile Ala Glu Leu Ser Gln Ala Met Asn Ser Gly Thr Leu Leu Ser
210 215 220

```
Lys Pro Ser Pro Pro Leu Pro Pro Lys Arg Arg Gly Arg Lys Arg Arg
225                 230                 235                 240

Ser Met Ser Val Met Val Leu Arg Thr Gln Gly Pro Glu Ala Pro Phe
                245                 250                 255

Glu Asp His Arg Leu Ile Leu His Thr Ser Ser Cys Asp Ala Glu Arg
            260                 265                 270

Ala Arg Arg Gly Arg Lys Arg Arg Ser Gly Glu Ser Lys Gly Pro Leu
        275                 280                 285

Asp Ser Ser Phe Ser Gln Tyr Leu Gly Arg Ser Cys Leu Leu Asp Gln
    290                 295                 300

Arg Glu Ala Lys Arg Lys Gly Glu Gly Leu Arg Gly Arg Lys Arg Arg
305                 310                 315                 320

Ser Cys Pro His Met Thr Glu Asp Asn Lys Asp Leu Ile Gln Gly Lys
                325                 330                 335

Asp Leu Leu Thr Ala Cys Tyr Asp Val Asp Tyr Glu Lys Asn Ala Lys
            340                 345                 350

Gly Ser Arg Gly Arg Lys Arg Arg Ser Gln Gly Lys Tyr Ile Leu Lys
        355                 360                 365

Val Cys Gly Cys Asp Glu Tyr Phe Leu Glu Lys Phe Pro Leu Ser Gln
    370                 375                 380

Tyr Lys Tyr Ile Arg Ser Cys Ile Met Leu Arg Gly Arg Lys Arg Arg
385                 390                 395                 400

Ser Thr Arg Gly Leu Ala Tyr Leu His Thr Glu Leu Pro Gln Gly Asp
                405                 410                 415

His Tyr Lys Pro Ala Ile Ser His Arg Asp Leu Asn Ser Arg Asn Val
            420                 425                 430

Leu Val Arg Gly Arg Lys Arg Arg Ser Lys Phe Ile Ser Val Leu Cys
        435                 440                 445

Thr Ser Leu Ala Thr Met Leu His Val Glu Leu Pro His Val Asn Leu
    450                 455                 460

Leu Ser Lys Met Asp Leu Ile Glu His Tyr Arg Gly Arg Lys Arg Arg
465                 470                 475                 480

Ser Ile His Arg Glu Gln Asn Ser Leu Ser Leu Leu Glu Ala Ser Glu
                485                 490                 495

Ala Asp Gly Asp Ala Val Asn Asp Lys Lys Arg Thr Pro Asn Glu Ala
            500                 505                 510

Pro Ser Arg Gly Arg Lys Arg Arg Ser Leu Arg Pro Ser Thr Leu Ser
        515                 520                 525

Gln Glu Val Tyr Lys Thr Val Ser Met Arg Leu Asn Val Val Ser Pro
    530                 535                 540

Asp Leu Ser Gly Lys Gly Leu Val Leu Pro Arg Gly Arg Lys Arg Arg
545                 550                 555                 560

Ser Glu Pro Lys Arg Asp Arg Arg Asp Pro Ser Thr Asp Lys Ser Gly
                565                 570                 575

Pro Asp Thr Phe Pro Val Glu Val Leu Glu Arg Lys Pro Pro Glu Lys
            580                 585                 590

Thr Tyr Arg Gly Arg Lys Arg Arg Ser Ala Cys Ser Ser Ser Tyr Asn
        595                 600                 605

Ser Ala Val Met Glu Ser Ser Ser Val Asn Val Ser Met Val His Ser
    610                 615                 620

Ser Ser Lys Glu Asn Leu Cys Pro Lys Lys Arg Gly Arg Lys Arg Arg
625                 630                 635                 640

Ser Ser Gly His Val Gly Leu Arg Asn Leu Gly Asn Thr Leu Pro Gln
```

-continued

```
                645                 650                 655

Cys Phe Leu Asn Ala Met Leu Gln Cys Leu Ser Ser Thr Arg Pro Leu
            660                 665                 670

Arg Asp Arg Gly Arg Lys Arg Arg Ser Arg Glu Ile Ala Val Glu His
        675                 680                 685

Asn Asn Leu Gly Lys Ala Val Tyr Ser Arg Met Ala Arg Ile Cys Lys
    690                 695                 700

Asn Asp Met Gly Gly Ser Gln Arg Val Leu Arg Gly Arg Lys Arg Arg
705                 710                 715                 720

Ser Ala Glu Asp Thr Gln Glu Asn Leu His Ser Gly Lys Ser Gln Ser
                725                 730                 735

Arg Ser Phe Pro Lys Val Leu Ala Asp Ser Asp Glu Ser Asp Met Glu
            740                 745                 750

Glu Thr Arg Gly Arg Lys Arg Arg Ser Pro Gly Leu Leu Ser Val Asp
        755                 760                 765

Leu Phe His Val Leu Val Ser Ala Val Leu Ala Phe Pro Ser Leu Tyr
    770                 775                 780

Trp Asp Asp Thr Val Asp Leu Gln Pro Ser Arg Gly Arg Lys Arg Arg
785                 790                 795                 800

Ser Glu Cys Lys Glu Ala Ala Val Ser His Ala Gly Ser Met His Arg
                805                 810                 815

Glu Arg Arg Thr Phe Leu Arg Ser Ala Leu Lys Glu Leu Ala Thr Val
            820                 825                 830

Leu Ser Arg Gly Arg Lys Arg Arg Ser Leu Cys Leu Met Gly His Lys
        835                 840                 845

Pro Val Leu Leu Arg Thr Gln Cys Arg Cys His Pro Ala Ile Ser Ala
    850                 855                 860

Ile Ala Asn Asp Leu Phe Tyr Glu Gly Ser Arg Gly Arg Lys Arg Arg
865                 870                 875                 880

Ser Arg Met Arg Glu Glu Gln Leu Ala Arg Glu Ala Glu Ala Trp Ala
                885                 890                 895

Glu Arg Glu Ala Glu Ala Arg Arg Arg Glu Glu Gln Glu Ala Arg Glu
            900                 905                 910

Lys Ala Arg Gly Arg Lys Arg Arg Ser Thr Ser Ala Ala Glu Thr Lys
        915                 920                 925

Pro Pro Leu Ala Pro Ser Ser Pro Pro Ala Pro Pro Gly Thr Met Val
    930                 935                 940

Ala Gly Ser Ser Leu Glu Gly Pro Ala Pro Arg Gly Arg Lys Arg Arg
945                 950                 955                 960

Ser Leu Ser Gln Thr Pro Pro Pro Ala Pro Pro Pro Ser Ala Gly Ser
                965                 970                 975

Glu Pro Leu Ala Arg Leu Pro Gln Lys Asp Ser Val Gly Lys His Ser
            980                 985                 990

Gly Ala Arg Gly Arg Lys Arg Arg  Ser Arg Ser Leu Gln  Glu Leu Leu
        995                 1000                1005

Ala Arg  Arg Thr Tyr Tyr Ser  Gly Asp Pro Leu Phe  Ser Val Asp
    1010                1015                1020

Ile Leu  Arg Asn Val Thr Asp  Thr Phe Lys Arg Arg  Gly Arg Lys
    1025                1030                1035

Arg Arg  Ser Asn Thr Gln Ile  Gln Lys Leu Thr Gly  Ser Pro Phe
    1040                1045                1050

Arg Ser  Arg Glu Tyr Val Gln  Thr Met Glu Ser Glu  Ser Glu His
    1055                1060                1065
```

-continued

```
Ser Tyr Pro Pro Pro Gly Arg Gly Arg Lys Arg Arg Ser Gly Gly
    1070                1075                1080

His Val Cys Trp Met Arg Glu Gly Val Glu Leu Cys Pro Gly Asn
    1085                1090                1095

Lys Tyr Glu Met Arg Arg His Gly Thr Thr His Ser Leu Val Ile
    1100                1105                1110

His Arg Gly Arg Lys Arg Arg Ser Thr Thr Thr Ser Arg Ala Ile
    1115                1120                1125

Cys Gln Leu Val Lys Glu Tyr Ile Gly Tyr Arg Asp Gly Ile Trp
    1130                1135                1140

Asp Val Ser Val Thr Arg Thr Gln Pro Ile Val Arg Gly Arg Lys
    1145                1150                1155

Arg Arg Ser Ser His Val Gln Arg Leu Val His Arg Asp Ser Thr
    1160                1165                1170

Ile Ser Asn Asp Ala Phe Ile Ser Val Asp Asp Leu Glu Pro Ser
    1175                1180                1185

Gly Pro Gln Asp Leu Glu Arg Gly Arg Lys Arg Arg Ser Glu Pro
    1190                1195                1200

Ile Glu Val Asn Leu Phe Gly Leu Ile Asn Val Thr Pro Asn Met
    1205                1210                1215

Leu Pro Leu Val Lys Lys Ala Arg Gly Arg Val Ile Asn Val Ser
    1220                1225                1230

Ser Arg Gly Arg Lys Arg Arg Ser Asn Gly Tyr Asp Thr Tyr Val
    1235                1240                1245

His Asp Ala Tyr Gly Leu Phe Gln Glu Cys Arg Ser Arg Val Ala
    1250                1255                1260

His Trp Gly Trp Pro Leu Gly Pro Ala Pro Leu Arg Gly Arg Lys
    1265                1270                1275

Arg Arg Ser Val Asp Phe Asn Lys Ile Cys Gly Gln Ala Tyr Asp
    1280                1285                1290

Ser Ala Thr Asn Phe Arg Val Lys Leu Asn Glu Val Val Ala Glu
    1295                1300                1305

Phe Lys Lys Glu Glu Pro Arg Gly Arg Lys Arg Arg Ser Ile Gln
    1310                1315                1320

Gly Trp Leu Gly Thr Lys Val Arg Thr Asn Leu Arg Arg Glu Pro
    1325                1330                1335

Phe Ser Leu Val Pro Lys Asn Ala Lys Asp Gly Asn Ser Phe Gln
    1340                1345                1350

Gly Arg Gly Arg Lys Arg Arg Ser Asn Cys Asn Phe Asp Phe Pro
    1355                1360                1365

Glu Glu Thr Cys Gly Trp Val Tyr Asp His Ala Lys Leu Leu Arg
    1370                1375                1380

Ser Thr Trp Ile Ser Ser Ala Asn Pro Asn Asp Arg Gly Arg Lys
    1385                1390                1395

Arg Arg Ser Gly Gly Lys Val Trp Asn Glu Gln Glu Lys Asn Thr
    1400                1405                1410

Tyr Ala Asp Lys Leu Phe Asp Cys Ile Glu Ala Tyr Ala Pro Gly
    1415                1420                1425

Phe Lys Arg Ser Val Leu Arg Gly Arg Lys Arg Arg Ser Ile Ser
    1430                1435                1440

Met Gly Gly His Met Ala Ser Leu Ala Val Cys Asn Trp Pro Lys
    1445                1450                1455
```

Pro Met Pro Leu Ile Pro Cys Leu Ser Trp Ser Thr Ala Ser Gly
    1460                1465                1470

Val Arg Gly Arg Lys Arg Arg Ser Trp Met Lys Cys Val Lys Gly
    1475                1480                1485

Gln Pro His Asp His Lys His Leu Met Pro Thr Gln Ile Ile Pro
    1490                1495                1500

Gly Ser Val Leu Thr Asp Leu Leu Asp Ala Met Arg Gly Arg Lys
    1505                1510                1515

Arg Arg Ser Gly Leu Ser Leu Asn Ile Lys Lys Tyr Leu Leu Val
    1520                1525                1530

Ser Met Pro Leu Trp Ala Lys His Met Ser Asp Glu Gln Ile Gln
    1535                1540                1545

Gly Phe Val Glu Asn Leu Arg Gly Arg Lys Arg Arg Ser Ser Ile
    1550                1555                1560

Leu Arg Asn His Arg Tyr Arg Arg Asp Ala Arg Thr Leu Glu Asp
    1565                1570                1575

Lys Glu Glu Met Trp Phe Asn Thr Asp Glu Asp Asp Met Glu Asp
    1580                1585                1590

Gly

<210> SEQ ID NO 51
<211> LENGTH: 1594
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Met Ala Asn Ala Val His Ser Met Glu Lys Val Met Asp Ile His Ser
1               5                   10                  15

Lys Tyr Cys Arg Cys Leu Gln Arg Leu Ser Ser Thr Val Gly His Ser
            20                  25                  30

Leu Ile Arg Gly Arg Lys Arg Arg Ser Asp His Leu Gln Leu Lys Asp
        35                  40                  45

Ile Leu Arg Lys Gln Asp Glu Tyr His Met Val His Leu Leu Cys Ala
    50                  55                  60

Ser Arg Ser Pro Pro Ser Ser Pro Lys Ser Arg Gly Arg Lys Arg Arg
65                  70                  75                  80

Ser Glu Val Pro Lys Pro Leu Phe Pro Val Ala Gly Val Pro Met Ile
                85                  90                  95

Gln Tyr His Ile Glu Ala Cys Ala Gln Val Pro Gly Met Gln Glu Ile
            100                 105                 110

Leu Leu Arg Gly Arg Lys Arg Arg Ser Trp Asn Thr Trp Leu Tyr Ala
        115                 120                 125

Pro Gly Leu Pro Pro Val Lys Pro Asn Tyr Asp Ala Thr Leu Thr Asn
    130                 135                 140

Ala Cys Ile Ala Leu Ser Gln Arg Trp Val Arg Gly Arg Lys Arg Arg
145                 150                 155                 160

Ser Ser Asn Glu Asp Arg Glu Trp His Glu Ser Phe Ser Leu Val Leu
                165                 170                 175

Gly Pro Asp Asp Pro Val Glu Ala Val Leu Gly Asp Val Thr Thr Ala
            180                 185                 190

Thr Val Arg Gly Arg Lys Arg Arg Ser Ala Gln Arg Asn Ser Asn Pro
        195                 200                 205

```
Ile Ile Ala Glu Leu Ser Gln Ala Met Asn Ser Gly Thr Leu Leu Ser
    210                 215                 220

Lys Pro Ser Pro Pro Leu Pro Pro Lys Arg Arg Gly Arg Lys Arg Arg
225                 230                 235                 240

Ser Met Ser Val Met Val Leu Arg Thr Gln Gly Pro Glu Ala Pro Phe
                245                 250                 255

Glu Asp His Arg Leu Ile Leu His Thr Ser Ser Cys Asp Ala Glu Arg
            260                 265                 270

Ala Arg Arg Gly Arg Lys Arg Arg Ser Gly Glu Ser Lys Gly Pro Leu
        275                 280                 285

Asp Ser Ser Phe Ser Gln Tyr Leu Gly Arg Ser Cys Leu Leu Asp Gln
    290                 295                 300

Arg Glu Ala Lys Arg Lys Gly Glu Gly Leu Arg Gly Arg Lys Arg Arg
305                 310                 315                 320

Ser Cys Pro His Met Thr Glu Asp Asn Lys Asp Leu Ile Gln Gly Lys
                325                 330                 335

Asp Leu Leu Thr Ala Cys Tyr Asp Val Asp Tyr Glu Lys Asn Ala Lys
            340                 345                 350

Gly Ser Arg Gly Arg Lys Arg Arg Ser Gln Gly Lys Tyr Ile Leu Lys
        355                 360                 365

Val Cys Gly Cys Asp Glu Tyr Phe Leu Glu Lys Phe Pro Leu Ser Gln
    370                 375                 380

Tyr Lys Tyr Ile Arg Ser Cys Ile Met Leu Arg Gly Arg Lys Arg Arg
385                 390                 395                 400

Ser Thr Arg Gly Leu Ala Tyr Leu His Thr Glu Leu Pro Gln Gly Asp
                405                 410                 415

His Tyr Lys Pro Ala Ile Ser His Arg Asp Leu Asn Ser Arg Asn Val
            420                 425                 430

Leu Val Arg Gly Arg Lys Arg Arg Ser Lys Phe Ile Ser Val Leu Cys
        435                 440                 445

Thr Ser Leu Ala Thr Met Leu His Val Glu Leu Pro His Val Asn Leu
    450                 455                 460

Leu Ser Lys Met Asp Leu Ile Glu His Tyr Arg Gly Arg Lys Arg Arg
465                 470                 475                 480

Ser Ile His Arg Glu Gln Asn Ser Leu Ser Leu Leu Glu Ala Ser Glu
                485                 490                 495

Ala Asp Gly Asp Ala Val Asn Asp Lys Lys Arg Thr Pro Asn Glu Ala
            500                 505                 510

Pro Ser Arg Gly Arg Lys Arg Arg Ser Leu Arg Pro Ser Thr Leu Ser
        515                 520                 525

Gln Glu Val Tyr Lys Thr Val Ser Met Arg Leu Asn Val Val Ser Pro
    530                 535                 540

Asp Leu Ser Gly Lys Gly Leu Val Leu Pro Arg Gly Arg Lys Arg Arg
545                 550                 555                 560

Ser Glu Pro Lys Arg Asp Arg Arg Asp Pro Ser Thr Asp Lys Ser Gly
                565                 570                 575

Pro Asp Thr Phe Pro Val Glu Val Leu Glu Arg Lys Pro Pro Glu Lys
            580                 585                 590

Thr Tyr Arg Gly Arg Lys Arg Arg Ser Ala Cys Ser Ser Ser Tyr Asn
        595                 600                 605

Ser Ala Val Met Glu Ser Ser Ser Val Asn Val Ser Met Val His Ser
    610                 615                 620

Ser Ser Lys Glu Asn Leu Cys Pro Lys Lys Arg Gly Arg Lys Arg Arg
```

```
625                 630                 635                 640

Ser Ser Gly His Val Gly Leu Arg Asn Leu Gly Asn Thr Leu Pro Gln
                645                 650                 655

Cys Phe Leu Asn Ala Met Leu Gln Cys Leu Ser Ser Thr Arg Pro Leu
            660                 665                 670

Arg Asp Arg Gly Arg Lys Arg Arg Ser Arg Glu Ile Ala Val Glu His
        675                 680                 685

Asn Asn Leu Gly Lys Ala Val Tyr Ser Arg Met Ala Arg Ile Cys Lys
    690                 695                 700

Asn Asp Met Gly Gly Ser Gln Arg Val Leu Arg Gly Arg Lys Arg Arg
705                 710                 715                 720

Ser Ala Glu Asp Thr Gln Glu Asn Leu His Ser Gly Lys Ser Gln Ser
                725                 730                 735

Arg Ser Phe Pro Lys Val Leu Ala Asp Ser Asp Glu Ser Asp Met Glu
            740                 745                 750

Glu Thr Arg Gly Arg Lys Arg Arg Ser Pro Gly Leu Leu Ser Val Asp
        755                 760                 765

Leu Phe His Val Leu Val Ser Ala Val Leu Ala Phe Pro Ser Leu Tyr
    770                 775                 780

Trp Asp Asp Thr Val Asp Leu Gln Pro Ser Arg Gly Arg Lys Arg Arg
785                 790                 795                 800

Ser Glu Cys Lys Glu Ala Ala Val Ser His Ala Gly Ser Met His Arg
                805                 810                 815

Glu Arg Arg Thr Phe Leu Arg Ser Ala Leu Lys Glu Leu Ala Thr Val
            820                 825                 830

Leu Ser Arg Gly Arg Lys Arg Arg Ser Leu Cys Leu Met Gly His Lys
        835                 840                 845

Pro Val Leu Leu Arg Thr Gln Cys Arg Cys His Pro Ala Ile Ser Ala
    850                 855                 860

Ile Ala Asn Asp Leu Phe Tyr Glu Gly Ser Arg Gly Arg Lys Arg Arg
865                 870                 875                 880

Ser Arg Met Arg Glu Glu Gln Leu Ala Arg Glu Ala Glu Ala Trp Ala
                885                 890                 895

Glu Arg Glu Ala Glu Ala Arg Arg Arg Glu Glu Gln Glu Ala Arg Glu
            900                 905                 910

Lys Ala Arg Gly Arg Lys Arg Arg Ser Thr Ser Ala Ala Glu Thr Lys
        915                 920                 925

Pro Pro Leu Ala Pro Ser Ser Pro Pro Ala Pro Pro Gly Thr Met Val
    930                 935                 940

Ala Gly Ser Ser Leu Glu Gly Pro Ala Pro Arg Gly Arg Lys Arg Arg
945                 950                 955                 960

Ser Leu Ser Gln Thr Pro Pro Pro Ala Pro Pro Pro Ser Ala Gly Ser
                965                 970                 975

Glu Pro Leu Ala Arg Leu Pro Gln Lys Asp Ser Val Gly Lys His Ser
            980                 985                 990

Gly Ala Arg Gly Arg Lys Arg Arg  Ser Arg Ser Leu Gln  Glu Leu Leu
        995                 1000                1005

Ala Arg  Arg Thr Tyr Tyr Ser  Gly Asp Pro Leu Phe  Ser Val Asp
    1010                1015                1020

Ile Leu  Arg Asn Val Thr Asp  Thr Phe Lys Arg Arg  Gly Arg Lys
    1025                1030                1035

Arg Arg  Ser Asn Thr Gln Ile  Gln Lys Leu Thr Gly  Ser Pro Phe
    1040                1045                1050
```

```
Arg Ser  Arg Glu Tyr Val Gln  Thr Met Glu Ser Glu  Ser Glu His
    1055                 1060                 1065

Ser Tyr  Pro Pro Pro Gly Arg  Gly Arg Lys Arg Arg  Ser Gly Gly
    1070                 1075                 1080

His Val  Cys Trp Met Arg Glu  Gly Val Glu Leu Cys  Pro Gly Asn
    1085                 1090                 1095

Lys Tyr  Glu Met Arg Arg His  Gly Thr Thr His Ser  Leu Val Ile
    1100                 1105                 1110

His Arg  Gly Arg Lys Arg Arg  Ser Thr Thr Thr Ser  Arg Ala Ile
    1115                 1120                 1125

Cys Gln  Leu Val Lys Glu Tyr  Ile Gly Tyr Arg Asp  Gly Ile Trp
    1130                 1135                 1140

Asp Val  Ser Val Thr Arg Thr  Gln Pro Ile Val Arg  Gly Arg Lys
    1145                 1150                 1155

Arg Arg  Ser Glu Pro Ile Glu  Val Asn Leu Phe Gly  Leu Ile Asn
    1160                 1165                 1170

Val Thr  Pro Asn Met Leu Pro  Leu Val Lys Lys Ala  Arg Gly Arg
    1175                 1180                 1185

Val Ile  Asn Val Ser Ser Arg  Gly Arg Lys Arg Arg  Ser Asn Gly
    1190                 1195                 1200

Tyr Asp  Thr Tyr Val His Asp  Ala Tyr Gly Leu Phe  Gln Glu Cys
    1205                 1210                 1215

Arg Ser  Arg Val Ala His Trp  Gly Trp Pro Leu Gly  Pro Ala Pro
    1220                 1225                 1230

Leu Arg  Gly Arg Lys Arg Arg  Ser Val Asp Phe Asn  Lys Ile Cys
    1235                 1240                 1245

Gly Gln  Ala Tyr Asp Ser Ala  Thr Asn Phe Arg Val  Lys Leu Asn
    1250                 1255                 1260

Glu Val  Val Ala Glu Phe Lys  Lys Glu Glu Pro Arg  Gly Arg Lys
    1265                 1270                 1275

Arg Arg  Ser Ile Gln Gly Trp  Leu Gly Thr Lys Val  Arg Thr Asn
    1280                 1285                 1290

Leu Arg  Arg Glu Pro Phe Ser  Leu Val Pro Lys Asn  Ala Lys Asp
    1295                 1300                 1305

Gly Asn  Ser Phe Gln Gly Arg  Gly Arg Lys Arg Arg  Ser Asn Cys
    1310                 1315                 1320

Asn Phe  Asp Phe Pro Glu Glu  Thr Cys Gly Trp Val  Tyr Asp His
    1325                 1330                 1335

Ala Lys  Leu Leu Arg Ser Thr  Trp Ile Ser Ser Ala  Asn Pro Asn
    1340                 1345                 1350

Asp Arg  Gly Arg Lys Arg Arg  Ser Gly Gly Lys Val  Trp Asn Glu
    1355                 1360                 1365

Gln Glu  Lys Asn Thr Tyr Ala  Asp Lys Leu Phe Asp  Cys Ile Glu
    1370                 1375                 1380

Ala Tyr  Ala Pro Gly Phe Lys  Arg Ser Val Leu Arg  Gly Arg Lys
    1385                 1390                 1395

Arg Arg  Ser Ile Ser Met Gly  Gly His Met Ala Ser  Leu Ala Val
    1400                 1405                 1410

Cys Asn  Trp Pro Lys Pro Met  Pro Leu Ile Pro Cys  Leu Ser Trp
    1415                 1420                 1425

Ser Thr  Ala Ser Gly Val Arg  Gly Arg Lys Arg Arg  Ser Trp Met
    1430                 1435                 1440
```

```
Lys Cys  Val Lys Gly Gln Pro  His Asp His Lys His  Leu Met Pro
    1445                 1450                 1455

Thr Gln  Ile Ile Pro Gly Ser  Val Leu Thr Asp Leu  Leu Asp Ala
    1460                 1465                 1470

Met Arg  Gly Arg Lys Arg Arg  Ser Gly Leu Ser Leu  Asn Ile Lys
    1475                 1480                 1485

Lys Tyr  Leu Leu Val Ser Met  Pro Leu Trp Ala Lys  His Met Ser
    1490                 1495                 1500

Asp Glu  Gln Ile Gln Gly Phe  Val Glu Asn Leu Arg  Gly Arg Lys
    1505                 1510                 1515

Arg Arg  Ser Ser Ile Leu Arg  Asn His Arg Tyr Arg  Arg Asp Ala
    1520                 1525                 1530

Arg Thr  Leu Glu Asp Lys Glu  Glu Met Trp Phe Asn  Thr Asp Glu
    1535                 1540                 1545

Asp Asp  Met Glu Asp Gly Arg  Gly Arg Lys Arg Arg  Ser Ser His
    1550                 1555                 1560

Val Gln  Arg Leu Val His Arg  Asp Ser Thr Ile Ser  Asn Asp Ala
    1565                 1570                 1575

Phe Ile  Ser Val Asp Asp Leu  Glu Pro Ser Gly Pro  Gln Asp Leu
    1580                 1585                 1590

Glu
```

<210> SEQ ID NO 52
<211> LENGTH: 194
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 52

```
Met Ser His Val Gln Arg Leu Val His Arg Asp Ser Thr Ile Ser Asn
1               5                   10                  15

Asp Ala Phe Ile Ser Val Asp Asp Leu Glu Pro Ser Gly Pro Gln Asp
            20                  25                  30

Leu Glu Arg Gly Arg Lys Arg Arg Ser Asp His Leu Gln Leu Lys Asp
        35                  40                  45

Ile Leu Arg Lys Gln Asp Glu Tyr His Met Val His Leu Leu Cys Ala
    50                  55                  60

Ser Arg Ser Pro Pro Ser Ser Pro Lys Ser Arg Gly Arg Lys Arg Arg
65                  70                  75                  80

Ser Trp Asn Thr Trp Leu Tyr Ala Pro Gly Leu Pro Pro Val Lys Pro
                85                  90                  95

Asn Tyr Asp Ala Thr Leu Thr Asn Ala Cys Ile Ala Leu Ser Gln Arg
            100                 105                 110

Trp Val Arg Gly Arg Lys Arg Arg Ser Ala Gln Arg Asn Ser Asn Pro
        115                 120                 125

Ile Ile Ala Glu Leu Ser Gln Ala Met Asn Ser Gly Thr Leu Leu Ser
    130                 135                 140

Lys Pro Ser Pro Pro Leu Pro Pro Lys Arg Arg Gly Arg Lys Arg Arg
145                 150                 155                 160

Ser Gly Glu Ser Lys Gly Pro Leu Asp Ser Ser Phe Ser Gln Tyr Leu
                165                 170                 175

Gly Arg Ser Cys Leu Leu Asp Gln Arg Glu Ala Lys Arg Lys Gly Glu
            180                 185                 190
```

Gly Leu

<210> SEQ ID NO 53
<211> LENGTH: 994
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

```
Met Ser His Val Gln Arg Leu Val His Arg Asp Ser Thr Ile Ser Asn
1               5                   10                  15

Asp Ala Phe Ile Ser Val Asp Asp Leu Glu Pro Ser Gly Pro Gln Asp
            20                  25                  30

Leu Glu Arg Gly Arg Lys Arg Arg Ser Asp His Leu Gln Leu Lys Asp
        35                  40                  45

Ile Leu Arg Lys Gln Asp Glu Tyr His Met Val His Leu Leu Cys Ala
    50                  55                  60

Ser Arg Ser Pro Pro Ser Ser Pro Lys Ser Arg Gly Arg Lys Arg Arg
65                  70                  75                  80

Ser Trp Asn Thr Trp Leu Tyr Ala Pro Gly Leu Pro Pro Val Lys Pro
                85                  90                  95

Asn Tyr Asp Ala Thr Leu Thr Asn Ala Cys Ile Ala Leu Ser Gln Arg
            100                 105                 110

Trp Val Arg Gly Arg Lys Arg Arg Ser Ala Gln Arg Asn Ser Asn Pro
        115                 120                 125

Ile Ile Ala Glu Leu Ser Gln Ala Met Asn Ser Gly Thr Leu Leu Ser
    130                 135                 140

Lys Pro Ser Pro Pro Leu Pro Pro Lys Arg Arg Gly Arg Lys Arg Arg
145                 150                 155                 160

Ser Gly Glu Ser Lys Gly Pro Leu Asp Ser Ser Phe Ser Gln Tyr Leu
                165                 170                 175

Gly Arg Ser Cys Leu Leu Asp Gln Arg Glu Ala Lys Arg Lys Gly Glu
            180                 185                 190

Gly Leu Arg Gly Arg Lys Arg Arg Ser Ser His Val Gln Arg Leu Val
        195                 200                 205

His Arg Asp Ser Thr Ile Ser Asn Asp Ala Phe Ile Ser Val Asp Asp
    210                 215                 220

Leu Glu Pro Ser Gly Pro Gln Asp Leu Glu Arg Gly Arg Lys Arg Arg
225                 230                 235                 240

Ser Asp His Leu Gln Leu Lys Asp Ile Leu Arg Lys Gln Asp Glu Tyr
                245                 250                 255

His Met Val His Leu Leu Cys Ala Ser Arg Ser Pro Pro Ser Ser Pro
            260                 265                 270

Lys Ser Arg Gly Arg Lys Arg Arg Ser Trp Asn Thr Trp Leu Tyr Ala
        275                 280                 285

Pro Gly Leu Pro Pro Val Lys Pro Asn Tyr Asp Ala Thr Leu Thr Asn
    290                 295                 300

Ala Cys Ile Ala Leu Ser Gln Arg Trp Val Arg Gly Arg Lys Arg Arg
305                 310                 315                 320

Ser Ala Gln Arg Asn Ser Asn Pro Ile Ile Ala Glu Leu Ser Gln Ala
                325                 330                 335

Met Asn Ser Gly Thr Leu Leu Ser Lys Pro Ser Pro Pro Leu Pro Pro
            340                 345                 350
```

```
Lys Arg Arg Gly Arg Lys Arg Arg Ser Gly Glu Ser Lys Gly Pro Leu
        355                 360                 365

Asp Ser Ser Phe Ser Gln Tyr Leu Gly Arg Ser Cys Leu Leu Asp Gln
    370                 375                 380

Arg Glu Ala Lys Arg Lys Gly Glu Gly Leu Arg Gly Arg Lys Arg Arg
385                 390                 395                 400

Ser Ser His Val Gln Arg Leu Val His Arg Asp Ser Thr Ile Ser Asn
                405                 410                 415

Asp Ala Phe Ile Ser Val Asp Asp Leu Glu Pro Ser Gly Pro Gln Asp
            420                 425                 430

Leu Glu Arg Gly Arg Lys Arg Arg Ser Asp His Leu Gln Leu Lys Asp
        435                 440                 445

Ile Leu Arg Lys Gln Asp Glu Tyr His Met Val His Leu Leu Cys Ala
    450                 455                 460

Ser Arg Ser Pro Pro Ser Ser Pro Lys Ser Arg Gly Arg Lys Arg Arg
465                 470                 475                 480

Ser Trp Asn Thr Trp Leu Tyr Ala Pro Gly Leu Pro Pro Val Lys Pro
                485                 490                 495

Asn Tyr Asp Ala Thr Leu Thr Asn Ala Cys Ile Ala Leu Ser Gln Arg
            500                 505                 510

Trp Val Arg Gly Arg Lys Arg Arg Ser Ala Gln Arg Asn Ser Asn Pro
        515                 520                 525

Ile Ile Ala Glu Leu Ser Gln Ala Met Asn Ser Gly Thr Leu Leu Ser
    530                 535                 540

Lys Pro Ser Pro Pro Leu Pro Pro Lys Arg Arg Gly Arg Lys Arg Arg
545                 550                 555                 560

Ser Gly Glu Ser Lys Gly Pro Leu Asp Ser Ser Phe Ser Gln Tyr Leu
                565                 570                 575

Gly Arg Ser Cys Leu Leu Asp Gln Arg Glu Ala Lys Arg Lys Gly Glu
            580                 585                 590

Gly Leu Arg Gly Arg Lys Arg Arg Ser Ser His Val Gln Arg Leu Val
        595                 600                 605

His Arg Asp Ser Thr Ile Ser Asn Asp Ala Phe Ile Ser Val Asp Asp
    610                 615                 620

Leu Glu Pro Ser Gly Pro Gln Asp Leu Glu Arg Gly Arg Lys Arg Arg
625                 630                 635                 640

Ser Asp His Leu Gln Leu Lys Asp Ile Leu Arg Lys Gln Asp Glu Tyr
                645                 650                 655

His Met Val His Leu Leu Cys Ala Ser Arg Ser Pro Pro Ser Ser Pro
            660                 665                 670

Lys Ser Arg Gly Arg Lys Arg Arg Ser Trp Asn Thr Trp Leu Tyr Ala
        675                 680                 685

Pro Gly Leu Pro Pro Val Lys Pro Asn Tyr Asp Ala Thr Leu Thr Asn
    690                 695                 700

Ala Cys Ile Ala Leu Ser Gln Arg Trp Val Arg Gly Arg Lys Arg Arg
705                 710                 715                 720

Ser Ala Gln Arg Asn Ser Asn Pro Ile Ile Ala Glu Leu Ser Gln Ala
                725                 730                 735

Met Asn Ser Gly Thr Leu Leu Ser Lys Pro Ser Pro Pro Leu Pro Pro
            740                 745                 750

Lys Arg Arg Gly Arg Lys Arg Arg Ser Gly Glu Ser Lys Gly Pro Leu
        755                 760                 765

Asp Ser Ser Phe Ser Gln Tyr Leu Gly Arg Ser Cys Leu Leu Asp Gln
```

770 775 780

Arg Glu Ala Lys Arg Lys Gly Glu Gly Leu Arg Gly Arg Lys Arg Arg
785 790 795 800

Ser Ser His Val Gln Arg Leu Val His Arg Asp Ser Thr Ile Ser Asn
805 810 815

Asp Ala Phe Ile Ser Val Asp Asp Leu Glu Pro Ser Gly Pro Gln Asp
820 825 830

Leu Glu Arg Gly Arg Lys Arg Arg Ser Asp His Leu Gln Leu Lys Asp
835 840 845

Ile Leu Arg Lys Gln Asp Glu Tyr His Met Val His Leu Leu Cys Ala
850 855 860

Ser Arg Ser Pro Pro Ser Ser Pro Lys Ser Arg Gly Arg Lys Arg Arg
865 870 875 880

Ser Trp Asn Thr Trp Leu Tyr Ala Pro Gly Leu Pro Pro Val Lys Pro
885 890 895

Asn Tyr Asp Ala Thr Leu Thr Asn Ala Cys Ile Ala Leu Ser Gln Arg
900 905 910

Trp Val Arg Gly Arg Lys Arg Arg Ser Ala Gln Arg Asn Ser Asn Pro
915 920 925

Ile Ile Ala Glu Leu Ser Gln Ala Met Asn Ser Gly Thr Leu Leu Ser
930 935 940

Lys Pro Ser Pro Pro Leu Pro Pro Lys Arg Arg Gly Arg Lys Arg Arg
945 950 955 960

Ser Gly Glu Ser Lys Gly Pro Leu Asp Ser Ser Phe Ser Gln Tyr Leu
965 970 975

Gly Arg Ser Cys Leu Leu Asp Gln Arg Glu Ala Lys Arg Lys Gly Glu
980 985 990

Gly Leu

<210> SEQ ID NO 54
<211> LENGTH: 219
<212> TYPE: PRT
<213> ORGANISM: Homo sapiens

<400> SEQUENCE: 54

Met Cys Pro Ala Arg Ser Leu Leu Leu Val Ala Thr Leu Val Leu Leu
1 5 10 15

Asp His Leu Ser Leu Ala Arg Asn Leu Pro Val Ala Thr Pro Asp Pro
20 25 30

Gly Met Phe Pro Cys Leu His His Ser Gln Asn Leu Leu Arg Ala Val
35 40 45

Ser Asn Met Leu Gln Lys Ala Arg Gln Thr Leu Glu Phe Tyr Pro Cys
50 55 60

Thr Ser Glu Glu Ile Asp His Glu Asp Ile Thr Lys Asp Lys Thr Ser
65 70 75 80

Thr Val Glu Ala Cys Leu Pro Leu Glu Leu Thr Lys Asn Glu Ser Cys
85 90 95

Leu Asn Ser Arg Glu Thr Ser Phe Ile Thr Asn Gly Ser Cys Leu Ala
100 105 110

Ser Arg Lys Thr Ser Phe Met Met Ala Leu Cys Leu Ser Ser Ile Tyr
115 120 125

Glu Asp Leu Lys Met Tyr Gln Val Glu Phe Lys Thr Met Asn Ala Lys
130 135 140

Leu Leu Met Asp Pro Lys Arg Gln Ile Phe Leu Asp Gln Asn Met Leu

```
145                 150                 155                 160

Ala Val Ile Asp Glu Leu Met Gln Ala Leu Asn Phe Asn Ser Glu Thr
                165                 170                 175

Val Pro Gln Lys Ser Ser Leu Glu Glu Pro Asp Phe Tyr Lys Thr Lys
            180                 185                 190

Ile Lys Leu Cys Ile Leu Leu His Ala Phe Arg Ile Arg Ala Val Thr
        195                 200                 205

Ile Asp Arg Val Met Ser Tyr Leu Asn Ala Ser
    210                 215


<210> SEQ ID NO 55
<211> LENGTH: 328
<212> TYPE: PRT
<213> ORGANISM: Homo sapiens

<400> SEQUENCE: 55

Met Cys His Gln Gln Leu Val Ile Ser Trp Phe Ser Leu Val Phe Leu
1               5                   10                  15

Ala Ser Pro Leu Val Ala Ile Trp Glu Leu Lys Lys Asp Val Tyr Val
            20                  25                  30

Val Glu Leu Asp Trp Tyr Pro Asp Ala Pro Gly Glu Met Val Val Leu
        35                  40                  45

Thr Cys Asp Thr Pro Glu Glu Asp Gly Ile Thr Trp Thr Leu Asp Gln
    50                  55                  60

Ser Ser Glu Val Leu Gly Ser Gly Lys Thr Leu Thr Ile Gln Val Lys
65                  70                  75                  80

Glu Phe Gly Asp Ala Gly Gln Tyr Thr Cys His Lys Gly Gly Glu Val
                85                  90                  95

Leu Ser His Ser Leu Leu Leu Leu His Lys Lys Glu Asp Gly Ile Trp
            100                 105                 110

Ser Thr Asp Ile Leu Lys Asp Gln Lys Glu Pro Lys Asn Lys Thr Phe
        115                 120                 125

Leu Arg Cys Glu Ala Lys Asn Tyr Ser Gly Arg Phe Thr Cys Trp Trp
    130                 135                 140

Leu Thr Thr Ile Ser Thr Asp Leu Thr Phe Ser Val Lys Ser Ser Arg
145                 150                 155                 160

Gly Ser Ser Asp Pro Gln Gly Val Thr Cys Gly Ala Ala Thr Leu Ser
                165                 170                 175

Ala Glu Arg Val Arg Gly Asp Asn Lys Glu Tyr Glu Tyr Ser Val Glu
            180                 185                 190

Cys Gln Glu Asp Ser Ala Cys Pro Ala Ala Glu Glu Ser Leu Pro Ile
        195                 200                 205

Glu Val Met Val Asp Ala Val His Lys Leu Lys Tyr Glu Asn Tyr Thr
    210                 215                 220

Ser Ser Phe Phe Ile Arg Asp Ile Ile Lys Pro Asp Pro Pro Lys Asn
225                 230                 235                 240

Leu Gln Leu Lys Pro Leu Lys Asn Ser Arg Gln Val Glu Val Ser Trp
                245                 250                 255

Glu Tyr Pro Asp Thr Trp Ser Thr Pro His Ser Tyr Phe Ser Leu Thr
            260                 265                 270

Phe Cys Val Gln Val Gln Gly Lys Ser Lys Arg Glu Lys Lys Asp Arg
        275                 280                 285

Val Phe Thr Asp Lys Thr Ser Ala Thr Val Ile Cys Arg Lys Asn Ala
    290                 295                 300
```

```
Ser Ile Ser Val Arg Ala Gln Asp Arg Tyr Tyr Ser Ser Ser Trp Ser
305                 310                 315                 320

Glu Trp Ala Ser Val Pro Cys Ser
                325


<210> SEQ ID NO 56
<211> LENGTH: 162
<212> TYPE: PRT
<213> ORGANISM: Homo sapiens

<400> SEQUENCE: 56

Met Arg Ile Ser Lys Pro His Leu Arg Ser Ile Ser Ile Gln Cys Tyr
1               5                   10                  15

Leu Cys Leu Leu Leu Asn Ser His Phe Leu Thr Glu Ala Gly Ile His
            20                  25                  30

Val Phe Ile Leu Gly Cys Phe Ser Ala Gly Leu Pro Lys Thr Glu Ala
        35                  40                  45

Asn Trp Val Asn Val Ile Ser Asp Leu Lys Lys Ile Glu Asp Leu Ile
    50                  55                  60

Gln Ser Met His Ile Asp Ala Thr Leu Tyr Thr Glu Ser Asp Val His
65                  70                  75                  80

Pro Ser Cys Lys Val Thr Ala Met Lys Cys Phe Leu Leu Glu Leu Gln
                85                  90                  95

Val Ile Ser Leu Glu Ser Gly Asp Ala Ser Ile His Asp Thr Val Glu
            100                 105                 110

Asn Leu Ile Ile Leu Ala Asn Asn Ser Leu Ser Ser Asn Gly Asn Val
        115                 120                 125

Thr Glu Ser Gly Cys Lys Glu Cys Glu Glu Leu Glu Glu Lys Asn Ile
    130                 135                 140

Lys Glu Phe Leu Gln Ser Phe Val His Ile Val Gln Met Phe Ile Asn
145                 150                 155                 160

Thr Ser


<210> SEQ ID NO 57
<211> LENGTH: 155
<212> TYPE: PRT
<213> ORGANISM: Homo sapiens

<400> SEQUENCE: 57

Met Thr Pro Gly Lys Thr Ser Leu Val Ser Leu Leu Leu Leu Leu Ser
1               5                   10                  15

Leu Glu Ala Ile Val Lys Ala Gly Ile Thr Ile Pro Arg Asn Pro Gly
            20                  25                  30

Cys Pro Asn Ser Glu Asp Lys Asn Phe Pro Arg Thr Val Met Val Asn
        35                  40                  45

Leu Asn Ile His Asn Arg Asn Thr Asn Thr Asn Pro Lys Arg Ser Ser
    50                  55                  60

Asp Tyr Tyr Asn Arg Ser Thr Ser Pro Trp Asn Leu His Arg Asn Glu
65                  70                  75                  80

Asp Pro Glu Arg Tyr Pro Ser Val Ile Trp Glu Ala Lys Cys Arg His
                85                  90                  95

Leu Gly Cys Ile Asn Ala Asp Gly Asn Val Asp Tyr His Met Asn Ser
            100                 105                 110

Val Pro Ile Gln Gln Glu Ile Leu Val Leu Arg Arg Glu Pro Pro His
        115                 120                 125

Cys Pro Asn Ser Phe Arg Leu Glu Lys Ile Leu Val Ser Val Gly Cys
```

```
    130                 135                 140

Thr Cys Val Thr Pro Ile Val His His Val Ala
145                 150                 155


<210> SEQ ID NO 58
<211> LENGTH: 99
<212> TYPE: PRT
<213> ORGANISM: Homo sapiens

<400> SEQUENCE: 58

Met Thr Ser Lys Leu Ala Val Ala Leu Leu Ala Ala Phe Leu Ile Ser
1               5                   10                  15

Ala Ala Leu Cys Glu Gly Ala Val Leu Pro Arg Ser Ala Lys Glu Leu
            20                  25                  30

Arg Cys Gln Cys Ile Lys Thr Tyr Ser Lys Pro Phe His Pro Lys Phe
        35                  40                  45

Ile Lys Glu Leu Arg Val Ile Glu Ser Gly Pro His Cys Ala Asn Thr
    50                  55                  60

Glu Ile Ile Val Lys Leu Ser Asp Gly Arg Glu Leu Cys Leu Asp Pro
65                  70                  75                  80

Lys Glu Asn Trp Val Gln Arg Val Val Glu Lys Phe Leu Lys Arg Ala
                85                  90                  95

Glu Asn Ser


<210> SEQ ID NO 59
<211> LENGTH: 91
<212> TYPE: PRT
<213> ORGANISM: Homo sapiens

<400> SEQUENCE: 59

Met Lys Val Ser Ala Ala Ala Leu Ala Val Ile Leu Ile Ala Thr Ala
1               5                   10                  15

Leu Cys Ala Pro Ala Ser Ala Ser Pro Tyr Ser Ser Asp Thr Thr Pro
            20                  25                  30

Cys Cys Phe Ala Tyr Ile Ala Arg Pro Leu Pro Arg Ala His Ile Lys
        35                  40                  45

Glu Tyr Phe Tyr Thr Ser Gly Lys Cys Ser Asn Pro Ala Val Val Phe
    50                  55                  60

Val Thr Arg Lys Asn Arg Gln Val Cys Ala Asn Pro Glu Lys Lys Trp
65                  70                  75                  80

Val Arg Glu Tyr Ile Asn Ser Leu Glu Met Ser
                85                  90


<210> SEQ ID NO 60
<211> LENGTH: 92
<212> TYPE: PRT
<213> ORGANISM: Homo sapiens

<400> SEQUENCE: 60

Met Gln Val Ser Thr Ala Ala Leu Ala Val Leu Leu Cys Thr Met Ala
1               5                   10                  15

Leu Cys Asn Gln Phe Ser Ala Ser Leu Ala Ala Asp Thr Pro Thr Ala
            20                  25                  30

Cys Cys Phe Ser Tyr Thr Ser Arg Gln Ile Pro Gln Asn Phe Ile Ala
        35                  40                  45

Asp Tyr Phe Glu Thr Ser Ser Gln Cys Ser Lys Pro Gly Val Ile Phe
    50                  55                  60
```

```
Leu Thr Lys Arg Ser Arg Gln Val Cys Ala Asp Pro Ser Glu Glu Trp
65                  70                  75                  80

Val Gln Lys Tyr Val Ser Asp Leu Glu Leu Ser Ala
                85                  90


<210> SEQ ID NO 61
<211> LENGTH: 141
<212> TYPE: PRT
<213> ORGANISM: Unknown
<220> FEATURE:
<223> OTHER INFORMATION: Description of Unknown:
      Survivin sequence

<400> SEQUENCE: 61

Met Gly Ala Pro Thr Leu Pro Pro Ala Trp Gln Pro Phe Leu Lys Asp
1               5                   10                  15

His Arg Ile Ser Thr Phe Lys Asn Trp Pro Phe Leu Glu Gly Cys Ala
            20                  25                  30

Cys Thr Pro Glu Arg Met Ala Glu Ala Gly Phe Ile His Cys Pro Thr
        35                  40                  45

Glu Asn Glu Pro Asp Leu Ala Gln Cys Phe Phe Cys Phe Lys Glu Leu
    50                  55                  60

Glu Gly Trp Glu Pro Asp Asp Asp Pro Ile Glu Glu His Lys Lys His
65                  70                  75                  80

Ser Ser Gly Cys Ala Phe Leu Ser Val Lys Lys Gln Phe Glu Glu Leu
                85                  90                  95

Thr Leu Gly Glu Phe Leu Lys Leu Asp Arg Glu Arg Ala Lys Asn Lys
            100                 105                 110

Ile Ala Lys Glu Thr Asn Asn Lys Lys Glu Phe Glu Glu Thr Ala Glu
        115                 120                 125

Lys Val Arg Arg Ala Ile Glu Gln Leu Ala Ala Met Asp
    130                 135                 140


<210> SEQ ID NO 62
<211> LENGTH: 574
<212> TYPE: PRT
<213> ORGANISM: Unknown
<220> FEATURE:
<223> OTHER INFORMATION: Description of Unknown:
      MAGE sequence

<400> SEQUENCE: 62

Met Ala Thr Ser Gln Ala Asp Ile Glu Thr Asp Pro Gly Ile Ser Glu
1               5                   10                  15

Pro Asp Gly Ala Thr Ala Gln Thr Ser Ala Asp Gly Ser Gln Ala Gln
            20                  25                  30

Asn Leu Glu Ser Arg Thr Ile Ile Arg Gly Lys Arg Thr Arg Lys Ile
        35                  40                  45

Asn Asn Leu Asn Val Glu Glu Asn Ser Ser Gly Asp Gln Arg Arg Ala
    50                  55                  60

Pro Leu Ala Ala Gly Thr Trp Arg Ser Ala Pro Val Pro Val Thr Thr
65                  70                  75                  80

Gln Asn Pro Pro Gly Ala Pro Pro Asn Val Leu Trp Gln Thr Pro Leu
                85                  90                  95

Ala Trp Gln Asn Pro Ser Gly Trp Gln Asn Gln Thr Ala Arg Gln Thr
            100                 105                 110

Pro Pro Ala Arg Gln Ser Pro Pro Ala Arg Gln Thr Pro Pro Ala Trp
        115                 120                 125
```

```
Gln Asn Pro Val Ala Trp Gln Asn Pro Val Ile Trp Pro Asn Pro Val
    130                 135                 140

Ile Trp Gln Asn Pro Val Ile Trp Pro Asn Pro Ile Val Trp Pro Gly
145                 150                 155                 160

Pro Val Val Trp Pro Asn Pro Leu Ala Trp Gln Asn Pro Pro Gly Trp
                165                 170                 175

Gln Thr Pro Pro Gly Trp Gln Thr Pro Pro Gly Trp Gln Gly Pro Pro
            180                 185                 190

Asp Trp Gln Gly Pro Pro Asp Trp Pro Leu Pro Pro Asp Trp Pro Leu
        195                 200                 205

Pro Pro Asp Trp Pro Leu Pro Thr Asp Trp Pro Leu Pro Pro Asp Trp
    210                 215                 220

Ile Pro Ala Asp Trp Pro Ile Pro Pro Asp Trp Gln Asn Leu Arg Pro
225                 230                 235                 240

Ser Pro Asn Leu Arg Pro Ser Pro Asn Ser Arg Ala Ser Gln Asn Pro
                245                 250                 255

Gly Ala Ala Gln Pro Arg Asp Val Ala Leu Leu Gln Glu Arg Ala Asn
            260                 265                 270

Lys Leu Val Lys Tyr Leu Met Leu Lys Asp Tyr Thr Lys Val Pro Ile
        275                 280                 285

Lys Arg Ser Glu Met Leu Arg Asp Ile Ile Arg Glu Tyr Thr Asp Val
    290                 295                 300

Tyr Pro Glu Ile Ile Glu Arg Ala Cys Phe Val Leu Glu Lys Lys Phe
305                 310                 315                 320

Gly Ile Gln Leu Lys Glu Ile Asp Lys Glu Glu His Leu Tyr Ile Leu
                325                 330                 335

Ile Ser Thr Pro Glu Ser Leu Ala Gly Ile Leu Gly Thr Thr Lys Asp
            340                 345                 350

Thr Pro Lys Leu Gly Leu Leu Leu Val Ile Leu Gly Val Ile Phe Met
        355                 360                 365

Asn Gly Asn Arg Ala Ser Glu Ala Val Leu Trp Glu Ala Leu Arg Lys
    370                 375                 380

Met Gly Leu Arg Pro Gly Val Arg His Pro Leu Leu Gly Asp Leu Arg
385                 390                 395                 400

Lys Leu Leu Thr Tyr Glu Phe Val Lys Gln Lys Tyr Leu Asp Tyr Arg
                405                 410                 415

Arg Val Pro Asn Ser Asn Pro Pro Glu Tyr Glu Phe Leu Trp Gly Leu
            420                 425                 430

Arg Ser Tyr His Glu Thr Ser Lys Met Lys Val Leu Arg Phe Ile Ala
        435                 440                 445

Glu Val Gln Lys Arg Asp Pro Arg Asp Trp Thr Ala Gln Phe Met Glu
    450                 455                 460

Ala Ala Asp Glu Ala Leu Asp Ala Leu Asp Ala Ala Ala Ala Glu Ala
465                 470                 475                 480

Glu Ala Arg Ala Glu Ala Arg Thr Arg Met Gly Ile Gly Asp Glu Ala
                485                 490                 495

Val Ser Gly Pro Trp Ser Trp Asp Asp Ile Glu Phe Glu Leu Leu Thr
            500                 505                 510

Trp Asp Glu Glu Gly Asp Phe Gly Asp Pro Trp Ser Arg Ile Pro Phe
        515                 520                 525

Thr Phe Trp Ala Arg Tyr His Gln Asn Ala Arg Ser Arg Phe Pro Gln
    530                 535                 540

Thr Phe Ala Gly Pro Ile Ile Gly Pro Gly Gly Thr Ala Ser Ala Asn
```

545 550 555 560

Phe Ala Ala Asn Phe Gly Ala Ile Gly Phe Phe Trp Val Glu
565 570

<210> SEQ ID NO 63
<211> LENGTH: 189
<212> TYPE: PRT
<213> ORGANISM: Unknown
<220> FEATURE:
<223> OTHER INFORMATION: Description of Unknown:
A10 sequence

<400> SEQUENCE: 63

Met Thr Asp Lys Thr Glu Lys Val Ala Val Asp Pro Glu Thr Val Phe
1 5 10 15

Lys Arg Pro Arg Glu Cys Asp Ser Pro Ser Tyr Gln Lys Arg Gln Arg
20 25 30

Met Ala Leu Leu Ala Arg Lys Gln Gly Ala Gly Asp Ser Leu Ile Ala
35 40 45

Gly Ser Ala Met Ser Lys Glu Lys Lys Leu Met Thr Gly His Ala Ile
50 55 60

Pro Pro Ser Gln Leu Asp Ser Gln Ile Asp Asp Phe Thr Gly Phe Ser
65 70 75 80

Lys Asp Gly Met Met Gln Lys Pro Gly Ser Asn Ala Pro Val Gly Gly
85 90 95

Asn Val Thr Ser Asn Phe Ser Gly Asp Asp Leu Glu Cys Arg Gly Ile
100 105 110

Ala Ser Ser Pro Lys Ser Gln Gln Glu Ile Asn Ala Asp Ile Lys Cys
115 120 125

Gln Val Val Lys Glu Ile Arg Cys Leu Gly Arg Lys Tyr Glu Lys Ile
130 135 140

Phe Glu Met Leu Glu Gly Val Gln Gly Pro Thr Ala Val Arg Lys Arg
145 150 155 160

Phe Phe Glu Ser Ile Ile Lys Glu Ala Ala Arg Cys Met Arg Arg Asp
165 170 175

Phe Val Lys His Leu Lys Lys Lys Leu Lys Arg Met Ile
180 185

<210> SEQ ID NO 64
<211> LENGTH: 661
<212> TYPE: PRT
<213> ORGANISM: Unknown
<220> FEATURE:
<223> OTHER INFORMATION: Description of Unknown:
gp100 sequence

<400> SEQUENCE: 64

Met Asp Leu Val Leu Lys Arg Cys Leu Leu His Leu Ala Val Ile Gly
1 5 10 15

Ala Leu Leu Ala Val Gly Ala Thr Lys Val Pro Arg Asn Gln Asp Trp
20 25 30

Leu Gly Val Ser Arg Gln Leu Arg Thr Lys Ala Trp Asn Arg Gln Leu
35 40 45

Tyr Pro Glu Trp Thr Glu Ala Gln Arg Leu Asp Cys Trp Arg Gly Gly
50 55 60

Gln Val Ser Leu Lys Val Ser Asn Asp Gly Pro Thr Leu Ile Gly Ala
65 70 75 80

Asn Ala Ser Phe Ser Ile Ala Leu Asn Phe Pro Gly Ser Gln Lys Val

```
                85                  90                  95

Leu Pro Asp Gly Gln Val Ile Trp Val Asn Asn Thr Ile Ile Asn Gly
            100                 105                 110

Ser Gln Val Trp Gly Gly Gln Pro Val Tyr Pro Gln Glu Thr Asp Asp
        115                 120                 125

Ala Cys Ile Phe Pro Asp Gly Gly Pro Cys Pro Ser Gly Ser Trp Ser
    130                 135                 140

Gln Lys Arg Ser Phe Val Tyr Val Trp Lys Thr Trp Gly Gln Tyr Trp
145                 150                 155                 160

Gln Val Leu Gly Gly Pro Val Ser Gly Leu Ser Ile Gly Thr Gly Arg
                165                 170                 175

Ala Met Leu Gly Thr His Thr Met Glu Val Thr Val Tyr His Arg Arg
            180                 185                 190

Gly Ser Arg Ser Tyr Val Pro Leu Ala His Ser Ser Ser Ala Phe Thr
        195                 200                 205

Ile Thr Asp Gln Val Pro Phe Ser Val Ser Val Ser Gln Leu Arg Ala
    210                 215                 220

Leu Asp Gly Gly Asn Lys His Phe Leu Arg Asn Gln Pro Leu Thr Phe
225                 230                 235                 240

Ala Leu Gln Leu His Asp Pro Ser Gly Tyr Leu Ala Glu Ala Asp Leu
                245                 250                 255

Ser Tyr Thr Trp Asp Phe Gly Asp Ser Ser Gly Thr Leu Ile Ser Arg
            260                 265                 270

Ala Leu Val Val Thr His Thr Tyr Leu Glu Pro Gly Pro Val Thr Ala
        275                 280                 285

Gln Val Val Leu Gln Ala Ala Ile Pro Leu Thr Ser Cys Gly Ser Ser
    290                 295                 300

Pro Val Pro Gly Thr Thr Asp Gly His Arg Pro Thr Ala Glu Ala Pro
305                 310                 315                 320

Asn Thr Thr Ala Gly Gln Val Pro Thr Thr Glu Val Val Gly Thr Thr
                325                 330                 335

Pro Gly Gln Ala Pro Thr Ala Glu Pro Ser Gly Thr Thr Ser Val Gln
            340                 345                 350

Val Pro Thr Thr Glu Val Ile Ser Thr Ala Pro Val Gln Met Pro Thr
        355                 360                 365

Ala Glu Ser Thr Gly Met Thr Pro Glu Lys Val Pro Val Ser Glu Val
    370                 375                 380

Met Gly Thr Thr Leu Ala Glu Met Ser Thr Pro Glu Ala Thr Gly Met
385                 390                 395                 400

Thr Pro Ala Glu Val Ser Ile Val Val Leu Ser Gly Thr Thr Ala Ala
                405                 410                 415

Gln Val Thr Thr Thr Glu Trp Val Glu Thr Thr Ala Arg Glu Leu Pro
            420                 425                 430

Ile Pro Glu Pro Glu Gly Pro Asp Ala Ser Ser Ile Met Ser Thr Glu
        435                 440                 445

Ser Ile Thr Gly Ser Leu Gly Pro Leu Leu Asp Gly Thr Ala Thr Leu
    450                 455                 460

Arg Leu Val Lys Arg Gln Val Pro Leu Asp Cys Val Leu Tyr Arg Tyr
465                 470                 475                 480

Gly Ser Phe Ser Val Thr Leu Asp Ile Val Gln Gly Ile Glu Ser Ala
                485                 490                 495

Glu Ile Leu Gln Ala Val Pro Ser Gly Glu Gly Asp Ala Phe Glu Leu
            500                 505                 510
```

```
Thr Val Ser Cys Gln Gly Gly Leu Pro Lys Glu Ala Cys Met Glu Ile
        515                 520                 525

Ser Ser Pro Gly Cys Gln Pro Pro Ala Gln Arg Leu Cys Gln Pro Val
    530                 535                 540

Leu Pro Ser Pro Ala Cys Gln Leu Val Leu His Gln Ile Leu Lys Gly
545                 550                 555                 560

Gly Ser Gly Thr Tyr Cys Leu Asn Val Ser Leu Ala Asp Thr Asn Ser
                565                 570                 575

Leu Ala Val Val Ser Thr Gln Leu Ile Met Pro Gly Gln Glu Ala Gly
            580                 585                 590

Leu Gly Gln Val Pro Leu Ile Val Gly Ile Leu Leu Val Leu Met Ala
        595                 600                 605

Val Val Leu Ala Ser Leu Ile Tyr Arg Arg Arg Leu Met Lys Gln Asp
    610                 615                 620

Phe Ser Val Pro Gln Leu Pro His Ser Ser Ser His Trp Leu Arg Leu
625                 630                 635                 640

Pro Arg Ile Phe Cys Ser Cys Pro Ile Gly Glu Asn Ser Pro Leu Leu
                645                 650                 655

Ser Gly Gln Gln Val
            660


<210> SEQ ID NO 65
<211> LENGTH: 943
<212> TYPE: PRT
<213> ORGANISM: Unknown
<220> FEATURE:
<223> OTHER INFORMATION: Description of Unknown:
      EGFRvIII sequence

<400> SEQUENCE: 65

Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Gly Asn Tyr
            20                  25                  30

Val Val Thr Asp His Gly Ser Cys Val Arg Ala Cys Gly Ala Asp Ser
        35                  40                  45

Tyr Glu Met Glu Glu Asp Gly Val Arg Lys Cys Lys Lys Cys Glu Gly
    50                  55                  60

Pro Cys Arg Lys Val Cys Asn Gly Ile Gly Ile Gly Glu Phe Lys Asp
65                  70                  75                  80

Ser Leu Ser Ile Asn Ala Thr Asn Ile Lys His Phe Lys Asn Cys Thr
                85                  90                  95

Ser Ile Ser Gly Asp Leu His Ile Leu Pro Val Ala Phe Arg Gly Asp
            100                 105                 110

Ser Phe Thr His Thr Pro Pro Leu Asp Pro Gln Glu Leu Asp Ile Leu
        115                 120                 125

Lys Thr Val Lys Glu Ile Thr Gly Phe Leu Leu Ile Gln Ala Trp Pro
    130                 135                 140

Glu Asn Arg Thr Asp Leu His Ala Phe Glu Asn Leu Glu Ile Ile Arg
145                 150                 155                 160

Gly Arg Thr Lys Gln His Gly Gln Phe Ser Leu Ala Val Val Ser Leu
                165                 170                 175

Asn Ile Thr Ser Leu Gly Leu Arg Ser Leu Lys Glu Ile Ser Asp Gly
            180                 185                 190

Asp Val Ile Ile Ser Gly Asn Lys Asn Leu Cys Tyr Ala Asn Thr Ile
```

```
        195                 200                 205

Asn Trp Lys Lys Leu Phe Gly Thr Ser Gly Gln Lys Thr Lys Ile Ile
    210                 215                 220

Ser Asn Arg Gly Glu Asn Ser Cys Lys Ala Thr Gly Gln Val Cys His
225                 230                 235                 240

Ala Leu Cys Ser Pro Glu Gly Cys Trp Gly Pro Glu Pro Arg Asp Cys
                245                 250                 255

Val Ser Cys Arg Asn Val Ser Arg Gly Arg Glu Cys Val Asp Lys Cys
            260                 265                 270

Asn Leu Leu Glu Gly Glu Pro Arg Glu Phe Val Glu Asn Ser Glu Cys
        275                 280                 285

Ile Gln Cys His Pro Glu Cys Leu Pro Gln Ala Met Asn Ile Thr Cys
    290                 295                 300

Thr Gly Arg Gly Pro Asp Asn Cys Ile Gln Cys Ala His Tyr Ile Asp
305                 310                 315                 320

Gly Pro His Cys Val Lys Thr Cys Pro Ala Gly Val Met Gly Glu Asn
                325                 330                 335

Asn Thr Leu Val Trp Lys Tyr Ala Asp Ala Gly His Val Cys His Leu
            340                 345                 350

Cys His Pro Asn Cys Thr Tyr Gly Cys Thr Gly Pro Gly Leu Glu Gly
        355                 360                 365

Cys Pro Thr Asn Gly Pro Lys Ile Pro Ser Ile Ala Thr Gly Met Val
    370                 375                 380

Gly Ala Leu Leu Leu Leu Leu Val Val Ala Leu Gly Ile Gly Leu Phe
385                 390                 395                 400

Met Arg Arg Arg His Ile Val Arg Lys Arg Thr Leu Arg Arg Leu Leu
                405                 410                 415

Gln Glu Arg Glu Leu Val Glu Pro Leu Thr Pro Ser Gly Glu Ala Pro
            420                 425                 430

Asn Gln Ala Leu Leu Arg Ile Leu Lys Glu Thr Glu Phe Lys Lys Ile
        435                 440                 445

Lys Val Leu Gly Ser Gly Ala Phe Gly Thr Val Tyr Lys Gly Leu Trp
    450                 455                 460

Ile Pro Glu Gly Glu Lys Val Lys Ile Pro Val Ala Ile Lys Glu Leu
465                 470                 475                 480

Arg Glu Ala Thr Ser Pro Lys Ala Asn Lys Glu Ile Leu Asp Glu Ala
                485                 490                 495

Tyr Val Met Ala Ser Val Asp Asn Pro His Val Cys Arg Leu Leu Gly
            500                 505                 510

Ile Cys Leu Thr Ser Thr Val Gln Leu Ile Thr Gln Leu Met Pro Phe
        515                 520                 525

Gly Cys Leu Leu Asp Tyr Val Arg Glu His Lys Asp Asn Ile Gly Ser
    530                 535                 540

Gln Tyr Leu Leu Asn Trp Cys Val Gln Ile Ala Lys Gly Met Asn Tyr
545                 550                 555                 560

Leu Glu Asp Arg Arg Leu Val His Arg Asp Leu Ala Ala Arg Asn Val
                565                 570                 575

Leu Val Lys Thr Pro Gln His Val Lys Ile Thr Asp Phe Gly Leu Ala
            580                 585                 590

Lys Leu Leu Gly Ala Glu Glu Lys Glu Tyr His Ala Glu Gly Gly Lys
        595                 600                 605

Val Pro Ile Lys Trp Met Ala Leu Glu Ser Ile Leu His Arg Ile Tyr
    610                 615                 620
```

Thr His Gln Ser Asp Val Trp Ser Tyr Gly Val Thr Val Trp Glu Leu
625 630 635 640

Met Thr Phe Gly Ser Lys Pro Tyr Asp Gly Ile Pro Ala Ser Glu Ile
645 650 655

Ser Ser Ile Leu Glu Lys Gly Glu Arg Leu Pro Gln Pro Pro Ile Cys
660 665 670

Thr Ile Asp Val Tyr Met Ile Met Val Lys Cys Trp Met Ile Asp Ala
675 680 685

Asp Ser Arg Pro Lys Phe Arg Glu Leu Ile Ile Glu Phe Ser Lys Met
690 695 700

Ala Arg Asp Pro Gln Arg Tyr Leu Val Ile Gln Gly Asp Glu Arg Met
705 710 715 720

His Leu Pro Ser Pro Thr Asp Ser Asn Phe Tyr Arg Ala Leu Met Asp
725 730 735

Glu Glu Asp Met Asp Asp Val Val Asp Ala Asp Glu Tyr Leu Ile Pro
740 745 750

Gln Gln Gly Phe Phe Ser Ser Pro Ser Thr Ser Arg Thr Pro Leu Leu
755 760 765

Ser Ser Leu Ser Ala Thr Ser Asn Asn Ser Thr Val Ala Cys Ile Asp
770 775 780

Arg Asn Gly Leu Gln Ser Cys Pro Ile Lys Glu Asp Ser Phe Leu Gln
785 790 795 800

Arg Tyr Ser Ser Asp Pro Thr Gly Ala Leu Thr Glu Asp Ser Ile Asp
805 810 815

Asp Thr Phe Leu Pro Val Pro Glu Tyr Ile Asn Gln Ser Val Pro Lys
820 825 830

Arg Pro Ala Gly Ser Val Gln Asn Pro Val Tyr His Asn Gln Pro Leu
835 840 845

Asn Pro Ala Pro Ser Arg Asp Pro His Tyr Gln Asp Pro His Ser Thr
850 855 860

Ala Val Gly Asn Pro Glu Tyr Leu Asn Thr Val Gln Pro Thr Cys Val
865 870 875 880

Asn Ser Thr Phe Asp Ser Pro Ala His Trp Ala Gln Lys Gly Ser His
885 890 895

Gln Ile Ser Leu Asp Asn Pro Asp Tyr Gln Gln Asp Phe Phe Pro Lys
900 905 910

Glu Ala Lys Pro Asn Gly Ile Phe Lys Gly Ser Thr Ala Glu Asn Ala
915 920 925

Glu Tyr Leu Arg Val Ala Pro Gln Ser Ser Glu Phe Ile Gly Ala
930 935 940

<210> SEQ ID NO 66
<211> LENGTH: 417
<212> TYPE: PRT
<213> ORGANISM: Unknown
<220> FEATURE:
<223> OTHER INFORMATION: Description of Unknown:
Calreticulin sequence

<400> SEQUENCE: 66

Met Leu Leu Ser Val Pro Leu Leu Leu Gly Leu Leu Gly Leu Ala Val
1 5 10 15

Ala Glu Pro Ala Val Tyr Phe Lys Glu Gln Phe Leu Asp Gly Asp Gly
20 25 30

Trp Thr Ser Arg Trp Ile Glu Ser Lys His Lys Ser Asp Phe Gly Lys

```
        35                  40                  45

Phe Val Leu Ser Ser Gly Lys Phe Tyr Gly Asp Glu Glu Lys Asp Lys
    50                  55                  60

Gly Leu Gln Thr Ser Gln Asp Ala Arg Phe Tyr Ala Leu Ser Ala Ser
65                  70                  75                  80

Phe Glu Pro Phe Ser Asn Lys Gly Gln Thr Leu Val Val Gln Phe Thr
                85                  90                  95

Val Lys His Glu Gln Asn Ile Asp Cys Gly Gly Gly Tyr Val Lys Leu
            100                 105                 110

Phe Pro Asn Ser Leu Asp Gln Thr Asp Met His Gly Asp Ser Glu Tyr
        115                 120                 125

Asn Ile Met Phe Gly Pro Asp Ile Cys Gly Pro Gly Thr Lys Lys Val
    130                 135                 140

His Val Ile Phe Asn Tyr Lys Gly Lys Asn Val Leu Ile Asn Lys Asp
145                 150                 155                 160

Ile Arg Cys Lys Asp Asp Glu Phe Thr His Leu Tyr Thr Leu Ile Val
                165                 170                 175

Arg Pro Asp Asn Thr Tyr Glu Val Lys Ile Asp Asn Ser Gln Val Glu
            180                 185                 190

Ser Gly Ser Leu Glu Asp Asp Trp Asp Phe Leu Pro Pro Lys Lys Ile
        195                 200                 205

Lys Asp Pro Asp Ala Ser Lys Pro Glu Asp Trp Asp Glu Arg Ala Lys
    210                 215                 220

Ile Asp Asp Pro Thr Asp Ser Lys Pro Glu Asp Trp Asp Lys Pro Glu
225                 230                 235                 240

His Ile Pro Asp Pro Asp Ala Lys Lys Pro Glu Asp Trp Asp Glu Glu
                245                 250                 255

Met Asp Gly Glu Trp Glu Pro Pro Val Ile Gln Asn Pro Glu Tyr Lys
            260                 265                 270

Gly Glu Trp Lys Pro Arg Gln Ile Asp Asn Pro Asp Tyr Lys Gly Thr
        275                 280                 285

Trp Ile His Pro Glu Ile Asp Asn Pro Glu Tyr Ser Pro Asp Pro Ser
    290                 295                 300

Ile Tyr Ala Tyr Asp Asn Phe Gly Val Leu Gly Leu Asp Leu Trp Gln
305                 310                 315                 320

Val Lys Ser Gly Thr Ile Phe Asp Asn Phe Leu Ile Thr Asn Asp Glu
                325                 330                 335

Ala Tyr Ala Glu Glu Phe Gly Asn Glu Thr Trp Gly Val Thr Lys Ala
            340                 345                 350

Ala Glu Lys Gln Met Lys Asp Lys Gln Asp Glu Glu Gln Arg Leu Lys
        355                 360                 365

Glu Glu Glu Glu Asp Lys Lys Arg Lys Glu Glu Glu Glu Ala Glu Asp
    370                 375                 380

Lys Glu Asp Asp Glu Asp Lys Asp Glu Asp Glu Glu Asp Glu Glu Asp
385                 390                 395                 400

Lys Glu Glu Asp Glu Glu Glu Asp Val Pro Gly Gln Ala Lys Asp Glu
                405                 410                 415

Leu
```

<210> SEQ ID NO 67
<211> LENGTH: 502
<212> TYPE: PRT
<213> ORGANISM: Unknown
<220> FEATURE:

<223> OTHER INFORMATION: Description of Unknown:
WT1 sequence

<400> SEQUENCE: 67

```
Met Asp Phe Leu Leu Leu Gln Asp Pro Ala Ser Thr Cys Val Pro Glu
1               5                   10                  15

Pro Ala Ser Gln His Thr Leu Arg Ser Gly Pro Gly Cys Leu Gln Gln
            20                  25                  30

Pro Glu Gln Gln Gly Val Arg Asp Pro Gly Gly Ile Trp Ala Lys Leu
        35                  40                  45

Gly Ala Ala Glu Ala Ser Ala Glu Arg Leu Gln Gly Arg Arg Ser Arg
    50                  55                  60

Gly Ala Ser Gly Ser Glu Pro Gln Gln Met Gly Ser Asp Val Arg Asp
65                  70                  75                  80

Leu Asn Ala Leu Leu Pro Ala Val Pro Ser Leu Gly Gly Gly Gly Gly
                85                  90                  95

Cys Ala Leu Pro Val Ser Gly Ala Ala Gln Trp Ala Pro Val Leu Asp
            100                 105                 110

Phe Ala Pro Pro Gly Ala Ser Ala Tyr Gly Ser Leu Gly Gly Pro Ala
        115                 120                 125

Pro Pro Pro Ala Pro Pro Pro Pro Pro Pro Pro Pro Pro His Ser Phe
    130                 135                 140

Ile Lys Gln Glu Pro Ser Trp Gly Gly Ala Glu Pro His Glu Glu Gln
145                 150                 155                 160

Cys Leu Ser Ala Phe Thr Val His Phe Ser Gly Gln Phe Thr Gly Thr
                165                 170                 175

Ala Gly Ala Cys Arg Tyr Gly Pro Phe Gly Pro Pro Pro Pro Ser Gln
            180                 185                 190

Ala Ser Ser Gly Gln Ala Arg Met Phe Pro Asn Ala Pro Tyr Leu Pro
        195                 200                 205

Ser Cys Leu Glu Ser Gln Pro Ala Ile Arg Asn Gln Gly Tyr Ser Thr
    210                 215                 220

Val Thr Phe Asp Gly Thr Pro Ser Tyr Gly His Thr Pro Ser His His
225                 230                 235                 240

Ala Ala Gln Phe Pro Asn His Ser Phe Lys His Glu Asp Pro Met Gly
                245                 250                 255

Gln Gln Gly Ser Leu Gly Glu Gln Gln Tyr Ser Val Pro Pro Pro Val
            260                 265                 270

Tyr Gly Cys His Thr Pro Thr Asp Ser Cys Thr Gly Ser Gln Ala Leu
        275                 280                 285

Leu Leu Arg Thr Pro Tyr Ser Ser Asp Asn Leu Tyr Gln Met Thr Ser
    290                 295                 300

Gln Leu Glu Cys Met Thr Trp Asn Gln Met Asn Leu Gly Ala Thr Leu
305                 310                 315                 320

Lys Gly His Ser Thr Gly Tyr Glu Ser Asp Asn His Thr Thr Pro Ile
                325                 330                 335

Leu Cys Gly Ala Gln Tyr Arg Ile His Thr His Gly Val Phe Arg Gly
            340                 345                 350

Ile Gln Asp Val Arg Arg Val Pro Gly Val Ala Pro Thr Leu Val Arg
        355                 360                 365

Ser Ala Ser Glu Thr Ser Glu Lys Arg Pro Phe Met Cys Ala Tyr Pro
    370                 375                 380

Gly Cys Asn Lys Arg Tyr Phe Lys Leu Ser His Leu Gln Met His Ser
385                 390                 395                 400
```

```
Arg Lys His Thr Gly Glu Lys Pro Tyr Gln Cys Asp Phe Lys Asp Cys
                405                 410                 415

Glu Arg Arg Phe Ser Arg Ser Asp Gln Leu Lys Arg His Gln Arg Arg
            420                 425                 430

His Thr Gly Val Lys Pro Phe Gln Cys Lys Thr Cys Gln Arg Lys Phe
        435                 440                 445

Ser Arg Ser Asp His Leu Lys Thr His Thr Arg Thr His Thr Gly Glu
    450                 455                 460

Lys Pro Phe Ser Cys Arg Trp Pro Ser Cys Gln Lys Lys Phe Ala Arg
465                 470                 475                 480

Ser Asp Glu Leu Val Arg His His Asn Met His Gln Arg Asn Met Thr
                485                 490                 495

Lys Leu Gln Leu Ala Leu
            500


<210> SEQ ID NO 68
<211> LENGTH: 2998
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 68

gctgcttcgc gatgtacggg ccagatatac gcgttgacat tgattattga ctagttatta      60

atagtaatca attacggggt cattagttca tagcccatat atggagttcc gcgttacata     120

acttacggta aatggcccgc ctggctgacc gcccaacgac ccccgcccat tgacgtcaat     180

aatgacgtat gttcccatag taacgccaat agggactttc cattgacgtc aatgggtgga     240

gtatttacgg taaactgccc acttggcagt acatcaagtg tatcatatgc caagtacgcc     300

ccctattgac gtcaatgacg gtaaatggcc cgcctggcat tatgcccagt acatgacctt     360

atgggacttt cctacttggc agtacatcta cgtattagtc atcgctatta ccatggtgat     420

gcggttttgg cagtacatca atgggcgtgg atagcggttt gactcacggg gatttccaag     480

tctccacccc attgacgtca atgggagttt gttttggcac caaaatcaac gggactttcc     540

aaaatgtcgt aacaactccg ccccattgac gcaaatgggc ggtaggcgtg tacggtggga     600

ggtctatata agcagagctc tctggctaac tagagaaccc actgcttact ggcttatcga     660

aattaatacg actcactata gggagaccca agctggctag cgtttaaact taagcttggt     720

accgagctcg gatccactag tccagtgtgg tggaattctg cagatatcca gcacagtggc     780

ggccgctcga gtctagaggg cccgtttaaa cccgctgatc agcctcgact gtgccttcta     840

gttgccagcc atctgttgtt tgcccctccc ccgtgccttc cttgaccctg gaaggtgcca     900

ctcccactgt cctttcctaa taaaatgagg aaattgcatc gcattgtctg agtaggtgtc     960

attctattct ggggggtggg gtggggcagg acagcaaggg ggaggattgg gaagacaata    1020

gcaggcatgc tggggatgcg gtgggctcta tggcttctac tgggcggttt tatggacagc    1080

aagcgaaccg gaattgccag ctggggcgcc ctctggtaag gttgggaagc cctgcaaagt    1140

aaactggatg gctttcttgc cgccaaggat ctgatggcgc aggggatcaa gctctgatca    1200

agagacagga tgaggatcgt ttcgcatgat tgaacaagat ggattgcacg caggttctcc    1260

ggccgcttgg gtggagaggc tattcggcta tgactgggca caacagacaa tcggctgctc    1320

tgatgccgcc gtgttccggc tgtcagcgca ggggcgcccg gttctttttg tcaagaccga    1380
```

-continued

```
cctgtccggt gccctgaatg aactgcaaga cgaggcagcg cggctatcgt ggctggccac   1440

gacgggcgtt ccttgcgcag ctgtgctcga cgttgtcact gaagcgggaa gggactggct   1500

gctattgggc gaagtgccgg ggcaggatct cctgtcatct caccttgctc ctgccgagaa   1560

agtatccatc atggctgatg caatgcggcg gctgcatacg cttgatccgg ctacctgccc   1620

attcgaccac caagcgaaac atcgcatcga gcgagcacgt actcggatgg aagccggtct   1680

tgtcgatcag gatgatctgg acgaagagca tcaggggctc gcgccagccg aactgttcgc   1740

caggctcaag gcgagcatgc ccgacggcga ggatctcgtc gtgacccatg gcgatgcctg   1800

cttgccgaat atcatggtgg aaaatggccg cttttctgga ttcatcgact gtggccggct   1860

gggtgtggcg gaccgctatc aggacatagc gttggctacc cgtgatattg ctgaagagct   1920

tggcggcgaa tgggctgacc gcttcctcgt gctttacggt atcgccgctc ccgattcgca   1980

gcgcatcgcc ttctatcgcc ttcttgacga gttcttctga attattaacg cttacaattt   2040

cctgatgcgg tattttctcc ttacgcatct gtgcggtatt tcacaccgca tcaggtggca   2100

cttttcgggg aaatgtgcgc ggaaccccta tttgtttatt tttctaaata cattcaaata   2160

tgtatccgct catgagacaa taaccctgat aaatgcttca ataatagcac gtgctaaaac   2220

ttcattttta atttaaaagg atctaggtga agatcctttt tgataatctc atgaccaaaa   2280

tcccttaacg tgagttttcg ttccactgag cgtcagaccc cgtagaaaag atcaaaggat   2340

cttcttgaga tccttttttt ctgcgcgtaa tctgctgctt gcaaacaaaa aaaccaccgc   2400

taccagcggt ggtttgtttg ccggatcaag agctaccaac tctttttccg aaggtaactg   2460

gcttcagcag agcgcagata ccaaatactg ttcttctagt gtagccgtag ttaggccacc   2520

acttcaagaa ctctgtagca ccgcctacat acctcgctct gctaatcctg ttaccagtgg   2580

ctgctgccag tggcgataag tcgtgtctta ccgggttgga ctcaagacga tagttaccgg   2640

ataaggcgca gcggtcgggc tgaacggggg gttcgtgcac acagcccagc ttggagcgaa   2700

cgacctacac cgaactgaga tacctacagc gtgagctatg agaaagcgcc acgcttcccg   2760

aagggagaaa ggcggacagg tatccggtaa gcggcagggt cggaacagga gagcgcacga   2820

gggagcttcc agggggaaac gcctggtatc tttatagtcc tgtcgggttt cgccacctct   2880

gacttgagcg tcgatttttg tgatgctcgt caggggggcg gagcctatgg aaaaacgcca   2940

gcaacgcggc ctttttacgg ttcctggcct tttgctggcc ttttgctcac atgttctt     2998
```

<210> SEQ ID NO 69
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 69

```
Met Asp Trp Thr Trp Ile Leu Phe Leu Val Ala Ala Ala Thr Arg Val
1               5                   10                  15
```

<210> SEQ ID NO 70
<211> LENGTH: 27
<212> TYPE: PRT
<213> ORGANISM: Artificial Sequence
<220> FEATURE:
<223> OTHER INFORMATION: Description of Artificial Sequence: Synthetic peptide

<400> SEQUENCE: 70

Arg Glu Gly Val Glu Leu Cys Pro Gly Asn Lys Tyr Glu Met Arg Arg
1 5 10 15

His Gly Thr Thr His Ser Leu Val Ile His Asp
20 25

<210> SEQ ID NO 71
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 71

Arg Glu Gly Val Glu Leu Cys Pro Gly Asn Lys Tyr Glu Met Arg
1 5 10 15

<210> SEQ ID NO 72
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 72

Glu Leu Cys Pro Gly Asn Lys Tyr Glu Met Arg Arg His Gly Thr
1 5 10 15

<210> SEQ ID NO 73
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 73

Gly Asn Lys Tyr Glu Met Arg Arg His Gly Thr Thr His Ser Leu
1 5 10 15

<210> SEQ ID NO 74
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 74

Glu Met Arg Arg His Gly Thr Thr His Ser Leu Val Ile His Asp
1 5 10 15

<210> SEQ ID NO 75
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 75

His Gly Thr Thr His Ser Leu Val Ile His Asp
1 5 10

<210> SEQ ID NO 76
<211> LENGTH: 27

<212> TYPE: PRT
<213> ORGANISM: Artificial Sequence
<220> FEATURE:
<223> OTHER INFORMATION: Description of Artificial Sequence: Synthetic peptide

<400> SEQUENCE: 76

Pro Ser Lys Pro Ser Phe Gln Glu Phe Val Asp Trp Glu Asn Val Ser
1 5 10 15

Pro Glu Leu Asn Ser Thr Asp Gln Pro Phe Leu
20 25

<210> SEQ ID NO 77
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 77

Pro Ser Lys Pro Ser Phe Gln Glu Phe Val Asp Trp Glu Asn Val
1 5 10 15

<210> SEQ ID NO 78
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 78

Ser Phe Gln Glu Phe Val Asp Trp Glu Asn Val Ser Pro Glu Leu
1 5 10 15

<210> SEQ ID NO 79
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 79

Phe Val Asp Trp Glu Asn Val Ser Pro Glu Leu Asn Ser Thr Asp
1 5 10 15

<210> SEQ ID NO 80
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 80

Glu Asn Val Ser Pro Glu Leu Asn Ser Thr Asp Gln Pro Phe Leu
1 5 10 15

<210> SEQ ID NO 81
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 81

Pro Glu Leu Asn Ser Thr Asp Gln Pro Phe Leu
1 5 10

<210> SEQ ID NO 82
<211> LENGTH: 27
<212> TYPE: PRT
<213> ORGANISM: Artificial Sequence
<220> FEATURE:
<223> OTHER INFORMATION: Description of Artificial Sequence: Synthetic peptide

<400> SEQUENCE: 82

Asp Ser Gly Ser Pro Phe Pro Ala Ala Val Ile Leu Arg Asp Ala Leu
1 5 10 15

His Met Ala Arg Gly Leu Lys Tyr Leu His Gln
20 25

<210> SEQ ID NO 83
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 83

Asp Ser Gly Ser Pro Phe Pro Ala Ala Val Ile Leu Arg Asp Ala
1 5 10 15

<210> SEQ ID NO 84
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 84

Pro Phe Pro Ala Ala Val Ile Leu Arg Asp Ala Leu His Met Ala
1 5 10 15

<210> SEQ ID NO 85
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 85

Ala Val Ile Leu Arg Asp Ala Leu His Met Ala Arg Gly Leu Lys
1 5 10 15

<210> SEQ ID NO 86
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 86

Arg Asp Ala Leu His Met Ala Arg Gly Leu Lys Tyr Leu His Gln
1 5 10 15

<210> SEQ ID NO 87
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 87

His Met Ala Arg Gly Leu Lys Tyr Leu His Gln
1 5 10

<210> SEQ ID NO 88
<211> LENGTH: 27
<212> TYPE: PRT
<213> ORGANISM: Artificial Sequence
<220> FEATURE:
<223> OTHER INFORMATION: Description of Artificial Sequence: Synthetic peptide

<400> SEQUENCE: 88

Gln Ala Ile Val Arg Gly Cys Ser Met Pro Gly Pro Trp Arg Ser Gly
1 5 10 15

Arg Leu Leu Val Ser Arg Arg Trp Ser Val Glu
20 25

<210> SEQ ID NO 89
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 89

Gln Ala Ile Val Arg Gly Cys Ser Met Pro Gly Pro Trp Arg Ser
1 5 10 15

<210> SEQ ID NO 90
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 90

Arg Gly Cys Ser Met Pro Gly Pro Trp Arg Ser Gly Arg Leu Leu
1 5 10 15

<210> SEQ ID NO 91
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 91

Met Pro Gly Pro Trp Arg Ser Gly Arg Leu Leu Val Ser Arg Arg
1 5 10 15

<210> SEQ ID NO 92
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 92

Trp Arg Ser Gly Arg Leu Leu Val Ser Arg Arg Trp Ser Val Glu
1 5 10 15

<210> SEQ ID NO 93
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 93

Arg Leu Leu Val Ser Arg Arg Trp Ser Val Glu
1 5 10

<210> SEQ ID NO 94
<211> LENGTH: 27
<212> TYPE: PRT
<213> ORGANISM: Artificial Sequence
<220> FEATURE:
<223> OTHER INFORMATION: Description of Artificial Sequence: Synthetic peptide

<400> SEQUENCE: 94

Pro Leu Leu Pro Phe Tyr Pro Pro Asp Glu Ala Leu Glu Ile Gly Leu
1 5 10 15

Glu Leu Asn Ser Ser Ala Leu Pro Pro Thr Glu
20 25

<210> SEQ ID NO 95
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 95

Pro Leu Leu Pro Phe Tyr Pro Pro Asp Glu Ala Leu Glu Ile Gly
1 5 10 15

<210> SEQ ID NO 96
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 96

Phe Tyr Pro Pro Asp Glu Ala Leu Glu Ile Gly Leu Glu Leu Asn
1 5 10 15

<210> SEQ ID NO 97
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 97

Asp Glu Ala Leu Glu Ile Gly Leu Glu Leu Asn Ser Ser Ala Leu
1 5 10 15

<210> SEQ ID NO 98
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Glu Ile Gly Leu Glu Leu Asn Ser Ser Ala Leu Pro Pro Thr Glu
1               5                   10                  15

<210> SEQ ID NO 99
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Glu Leu Asn Ser Ser Ala Leu Pro Pro Thr Glu
1               5                   10

<210> SEQ ID NO 100
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Val Ile Leu Pro Gln Ala Pro Ser Gly Pro Ser Tyr Ala Thr Tyr Leu
1               5                   10                  15

Gln Pro Ala Gln Ala Gln Met Leu Thr Pro Pro
            20                  25

<210> SEQ ID NO 101
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Val Ile Leu Pro Gln Ala Pro Ser Gly Pro Ser Tyr Ala Thr Tyr
1               5                   10                  15

<210> SEQ ID NO 102
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Gln Ala Pro Ser Gly Pro Ser Tyr Ala Thr Tyr Leu Gln Pro Ala
1               5                   10                  15

<210> SEQ ID NO 103
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 103

Gly Pro Ser Tyr Ala Thr Tyr Leu Gln Pro Ala Gln Ala Gln Met
1 5 10 15

<210> SEQ ID NO 104
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 104

Ala Thr Tyr Leu Gln Pro Ala Gln Ala Gln Met Leu Thr Pro Pro
1 5 10 15

<210> SEQ ID NO 105
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 105

Gln Pro Ala Gln Ala Gln Met Leu Thr Pro Pro
1 5 10

<210> SEQ ID NO 106
<211> LENGTH: 66
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: CDS
<222> LOCATION: (1)..(66)

<400> SEQUENCE: 106 gga agc gga gct act aac ttc agc ctg ctg aag cag gct gga gac gtg 48
Gly Ser Gly Ala Thr Asn Phe Ser Leu Leu Lys Gln Ala Gly Asp Val
1 5 10 15 gag gag aac cct gga cct 66
Glu Glu Asn Pro Gly Pro
20

<210> SEQ ID NO 107
<211> LENGTH: 22
<212> TYPE: PRT
<213> ORGANISM: Artificial Sequence
<220> FEATURE:
<223> OTHER INFORMATION: Description of Artificial Sequence: Synthetic peptide

<400> SEQUENCE: 107

Gly Ser Gly Ala Thr Asn Phe Ser Leu Leu Lys Gln Ala Gly Asp Val
1 5 10 15

Glu Glu Asn Pro Gly Pro
20

<210> SEQ ID NO 108
<211> LENGTH: 63

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(63)

<400> SEQUENCE: 108

gga agc gga gag ggc aga gga agt ctg cta aca tgc ggt gac gtc gag       48
Gly Ser Gly Glu Gly Arg Gly Ser Leu Leu Thr Cys Gly Asp Val Glu
1               5                   10                  15

gag aat cct gga cct                                                   63
Glu Asn Pro Gly Pro
            20


<210> SEQ ID NO 109
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Gly Ser Gly Glu Gly Arg Gly Ser Leu Leu Thr Cys Gly Asp Val Glu
1               5                   10                  15

Glu Asn Pro Gly Pro
            20


<210> SEQ ID NO 110
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(69)

<400> SEQUENCE: 110

gga agc gga cag tgt act aat tat gct ctc ttg aaa ttg gct gga gat       48
Gly Ser Gly Gln Cys Thr Asn Tyr Ala Leu Leu Lys Leu Ala Gly Asp
1               5                   10                  15

gtt gag agc aac cct gga cct                                           69
Val Glu Ser Asn Pro Gly Pro
            20


<210> SEQ ID NO 111
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Gly Ser Gly Gln Cys Thr Asn Tyr Ala Leu Leu Lys Leu Ala Gly Asp
1               5                   10                  15

Val Glu Ser Asn Pro Gly Pro
            20


<210> SEQ ID NO 112
<211> LENGTH: 75
<212> TYPE: DNA
```

<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(75)

<400> SEQUENCE: 112 gga agc gga gtg aaa cag act ttg aat ttt gac ctt ctc aag ttg gcg 48
Gly Ser Gly Val Lys Gln Thr Leu Asn Phe Asp Leu Leu Lys Leu Ala
1 5 10 15 gga gac gtg gag tcc aac cct gga cct 75
Gly Asp Val Glu Ser Asn Pro Gly Pro
20 25

<210> SEQ ID NO 113
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Gly Ser Gly Val Lys Gln Thr Leu Asn Phe Asp Leu Leu Lys Leu Ala
1 5 10 15

Gly Asp Val Glu Ser Asn Pro Gly Pro
20 25

<210> SEQ ID NO 114
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 114

His His His His His His
1 5

<210> SEQ ID NO 115
<211> LENGTH: 1446
<212> TYPE: DNA
<213> ORGANISM: Artificial Sequence
<220> FEATURE:
<223> OTHER INFORMATION: Plasmid 1

<400> SEQUENCE: 115
ggatccgcca ccatgcacct cggcaacttc gcttcctcac tgtctggggg tcagatgtat 60
ggtcctggtt ctccactcgg gggagcacct ctcggcggcg cccctaccgc cgctaggggc 120
agaaagagga gatctgctca gagaaacagc aacccaatca tcgccgagct gtcccaggct 180
atgaactctg gcacactgct gtccaagccc tctccccctc tgccacccaa gaggaggga 240 aggaagagga gaagcggaga gtccaaggga cctctggaca gctccttcag ccagtacctg 300
ggccggtcct gcctgctgga tcagagagag gccaagcgga agggagaggg actgagggga 360
aggaagcggc gcagcctggc cagggacgag ttcaacctgc agaagatgat ggtcatggtg 420
accgcttccg gcaagctgtt tggaatcgag tctagctccg gcacaatcct gtggagggga 480
agaaagagga gaagcgagac aacagtgaag tacctggacg gcgagaagct gagcgtgctg 540
tgccacgaca actacctgac ccaggattcc gaggagatgg tgtgcaagga tggaagaggc 600

```
aggaagcggc gctctgacag cttccagatc atcctggatt ctctgctgct gtttggccag    660

tgctctagca cacctctgag cgaggccttc cacccaaccg tgacaggcga gtctagggga    720

cgcaaaagga gaagcgagtg taaggaggcc gccgtgagcc acgctggatc tatgcacagg    780

gagaggcgca cctttctgag gtccgccctg aaggagctgg ctacagtgct gtcccggggc    840

cgcaagagga gatctcaggg aaagtacatc ctgaaggtgt gcggctgtga cgagtacttc    900

ctggagaagt ttccactgag ccagtacaag tacatcagat cctgcatcat gctgaggggga    960

agaaagcggc gcagcaagtt tatcagcgtg ctgtgcacct ccctggccac aatgctgcac   1020

gtggagctgc cccacgtgaa cctgctgtct aagatggacc tgatcgagca ctatagaggt   1080

agaaagagga gatctgccga ggatacccag gagaacctgc acagcggaaa gtcccagtct   1140

agaagcttcc ccaaggtgct ggctgactct gatgagagcg atatggagga gacaaggggc   1200

agaaagcggc gctcctctgg acacgtggga ctgaggaacc tgggaaacac cctgccacag   1260

tgctttctga acgctatgct gcagtgtctg agctccacaa gacccctgcg ggaccgcgga   1320

aggaagagga gatccgagcc aaagcgggac cggcgcgatc cttctaccga taagagcggt   1380

cctgatacct tccccgtgga agtgctggag agaaagcccc ctgaaaaaac atactgataa   1440

ctcgag                                                               1446
```

```
<210> SEQ ID NO 116
<211> LENGTH: 474
<212> TYPE: PRT
<213> ORGANISM: Artificial Sequence
<220> FEATURE:
<223> OTHER INFORMATION: peptide encoded plasmid1

<400> SEQUENCE: 116

Met His Leu Gly Asn Phe Ala Ser Ser Leu Ser Gly Gly Gln Met Tyr
1               5                   10                  15

Gly Pro Gly Ser Pro Leu Gly Gly Ala Pro Leu Gly Gly Ala Pro Thr
            20                  25                  30

Ala Ala Arg Gly Arg Lys Arg Arg Ser Ala Gln Arg Asn Ser Asn Pro
        35                  40                  45

Ile Ile Ala Glu Leu Ser Gln Ala Met Asn Ser Gly Thr Leu Leu Ser
    50                  55                  60

Lys Pro Ser Pro Pro Leu Pro Pro Lys Arg Arg Gly Arg Lys Arg Arg
65                  70                  75                  80

Ser Gly Glu Ser Lys Gly Pro Leu Asp Ser Ser Phe Ser Gln Tyr Leu
                85                  90                  95

Gly Arg Ser Cys Leu Leu Asp Gln Arg Glu Ala Lys Arg Lys Gly Glu
            100                 105                 110

Gly Leu Arg Gly Arg Lys Arg Arg Ser Leu Ala Arg Asp Glu Phe Asn
        115                 120                 125

Leu Gln Lys Met Met Val Met Val Thr Ala Ser Gly Lys Leu Phe Gly
    130                 135                 140

Ile Glu Ser Ser Ser Gly Thr Ile Leu Trp Arg Gly Arg Lys Arg Arg
145                 150                 155                 160

Ser Glu Thr Thr Val Lys Tyr Leu Asp Gly Glu Lys Leu Ser Val Leu
                165                 170                 175

Cys His Asp Asn Tyr Leu Thr Gln Asp Ser Glu Glu Met Val Cys Lys
            180                 185                 190

Asp Gly Arg Gly Arg Lys Arg Arg Ser Asp Ser Phe Gln Ile Ile Leu
        195                 200                 205
```

```
Asp Ser Leu Leu Leu Phe Gly Gln Cys Ser Ser Thr Pro Leu Ser Glu
    210                 215                 220

Ala Phe His Pro Thr Val Thr Gly Glu Ser Arg Gly Arg Lys Arg Arg
225                 230                 235                 240

Ser Glu Cys Lys Glu Ala Ala Val Ser His Ala Gly Ser Met His Arg
                245                 250                 255

Glu Arg Arg Thr Phe Leu Arg Ser Ala Leu Lys Glu Leu Ala Thr Val
            260                 265                 270

Leu Ser Arg Gly Arg Lys Arg Arg Ser Gln Gly Lys Tyr Ile Leu Lys
        275                 280                 285

Val Cys Gly Cys Asp Glu Tyr Phe Leu Glu Lys Phe Pro Leu Ser Gln
    290                 295                 300

Tyr Lys Tyr Ile Arg Ser Cys Ile Met Leu Arg Gly Arg Lys Arg Arg
305                 310                 315                 320

Ser Lys Phe Ile Ser Val Leu Cys Thr Ser Leu Ala Thr Met Leu His
                325                 330                 335

Val Glu Leu Pro His Val Asn Leu Leu Ser Lys Met Asp Leu Ile Glu
            340                 345                 350

His Tyr Arg Gly Arg Lys Arg Arg Ser Ala Glu Asp Thr Gln Glu Asn
        355                 360                 365

Leu His Ser Gly Lys Ser Gln Ser Arg Ser Phe Pro Lys Val Leu Ala
    370                 375                 380

Asp Ser Asp Glu Ser Asp Met Glu Glu Thr Arg Gly Arg Lys Arg Arg
385                 390                 395                 400

Ser Ser Gly His Val Gly Leu Arg Asn Leu Gly Asn Thr Leu Pro Gln
                405                 410                 415

Cys Phe Leu Asn Ala Met Leu Gln Cys Leu Ser Ser Thr Arg Pro Leu
            420                 425                 430

Arg Asp Arg Gly Arg Lys Arg Arg Ser Glu Pro Lys Arg Asp Arg Arg
        435                 440                 445

Asp Pro Ser Thr Asp Lys Ser Gly Pro Asp Thr Phe Pro Val Glu Val
    450                 455                 460

Leu Glu Arg Lys Pro Pro Glu Lys Thr Tyr
465                 470
```

<210> SEQ ID NO 117
<211> LENGTH: 1446
<212> TYPE: DNA
<213> ORGANISM: Artificial Sequence
<220> FEATURE:
<223> OTHER INFORMATION: plasmid 2

<400> SEQUENCE: 117

```
ggatccgcca ccatgaactc aggggtcgat aacgccatta caaaaagcga gatgctggtc      60

gatcagtatt tcccactcac tcaggaagag ctggagatgg aggccaagaa ggtgcgggga     120

aggaagagga gaagcctgcg gccttccacc ctgtctcagg aggtgtacaa gacagtgtcc     180

atgcgcctga acgtggtgtc tccagacctg agcggcaagg gactggtgct gcccaggggc     240

agaaagcggc gctccttcct gcagctgaag ctggtggtga agaagggaaa gcagaccgag     300

aacctgtaca tcgagctgac actgccacag ttctactcct ttctgcacga gatgcggggc     360

cgcaagagga gatctctgac ccacccttac ggcaagggat gggacctgat gcagaacatc     420

atggacgatg tgccaatcta catgtacagc gtgtgcaacg tggtgagcgg cgatagggga     480

agaaagcggc gctccgcctg tagctcctct tacaactctg ctgtgatgga gagctcctct     540
```

```
gtgaacgtgt ccatggtgca cagctcctct aaggagaacc tgtgccccaa gaagcggggt    600

agaaagagga gatctcagca cgtgatccac aagtacttcc tgcctagggc ctacgctgtg    660

ctgctgccac tgcctgctgg cctgctgctg ctgctgtttg tgggcaagag ccccagggga    720

aggaaacggc gctcccagca cggcatccag ctgctgaacg gacacgctcc tgctgctgga    780

ccaaacctga gcggactgcc acaggctaac aggcaccacg gcctgctggg cggaagggga    840

aggaagagga ggagcaggga cccctacgct ctggacctga tcgataagct gctggtgcca    900

gaccccgctc agaggatcga tagcgacgat gctctgaacc acgatttctt ttggagaggt    960

agaaagcggc gctctcgcga gatcgctgtg gagcacaaca acctgggaaa ggccgtgtac   1020

agcaggatgg ctagaatctg taagaacgac atgggcggat ctcagagagt gctgagggga   1080

cgcaagagga gaagcaacac ccagatccag aagctgacag gcagcccctt caggagcagg   1140

gagtacgtgc agaccatgga gagcgagtcc gagcactctt accctcctcc cggaagggga   1200

aggaagcggc gctctctgag ccagacaccc cctccagccc ctcctcccag cgccggctcc   1260

gagccactgg ctaggctgcc tcagaaggat agcgtgggaa agcactccgg cgctagggga   1320

agaaagagga gaagccggat gagggaggag cagctggcca gagaggctga ggcttgggca   1380

gaacgggagg cagaggcaag acgcagggag gaacaggaag caagggaaaa agcatgataa   1440

ctcgag                                                              1446
```

<210> SEQ ID NO 118
<211> LENGTH: 474
<212> TYPE: PRT
<213> ORGANISM: Artificial Sequence
<220> FEATURE:
<223> OTHER INFORMATION: peptide from plasmid 2

<400> SEQUENCE: 118

```
Met Asn Ser Gly Val Asp Asn Ala Ile Thr Lys Ser Glu Met Leu Val
1               5                   10                  15

Asp Gln Tyr Phe Pro Leu Thr Gln Glu Glu Leu Glu Met Glu Ala Lys
            20                  25                  30

Lys Val Arg Gly Arg Lys Arg Arg Ser Leu Arg Pro Ser Thr Leu Ser
        35                  40                  45

Gln Glu Val Tyr Lys Thr Val Ser Met Arg Leu Asn Val Val Ser Pro
    50                  55                  60

Asp Leu Ser Gly Lys Gly Leu Val Leu Pro Arg Gly Arg Lys Arg Arg
65                  70                  75                  80

Ser Phe Leu Gln Leu Lys Leu Val Val Lys Lys Gly Lys Gln Thr Glu
                85                  90                  95

Asn Leu Tyr Ile Glu Leu Thr Leu Pro Gln Phe Tyr Ser Phe Leu His
            100                 105                 110

Glu Met Arg Gly Arg Lys Arg Arg Ser Leu Thr His Pro Tyr Gly Lys
        115                 120                 125

Gly Trp Asp Leu Met Gln Asn Ile Met Asp Asp Val Pro Ile Tyr Met
    130                 135                 140

Tyr Ser Val Cys Asn Val Val Ser Gly Asp Arg Gly Arg Lys Arg Arg
145                 150                 155                 160

Ser Ala Cys Ser Ser Ser Tyr Asn Ser Ala Val Met Glu Ser Ser Ser
                165                 170                 175

Val Asn Val Ser Met Val His Ser Ser Ser Lys Glu Asn Leu Cys Pro
            180                 185                 190

Lys Lys Arg Gly Arg Lys Arg Arg Ser Gln His Val Ile His Lys Tyr
```

```
        195                 200                 205

Phe Leu Pro Arg Ala Tyr Ala Val Leu Leu Pro Leu Pro Ala Gly Leu
    210                 215                 220

Leu Leu Leu Leu Phe Val Gly Lys Ser Pro Arg Gly Arg Lys Arg Arg
225                 230                 235                 240

Ser Gln His Gly Ile Gln Leu Leu Asn Gly His Ala Pro Ala Ala Gly
                245                 250                 255

Pro Asn Leu Ser Gly Leu Pro Gln Ala Asn Arg His His Gly Leu Leu
            260                 265                 270

Gly Gly Arg Gly Arg Lys Arg Arg Ser Arg Asp Pro Tyr Ala Leu Asp
        275                 280                 285

Leu Ile Asp Lys Leu Leu Val Pro Asp Pro Ala Gln Arg Ile Asp Ser
    290                 295                 300

Asp Asp Ala Leu Asn His Asp Phe Phe Trp Arg Gly Arg Lys Arg Arg
305                 310                 315                 320

Ser Arg Glu Ile Ala Val Glu His Asn Asn Leu Gly Lys Ala Val Tyr
                325                 330                 335

Ser Arg Met Ala Arg Ile Cys Lys Asn Asp Met Gly Gly Ser Gln Arg
            340                 345                 350

Val Leu Arg Gly Arg Lys Arg Arg Ser Asn Thr Gln Ile Gln Lys Leu
        355                 360                 365

Thr Gly Ser Pro Phe Arg Ser Arg Glu Tyr Val Gln Thr Met Glu Ser
    370                 375                 380

Glu Ser Glu His Ser Tyr Pro Pro Pro Gly Arg Gly Arg Lys Arg Arg
385                 390                 395                 400

Ser Leu Ser Gln Thr Pro Pro Pro Ala Pro Pro Pro Ser Ala Gly Ser
                405                 410                 415

Glu Pro Leu Ala Arg Leu Pro Gln Lys Asp Ser Val Gly Lys His Ser
            420                 425                 430

Gly Ala Arg Gly Arg Lys Arg Arg Ser Arg Met Arg Glu Glu Gln Leu
        435                 440                 445

Ala Arg Glu Ala Glu Ala Trp Ala Glu Arg Glu Ala Glu Ala Arg Arg
    450                 455                 460

Arg Glu Glu Gln Glu Ala Arg Glu Lys Ala
465                 470


<210> SEQ ID NO 119
<211> LENGTH: 1446
<212> TYPE: DNA
<213> ORGANISM: Artificial Sequence
<220> FEATURE:
<223> OTHER INFORMATION: plasmid 3

<400> SEQUENCE: 119

ggatccgcca ccatggaggg ggagtcaacc aatacatcaa aagtcgctaa aaagtcatca      60

gtccactaca gcctgctcgc cgaacacgaa gaaacccagt ccctgggcac caagcgggga     120

cgcaagagga gatccacagg ctctatgaac gtgatccaca tgctggagtc tttcaccttt     180

aggaacaacg tgtgcatggc cttcgagctg ctgtctatcg acctgtacga gctgaggggc     240

agaaagcggc gcagcaactg caacttcgac tttcccgagg agacatgtgg atgggtgtac     300

gatcacgcca agctgctgag gtctacatgg atcagctccg ctaaccctaa cgacagggga     360

aggaagagga gaagcctgcc agccagactg gagatccagg gaaccgatcc tatgtccgct     420

gtgacactgt ctctgctgga ccctgagaca caggaggacc ccagcagctg gacaaggggc     480
```

```
aggaaacggc gcagcggact gtccctgaac atcaagaagt acctgctggt gtctatgcct    540

ctgtgggcta agcacatgag cgatgagcag atccagggct ttgtggagaa cctgagaggc    600

cgcaagagga gaagcatctc catgggcgga cacatggcta gcctggccgt gtgcaactgg    660

cccaagccta tgccactgat cccatgtctg tcttggagca ccgcttccgg cgtgaggga    720

agaaagcggc gctctgagcc catcgaggtg aacctgttcg gcctgatcaa cgtgacaccc    780

aacatgctgc ctctggtgaa gaaggctcgg ggccgcgtga tcaacgtgtc ctctagggga    840

agaaagagga gatccgtgga ctttaacaag atctgtggac aggcctacga ttctgctaca    900

aacttccggg tgaagctgaa cgaggtggtg gccgagttta agaaggagga gccacggggc    960

aggaagcggc gcagcgccga ggtgctgatc gacgctctgg tggatggaca ggtggtggcc   1020

ctgctggtgc agaacctgga gcggctggac gagagcgtgc gcgaggaggc tgataggggc   1080

agaaagagga gatccgacga ggaggagtct gtggatctga gcatccccgg agcctgctac   1140

ctgagactgc tgaccatcac agctccatcc gtgctgcccg ctctggagga gttccgggga   1200

cgcaagcggc gcagcaagct gctggtgtac tccgctcacg acaccacact ggtggccctg   1260

cagatggctc tgaacctgta caacggcaag caggcccctt acgctagctg tcacagaggc   1320

aggaaaagga gatccggcga ggacgaggga gataagccag aggccaagca ggtggtgctg   1380

attgggtcat cctacctctg ccagttttgt ccttctaaat tctccaccta cttttgataa   1440

ctcgag                                                               1446


<210> SEQ ID NO 120
<211> LENGTH: 474
<212> TYPE: PRT
<213> ORGANISM: Artificial Sequence
<220> FEATURE:
<223> OTHER INFORMATION: peptide from plasmid 3

<400> SEQUENCE: 120

Met Glu Gly Glu Ser Thr Asn Thr Ser Lys Val Ala Lys Lys Ser Ser
1               5                   10                  15

Val His Tyr Ser Leu Leu Ala Glu His Glu Glu Thr Gln Ser Leu Gly
            20                  25                  30

Thr Lys Arg Gly Arg Lys Arg Arg Ser Thr Gly Ser Met Asn Val Ile
        35                  40                  45

His Met Leu Glu Ser Phe Thr Phe Arg Asn Asn Val Cys Met Ala Phe
    50                  55                  60

Glu Leu Leu Ser Ile Asp Leu Tyr Glu Leu Arg Gly Arg Lys Arg Arg
65                  70                  75                  80

Ser Asn Cys Asn Phe Asp Phe Pro Glu Glu Thr Cys Gly Trp Val Tyr
                85                  90                  95

Asp His Ala Lys Leu Leu Arg Ser Thr Trp Ile Ser Ser Ala Asn Pro
            100                 105                 110

Asn Asp Arg Gly Arg Lys Arg Arg Ser Leu Pro Ala Arg Leu Glu Ile
        115                 120                 125

Gln Gly Thr Asp Pro Met Ser Ala Val Thr Leu Ser Leu Leu Asp Pro
    130                 135                 140

Glu Thr Gln Glu Asp Pro Ser Ser Trp Thr Arg Gly Arg Lys Arg Arg
145                 150                 155                 160

Ser Gly Leu Ser Leu Asn Ile Lys Lys Tyr Leu Leu Val Ser Met Pro
                165                 170                 175

Leu Trp Ala Lys His Met Ser Asp Glu Gln Ile Gln Gly Phe Val Glu
            180                 185                 190
```

```
Asn Leu Arg Gly Arg Lys Arg Arg Ser Ile Ser Met Gly Gly His Met
        195                 200                 205

Ala Ser Leu Ala Val Cys Asn Trp Pro Lys Pro Met Pro Leu Ile Pro
    210                 215                 220

Cys Leu Ser Trp Ser Thr Ala Ser Gly Val Arg Gly Arg Lys Arg Arg
225                 230                 235                 240

Ser Glu Pro Ile Glu Val Asn Leu Phe Gly Leu Ile Asn Val Thr Pro
                245                 250                 255

Asn Met Leu Pro Leu Val Lys Lys Ala Arg Gly Arg Val Ile Asn Val
            260                 265                 270

Ser Ser Arg Gly Arg Lys Arg Arg Ser Val Asp Phe Asn Lys Ile Cys
        275                 280                 285

Gly Gln Ala Tyr Asp Ser Ala Thr Asn Phe Arg Val Lys Leu Asn Glu
    290                 295                 300

Val Val Ala Glu Phe Lys Lys Glu Glu Pro Arg Gly Arg Lys Arg Arg
305                 310                 315                 320

Ser Ala Glu Val Leu Ile Asp Ala Leu Val Asp Gly Gln Val Val Ala
                325                 330                 335

Leu Leu Val Gln Asn Leu Glu Arg Leu Asp Glu Ser Val Arg Glu Glu
            340                 345                 350

Ala Asp Arg Gly Arg Lys Arg Arg Ser Asp Glu Glu Glu Ser Val Asp
        355                 360                 365

Leu Ser Ile Pro Gly Ala Cys Tyr Leu Arg Leu Leu Thr Ile Thr Ala
    370                 375                 380

Pro Ser Val Leu Pro Ala Leu Glu Glu Phe Arg Gly Arg Lys Arg Arg
385                 390                 395                 400

Ser Lys Leu Leu Val Tyr Ser Ala His Asp Thr Thr Leu Val Ala Leu
                405                 410                 415

Gln Met Ala Leu Asn Leu Tyr Asn Gly Lys Gln Ala Pro Tyr Ala Ser
            420                 425                 430

Cys His Arg Gly Arg Lys Arg Arg Ser Gly Glu Asp Glu Gly Asp Lys
        435                 440                 445

Pro Glu Ala Lys Gln Val Val Leu Ile Gly Ser Ser Tyr Leu Cys Gln
    450                 455                 460

Phe Cys Pro Ser Lys Phe Ser Thr Tyr Phe
465                 470
```

<210> SEQ ID NO 121
<211> LENGTH: 1446
<212> TYPE: DNA
<213> ORGANISM: Artificial Sequence
<220> FEATURE:
<223> OTHER INFORMATION: plasmid 4

<400> SEQUENCE: 121

```
ggatccgcca ccatgctcct cgctcgcact caccctggtt gtggtaatat cgtcactttt      60

gctcatttcc tctttatcgc agtcgaaggt ttcctgttcg aggctaacct gggaagaggc     120

aggaagcgca gatcttccca cgtgcagaga ctggtgcaca gggacagcac aatctccaac     180

gacgccttta tctccgtgga cgatctggag ccatccggac cacaggatct ggagcgggga     240

aggaagagga gatccgacta catcgctctg aacgaggatc tgaagacctg gacagctgcc     300

gctatggctg ccctgatcac aaagcacaag tgggagcagg ccggcgaggc tgagagggga     360

agaaagcgga ggtccggcgg aaaggtgtgg aacgagcagg agaagaacac ctacgccgac     420
```

```
aagctgttcg attgtatcga ggcttacgct cctggattca agagaagcgt gctgagaggc    480

cggaagcgca gatccaagct ggtgttcgtg agcacctctg gcggatctct gtggaacctg    540

aaggccatcc actccatgtg caggatcgag caggagcagg agggaagcgt gcggagagga    600

aggaagcgca ggtccccaaa gatgtgctct cagcctgctg tgagccagct gcagtctaac    660

atcagatccc agtgcatctc ccacaccgcc ctggtgctgc agggcagcct gacaagagga    720

aggaagagac ggtccatcca gggatggctg ggcaccaagg tgaggacaaa cctgcggaga    780

gagccattct ctctggtgcc taagaacgct aaggacggaa actccttcca gggacgcgga    840

aggaagagac gctctaacac catgacaacc aaggagtgcc tgcacaggtt ttgtgccgac    900

tgtatcatca ccggcctgag gagcggaaac aaggagtgcc ctacctgcag aaagaggggc    960

agaaagcgga gaagcaacgg atacgataca tacgtgcacg atgcctacgg actgttccag   1020

gagtgcaggt ctagggtggc ccactggggc tggcctctgg gacccgcccc actgagagga   1080

agaaagagga ggtccgacca cctgcagctg aaggacatcc tgagaaagca ggacgagtac   1140

cacatggtgc acctgctgtg cgcctctaga tcccctccca gctcccccaa gtccagggga   1200

cggaagaggc ggagcgcccc agagctgaca ttcgacttta ccatcgagac cgtgctgtgc   1260

ctgcaggaca gcgtgctggc cttctggagc cacggaatgc agggacggtc cctgagagga   1320

cgcaagagga gaagcacaac aaccagcagg gccatctgcc agctggtgaa ggagtacatt   1380

ggatacaggg atggcatttg ggatgtcagc gtcacacgga ctcagcctat tgtctgataa   1440

ctcgag                                                              1446
```

<210> SEQ ID NO 122
<211> LENGTH: 474
<212> TYPE: PRT
<213> ORGANISM: Artificial Sequence
<220> FEATURE:
<223> OTHER INFORMATION: peptide from plasmid 4

<400> SEQUENCE: 122

```
Met Leu Leu Ala Arg Thr His Pro Gly Cys Gly Asn Ile Val Thr Phe
1               5                   10                  15

Ala His Phe Leu Phe Ile Ala Val Glu Gly Phe Leu Phe Glu Ala Asn
            20                  25                  30

Leu Gly Arg Gly Arg Lys Arg Arg Ser Ser His Val Gln Arg Leu Val
        35                  40                  45

His Arg Asp Ser Thr Ile Ser Asn Asp Ala Phe Ile Ser Val Asp Asp
    50                  55                  60

Leu Glu Pro Ser Gly Pro Gln Asp Leu Glu Arg Gly Arg Lys Arg Arg
65                  70                  75                  80

Ser Asp Tyr Ile Ala Leu Asn Glu Asp Leu Lys Thr Trp Thr Ala Ala
                85                  90                  95

Ala Met Ala Ala Leu Ile Thr Lys His Lys Trp Glu Gln Ala Gly Glu
            100                 105                 110

Ala Glu Arg Gly Arg Lys Arg Arg Ser Gly Gly Lys Val Trp Asn Glu
        115                 120                 125

Gln Glu Lys Asn Thr Tyr Ala Asp Lys Leu Phe Asp Cys Ile Glu Ala
    130                 135                 140

Tyr Ala Pro Gly Phe Lys Arg Ser Val Leu Arg Gly Arg Lys Arg Arg
145                 150                 155                 160

Ser Lys Leu Val Phe Val Ser Thr Ser Gly Gly Ser Leu Trp Asn Leu
                165                 170                 175
```

```
Lys Ala Ile His Ser Met Cys Arg Ile Glu Gln Glu Gln Glu Gly Ser
            180                 185                 190

Val Arg Arg Gly Arg Lys Arg Arg Ser Pro Lys Met Cys Ser Gln Pro
        195                 200                 205

Ala Val Ser Gln Leu Gln Ser Asn Ile Arg Ser Gln Cys Ile Ser His
    210                 215                 220

Thr Ala Leu Val Leu Gln Gly Ser Leu Thr Arg Gly Arg Lys Arg Arg
225                 230                 235                 240

Ser Ile Gln Gly Trp Leu Gly Thr Lys Val Arg Thr Asn Leu Arg Arg
                245                 250                 255

Glu Pro Phe Ser Leu Val Pro Lys Asn Ala Lys Asp Gly Asn Ser Phe
            260                 265                 270

Gln Gly Arg Gly Arg Lys Arg Arg Ser Asn Thr Met Thr Thr Lys Glu
        275                 280                 285

Cys Leu His Arg Phe Cys Ala Asp Cys Ile Ile Thr Gly Leu Arg Ser
    290                 295                 300

Gly Asn Lys Glu Cys Pro Thr Cys Arg Lys Arg Gly Arg Lys Arg Arg
305                 310                 315                 320

Ser Asn Gly Tyr Asp Thr Tyr Val His Asp Ala Tyr Gly Leu Phe Gln
                325                 330                 335

Glu Cys Arg Ser Arg Val Ala His Trp Gly Trp Pro Leu Gly Pro Ala
            340                 345                 350

Pro Leu Arg Gly Arg Lys Arg Arg Ser Asp His Leu Gln Leu Lys Asp
        355                 360                 365

Ile Leu Arg Lys Gln Asp Glu Tyr His Met Val His Leu Leu Cys Ala
    370                 375                 380

Ser Arg Ser Pro Pro Ser Ser Pro Lys Ser Arg Gly Arg Lys Arg Arg
385                 390                 395                 400

Ser Ala Pro Glu Leu Thr Phe Asp Phe Thr Ile Glu Thr Val Leu Cys
                405                 410                 415

Leu Gln Asp Ser Val Leu Ala Phe Trp Ser His Gly Met Gln Gly Arg
            420                 425                 430

Ser Leu Arg Gly Arg Lys Arg Arg Ser Thr Thr Thr Ser Arg Ala Ile
        435                 440                 445

Cys Gln Leu Val Lys Glu Tyr Ile Gly Tyr Arg Asp Gly Ile Trp Asp
    450                 455                 460

Val Ser Val Thr Arg Thr Gln Pro Ile Val
465                 470
```

<210> SEQ ID NO 123
<211> LENGTH: 1446
<212> TYPE: DNA
<213> ORGANISM: Artificial Sequence
<220> FEATURE:
<223> OTHER INFORMATION: plasmid 5 insert

<400> SEQUENCE: 123

```
ggatccgcca ccatggggaa caatatcact gtgaaaaccg agagcaccgt caaaaccaat     60

gtctttagct gtaatctggg ggagaaattc gatgaaacca ccgccgacgg caggagagga    120

agaaagcggc gctccgtgga gcacaagaag cggccaaagg tggagctgat gcccggcatg    180

aggagactgc agtctctgct ggataccaga tgcgtgtaca tcctggactg ttggagggga    240

aggaagcggc gcagcacaca gggatgcaag ctggtggata ccaacaagac acgcaccaca    300

tgcgcctgta ggcacctgac aaacttcgcc atcctgatgg ctcaccgcga gatcaggggc    360
```

agaaagagga gatctcagag caagaagagg ctgcacatcg aggattactc cgtgtctcag 420
cctaccctgg accaggtgtt cgtgaacttt gctaaggatc agagcgacga tgacagaggc 480
aggaagcggc gctcctggaa cacatggctg tacgcccctg gactgccccc tgtgaagcca 540
aactacgacg ctaccctgac aaacgcctgc atcgctctgt cccagagatg ggtgaggggt 600
aggaagagga gatccctggg atcttacacc gaggataacg cttctcaggc tcgggtggac 660
ggacacagat gtatcgtgag ggccctgaag gaccccaacg ctttcctgtt tgacagaggt 720
aggaagcggc gcagccagag ggacaacctg acacagttct ttccccagaa ctacttccct 780
ctgctgggac aggagctggt gcaggccctg aaggctgtgg tgaactttct gcagagaggt 840
agaaagagga gaagcaccgc ttccggaaca caggaccccc actccgctga gacactggga 900
gtgtgccgca gcccaccccc tccatgttcc cctatcctgg aggcttctga tgacagaggg 960
aggaagcggc gctctggaca ggtcatccag gctcagggaa gagctagccc aaccatggcc 1020
acactgcctg ctccaatggc ctccgctccc cctctgtctg agctgtaccc aaacagggga 1080
agaaagagga gaagcgactc caagcggcgc aaggagcagt tccccgtgct gtctcacctg 1140
ctgagcatcg cccagctgcc acccaacaag gatgctacct acctgtctcg gagccgcggc 1200
aggaagagga gaagctccat cctgcgcaac cacaggtaca ggagggatgc taggaccctg 1260
gaggacaagg aggagatgtg gtttaacaca gatgaggatg acatggagga cggcagagga 1320
cggaagagga gaagctggat gaagtgcgtg aagggacagc ctcacgacca caagcacctc 1380
atgccaactc agattattcc cggctccgtg ctcacagacc tcctggatgc tatgtgataa 1440
ctcgag 1446

<210> SEQ ID NO 124
<211> LENGTH: 474
<212> TYPE: PRT
<213> ORGANISM: Artificial Sequence
<220> FEATURE:
<223> OTHER INFORMATION: peptide from insert 5

<400> SEQUENCE: 124

Met Gly Asn Asn Ile Thr Val Lys Thr Glu Ser Thr Val Lys Thr Asn
1 5 10 15

Val Phe Ser Cys Asn Leu Gly Glu Lys Phe Asp Glu Thr Thr Ala Asp
20 25 30

Gly Arg Arg Gly Arg Lys Arg Arg Ser Val Glu His Lys Lys Arg Pro
35 40 45

Lys Val Glu Leu Met Pro Gly Met Arg Arg Leu Gln Ser Leu Leu Asp
50 55 60

Thr Arg Cys Val Tyr Ile Leu Asp Cys Trp Arg Gly Arg Lys Arg Arg
65 70 75 80

Ser Thr Gln Gly Cys Lys Leu Val Asp Thr Asn Lys Thr Arg Thr Thr
85 90 95

Cys Ala Cys Arg His Leu Thr Asn Phe Ala Ile Leu Met Ala His Arg
100 105 110

Glu Ile Arg Gly Arg Lys Arg Arg Ser Gln Ser Lys Lys Arg Leu His
115 120 125

Ile Glu Asp Tyr Ser Val Ser Gln Pro Thr Leu Asp Gln Val Phe Val
130 135 140

Asn Phe Ala Lys Asp Gln Ser Asp Asp Asp Arg Gly Arg Lys Arg Arg
145 150 155 160

Ser Trp Asn Thr Trp Leu Tyr Ala Pro Gly Leu Pro Pro Val Lys Pro

```
                165                 170                 175

Asn Tyr Asp Ala Thr Leu Thr Asn Ala Cys Ile Ala Leu Ser Gln Arg
            180                 185                 190

Trp Val Arg Gly Arg Lys Arg Arg Ser Leu Gly Ser Tyr Thr Glu Asp
        195                 200                 205

Asn Ala Ser Gln Ala Arg Val Asp Gly His Arg Cys Ile Val Arg Ala
    210                 215                 220

Leu Lys Asp Pro Asn Ala Phe Leu Phe Asp Arg Gly Arg Lys Arg Arg
225                 230                 235                 240

Ser Gln Arg Asp Asn Leu Thr Gln Phe Phe Pro Gln Asn Tyr Phe Pro
                245                 250                 255

Leu Leu Gly Gln Glu Leu Val Gln Ala Leu Lys Ala Val Val Asn Phe
            260                 265                 270

Leu Gln Arg Gly Arg Lys Arg Arg Ser Thr Ala Ser Gly Thr Gln Asp
        275                 280                 285

Pro His Ser Ala Glu Thr Leu Gly Val Cys Arg Ser Pro Pro Pro Pro
    290                 295                 300

Cys Ser Pro Ile Leu Glu Ala Ser Asp Asp Arg Gly Arg Lys Arg Arg
305                 310                 315                 320

Ser Gly Gln Val Ile Gln Ala Gln Gly Arg Ala Ser Pro Thr Met Ala
                325                 330                 335

Thr Leu Pro Ala Pro Met Ala Ser Ala Pro Pro Leu Ser Glu Leu Tyr
            340                 345                 350

Pro Asn Arg Gly Arg Lys Arg Arg Ser Asp Ser Lys Arg Arg Lys Glu
        355                 360                 365

Gln Phe Pro Val Leu Ser His Leu Leu Ser Ile Ala Gln Leu Pro Pro
    370                 375                 380

Asn Lys Asp Ala Thr Tyr Leu Ser Arg Ser Arg Gly Arg Lys Arg Arg
385                 390                 395                 400

Ser Ser Ile Leu Arg Asn His Arg Tyr Arg Arg Asp Ala Arg Thr Leu
                405                 410                 415

Glu Asp Lys Glu Glu Met Trp Phe Asn Thr Asp Glu Asp Asp Met Glu
            420                 425                 430

Asp Gly Arg Gly Arg Lys Arg Arg Ser Trp Met Lys Cys Val Lys Gly
        435                 440                 445

Gln Pro His Asp His Lys His Leu Met Pro Thr Gln Ile Ile Pro Gly
    450                 455                 460

Ser Val Leu Thr Asp Leu Leu Asp Ala Met
465                 470
```

<210> SEQ ID NO 125
<211> LENGTH: 1443
<212> TYPE: DNA
<213> ORGANISM: Artificial Sequence
<220> FEATURE:
<223> OTHER INFORMATION: plasmid insert 6

<400> SEQUENCE: 125

```
ggatccgcca ccatggcaac tgatatgtcc cagggagaac tgattcatcc taaggctttt     60

ccactcattg tcggggcaca gctcattcac gcagataagc tgggcgagaa gaggggaaga    120

aagaggagaa gcacatgcta cctggacgct ggcctggcta ggaccacaac cggaaacaag    180

ttctttggcg ccctgaaggg agctgtggat ggcggactgt ccatcccaca caggggaagg    240

aagcggcgca gctggctgct gtccagacct gaggccccag aggacttcca gacctttcac    300
```

gctagcctgc agctgaggaa gcagtccctg gctcgcaagc acatctacct gaggggcaga 360
aagaggagat ccgccaacgc tgtgcactct atggagaaag tgatggatat ccactccaag 420
tactgcaggt gtctgcagag actgagctcc acagtgggcc actctctgat tagaggaagg 480
aagcggcgct ctcccggcct gctgagcgtg gacctgttcc acgtgctggt gtctgccgtg 540
ctggcttttc caagcctgta ctgggacgat accgtggatc tgcagccctc caggggcagg 600
aaaaggagat ctgaggtgcc caagcctctg ttccctgtgg ccggagtgcc aatgatccag 660
taccacatcg aggcctgcgc tcaggtgcct ggcatgcagg agatcctgct gcgcggcagg 720
aagcggcgct ctagcaacga ggacagggag tggcacgagt ccttttctct ggtgctggga 780
ccagacgatc ctgtggaggc cgtgctgggc gatgtgacaa ccgctacagt gaggggtagg 840
aagaggagga gcctgtgcct gatgggacac aagcccgtgc tgctgaggac ccagtgcagg 900
tgtcaccctg ccatctctgc catcgctaac gacctgttct acgagggcag ccggggaaga 960
aaacggcgca gcacatccgc cgctgagaca aagcccctc tggctccttc ctctccaccc 1020
gctcctccag gcacaatggt ggctggaagc tccctggagg gaccagctcc caggggaagg 1080
aaaaggagat ctatgagcgt gatggtgctg agaacacagg gaccagaggc tccctttgag 1140
gaccaccggc tgatcctgca cacctctagc tgcgatgctg agagggctag aagaggaaga 1200
aagaggagat ccctgtctgg aaaggacgag caggagaaca gcaacctggc taccccctgag 1260 taccaggtgt ccgaggctgc tagagagctg ggcctggcta cagctgagga gcgcggtagg 1320
aagcggcgct cctgtccaca catgaccgag gacaacaagg atctgatcca gggtaaagac 1380
ctcctgactg cttgctatga tgtggactac gaaaagaatg ccaaaggctc ttgataactc 1440
gag 1443

<210> SEQ ID NO 126
<211> LENGTH: 473
<212> TYPE: PRT
<213> ORGANISM: Artificial Sequence
<220> FEATURE:
<223> OTHER INFORMATION: peptide from insert 6

<400> SEQUENCE: 126

Met Ala Thr Asp Met Ser Gln Gly Glu Leu Ile His Pro Lys Ala Phe
1               5                   10                  15

Pro Leu Ile Val Gly Ala Gln Leu Ile His Ala Asp Lys Leu Gly Glu
            20                  25                  30

Lys Arg Gly Arg Lys Arg Arg Ser Thr Cys Tyr Leu Asp Ala Gly Leu
        35                  40                  45

Ala Arg Thr Thr Thr Gly Asn Lys Phe Phe Gly Ala Leu Lys Gly Ala
    50                  55                  60

Val Asp Gly Gly Leu Ser Ile Pro His Arg Gly Arg Lys Arg Arg Ser
65                  70                  75                  80

Trp Leu Leu Ser Arg Pro Glu Ala Pro Glu Asp Phe Gln Thr Phe His
                85                  90                  95

Ala Ser Leu Gln Leu Arg Lys Gln Ser Leu Ala Arg Lys His Ile Tyr
            100                 105                 110

Leu Arg Gly Arg Lys Arg Arg Ser Ala Asn Ala Val His Ser Met Glu
        115                 120                 125

Lys Val Met Asp Ile His Ser Lys Tyr Cys Arg Cys Leu Gln Arg Leu
    130                 135                 140

Ser Ser Thr Val Gly His Ser Leu Ile Arg Gly Arg Lys Arg Arg Ser
145                 150                 155                 160

Pro Gly Leu Leu Ser Val Asp Leu Phe His Val Leu Val Ser Ala Val
165 170 175

Leu Ala Phe Pro Ser Leu Tyr Trp Asp Asp Thr Val Asp Leu Gln Pro
180 185 190

Ser Arg Gly Arg Lys Arg Arg Ser Glu Val Pro Lys Pro Leu Phe Pro
195 200 205

Val Ala Gly Val Pro Met Ile Gln Tyr His Ile Glu Ala Cys Ala Gln
210 215 220

Val Pro Gly Met Gln Glu Ile Leu Leu Arg Gly Arg Lys Arg Arg Ser
225 230 235 240

Ser Asn Glu Asp Arg Glu Trp His Glu Ser Phe Ser Leu Val Leu Gly
245 250 255

Pro Asp Asp Pro Val Glu Ala Val Leu Gly Asp Val Thr Thr Ala Thr
260 265 270

Val Arg Gly Arg Lys Arg Arg Ser Leu Cys Leu Met Gly His Lys Pro
275 280 285

Val Leu Leu Arg Thr Gln Cys Arg Cys His Pro Ala Ile Ser Ala Ile
290 295 300

Ala Asn Asp Leu Phe Tyr Glu Gly Ser Arg Gly Arg Lys Arg Arg Ser
305 310 315 320

Thr Ser Ala Ala Glu Thr Lys Pro Pro Leu Ala Pro Ser Ser Pro Pro
325 330 335

Ala Pro Pro Gly Thr Met Val Ala Gly Ser Ser Leu Glu Gly Pro Ala
340 345 350

Pro Arg Gly Arg Lys Arg Arg Ser Met Ser Val Met Val Leu Arg Thr
355 360 365

Gln Gly Pro Glu Ala Pro Phe Glu Asp His Arg Leu Ile Leu His Thr
370 375 380

Ser Ser Cys Asp Ala Glu Arg Ala Arg Arg Gly Arg Lys Arg Arg Ser
385 390 395 400

Leu Ser Gly Lys Asp Glu Gln Glu Asn Ser Asn Leu Ala Thr Pro Glu
405 410 415

Tyr Gln Val Ser Glu Ala Ala Arg Glu Leu Gly Leu Ala Thr Ala Glu
420 425 430

Glu Arg Gly Arg Lys Arg Arg Ser Cys Pro His Met Thr Glu Asp Asn
435 440 445

Lys Asp Leu Ile Gln Gly Lys Asp Leu Leu Thr Ala Cys Tyr Asp Val
450 455 460

Asp Tyr Glu Lys Asn Ala Lys Gly Ser
465 470

<210> SEQ ID NO 127
<211> LENGTH: 1443
<212> TYPE: DNA
<213> ORGANISM: Artificial Sequence
<220> FEATURE:
<223> OTHER INFORMATION: plasmid insert 7

<400> SEQUENCE: 127
ggatccgcca ccatggctgc tacatcagaa gggctcctgt tcgccgcatc aatcgagaaa 60
acttggggtt cagtcgtcag gtcaccagag ggtactccac agaaggtgag gagaggaagg 120
aagcggcgct ccacaagagg cctggcctac ctgcacaccg agctgccaca gggcgaccac 180
tacaagcccg ctatctctca cagagatctg aacagccgga acgtgctggt gagaggccgg 240

```
aagaggagat ccatccaccg ggagcagaac tccctgtctc tgctggaggc ctctgaggct    300

gacggcgatg ccgtgaacga caagaagagg acacccaacg aggctccttc tcgcggaagg    360

aagcggcgca gctaccaggt gaagggcaag aagaacatca gagccacaga gcgggctctg    420

agctgggatt ccttcaacac cggcgactgc ctgatcctgg atctgggcca gagaggacgg    480

aagaggagaa gcaggtccct gcaggagctg ctggctagga ggacctacta ctccggcgac    540

cccctgttct ctgtggatat cctgcggaac gtgacagaca cctttaagag aaggggcaga    600

aagcggcgct ccggcggaca cgtgtgctgg atgagagagg gcgtggagct gtgcccagga    660

aacaagtacg agatgaggag acacggaacc acacacagcc tggtcatcca caggggccgc    720

aagcggcgca gctccatggc tctgtccctg cgcctggccc tggctaggtc tagcatcgag    780

agatcctcta cagctagcga cccccaggga gatctgctgt ttctgctgga taggggtcgg    840

aagaggagat ctctgagcaa gcacaagcag atccctggac tgatccagaa catgaccgtg    900

aggtgctgtg agctgcccta ccctgagcag gcttgctgtg gagaggagga gaggggcagg    960

aaacggcgca gctccaacag cggaccaaga ccctccaaca ccacaacctc tagcaactcc   1020

cagtctaaca gcctgcctcg cccatctaac aggggcagca tctctaacta caggggacgg   1080

aagaggagat ctgctggcag cccaggaatg cagcggcgca ggagacgggt gctgaacaca   1140

agcgtggcct acgtgagagg cgaggagaac ctggctggat ggcggcccag gaggggacgc   1200

aagagacggt ccatcaagtc ttgccctgag tgtcggatca ccagcaactt cgtgatccca   1260

tccgagtact gggtggagga gaaggaggag aagcagaagc tgatccagaa gaggggaagg   1320

aagcgcagga gcgccgagga cgagatcgag gatatccagc aggagatcac agctctcagc   1380

cagtgtgata gcccttacat taccagatac ttcggttcct acctcaaatc ctgataactc   1440

gag                                                                 1443
```

<210> SEQ ID NO 128
<211> LENGTH: 473
<212> TYPE: PRT
<213> ORGANISM: Artificial Sequence
<220> FEATURE:
<223> OTHER INFORMATION: peptide from insert 7

<400> SEQUENCE: 128

```
Met Ala Ala Thr Ser Glu Gly Leu Leu Phe Ala Ala Ser Ile Glu Lys
1               5                   10                  15

Thr Trp Gly Ser Val Val Arg Ser Pro Glu Gly Thr Pro Gln Lys Val
            20                  25                  30

Arg Arg Gly Arg Lys Arg Arg Ser Thr Arg Gly Leu Ala Tyr Leu His
        35                  40                  45

Thr Glu Leu Pro Gln Gly Asp His Tyr Lys Pro Ala Ile Ser His Arg
    50                  55                  60

Asp Leu Asn Ser Arg Asn Val Leu Val Arg Gly Arg Lys Arg Arg Ser
65                  70                  75                  80

Ile His Arg Glu Gln Asn Ser Leu Ser Leu Leu Glu Ala Ser Glu Ala
                85                  90                  95

Asp Gly Asp Ala Val Asn Asp Lys Lys Arg Thr Pro Asn Glu Ala Pro
            100                 105                 110

Ser Arg Gly Arg Lys Arg Arg Ser Tyr Gln Val Lys Gly Lys Lys Asn
        115                 120                 125

Ile Arg Ala Thr Glu Arg Ala Leu Ser Trp Asp Ser Phe Asn Thr Gly
    130                 135                 140
```

```
Asp Cys Leu Ile Leu Asp Leu Gly Gln Arg Gly Arg Lys Arg Arg Ser
145                 150                 155                 160

Arg Ser Leu Gln Glu Leu Leu Ala Arg Arg Thr Tyr Tyr Ser Gly Asp
                165                 170                 175

Pro Leu Phe Ser Val Asp Ile Leu Arg Asn Val Thr Asp Thr Phe Lys
            180                 185                 190

Arg Arg Gly Arg Lys Arg Arg Ser Gly Gly His Val Cys Trp Met Arg
        195                 200                 205

Glu Gly Val Glu Leu Cys Pro Gly Asn Lys Tyr Glu Met Arg Arg His
    210                 215                 220

Gly Thr Thr His Ser Leu Val Ile His Arg Gly Arg Lys Arg Arg Ser
225                 230                 235                 240

Ser Met Ala Leu Ser Leu Arg Leu Ala Leu Ala Arg Ser Ser Ile Glu
                245                 250                 255

Arg Ser Ser Thr Ala Ser Asp Pro Gln Gly Asp Leu Leu Phe Leu Leu
            260                 265                 270

Asp Arg Gly Arg Lys Arg Arg Ser Leu Ser Lys His Lys Gln Ile Pro
        275                 280                 285

Gly Leu Ile Gln Asn Met Thr Val Arg Cys Cys Glu Leu Pro Tyr Pro
    290                 295                 300

Glu Gln Ala Cys Cys Gly Glu Glu Glu Arg Gly Arg Lys Arg Arg Ser
305                 310                 315                 320

Ser Asn Ser Gly Pro Arg Pro Ser Asn Thr Thr Thr Ser Ser Asn Ser
                325                 330                 335

Gln Ser Asn Ser Leu Pro Arg Pro Ser Asn Arg Gly Ser Ile Ser Asn
            340                 345                 350

Tyr Arg Gly Arg Lys Arg Arg Ser Ala Gly Ser Pro Gly Met Gln Arg
        355                 360                 365

Arg Arg Arg Arg Val Leu Asn Thr Ser Val Ala Tyr Val Arg Gly Glu
    370                 375                 380

Glu Asn Leu Ala Gly Trp Arg Pro Arg Arg Gly Arg Lys Arg Arg Ser
385                 390                 395                 400

Ile Lys Ser Cys Pro Glu Cys Arg Ile Thr Ser Asn Phe Val Ile Pro
                405                 410                 415

Ser Glu Tyr Trp Val Glu Glu Lys Glu Glu Lys Gln Lys Leu Ile Gln
            420                 425                 430

Lys Arg Gly Arg Lys Arg Arg Ser Ala Glu Asp Glu Ile Glu Asp Ile
        435                 440                 445

Gln Gln Glu Ile Thr Ala Leu Ser Gln Cys Asp Ser Pro Tyr Ile Thr
    450                 455                 460

Arg Tyr Phe Gly Ser Tyr Leu Lys Ser
465                 470
```

<210> SEQ ID NO 129
<211> LENGTH: 3257
<212> TYPE: DNA
<213> ORGANISM: Artificial Sequence
<220> FEATURE:
<223> OTHER INFORMATION: plasmid sequence 11

<400> SEQUENCE: 129

```
gctgcttcgc gatgtacggg ccagatatac gcgttgacat tgattattga ctagttatta      60

atagtaatca attacggggt cattagttca tagcccatat atggagttcc gcgttacata     120

acttacggta aatggcccgc ctggctgacc gcccaacgac ccccgcccat tgacgtcaat     180
```

```
aatgacgtat gttcccatag taacgccaat agggactttc cattgacgtc aatgggtgga    240
gtatttacgg taaactgccc acttggcagt acatcaagtg tatcatatgc caagtacgcc    300
ccctattgac gtcaatgacg gtaaatggcc cgcctggcat tatgcccagt acatgacctt    360
atgggacttt cctacttggc agtacatcta cgtattagtc atcgctatta ccatggtgat    420
gcggttttgg cagtacatca atgggcgtgg atagcggttt gactcacggg gatttccaag    480
tctccacccc attgacgtca atgggagttt gttttggcac caaaatcaac gggactttcc    540
aaaatgtcgt aacaactccg ccccattgac gcaaatgggc ggtaggcgtg tacggtggga    600
ggtctatata agcagagctc tctggctaac tagagaaccc actgcttact ggcttatcga    660
aattaatacg actcactata gggagaccca agctggctag cgtttaaact taagcttggt    720
accgagctcg gatccgccac catggactgg acctggattc tgttcctggt ggccgctgcc    780
acacgggtgc acagccgcga gggagtggag ctgtgcccag gaaacaagta cgagatgagg    840
agacacggca ccacacactc cctggtcatc cacgacccat ctaagcccag cttccaggag    900
tttgtggatt gggagaacgt gtcccctgag ctgaactcta ccgaccagcc attcctggat    960
agcggctccc cctttcctgc tgccgtgatc ctgagggatg ctctgcacat ggcccgggga   1020
ctgaagtacc tgcaccagtg ataactcgag tctagagggc ccgtttaaac ccgctgatca   1080
gcctcgactg tgccttctag ttgccagcca tctgttgttt gcccctcccc cgtgccttcc   1140
ttgaccctgg aaggtgccac tcccactgtc ctttcctaat aaaatgagga aattgcatcg   1200
cattgtctga gtaggtgtca ttctattctg gggggtgggg tggggcagga cagcaagggg   1260
gaggattggg aagacaatag caggcatgct ggggatgcgg tgggctctat ggcttctact   1320
gggcggtttt atggacagca agcgaaccgg aattgccagc tggggcgccc tctggtaagg   1380
ttgggaagcc ctgcaaagta aactggatgg ctttcttgcc gccaaggatc tgatggcgca   1440
ggggatcaag ctctgatcaa gagacaggat gaggatcgtt tcgcatgatt gaacaagatg   1500
gattgcacgc aggttctccg gccgcttggg tggagaggct attcggctat gactgggcac   1560
aacagacaat cggctgctct gatgccgccg tgttccggct gtcagcgcag gggcgcccgg   1620
ttctttttgt caagaccgac ctgtccggtg ccctgaatga actgcaagac gaggcagcgc   1680
ggctatcgtg gctggccacg acgggcgttc cttgcgcagc tgtgctcgac gttgtcactg   1740
aagcgggaag ggactggctg ctattgggcg aagtgccggg gcaggatctc ctgtcatctc   1800
accttgctcc tgccgagaaa gtatccatca tggctgatgc aatgcggcgg ctgcatacgc   1860
ttgatccggc tacctgccca ttcgaccacc aagcgaaaca tcgcatcgag cgagcacgta   1920
ctcggatgga agccggtctt gtcgatcagg atgatctgga cgaagagcat caggggctcg   1980
cgccagccga actgttcgcc aggctcaagg cgagcatgcc cgacggcgag gatctcgtcg   2040
tgacccatgg cgatgcctgc ttgccgaata tcatggtgga aaatggccgc ttttctggat   2100
tcatcgactg tggccggctg ggtgtggcgg accgctatca ggacatagcg ttggctaccc   2160
gtgatattgc tgaagagctt ggcggcgaat gggctgaccg cttcctcgtg ctttacggta   2220
tcgccgctcc cgattcgcag cgcatcgcct tctatcgcct tcttgacgag ttcttctgaa   2280
ttattaacgc ttacaatttc ctgatgcggt attttctcct tacgcatctg tgcggtattt   2340
cacaccgcat caggtggcac ttttcgggga aatgtgcgcg gaacccctat ttgtttattt   2400
ttctaaatac attcaaatat gtatccgctc atgagacaat aaccctgata aatgcttcaa   2460
taatagcacg tgctaaaact tcatttttaa tttaaaagga tctaggtgaa gatccttttt   2520
gataatctca tgaccaaaat cccttaacgt gagttttcgt tccactgagc gtcagacccc   2580
```

gtagaaaaga tcaaaggatc ttcttgagat cctttttttc tgcgcgtaat ctgctgcttg 2640
caaacaaaaa aaccaccgct accagcggtg gtttgtttgc cggatcaaga gctaccaact 2700
ctttttccga aggtaactgg cttcagcaga gcgcagatac caaatactgt tcttctagtg 2760
tagccgtagt taggccacca cttcaagaac tctgtagcac cgcctacata cctcgctctg 2820
ctaatcctgt taccagtggc tgctgccagt ggcgataagt cgtgtcttac cgggttggac 2880
tcaagacgat agttaccgga taaggcgcag cggtcgggct gaacgggggg ttcgtgcaca 2940
cagcccagct tggagcgaac gacctacacc gaactgagat acctacagcg tgagctatga 3000
gaaagcgcca cgcttcccga agggagaaag gcggacaggt atccggtaag cggcagggtc 3060
ggaacaggag agcgcacgag ggagcttcca gggggaaacg cctggtatct ttatagtcct 3120
gtcgggtttc gccacctctg acttgagcgt cgatttttgt gatgctcgtc aggggggcgg 3180
agcctatgga aaaacgccag caacgcggcc tttttacggt tcctggcctt ttgctggcct 3240
tttgctcaca tgttctt 3257

<210> SEQ ID NO 130
<211> LENGTH: 3257
<212> TYPE: DNA
<213> ORGANISM: Artificial Sequence
<220> FEATURE:
<223> OTHER INFORMATION: plasmid sequence 12

<400> SEQUENCE: 130
gctgcttcgc gatgtacggg ccagatatac gcgttgacat tgattattga ctagttatta 60
atagtaatca attacggggt cattagttca tagcccatat atggagttcc gcgttacata 120
acttacggta aatggcccgc ctggctgacc gcccaacgac ccccgcccat tgacgtcaat 180
aatgacgtat gttcccatag taacgccaat agggactttc cattgacgtc aatgggtgga 240
gtatttacgg taaactgccc acttggcagt acatcaagtg tatcatatgc caagtacgcc 300
ccctattgac gtcaatgacg gtaaatggcc cgcctggcat tatgcccagt acatgacctt 360
atgggacttt cctacttggc agtacatcta cgtattagtc atcgctatta ccatggtgat 420
gcggttttgg cagtacatca atgggcgtgg atagcggttt gactcacggg gatttccaag 480
tctccacccc attgacgtca atgggagttt gttttggcac caaaatcaac gggactttcc 540
aaaatgtcgt aacaactccg ccccattgac gcaaatgggc ggtaggcgtg tacggtggga 600
ggtctatata agcagagctc tctggctaac tagagaaccc actgcttact ggcttatcga 660
aattaatacg actcactata gggagaccca agctggctag cgtttaaact taagcttggt 720
accgagctcg gatccgccac catggactgg acctggattc tgttcctggt ggccgctgcc 780
acaagggtgc actctcaggc tatcgtgcgg ggatgcagca tgccaggacc ttggcggtcc 840
ggccgcctgc tggtgtccag gagatggtct gtggagccac tgctgccctt ctaccctccc 900
gatgaggctc tggagatcgg actggagctg aacagctccg ccctgccacc caccgaagtg 960
atcctgcctc aggctccatc tggccccagc tacgccacct acctgcagcc tgctcaggcc 1020
cagatgctga cacctccatg ataactcgag tctagagggc ccgtttaaac ccgctgatca 1080
gcctcgactg tgccttctag ttgccagcca tctgttgttt gcccctcccc cgtgccttcc 1140
ttgaccctgg aaggtgccac tcccactgtc ctttcctaat aaaatgagga aattgcatcg 1200
cattgtctga gtaggtgtca ttctattctg gggggtgggg tggggcagga cagcaagggg 1260
gaggattggg aagacaatag caggcatgct ggggatgcgg tgggctctat ggcttctact 1320

-continued

```
gggcggtttt atggacagca agcgaaccgg aattgccagc tggggcgccc tctggtaagg   1380
ttgggaagcc ctgcaaagta aactggatgg ctttcttgcc gccaaggatc tgatggcgca   1440
ggggatcaag ctctgatcaa gagacaggat gaggatcgtt tcgcatgatt gaacaagatg   1500
gattgcacgc aggttctccg gccgcttggg tggagaggct attcggctat gactgggcac   1560
aacagacaat cggctgctct gatgccgccg tgttccggct gtcagcgcag gggcgcccgg   1620
ttctttttgt caagaccgac ctgtccggtg ccctgaatga actgcaagac gaggcagcgc   1680
ggctatcgtg gctggccacg acgggcgttc cttgcgcagc tgtgctcgac gttgtcactg   1740
aagcgggaag ggactggctg ctattgggcg aagtgccggg gcaggatctc ctgtcatctc   1800
accttgctcc tgccgagaaa gtatccatca tggctgatgc aatgcggcgg ctgcatacgc   1860
ttgatccggc tacctgccca ttcgaccacc aagcgaaaca tcgcatcgag cgagcacgta   1920
ctcggatgga agccggtctt gtcgatcagg atgatctgga cgaagagcat caggggctcg   1980
cgccagccga actgttcgcc aggctcaagg cgagcatgcc cgacggcgag gatctcgtcg   2040
tgacccatgg cgatgcctgc ttgccgaata tcatggtgga aaatggccgc ttttctggat   2100
tcatcgactg tggccggctg ggtgtggcgg accgctatca ggacatagcg ttggctaccc   2160
gtgatattgc tgaagagctt ggcggcgaat gggctgaccg cttcctcgtg ctttacggta   2220
tcgccgctcc cgattcgcag cgcatcgcct tctatcgcct tcttgacgag ttcttctgaa   2280
ttattaacgc ttacaatttc ctgatgcggt attttctcct tacgcatctg tgcggtattt   2340
cacaccgcat caggtggcac ttttcgggga aatgtgcgcg gaacccctat ttgtttattt   2400
ttctaaatac attcaaatat gtatccgctc atgagacaat aaccctgata aatgcttcaa   2460
taatagcacg tgctaaaact tcatttttaa tttaaaagga tctaggtgaa gatccttttt   2520
gataatctca tgaccaaaat cccttaacgt gagttttcgt tccactgagc gtcagacccc   2580
gtagaaaaga tcaaaggatc ttcttgagat cctttttttc tgcgcgtaat ctgctgcttg   2640
caaacaaaaa aaccaccgct accagcggtg gtttgtttgc cggatcaaga gctaccaact   2700
ctttttccga aggtaactgg cttcagcaga gcgcagatac caaatactgt tcttctagtg   2760
tagccgtagt taggccacca cttcaagaac tctgtagcac cgcctacata cctcgctctg   2820
ctaatcctgt taccagtggc tgctgccagt ggcgataagt cgtgtcttac cgggttggac   2880
tcaagacgat agttaccgga taaggcgcag cggtcgggct gaacgggggg ttcgtgcaca   2940
cagcccagct tggagcgaac gacctacacc gaactgagat acctacagcg tgagctatga   3000
gaaagcgcca cgcttcccga agggagaaag gcggacaggt atccggtaag cggcagggtc   3060
ggaacaggag agcgcacgag ggagcttcca gggggaaacg cctggtatct ttatagtcct   3120
gtcgggtttc gccacctctg acttgagcgt cgatttttgt gatgctcgtc aggggggcgg   3180
agcctatgga aaaacgccag caacgcggcc tttttacggt tcctggcctt ttgctggcct   3240
tttgctcaca tgttctt                                                  3257
```